United States Patent
Braun, III et al.

(10) Patent No.: US 10,801,057 B2
(45) Date of Patent: Oct. 13, 2020

(54) SELECTION OF MATURE FRUIT COLOR IN PEPPER PLANTS

(71) Applicant: SEMINIS VEGETABLE SEEDS, INC., St. Louis, MO (US)

(72) Inventors: Carl Joseph Braun, III, Woodland, CA (US); Eva King-Fan Chan, Rosebery (AU); Graeme S. Garvey, Woodland, CA (US); Carl Martin Jones, Sacramento, CA (US); Brian J. Just, Fort Myers, FL (US); Joel M. Kniskern, Sacramento, CA (US); Jonathan R. Mein, Concord, NC (US); Thomas C. Osborn, Kirkwood, MO (US); Petrus M. J. A. van Poppel, Wageningen (NL)

(73) Assignee: Seminis Vegetable Seeds, Inc., St. Louis, MO (US)

( * ) Notice: Subject to any disclaimer, the term of this patent is extended or adjusted under 35 U.S.C. 154(b) by 119 days.

(21) Appl. No.: 15/643,317

(22) Filed: Jul. 6, 2017

(65) Prior Publication Data
US 2017/0367288 A1 Dec. 28, 2017

Related U.S. Application Data

(62) Division of application No. 14/304,722, filed on Jun. 13, 2014, now Pat. No. 9,723,797.

(60) Provisional application No. 61/863,765, filed on Aug. 8, 2013, provisional application No. 61/838,094, filed on Jun. 21, 2013.

(51) Int. Cl.
| | |
|---|---|
| *C12Q 1/68* | (2018.01) |
| *A01H 1/04* | (2006.01) |
| *A01H 6/82* | (2018.01) |
| *A01H 5/08* | (2018.01) |
| *C12Q 1/6827* | (2018.01) |
| *C12Q 1/6895* | (2018.01) |

(52) U.S. Cl.
CPC ............ *C12Q 1/6827* (2013.01); *A01H 1/04* (2013.01); *A01H 6/822* (2018.05); *C12Q 1/6895* (2013.01); *C12Q 2600/13* (2013.01); *C12Q 2600/156* (2013.01)

(58) Field of Classification Search
None
See application file for complete search history.

(56) References Cited

U.S. PATENT DOCUMENTS

| | | |
|---|---|---|
| 8,026,424 B2 | 9/2011 | Van Der Heiden |
| 8,044,273 B2 | 10/2011 | Van Der Heiden |
| 8,067,681 B2 | 11/2011 | Van Der Heiden |
| 8,415,536 B2 | 4/2013 | Leij |
| 8,420,905 B2 | 4/2013 | Leij |
| 8,536,419 B2 | 9/2013 | Lindeman |

FOREIGN PATENT DOCUMENTS

| | | |
|---|---|---|
| WO | 2004089067 A1 | 10/2004 |
| WO | WO 2011/028120 | 3/2011 |

OTHER PUBLICATIONS

Bouvier et al. Journal of Biological Chemistry 46(15): 28861-28867 (1996).*
"Baloian Farms added to specialty packs with BellaFina baby bell peppers," article 103896; available at <http://www.freshplaza.com/article/103896/Baloian-Farms-adds-to-specialty-packs-with-BellaFina-baby-bell-peppers>, Dec. 6, 2012.
Borovsky et al., "Induced mutation in β-Carotene Hydroxylase results in accumulation of β-carotene and conversion of red to orange color in pepper fruit," *Theoret Appl Genet* 126:557-565, 2013.
Borovsky et al., "Chlorophyll breakdown during pepper fruit ripening in the *chlorophyll retainer* mutation is impaired at the homolog of the senescence-inducible stay-green gene," *Theoret Appl Genet* 117:235-240; 2008.
Brand et al., "pc8.1,a major QTL for pigment content in pepper fruit, is associated with variation in plastid compartment size," Planta 235(3):579-588, (2012).
Britton, "Structure and properties of carotenoids in relation to function," *FASEB J* 9:1551-1558, 1995.
European Extended Search Report regarding European Application No. 14814153.4, dated Dec. 16, 2016.
Farré et al., "Travel advice on the road to carotenoids in plants," Plant Science 179:28-48, 2010.
GenBank Accession No. DQ907615.1, "Capsicum annuum cultivar Nockwang capsanthin/capsorubin synthase, promoter region and partial sequence," dated Sep. 1, 2007.
GenBank Accession No. X77289, "C.annuum capsanthin/capsorubin synthase gene," dated Aug. 23, 1994.
GenBank Accession No. X91491, "C.annuum mRNA for xanthophyll epoxidase," dated Sep. 9, 2004.
Genbank Accession No. X68017.1, "C.annuum psyl mRNA for phytoene synthase," dated Feb. 5, 1994.
Guzman et al., "Variability of carotenoid biosynthesis in orange colored *Capsicum* spp.," *Plant Science* 179:49-59, 2010.

(Continued)

*Primary Examiner* — David T Fox
(74) *Attorney, Agent, or Firm* — Dentons US LLP; Matthew L. Madsen, Esq.

(57) ABSTRACT

The invention provides methods and compositions for breeding pepper (*Capsicum* sp. such as *Capsicum annuum*) lines, including isogenic and nearly isogenic lines, displaying one or more mature fruit color(s) of interest. Predictive genetic markers and associated sequences and primers, associated with phenotypic diversity at the Ccs locus encoding Capsanthin-Capsorubin Synthase, and the Ze locus encoding Zeaxanthin Epoxidase are also provided, as well as methods for breeding pepper lines. Further provided are pepper plants, and plant parts including seeds, seed mixtures, fruit, and packaged fruit, which display mature fruit color(s) of interest.

16 Claims, 77 Drawing Sheets

Specification includes a Sequence Listing.

(56) References Cited

OTHER PUBLICATIONS

Ha et al., "A comparison of the carotenoid accumulation in *Capsicum* varieties that show different ripening colours: deletion of the capsanthin-capsorubin synthase gene is not a prerequisite for the formation of a yellow pepper," *J Experim Botany* 58:3135-3144, 2007.

Hill et al., "Linkage disequilibrium of finite populations," *Theoret Appl Genet* 38:226-231, 1968.

Kim et al., "A splicing mutation in the gene encoding phytoene synthase causes orange coloration in habanero pepper fruits," *Mol Cells* 30:569-574, 2010.

Lang et al., "Orange fruit color in *Capsicum* due to deletion of Capsanthin-capsorubin synthesis gene," *Breeding Science* 54:33-39, 2004.

Lefebvre et al., "The capsanthin capsorubin synthase gene: a candidate gene for the y locus controlling the red fruit colour in pepper," *Plant Mol Biol* 36:785-789, 1998.

Popovsky et al., "Molecular genetics of the y locus in pepper: its relation to capsanthin-capsorubin synthase and to fruit color," *Theoret Appl Genet* 101:86-89, 2000.

Purcell et al., "PLINK: A tool set for whole-genome association and population-based linkage analyses," *Am J Hum Genet* 81:559-575, 2007.

Ramchiary et al., "Application of genetics and genomics towards Capsicum translational research," Plant Biotechnology Reports 8(2):101-123, 2013.

Romer et al., "Genetic Engineering of a Zeaxanthin-rich Potato by Antisense Inactivation and Co-suppression of Carotenoid Epoxidation," Metabolic Engineering 4:263-272, 2002.

Thorup et al., "Candidate gene analysis of organ pigmentation loci in the Solanaceae," *PNAS USA* 97:11192-11197, 2000.

Wahyuni et al., "Metabolite biodiversity in pepper (Capsicum) fruits of thirty-two diverse accessions: Variation in health-related compounds and implications for breeding," Phytochemistry 72:1358-1370, 2011.

International Search Report and Written Opinion of the ISA for PCT/US2014/042392, dated Nov. 4, 2014.

Extended European Search Report regarding Europe Application No. 20163450.8, dated May 29, 2020.

Matsufuji et al., Anti-oxidant content of different coloured sweet peppers, white, green, yellow, orange and red (*Capsicum annuum* L.), International Journal of Food Science and Technology, 42(12):1482-1488, 2007.

\* cited by examiner

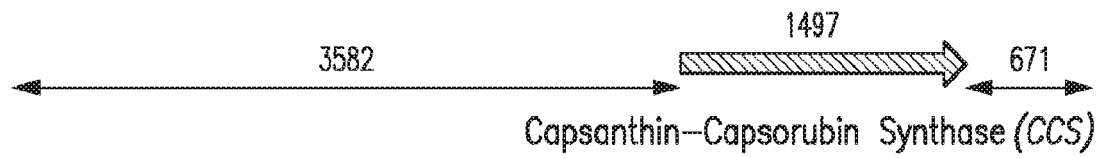
Capsanthin–Capsorubin Synthase (CCS)
FIG. 3A
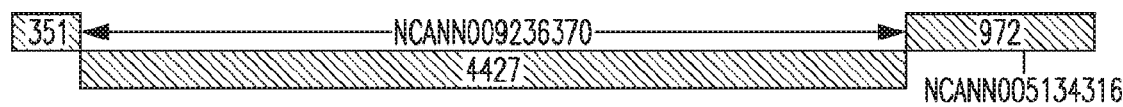
FIG. 3B
| line | Fruit color | NCANN009236370 | NCANN005134316 |
|---|---|---|---|
| 10CA_3745-M | red | INS | A |
| HAS-30-1017 | red | INS | A |
| SZZ-8T10901 | red | INS | A |
| SBR-27-146 | red | INS | A |
| SBR-99-1193 | red | INS | T |
| SBR-99-1299 | red | INS | T |
| SBR-99-1300 | red | INS | T |
| SBY-148-5201 | yellow | DEL | A |
| SBY-29-469 | yellow | DEL | A |
| SBY-99-1179 | yellow | DEL | A |
| SBY-99-1273 | yellow | DEL | A |
| SBY-99-1296 | yellow | DEL | A |
| SBY-99-1339 | yellow | DEL | A |
| SMO-28-1234 | orange | DEL | A |
FIG. 3C

```
contig36343     CCCAATAACCCAATACTAATAACTTAATAATATTTTATCGGTTCGATTTATCGATCGGCTCAACTACCAAAAGGAACAAAAAAATAAATAGAGTA    96
Ze_gDNA_yellow  CCCAATAATCCAATACTAATAACTTAATAATATTTTATCGGTTCGATTTATCGATCGGCTCAACTACCAAAAGGAACAAAAAAATAAATAGAGTA    96
Ze_gDNA_orange  CCCAATAACCCAATACTAATAACTTAATAATATTTTATCGGTTCGATTTATCGATCGGCTCAACTACCAAAAGGAACAAAAAAATAAATAGAGTA    96
Ze_CDS          ------------------------------------------------------------------------------------------------    0
                        NCANN0091989790
                        * contig36343     CTACAACAACCATAGATGAGTGAACAAGCGTCAAACATCAGCCTCAGTTTAGTAACCAAACAAGCTACAATGACAAGCCACCTGGCCATAAAATC   192
Ze_gDNA_yellow  CTACAACAACCATAGATGAGTGAACAAGCGTCAAACATCAGCCTCAGTTTAGTAACCAAACAAGCTACAATGACAAGCCACCTGGCCATAAAATC   192
Ze_gDNA_orange  CTACAACAACCATAGATGAGTGAACAAGCGTCAAACATCAGCCTCAGTTTAGTAACCAAACAAGCTACAATGACAAGCCACCTGGCCATAAAATC   192
Ze_CDS          ------------------------------------------------------------------------------------------------    0 contig36343     TTCACCATTGCTGCTTCATGGACCATTGATTGGTTCTCAATCTTCTTTGCCCACCACCACCCTCACTATCACCCACAATTTCCACTTCC         288
Ze_gDNA_yellow  TTCACCATTGCTGCTTCATGGACCATTGATTGGTTCTCAATCTTCTTTGCCCACCACCACCCTCACTATCACCCACAATTTCCACTTCC         288
Ze_gDNA_orange  TTCACCATTGCTGCTTCATGGACCATTGATTGGTTCTCAATCTTCTTTGCCCACCACCACCCTCACTATCACCCACAATTTCCACTTCC         288
Ze_CDS          ------------------------------------------------------------------------------------------------    0 contig36343     TTTTTTCCCTCCTCAAAAGCTAACTAACACACATTGGCCTAACTAAAATTCTCATAAATAATCACCTTCACTTCTTTTTTTCATTAGATTATACATTA    384
Ze_gDNA_yellow  TTTTTTCCCTCCTCAAAAGCTAACTAACACACATTGGCCTAACTAAAATTCTCATAAATAATCACCTTCACTTCTTTTTTTCATTAGATTATACATTA    384
Ze_gDNA_orange  TTTTTTCCCTCCTCAAAAGCTAACTAACACACATTGGCCTAACTAAAATTCTCATAAATAATCACCTTCACTTCTTTTTTTCATTAGATTATACATTA    384
Ze_CDS          ------------------------------------------------------------------------------------------------    0 contig36343     GTTGTTTGGTCTCAATCTTCCTTCACTTCCTTTGGCCTAATTAACAGTTTATATAAATCAACTTCACTTCTTTTTTTCACTAAAACATACAGTGA     480
Ze_gDNA_yellow  GTTGTTTGGTCTCAATCTTCCTTCACTTCCTTTGGCCTAATTAACAGTTTATATAAATCAACTTCACTTCTTTTTTTCACTAAAACATACAGTGA     480
Ze_gDNA_orange  GTTGTTTGGTCTCAATCTTCCTTCACTTCCTTTGGCCTAATTAACAGTTTATATAAATCAACTTCACTTCTTTTTTTCACTAAAACATACAGTGA     480
Ze_CDS          ------------------------------------------------------------------------------------------------    0 contig36343     AAGAGAAACACAAGAGTCTTTCTTGAACTGGAGTTCTAGTGAAAGATGTATTCAACTGTGTTTACACTTCAGTTCATCCCTCCACTTCAGTTTT    576
Ze_gDNA_yellow  AAGAGAAACACAAGAGTCTTTCTTGAACTGGAGTTCTAGTGAAAGATGTATTCAACTGTGTTTACACTTCAGTTCATCCCTCCACTTCAGTTTT    576
Ze_gDNA_orange  AAGAGAAACACAAGAGTCTTTCTTGAACTGGAGTTCTAGTGAAAGATGTATTCAACTGTGTTTACACTTCAGTTCATCCCTCCACTTCAGTTTT    576
Ze_CDS          ---------------------------------------ATGTATTCAACTGTGTTTACACTTCAGTTCATCCCTCCACTTCAGTTTT          50
                                                        Start contig36343     TTCAAGAAAACAGCTACCTTTATTGATATCCAAGGACTTCCTGCAGAGTTGTATCATTCTTTACCTTGTAAGAGTTTGGAAAATGGGCATATCAA    672
Ze_gDNA_yellow  TTCAAGAAAACAGCTACCTTTATTGATATCCAAGGACTTCCTGCAGAGTTGTATCATTCTTTACCTTGTAAGAGTTTGGAAAATGGGCATATCAA    672
Ze_gDNA_orange  TTCAAGAAAACAGCTACCTTTATTGATATCCAAGGACTTCCTGCAGAGTTGTATCATTCTTTACCTTGTAAGAGTTTGGAAAATGGGCATATCAA    672
Ze_CDS          TTCAAGAAAACAGCTACCTTTATTGATATCCAAGGACTTCCTGCAGAGTTGTATCATTCTTTACCTTGTAAGAGTTTGGAAAATGGGCATATCAA    146 contig36343     GAAGGTTAAAGGAGTAAAAGCCACACTAGCTGAAGCTCCAGCTGAAGCTCCAGCTCCAGCTCGAAGCTCGAGGTTCCACAGAAGAAGTTGAAAGTACT  768
Ze_gDNA_yellow  GAAGGTTAAAGGAGTAAAAGCCACACTAGCTGAAGCTCCAGCTGAAGCTCCAGCTCCAGCTCGAAGCTCGAGGTTCCACAGAAGAAGTTGAAAGTACT  768
Ze_gDNA_orange  GAAGGTTAAAGGAGTAAAAGCCACACTAGCTGAAGCTCCAGCTGAAGCTCCAGCTCCAGCTCGAAGCTCGAGGTTCCACAGAAGAAGTTGAAAGTACT  768
Ze_CDS          GAAGGTTAAAGGAGTAAAAGCCACACTAGCTGAAGCTCCAGCTGAAGCTCCAGCTCCAGCTCGAAGCTCGAGGTTCCACAGAAGAAGTTGAAAGTACT  242 contig36343     TGTGGCAGGTGGTGGGATTGGAGGATTAGTTTTTGCTTTGGCAGCAGCAAAGAAAAAGGGGTTTGATGTATTGGTGTTTGAGAGAGATTAAGTGCTAT  864
Ze_gDNA_yellow  TGTGGCAGGTGGTGGGATTGGAGGATTAGTTTTTGCTTTGGCAGCAGCAAAGAAAAAGGGGTTTGATGTATTGGTGTTTGAGAGAGATTAAGTGCTAT  864
Ze_gDNA_orange  TGTGGCAGGTGGTGGGATTGGAGGATTAGTTTTTGCTTTGGCAGCAGCAAAGAAAAAGGGGTTTGATGTATTGGTGTTTGAGAGAGATTAAGTGCTAT  864
Ze_CDS          TGTGGCAGGTGGTGGGATTGGAGGATTAGTTTTTGCTTTGGCAGCAGCAAAGAAAAAGGGGTTTGATGTATTGGTGTTTGAGAGAGATTAAGTGCTAT  338
```

```
contig36343      GGTGTGACAACGTTATAGACCTATTAGTTGCCACAGATGAAGATGCAATTCTTCGTCGTGACATCTATGATAGACCGCCAACATTTAATTGGGGAA  2880
Ze_gDNA_yellow   GGTGTGACAACGTTATAGACCTATTAGTTGCCACAGATGAAGATGCAATTCTTCGTCGTGACATCTATGATAGACCGCCAACATTTAATTGGGGAA  2880
Ze_gDNA_orange   GGTGTGACAACGTTATAGACCTATTAGTTGCCACAGATGAAGATGCAATTCTTCGTCGTGACATCTATGATAGACCGCCAACATTTAATTGGGGAA  2880
Ze_CDS           GGTGTGACAACGTTATAGACCTATTAGTTGCCACAGATGAAGATGCAATTCTTCGTCGTGACATCTATGATAGACCGCCAACATTTAATTGGGGAA  1084 contig36343      GAGGTCGTGTGTTACATTGCTTGGGGACTCAGTCCATGCTATGCCATGTCAGCCTAATTTGGTCAAGGAGGAGGATGCATGGCCATAGAGGTACACCACTGTGTTT  2976
Ze_gDNA_yellow   GAGGTCGTGTGTTACATTGCTTGGGGACTCAGTCCATGCTATGCCATGTCAGCCTAATTTGGTCAAGGAGGAGGATGCATGGCCATAGAGGTACACCACTGTGTTT  2976
Ze_gDNA_orange   GAGGTCGTGTGTTACATTGCTTGGGGACTCAGTCCATGCTATGCCATGTCAGCCTAATTTGGTCAAGGAGGAGGATGCATGGCCATAGAGGTACACCACTGTGTTT  2976
Ze_CDS           GAGGTCGTGTGTTACATTGCTTGGGGACTCAGTCCATGCTATGCCATGTCAGCCTAATTTGGTCAAGGAGGAGGATGCATGGCCATAGAG              1164 contig36343      ATCATCTTTGTCAAATACACAGTATTGTAAGGTTGTGTATGACACTGAAACTTTCCATGTACAACTACAGGATAGCTATCAACTAGCACTGGAACT  3072
Ze_gDNA_yellow   ATCATCTTTGTCAAATACACAGTATTGTAAGGTTGTGTATGACACTGAAACTTTCCATGTACAACTACAGGATAGCTATCAACTAGCACTGGAACT  3072
Ze_gDNA_orange   ATCATCTTTGTCAAATACACAGTATTGTAAGGTTGTGTATGACACTGAAACTTTCCATGTACAACTACAGGATAGCTATCAACTAGCACTGGAACT  3072
Ze_CDS                                                                           GATAGCTATCAACTAGCACTGGAACT  1190 contig36343      TGAGAAAGCATGGAGCCGAAGTGCTGAGTCCGGAGCCCTATGGATGTCATCATCTTTAAGGAGGTAATCCATTATTATTTATTGGCTCAAGTGCTG  3168
Ze_gDNA_yellow   TGAGAAAGCATGGAGCCGAAGTGCTGAGTCCGGAGCCCTATGGATGTCATCATCTTTAAGGAGGTAATCCATTATTATTTATTGGCTCAAGTGCTG  3168
Ze_gDNA_orange   TGAGAAAGCATGGAGCCGAAGTGCTGAGTCCGGAGCCCTATGGATGTCATCATCTTTAAGGAGGTAATCCATTATTATTTATTGGCTCAAGTGCTG  3168
Ze_CDS           TGAGAAAGCATGGAGCCGAAGTGCTGAGTCCGGAGCCCTATGGATGTCATCATCTCATCTTTAAGG                                1254 contig36343      TAGTCTGGTTGGTTGGTTGAGTACAGGCTGCCAGTTCATGATAATTGAAAAAACATTTGCAATTGGTTGAGGTCTTTAACTTCACCCACCAGCCCA  3264
Ze_gDNA_yellow   TAGTCTGGTTGGTTGGTTGAGTACAGGCTGCCAGTTCATGATAATTGAAAAAACATTTGCAATTGGTTGAGGTCTTTAACTTCACCCACCAGCCCA  3264
Ze_gDNA_orange   TAGTCTGGTTGGTTGGTTGAGTACAGGCTGCCAGTTCATGATAATTGAAAAAACATTTGCAATTGGTTGAGGTCTTTAACTTCACCCACCAGCCCA  3264
Ze_CDS                                                                                                        1254 contig36343      GTAGGACTGCTTTAAATGCCTCAACTGAAAATGCCTCAACTGAAAATGGATTCATTTGAACAGCTGCCGTCTCGCCGATCCTTTAATGAATTCCTTTTTCT  3360
Ze_gDNA_yellow   GTAGGACTGCTTTAAATGCCTCAACTGAAAATGCCTCAACTGAAAATGGATTCATTTGAACAGCTGCCGTCTCGCCGATCCTTTAATGAATTCCTTTTTCT  3360
Ze_gDNA_orange   GTAGGACTGCTTTAAATGCCTCAACTGAAAATGCCTCAACTGAAAATGGATTCATTTGAACAGCTGCCGTCTCGCCGATCCTTTAATGAATTCCTTTTTCT  3360
Ze_CDS                                                                                                         1254 contig36343      GCAGCTATGAAAGTGCTAGAAAACTTCGAGTTGGAGTTATCCATGGACTGCTAGAATGGCTGCAATCATGGACCAATTGAATTGCGCAGGCCTATCTTG  3456
Ze_gDNA_yellow   GCAGCTATGAAAGTGCTAGAAAACTTCGAGTTGGAGTTATCCATGGACTGCTAGAATGGCTGCAATCATGGACCAATTGAATTGCGCAGGCCTATCTTG  3456
Ze_gDNA_orange   GCAGCTATGAAAGTGCTAGAAAACTTCGAGTTGGAGTTATCCATGGACTGCTAGAATGGCTGCAATCATGGACCAATTGAATTGCGCAGGCCTATCTTG  3456
Ze_CDS           --AGCTATGAAAGTGCTAGAAAACTTCGAGTTGGAGTTATCCATGGACTGCTAGAATGGCTGCAATCATGGACCAATTGAATTGCGCAGGCCTATCTTG  1348 contig36343      GTGTCGGACTTGGTCCATTATCAGTATGGAAAACTATCTATCACTTGAAATTGAAATTGCGTGATTGCGCAGAGCTCTTCTTA  3552
Ze_gDNA_yellow   GTGTCGGACTTGGTCCATTATCAGTATGGAAAACTATCTATCACTTGAAATTGAAATTGCGTGATTGCGCAGAGCTCTTCTTA  3552
Ze_gDNA_orange   GTGTCGGACTTGGTCCATTATCAGTATGGAAAACTATCTATCACTTGAAATTGAAATTGCGTGATTGCGCAGAGCTCTTCTTA  3552
Ze_CDS           GTGTCGGACTTGGTCCATTATCAGTATGG                                                        1377 contig36343      TAATAGATGTTTTTTCTATTATTTGTCAGTTTTGTCAGTTTTGACCAAGTATAGGATACCACATCCTGGAAGAGTATTTGTGGACTTGGG  3648
Ze_gDNA_yellow   TAATAGATGTTTTTTCTATTATTTGTCAGTTTTGTCAGTTTTGACCAAGTATAGGATACCACATCCTGGAAGAGTATTTGTGGACTTGGG  3648
Ze_gDNA_orange   TAATAGATGTTTTTTCTATTATTTGTCAGTTTTGTCAGTTTTGACCAAGTATAGGATACCACATCCTGGAAGAGTATTTGTGGACTTGGG  3648
Ze_CDS                                                           ACCAAGTATAGGATACCACATCCTGGAAGAGTATTTGTGGACTTGGG  1436 contig36343      AATGCCTCTAATGTTAAGTTGGGTTCTAGGAGGCAACGGTCAACCGGTCAACGGCAACCGGTCAACCGGCAACGGTCAGCGAGCTGTATTCCAGCATTTCTTGCTTCTTGCTTCAGTATTTGAACATGAT  3744
Ze_gDNA_yellow   AATGCCTCTAATGTTAAGTTGGGTTCTAGGAGGCAACGGTCAACCGGTCAACGGCAACCGGTCAACCGGCAACGGTCAGCGAGCTGTATTCCAGCATTTCTTGCTTCTTGCTTCAGTATTTGAACATGAT  3744
Ze_gDNA_orange   AATGCCTCTAATGTTAAGTTGGGTTCTAGGAGGCAACGGTCAACCGGTCAACGGCAACCGGTCAACCGGCAACGGTCAGCGAGCTGTATTCCAGCATTTCTTGCTTCTTGCTTCAGTATTTGAACATGAT  3744
Ze_CDS           AATGCCTCTAATGTTAAGTTGGGTTCTAGGAGGCAACGG                                                                                            1476
```

```
contig36343    GTTTCCTTCATGAATTTCTTTTATAGATTTTCGTATTTGTAAGTCTTCATTCAAAATTAACTACTATTTTTACTTTTATTTCTAACTTGCATTAT  5664
Ze_gDNA_yellow GTTTCCTTCATGAATTTCTTTTATAGATTTTCGTATTTGTAAGTCTTCATTCAAAATTAACTACTATTTTTACTTTTATTTCTAACGTGCATTAT  5664
Ze_gDNA_orange GTTTCCTTCATGAATTTCTTTTATAGATTTTCGTATTTGTAAGTCTTCATTCAAAATTAACTACTATTTTTACTTTTATTTCTAACTTGCATTAT  5664
Ze_CDS         --------------------------------------------------------------------------------------T-------  1971
                                                                                              NCANN00919917O
                                                                                                   *
contig36343    TTTTTACTTTTTATTTCTAACTTGCATTTTATGTTCATTGTTGATTTTATACATAATAAATGAAACAAATAGAAAAAAATAATAAATT  5752
Ze_gDNA_yellow TTTTTACTTTTTATTTCTAACTTGCATTTTATGTTCATTGTTGATTTTATACATAATAAATGAAACAAATAGAAAAAAATAATAAATT  5752
Ze_gDNA_orange TTTTTACTTTTTATTTCTAACTTGCATTTTATGTTCATTGTTGATTTTATACATAATAATAAATGAAACAAATAGAAAAAAATAATAAATT  5752
Ze_CDS         --------------------------------------------------------------------------------------  1971
```

FIG.5 (continued)

```
SBY-99-1273      TGTTGAATGGAAAATATTGGAAGAGAATTTCATTTCATTTTTACAAAAATAAAGAGTGTAGAG   60
SMO-28-1234      TGTTGAATGGAAAATATTGGAAGAGAATTTCATTTCATTTTTACAAAAATAAAGAGTGTAGAG   60
SBY-99-1339      TGTTGAATGGAAAATATTGGAAGAGAATTTCATTTCATTTTTACAAAAATAAAGAGTGTAGAG   60
SBY-99-1296      TGTTGAATGGAAAATATTGGAAGAGAATTTCATTTCATTTTTACAAAAATAAAGAGTGTAGAG   60
SBY-99-1179      TGTTGAATGGAAAATATTGGAAGAGAATTTCATTTCATTTTTACAAAAATAAAGAGTGTAGAG   60
SBY-29-469       TGTTGAATGGAAAATATTGGAAGAGAATTTCATTTCATTTTTACAAAAATAAAGAGTGTAGAG   60
SBY-148-5201     TGTTGAATGGAAAATATTGGAAGAGAATTTCATTTCATTTTTACAAAAATAAAGAGTGTAGAG   60
SBR-27-146       TGTTGAATGGAAAATATTGGAAGAGAATTTCATTTCATTTTTACAAAAATAAAGAGTGTAGAG   60
Jimmy Nardello   TGTTGAATGGAAAATATTGGAAGAGAATTTCATTTCATTTTTACAAAAATAAAGAGTGTAGAG   60
10CA 3745-M      TGTTGAATGGAAAATATTGGAAGAGAATTTCATTTCATTTTTACAAAAATAAAGAGTGTAGAG   60
SBR-99-1193      TGTTGAATGGAAAATATTGGAAGAGAATTTCATTTCATTTTTACAAAAATAAAGAGTGTAGAG   60
SBR-99-1299      TGTTGAATGGAAAATATTGGAAGAGAATTTCATTTCATTTTTACAAAAATAAAGAGTGTAGAG   60
SBR-99-1300      TGTTGAATGGAAAATATTGGAAGAGAATTTCATTTCATTTTTACAAAAATAAAGAGTGTAGAG   60
HAS-30-1017      TGTTGAATGGAAAATATTGGAAGAGAATTTCATTTCATTTTTACAAAAATAAAGAGTGTAGAG   60

SBY-99-1273      GGTATTTTTGTAAATCAATATTTTTTCTATAAAAAAATATAAGAAATATTATTTTAATA   120
SMO-28-1234      GGTATTTTTGTAAATCAATATTTTTTCTATAAAAAAATATAAGAAATATTATTTTAATA   120
SBY-99-1339      GGTATTTTTGTAAATCAATATTTTTTCTATAAAAAAATATAAGAAATATTATTTTAATA   120
SBY-99-1296      GGTATTTTTGTAAATCAATATTTTTTCTATAAAAAAATATAAGAAATATTATTTTAATA   120
SBY-99-1179      GGTATTTTTGTAAATCAATATTTTTTCTATAAAAAAATATAAGAAATATTATTTTAATA   120
SBY-29-469       GGTATTTTTGTAAATCAATATTTTTTCTATAAAAAAATATAAGAAATATTATTTTAATA   120
SBY-148-5201     GGTATTTTTGTAAATCAATATTTTTTCTATAAAAAAATATAAGAAATATTATTTTAATA   120
SBR-27-146       GGTATTTTTGTAAATCAATATTTTTTCTATAAAAAAATATAAGAAATATTATTTTAATA   120
Jimmy Nardello   GGTATTTTTGTAAATCAATATTTTTTCTATAAAAAAATATAAGAAATATTATTTTAATA   120
10CA 3745-M      GGTATTTTTGTAAATCAATATTTTTTCTATAAAAAAATATAAGAAATATTATTTTAATA   120
SBR-99-1193      GGTATTTTTGTAAATCAATATTTTTTCTATAAAAAAATATAAGAAATATTATTTTAATA   120
SBR-99-1299      GGTATTTTTGTAAATCAATATTTTTTCTATAAAAAAATATAAGAAATATTATTTTAATA   120
SBR-99-1300      GGTATTTTTGTAAATCAATATTTTTTCTATAAAAAAATATAAGAAATATTATTTTAATA   120
HAS-30-1017      GGTATTTTTGTAAATCAATATTTTTTCTATAAAAAAATATAAGAAATATTATTTTAATA   120
```

| | | |
|---|---|---|
| SBY-99-1273 | CTACCAAACGACCCTAAGTGTGTATCTATATCCTCCGAGAATTTGGAATTTGCAAATTCC | 300 |
| SMO-28-1234 | CTACCAAACGACCCTAAGTGTGTATCTATATCCTCCGAGAATTTGGAATTTGCAAATTCC | 300 |
| SBY-99-1339 | CTACCAAACGACCCTAAGTGTGTATCTATATCCTCCGAGAATTTGGAATTTGCAAATTCC | 300 |
| SBY-99-1296 | CTACCAAACGACCCTAAGTGTGTATCTATATCCTCCGAGAATTTGGAATTTGCAAATTCC | 300 |
| SBY-99-1179 | CTACCAAACGACCCTAAGTGTGTATCTATATCCTCCGAGAATTTGGAATTTGCAAATTCC | 300 |
| SBY-29-469 | CTACCAAACGACCCTAAGTGTGTATCTATATCCTCCGAGAATTTGGAATTTGCAAATTCC | 300 |
| SBY-148-5201 | CTACCAAACGACCCTAAGTGTGTATCTATATCCTCCGAGAATTTGGAATTTGCAAATTCC | 300 |
| SBR-27-146 | CTACCAAACGACCCTAAGTGTGTATCTATATCCTCCGAGAATTTGGAATTTGCAAATTCC | 300 |
| Jimmy Nardello | CTACCAAACGACCCTAAGTGTGTATCTATATCCTCCGAGAATTTGGAATTTGCAAATTCC | 300 |
| 10CA_3745-M | CTACCAAACGACCCTAAGTGTGTATCTATATCCTCCGAGAATTTGGAATTTGCAAATTCC | 300 |
| SBR-99-1193 | CTACCAAACGACCCTAAGTGTGTATCTATATCCTCCGAGAATTTGGAATTTGCAAATTCC | 300 |
| SBR-99-1299 | CTACCAAACGACCCTAAGTGTGTATCTATATCCTCCGAGAATTTGGAATTTGCAAATTCC | 300 |
| SBR-99-1300 | CTACCAAACGACCCTAAGTGTGTATCTATATCCTCCGAGAATTTGGAATTTGCAAATTCC | 300 |
| HAS-30-1017 | CTACCAAACGACCCTAAGTGTGTATCTATATCCTCCGAGAATTTGGAATTTGCAAATTCC | 300 |

| | | |
|---|---|---|
| SBY-99-1273 | AAGTTTTGTATCTCCCTTTCCCAGAAAATTAAGATAATTCTGGTGCTTTTAG---------- | 351 |
| SMO-28-1234 | AAGTTTTGTATCTCCCTTTCCCAGAAAATTAAGATAATTCTGGTGCTTTTAG---------- | 351 |
| SBY-99-1339 | AAGTTTTGTATCTCCCTTTCCCAGAAAATTAAGATAATTCTGGTGCTTTTAG---------- | 351 |
| SBY-99-1296 | AAGTTTTGTATCTCCCTTTCCCAGAAAATTAAGATAATTCTGGTGCTTTTAG---------- | 351 |
| SBY-99-1179 | AAGTTTTGTATCTCCCTTTCCCAGAAAATTAAGATAATTCTGGTGCTTTTAG---------- | 351 |
| SBY-29-469 | AAGTTTTGTATCTCCCTTTCCCAGAAAATTAAGATAATTCTGGTGCTTTTAG---------- | 351 |
| SBY-148-5201 | AAGTTTTGTATCTCCCTTTCCCAGAAAATTAAGATAATTCTGGTGCTTTTAG---------- | 351 |
| SBR-27-146 | AAGTTTTGTATCTCCCTTTCCCAGAAAATTAAGATAATTCTGGTGCTTTTAGCATTAGAAA | 360 |
| Jimmy Nardello | AAGTTTTGTATCTCCCTTTCCCAGAAAATTAAGATAATTCTGGTGCTTTTAGCATTAGAAA | 360 |
| 10CA_3745-M | AAGTTTTGTATCTCCCTTTCCCAGAAAATTAAGATAATTCTGGTGCTTTTAGCATTAGAAA | 360 |
| SBR-99-1193 | AAGTTTTGTATCTCCCTTTCCCAGAAAATTAAGATAATTCTGGTGCTTTTAGCATTAGAAA | 360 |
| SBR-99-1299 | AAGTTTTGTATCTCCCTTTCCCAGAAAATTAAGATAATTCTGGTGCTTTTAGCATTAGAAA | 360 |
| SBR-99-1300 | AAGTTTTGTATCTCCCTTTCCCAGAAAATTAAGATAATTCTGGTGCTTTTAGCATTAGAAA | 360 |
| HAS-30-1017 | AAGTTTTGTATCTCCCTTTCCCAGAAAATTAAGATAATTCTGGTGCTTTTAGCATTAGAAA | 360 |
| | **********                                                   |  |

FIG. 8 (continued)

```
SBY-99-1273    ----------------------------------------------------------------
SMO-28-1234    ----------------------------------------------------------------
SBY-99-1339    ----------------------------------------------------------------
SBY-99-1296    ----------------------------------------------------------------
SBY-99-1179    ----------------------------------------------------------------
SBY-29-469     ----------------------------------------------------------------
SBY-148-5201   ----------------------------------------------------------------
SBR-27-146     AGTATTTATTGGGTAGGGAAATGTCATGACTTCACAGCATTAAGCATCAAGGGTATAACT 420
Jimmy Nardello AGTATTTATTGGGTAGGGAAATGTCATGACTTCACAGCATTAAGCATCAAGGGTATAACT 420
10CA 3745-M    AGTATTTATTGGGTAGGGAAATGTCATGACTTCACAGCATTAAGCATCAAGGGTATAACT 420
SBR-99-1193    AGTATTTATTGGGTAGGGAAATGTCATGACTTCACAGCATTAAGCATCAAGGGTATAACT 420
SBR-99-1299    AGTATTTATTGGGTAGGGAAATGTCATGACTTCACAGCATTAAGCATCAAGGGTATAACT 420
SBR-99-1300    AGTATTTATTGGGTAGGGAAATGTCATGACTTCACAGCATTAAGCATCAAGGGTATAACT 420
HAS-30-1017    AGTATTTATTGGGTAGGGAAATGTCATGACTTCACAGCATTAAGCATCAAGGGTATAACT 420
               ************************************************************

SBY-99-1273    ----------------------------------------------------------------
SMO-28-1234    ----------------------------------------------------------------
SBY-99-1339    ----------------------------------------------------------------
SBY-99-1296    ----------------------------------------------------------------
SBY-99-1179    ----------------------------------------------------------------
SBY-29-469     ----------------------------------------------------------------
SBY-148-5201   ----------------------------------------------------------------
SBR-27-146     TAATGAAATAGTGGTCAATGAATTATATTGAGAATGACGAGGTCTCTGTTCCAACTTTGG 480
Jimmy Nardello TAATGAAATAGTGGTCAATGAATTATATTGAGAATGACGAGGTCTCTGTTCCAACTTTGG 480
10CA 3745-M    TAATGAAATAGTGGTCAATGAATTATATTGAGAATGACGAGGTCTCTGTTCCAACTTTGG 480
SBR-99-1193    TAATGAAATAGTGGTCAATGAATTATATTGAGAATGACGAGGTCTCTGTTCCAACTTTGG 480
SBR-99-1299    TAATGAAATAGTGGTCAATGAATTATATTGAGAATGACGAGGTCTCTGTTCCAACTTTGG 480
SBR-99-1300    TAATGAAATAGTGGTCAATGAATTATATTGAGAATGACGAGGTCTCTGTTCCAACTTTGG 480
HAS-30-1017    TAATGAAATAGTGGTCAATGAATTATATTGAGAATGACGAGGTCTCTGTTCCAACTTTGG 480
               ************************************************************
```

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | CTCTTCTTTTTTACGACTCTATTTGACCTAGGCATTGGCCAACTTGGCTAACCACTT | 660 |
| Jimmy Nardello | CTCTTCTTTTTTACGACTCTATTTGACCTAGGCATTGGCCAACTTGGCTAACCACTT | 660 |
| 10CA 3745-M | CTCTTCTTTTTTACGACTCTATTTGACCTAGGCATTGGCCAACTTGGCTAACCACTT | 660 |
| SBR-99-1193 | CTCTTCTTTTTTACGACTCTATTTGACCTAGGCATTGGCCAACTTGGCTAACCACTT | 660 |
| SBR-99-1299 | CTCTTCTTTTTTACGACTCTATTTGACCTAGGCATTGGCCAACTTGGCTAACCACTT | 660 |
| SBR-99-1300 | CTCTTCTTTTTTACGACTCTATTTGACCTAGGCATTGGCCAACTTGGCTAACCACTT | 660 |
| HAS-30-1017 | CTCTTCTTTTTTACGACTCTATTTGACCTAGGCATTGGCCAACTTGGCTAACCACTT | 660 |
| | *********************************************************** | |

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | GAGGAACTAGAGTTCGGATTCAATAGAATCTAATAATTTTAATCAAAAGACTTCATGTAT | 720 |
| Jimmy Nardello | GAGGAACTAGAGTTCGGATTCAATAGAATCTAATAATTTTAATCAAAAGACTTCATGTAT | 720 |
| 10CA 3745-M | GAGGAACTAGAGTTCGGATTCAATAGAATCTAATAATTTTAATCAAAAGACTTCATGTAT | 720 |
| SBR-99-1193 | GAGGAACTAGAGTTCGGATTCAATAGAATCTAATAATTTTAATCAAAAGACTTCATGTAT | 720 |
| SBR-99-1299 | GAGGAACTAGAGTTCGGATTCAATAGAATCTAATAATTTTAATCAAAAGACTTCATGTAT | 720 |
| SBR-99-1300 | GAGGAACTAGAGTTCGGATTCAATAGAATCTAATAATTTTAATCAAAAGACTTCATGTAT | 720 |
| HAS-30-1017 | GAGGAACTAGAGTTCGGATTCAATAGAATCTAATAATTTTAATCAAAAGACTTCATGTAT | 720 |
| | *********************************************************** | |

```
SBY-99-1273                                                                                                                            -
SMO-28-1234                                                                                                                            -
SBY-99-1339                                                                                                                            -
SBY-99-1296                                                                                                                            -
SBY-99-1179                                                                                                                            -
SBY-29-469                                                                                                                             -
SBY-148-5201  -
SBR-27-146     TTCCACTAATACAGCTGCCGTGCCGTCCATGCCGTCCATGCCGTCCATGCCGTCCATGCCACTACAAGACAAGACAAATACACCACTATGTTTGTTAG 900
Jimmy Nardello TTCCACTAATACAGCTGCCGTGCCGTCCATGCCGTCCATGCCGTCCATGCCGTCCATGCCACTACAAGACAAGACAAATACACCACTATGTTTGTTAG 900
10CA 3745-M    TTCCACTAATACAGCTGCCGTGCCGTCCATGCCGTCCATGCCGTCCATGCCGTCCATGCCACTACAAGACAAGACAAATACACCACTATGTTTGTTAG 900
SBR-99-1193    TTCCACTAATACAGCTGCCGTGCCGTCCATGCCGTCCATGCCGTCCATGCCGTCCATGCCACTACAAGACAAGACAAATACACCACTATGTTTGTTAG 900
SBR-99-1299    TTCCACTAATACAGCTGCCGTGCCGTCCATGCCGTCCATGCCGTCCATGCCGTCCATGCCACTACAAGACAAGACAAATACACCACTATGTTTGTTAG 900
SBR-99-1300    TTCCACTAATACAGCTGCCGTGCCGTCCATGCCGTCCATGCCGTCCATGCCGTCCATGCCACTACAAGACAAGACAAATACACCACTATGTTTGTTAG 900
HAS-30-1017    TTCCACTAATACAGCTGCCGTGCCGTCCATGCCGTCCATGCCGTCCATGCCGTCCATGCCACTACAAGACAAGACAAATACACCACTATGTTTGTTAG 900
                             *********************************************

SBY-99-1273                                                                                                                            -
SMO-28-1234                                                                                                                            -
SBY-99-1339                                                                                                                            -
SBY-99-1296                                                                                                                            -
SBY-99-1179                                                                                                                            -
SBY-29-469                                                                                                                             -
SBY-148-5201  -
SBR-27-146     TGCTTGGTAAATGTAAAACAAACTTTTGATGAGAATCTATTCGTTGCCATCGAAGTGCTGC 960
Jimmy Nardello TGCTTGGTAAATGTAAAACAAACTTTTGATGAGAATCTATTCGTTGCCATCGAAGTGCTGC 960
10CA 3745-M    TGCTTGGTAAATGTAAAACAAACTTTTGATGAGAATCTATTCGTGGCCATCGAAGTGCTGC 960
SBR-99-1193    TGCTTGGTAAATGTAAAACAAACTTTTGATGAGAATCTATTCGTGGCCATCGAAGTGCTGC 960
SBR-99-1299    TGCTTGGTAAATGTAAAACAAACTTTTGATGAGAATCTATTCGTGGCCATCGAAGTGCTGC 960
SBR-99-1300    TGCTTGGTAAATGTAAAACAAACTTTTGATGAGAATCTATTCGTGGCCATCGAAGTGCTGC 960
HAS-30-1017    TGCTTGGTAAATGTAAAACAAACTTTTGATGAGAATCTATTCGTGGCCATCGAAGTGCTGC 960
                              ***********************************************
```

| | | |
|---|---|---|
| SBY-99-1273 | ---------------------------------------------------------- | |
| SMO-28-1234 | ---------------------------------------------------------- | |
| SBY-99-1339 | ---------------------------------------------------------- | |
| SBY-99-1296 | ---------------------------------------------------------- | |
| SBY-99-1179 | ---------------------------------------------------------- | |
| SBY-29-469 | ---------------------------------------------------------- | |
| SBY-148-5201 | ---------------------------------------------------------- | |
| SBR-27-146 | TTGGGAAGAGGAGTACTGCAAGGTAGGACCTCCAACAATTATCAATATCTAAATTGCAAA | 1500 |
| Jimmy Nardello | TTGGGAAGAGGAGTACTGCAAGGTAGGACCTCCAACAATTATCAATATCTAAATTGCAAA | 1500 |
| 10CA 3745-M | TTGGGAAGAGGAGTACTGCAAGGTAGGACCTCCAACAATTATCAATATCTAAATTGCAAA | 1500 |
| SBR-99-1193 | TTGGGAAGAGGAGTACTGCAAGGTAGGACCTCCAACAATTATCAATATCTAAATTGCAAA | 1500 |
| SBR-99-1299 | TTGGGAAGAGGAGTACTGCAAGGTAGGACCTCCAACAATTATCAATATCTAAATTGCAAA | 1500 |
| SBR-99-1300 | TTGGGAAGAGGAGTACTGCAAGGTAGGACCTCCAACAATTATCAATATCTAAATTGCAAA | 1500 |
| HAS-30-1017 | TTGGGAAGAGGAGTACTGCAAGGTAGGACCTCCAACAATTATCAATATCTAAATTGCAAA | 1500 |
| | ************************************************************ | |

| | | |
|---|---|---|
| SBY-99-1273 | ---------------------------------------------------------- | |
| SMO-28-1234 | ---------------------------------------------------------- | |
| SBY-99-1339 | ---------------------------------------------------------- | |
| SBY-99-1296 | ---------------------------------------------------------- | |
| SBY-99-1179 | ---------------------------------------------------------- | |
| SBY-29-469 | ---------------------------------------------------------- | |
| SBY-148-5201 | ---------------------------------------------------------- | |
| SBR-27-146 | AATTTCAGTTCGTTTTTAGTTTCTGTTTCGGGAAGAGGAATACTACAAGTTCGTTTTTTA | 1560 |
| Jimmy Nardello | AATTTCAGTTCGTTTTTAGTTTCTGTTTCGGGAAGAGGAATACTACAAGTTCGTTTTTTA | 1560 |
| 10CA 3745-M | AATTTCAGTTCGTTTTTAGTTTCTGTTTCGGGAAGAGGAATACTACAAGTTCGTTTTTTA | 1560 |
| SBR-99-1193 | AATTTCAGTTCGTTTTTAGTTTCTGTTTCGGGAAGAGGAATACTACAAGTTCGTTTTTTA | 1560 |
| SBR-99-1299 | AATTTCAGTTCGTTTTTAGTTTCTGTTTCGGGAAGAGGAATACTACAAGTTCGTTTTTTA | 1560 |
| SBR-99-1300 | AATTTCAGTTCGTTTTTAGTTTCTGTTTCGGGAAGAGGAATACTACAAGTTCGTTTTTTA | 1560 |
| HAS-30-1017 | AATTTCAGTTCGTTTTTAGTTTCTGTTTCGGGAAGAGGAATACTACAAGTTCGTTTTTTA | 1560 |
| | ************************************************************ | |

| | |
|---|---|
| SBY-99-1273 | ---- |
| SMO-28-1234 | ---- |
| SBY-99-1339 | ---- |
| SBY-99-1296 | ---- |
| SBY-99-1179 | ---- |
| SBY-29-469 | ---- |
| SBY-148-5201 | ---- |
| SBR-27-146 | AACAATCATCAGTACCTAAATTGCAAAAATTTCAGTTCGTTTTTTAGTTTTATGTTTGGGA 1740 |
| Jimmy Nardello | AACAATCATCAGTACCTAAATTGCAAAAATTTCAGTTCGTTTTTTAGTTTATGTTTGGGA 1740 |
| 10CA 3745-M | AACAATCATCAGTACCTAAATTGCAAAAATTTCAGTTCGTTTTTTAGTTTATGTTTGGGA 1740 |
| SBR-99-1193 | AACAATCATCAGTACCTAAATTGCAAAAATTTCAGTTCGTTTTTTAGTTTATGTTTGGGA 1740 |
| SBR-99-1299 | AACAATCATCAGTACCTAAATTGCAAAAATTTCAGTTCGTTTTTTAGTTTATGTTTGGGA 1740 |
| SBR-99-1300 | AACAATCATCAGTACCTAAATTGCAAAAATTTCAGTTCGTTTTTTAGTTTTATGTTTGGGA 1740 |
| HAS-30-1017 | AACAATCATCAGTACCTAAATTGCAAAAATTTCAGTTCGTTTTTTAGTTTTATGTTTGGGA 1740 |
| | ************************************************************ |
| SBY-99-1273 | ---- |
| SMO-28-1234 | ---- |
| SBY-99-1339 | ---- |
| SBY-99-1296 | ---- |
| SBY-99-1179 | ---- |
| SBY-29-469 | ---- |
| SBY-148-5201 | ---- |
| SBR-27-146 | AGAAGAATACTACAAGGCAGTGGCGGAGCTACCTTATGATTAGGGGTTCATCCGAACCT 1800 |
| Jimmy Nardello | AGAAGAATACTACAAGGCAGTGGCGGAGCTACCTTATGATTAGGGGTTCATCCGAACCT 1800 |
| 10CA 3745-M | AGAAGAATACTACAAGGCAGTGGCGGAGCTACCTTATGATTAGGGGTTCATCCGAACCT 1800 |
| SBR-99-1193 | AGAAGAATACTACAAGGCAGTGGCGGAGCTACCTTATGATTAGGGGTTCATCCGAACCT 1800 |
| SBR-99-1299 | AGAAGAATACTACAAGGCAGTGGCGGAGCTACCTTATGATTAGGGGTTCATCCGAACCT 1800 |
| SBR-99-1300 | AGAAGAATACTACAAGGCAGTGGCGGAGCTACCTTATGATTAGGGGTTCATCCGAACCT 1800 |
| HAS-30-1017 | AGAAGAATACTACAAGGCAGTGGCGGAGCTACCTTATGATTAGGGGTTCATCCGAACCT 1800 |
| | ************************************************************ |

| | |
|---|---|
| SBY-99-1273 | ------------------------------------------------------------ |
| SMO-28-1234 | ------------------------------------------------------------ |
| SBY-99-1339 | ------------------------------------------------------------ |
| SBY-99-1296 | ------------------------------------------------------------ |
| SBY-99-1179 | ------------------------------------------------------------ |
| SBY-29-469 | ------------------------------------------------------------ |
| SBY-148-5201 | ------------------------------------------------------------ |
| SBR-27-146 | ACCTAAATTGTAAAAATTTCAGTTCGTTTTTAGTTTCTCGTTTTGGGAAGAGGAATACTA 2460 |
| Jimmy Nardello | ACCTAAATTGTAAAAATTTCAGTTCGTTTTTTAGTTTCTCGTTTTGGGAAGAGGAATACTA 2460 |
| 10CA_3745-M | ACCTAAATTGTAAAAATTTCAGTTCGTTTTTTAGTTTCTCGTTTTGGGAAGAGGAATACTA 2460 |
| SBR-99-1193 | ACCTAAATTGTAAAAATTTCAGTTCGTTTTTTAGTTTCTCGTTTTGGGAAGAGGAATACTA 2460 |
| SBR-99-1299 | ACCTAAATTGTAAAAATTTCAGTTCGTTTTTTAGTTTCTGTTTTGGGAAGAGGAATACTA 2460 |
| SBR-99-1300 | ACCTAAATTGTAAAAATTTCAGTTCGTTTTTTAGTTTCTCGTTTTGGAAGAGGAATACTA 2460 |
| HAS-30-1017 | ACCTAAATTGTAAAAATTTCAGTTCGTTTTTTAGTTTCTCGTTTTGGAAGAGGAATACTA 2460 |
| | ************************************************************ |
| | |
| SBY-99-1273 | ------------------------------------------------------------ |
| SMO-28-1234 | ------------------------------------------------------------ |
| SBY-99-1339 | ------------------------------------------------------------ |
| SBY-99-1296 | ------------------------------------------------------------ |
| SBY-99-1179 | ------------------------------------------------------------ |
| SBY-29-469 | ------------------------------------------------------------ |
| SBY-148-5201 | ------------------------------------------------------------ |
| SBR-27-146 | CAAGGTAGGGCCTTCAACAATCAGCAATACCTAAATTACAAAAATTTCAATTCGTTTTTT 2520 |
| Jimmy Nardello | CAAGGTAGGGCCTTCAACAATCAGCAATACCTAAATTACAAAAATTTCAATTCGTTTTTT 2520 |
| 10CA_3745-M | CAAGGTAGGGCCTTCAACAATCAGCAATACCTAAATTACAAAAATTTCAATTCGTTTTTT 2520 |
| SBR-99-1193 | CAAGGTAGGGCCTTCAACAATCAGCAATACCTAAATTACAAAAATTTCAATTCGTTTTTT 2520 |
| SBR-99-1299 | CAAGGTAGGGCCTTCAACAATCAGCAATACCTAAATTACAAAAATTTCAATTCGTTTTTT 2520 |
| SBR-99-1300 | CAAGGTAGGGCCTTCAACAATCAGCAATACCTAAATTACAAAAATTTCAATTCGTTTTTT 2520 |
| HAS-30-1017 | CAAGGTAGGGCCTTCAACAATCAGCAATACCTAAATTACAAAAATTTCAATTCGTTTTTT 2520 |
| | ************************************************************ |

FIG. 8 (continued)

| | | |
|---|---|---|
| SBY-99-1273 | ---------------------------------------------------------------- | |
| SMO-28-1234 | ---------------------------------------------------------------- | |
| SBY-99-1339 | ---------------------------------------------------------------- | |
| SBY-99-1296 | ---------------------------------------------------------------- | |
| SBY-99-1179 | ---------------------------------------------------------------- | |
| SBY-29-469 | ---------------------------------------------------------------- | |
| SBY-148-5201 | ---------------------------------------------------------------- | |
| SBR-27-146 | AGTTTCTGTTTTGGGAAGAGGAATACTACAAGGCAGTGGCGGAGCTACCTTATGATTAGG | 2580 |
| Jimmy Nardello | AGTTTCTGTTTTGGGAAGAGGAATACTACAAGGCAGTGGCGGAGCTACCTTATGATTAGG | 2580 |
| 1OCA_3745-M | AGTTTCTGTTTTGGGAAGAGGAATACTACAAGGCAGTGGCGGAGCTACCTTATGATTAGG | 2580 |
| SBR-99-1193 | AGTTTCTGTTTTGGGAAGAGGAATACTACAAGGCAGTGGCGGAGCTACCTTATGATTAGG | 2580 |
| SBR-99-1299 | AGTTTCTGTTTTGGGAAGAGGAATACTACAAGGCAGTGGCGGAGCTACCTTATGATTAGG | 2580 |
| SBR-99-1300 | AGTTTCTGTTTTGGGAAGAGGAATACTACAAGGCAGTGGCGGAGCTACCTTATGATTAGG | 2580 |
| HAS-30-1017 | AGTTTCTGTTTTGGGAAGAGGAATACTACAAGGCAGTGGCGGAGCTACCTTATGATTAGG | 2580 |
| | ************************************************************ | |
| SBY-99-1273 | ---------------------------------------------------------------- | |
| SMO-28-1234 | ---------------------------------------------------------------- | |
| SBY-99-1339 | ---------------------------------------------------------------- | |
| SBY-99-1296 | ---------------------------------------------------------------- | |
| SBY-99-1179 | ---------------------------------------------------------------- | |
| SBY-29-469 | ---------------------------------------------------------------- | |
| SBY-148-5201 | ---------------------------------------------------------------- | |
| SBR-27-146 | GGTTCATCCGAACCTCCTTCGACGGAAAATTATACTATTTTTATATAGTAAAAATTATTT | 2640 |
| Jimmy Nardello | GGTTCATCCGAACCTCCTTCGACGGAAAATTATACTATTTTTATATAGTAAAAATTATTT | 2640 |
| 1OCA_3745-M | GGTTCATCCGAACCTCCTTCGACGGAAAATTATACTATTTTTATATAGTAAAAATTATTT | 2640 |
| SBR-99-1193 | GGTTCATCCGAACCTCCTTCGACGGAAAATTATACTATTTTTATATAGTAAAAATTATTT | 2640 |
| SBR-99-1299 | GGTTCATCCGAACCTCCTTCGACGGAAAATTATACTATTTTTATATAGTAAAAATTATTT | 2640 |
| SBR-99-1300 | GGTTCATCCGAACCTCCTTCGACGGAAAATTATACTATTTTTATATAGTAAAAATTATTT | 2640 |
| HAS-30-1017 | GGTTCATCCGAACCTCCTTCGACGGAAAATTATACTATTTTTATATAGTAAAAATTATTT | 2640 |
| | ************************************************************ | |

| | |
|---|---|
| SBY-99-1273 | ---------------------------------------------------------- |
| SMO-28-1234 | ---------------------------------------------------------- |
| SBY-99-1339 | ---------------------------------------------------------- |
| SBY-99-1296 | ---------------------------------------------------------- |
| SBY-99-1179 | ---------------------------------------------------------- |
| SBY-29-469 | ---------------------------------------------------------- |
| SBY-148-5201 | ---------------------------------------------------------- |
| SBR-27-146 | AACAATCACCAATACCAATACCTAAATTGCAAAAAATTTCAGTTCGTTTTTTTAATTTCTGTTTTTGGG 2820 |
| Jimmy Nardello | AACAATCACCAATACCAATACCTAAATTGCAAAAAATTTCAGTTCGTTTTTTTAATTTCTGTTTTTGGG 2820 |
| 10CA_3745-M | AACAATCACCAATACCAATACCTAAATTGCAAAAAATTTCAGTTCGTTTTTTTAATTTCTGTTTTTGGG 2820 |
| SBR-99-1193 | AACAATCACCAATACCAATACCTAAATTGCAAAAAATTTCAGTTCGTTTTTTTAATTTCTGTTTTTGGG 2820 |
| SBR-99-1299 | AACAATCACCAATACCAATACCTAAATTGCAAAAAATTTCAGTTCGTTTTTTTAATTTCTGTTTTTGGG 2820 |
| SBR-99-1300 | AACAATCACCAATACCAATACCTAAATTGCAAAAAATTTCAGTTCGTTTTTTTAATTTCTGTTTTTGGG 2820 |
| HAS-30-1017 | AACAATCACCAATACCAATACCTAAATTGCAAAAAATTTCAGTTCGTTTTTTTAATTTCTGTTTTTGGG 2820 |
| | ************************************************************ |
| SBY-99-1273 | ---------------------------------------------------------- |
| SMO-28-1234 | ---------------------------------------------------------- |
| SBY-99-1339 | ---------------------------------------------------------- |
| SBY-99-1296 | ---------------------------------------------------------- |
| SBY-99-1179 | ---------------------------------------------------------- |
| SBY-29-469 | ---------------------------------------------------------- |
| SBY-148-5201 | ---------------------------------------------------------- |
| SBR-27-146 | AAGAGGAATACTACAAGGCCTCCAACAATCACCAATACCAATACCTAAATTGCAAAAATTTCAGTT 2880 |
| Jimmy Nardello | AAGAGGAATACTACAAGGCCTCCAACAATCACCAATACCAATACCTAAATTGCAAAAATTTCAGTT 2880 |
| 10CA_3745-M | AAGAGGAATACTACAAGGCCTCCAACAATCACCAATACCAATACCTAAATTGCAAAAATTTCAGTT 2880 |
| SBR-99-1193 | AAGAGGAATACTACAAGGCCTCCAACAATCACCAATACCAATACCTAAATTGCAAAAATTTCAGTT 2880 |
| SBR-99-1299 | AAGAGGAATACTACAAGGCCTCCAACAATCACCAATACCAATACCTAAATTGCAAAAATTTCAGTT 2880 |
| SBR-99-1300 | AAGAGGAATACTACAAGGCCTCCAACAATCACCAATACCAATACCTAAATTGCAAAAATTTCAGTT 2880 |
| HAS-30-1017 | AAGAGGAATACTACAAGGCCTCCAACAATCACCAATACCAATACCTAAATTGCAAAAATTTCAGTT 2880 |
| | ************************************************************ |

FIG. 8 (continued)

| | |
|---|---|
| SBY-99-1273 | |
| SMO-28-1234 | |
| SBY-99-1339 | |
| SBY-99-1296 | |
| SBY-99-1179 | |
| SBY-29-469 | |
| SBY-148-5201 | TGTTTTTTAGTTTCTGTTTCTGTTTTGGGAAGAAGAGGAATACTACAAGGTAAGGCCTCCAACAATCAC 2940 |
| SBR-27-146 | TGTTTTTTAGTTTCTGTTTCTGTTTTGGGAAGAAGAGGAATACTACAAGGTAAGGCCTCCAACAATCAC 2940 |
| Jimmy Nardello | TGTTTTTTAGTTTCTGTTTCTGTTTTGGGAAGAAGAGGAATACTACAAGGTAAGGCCTCCAACAATCAC 2940 |
| 10CA 3745-M | TGTTTTTTAGTTTCTGTTTCTGTTTTGGGAAGAAGAGGAATACTACAAGGTAAGGCCTCCAACAATCAC 2940 |
| SBR-99-1193 | TGTTTTTTAGTTTCTGTTTCTGTTTTGGGAAGAAGAGGAATACTACAAGGTAAGGCCTCCAACAATCAC 2940 |
| SBR-99-1299 | TGTTTTTTAGTTTCTGTTTCTGTTTTGGGAAGAAGAGGAATACTACAAGGTAAGGCCTCCAACAATCAC 2940 |
| SBR-99-1300 | TGTTTTTTAGTTTCTGTTTCTGTTTTGGGAAGAAGAGGAATACTACAAGGTAAGGCCTCCAACAATCAC 2940 |
| HAS-30-1017 | TGTTTTTTAGTTTCTGTTTCTGTTTTGGGAAGAAGAGGAATACTACAAGGTAAGGCCTCCAACAATCAC 2940 |
| | ****************************************** |
| SBY-99-1273 | |
| SMO-28-1234 | |
| SBY-99-1339 | |
| SBY-99-1296 | |
| SBY-99-1179 | |
| SBY-29-469 | |
| SBY-148-5201 | CAATACCTAAATTGCAAAAATTTCAGTTCGTTTCTATTTCGTTTCTATTTTGGGAAGTGGAAT 3000 |
| SBR-27-146 | CAATACCTAAATTGCAAAAATTTCAGTTCGTTTCTATTTCGTTTCTATTTTGGGAAGTGGAAT 3000 |
| Jimmy Nardello | CAATACCTAAATTGCAAAAATTTCAGTTCGTTTCTATTTCGTTTCTATTTTGGGAAGTGGAAT 3000 |
| 10CA 3745-M | CAATACCTAAATTGCAAAAATTTCAGTTCGTTTCTATTTCGTTTCTATTTTGGGAAGTGGAAT 3000 |
| SBR-99-1193 | CAATACCTAAATTGCAAAAATTTCAGTTCGTTTCTATTTCGTTTCTATTTTGGGAAGTGGAAT 3000 |
| SBR-99-1299 | CAATACCTAAATTGCAAAAATTTCAGTTCGTTTCTATTTCGTTTCTATTTTGGGAAGTGGAAT 3000 |
| SBR-99-1300 | CAATACCTAAATTGCAAAAATTTCAGTTCGTTTCTATTTCGTTTCTATTTTGGGAAGTGGAAT 3000 |
| HAS-30-1017 | CAATACCTAAATTGCAAAAATTTCAGTTCGTTTCTATTTCGTTTCTATTTTGGGAAGTGGAAT 3000 |
| | ****************************************** |

FIG. 8 (continued)

| | | |
|---|---|---|
| SBY-99-1273 | | |
| SMO-28-1234 | | |
| SBY-99-1339 | | |
| SBY-99-1296 | | |
| SBY-99-1179 | | |
| SBY-29-469 | | |
| SBY-148-5201 | | |
| SBR-27-146 | AGTATAAGGTAGGACCTCCAACAATCACCAATTGCAAAAGTTCCGATTCATT | 3060 |
| Jimmy Nardello | AGTATAAGGTAGGACCTCCAACAATCACCAATTGCAAAAGTTCCGATTCATT | 3060 |
| 10CA 3745-M | AGTATAAGGTAGGACCTCCAACAATCACCAATTGCAAAAGTTCCGATTCATT | 3060 |
| SBR-99-1193 | AGTATAAGGTAGGACCTCCAACAATCACCAATTGCAAAAGTTCCGATTCATT | 3060 |
| SBR-99-1299 | AGTATAAGGTAGGACCTCCAACAATCACCAATTGCAAAAGTTCCGATTCATT | 3060 |
| SBR-99-1300 | AGTATAAGGTAGGACCTCCAACAATCACCAATTGCAAAAGTTCCGATTCATT | 3060 |
| HAS-30-1017 | AGTATAAGGTAGGACCTCCAACAATCACCAATTGCAAAAGTTCCGATTCATT | 3060 |
| | ************************************************ | |
| SBY-99-1273 | | |
| SMO-28-1234 | | |
| SBY-99-1339 | | |
| SBY-99-1296 | | |
| SBY-99-1179 | | |
| SBY-29-469 | | |
| SBY-148-5201 | | |
| SBR-27-146 | TTTTAGTTTCTGTTTTGGAAAGAGAGAAATACTACAAGGTAGGGTCTCCAACAATCACCAGT | 3120 |
| Jimmy Nardello | TTTTAGTTTCTGTTTTGGAAAGAGAGAAATACTACAAGGTAGGGTCTCCAACAATCACCAGT | 3120 |
| 10CA 3745-M | TTTTAGTTTCTGTTTTGGAAAGAGAGAAATACTACAAGGTAGGGTCTCCAACAATCACCAGT | 3120 |
| SBR-99-1193 | TTTTAGTTTCTGTTTTGGAAAGAGAGAAATACTACAAGGTAGGGTCTCCAACAATCACCAGT | 3120 |
| SBR-99-1299 | TTTTAGTTTCTGTTTTGGAAAGAGAGAAATACTACAAGGTAGGGTCTCCAACAATCACCAGT | 3120 |
| SBR-99-1300 | TTTTAGTTTCTGTTTTGGAAAGAGAGAAATACTACAAGGTAGGGTCTCCAACAATCACCAGT | 3120 |
| HAS-30-1017 | TTTTAGTTTCTGTTTTGGAAAGAGAGAAATACTACAAGGTAGGGTCTCCAACAATCACCAGT | 3120 |
| | ************************************************ | |

FIG. 8 (continued)

| | |
|---|---|
| SBY-99-1273 | |
| SMO-28-1234 | |
| SBY-99-1339 | |
| SBY-99-1296 | |
| SBY-99-1179 | |
| SBY-29-469 | |
| SBY-148-5201 | |
| SBR-27-146 | ACCTAAATTGTAAAAATTTCAGTTCGTTTTTCTATTTCTATTTTGGAAGTGGAATAGTA 3180 |
| Jimmy Nardello | ACCTAAATTGTAAAAATTTCAGTTCGTTTTTCTATTTCTATTTTGGAAGTGGAATAGTA 3180 |
| 10CA 3745-M | ACCTAAATTGTAAAAATTTCAGTTCGTTTTTCTATTTCTATTTTGGAAGTGGAATAGTA 3180 |
| SBR-99-1193 | ACCTAAATTGTAAAAATTTCAGTTCGTTTTTCTATTTCTATTTTGGAAGTGGAATAGTA 3180 |
| SBR-99-1299 | ACCTAAATTGTAAAAATTTCAGTTCGTTTTTCTATTTCTATTTTGGAAGTGGAATAGTA 3180 |
| SBR-99-1300 | ACCTAAATTGTAAAAATTTCAGTTCGTTTTTCTATTTCTATTTTGGAAGTGGAATAGTA 3180 |
| HAS-30-1017 | ACCTAAATTGTAAAAATTTCAGTTCGTTTTTCTATTTCTATTTTGGAAGTGGAATAGTA 3180 |
| | ****************************************** |

| | |
|---|---|
| SBY-99-1273 | |
| SMO-28-1234 | |
| SBY-99-1339 | |
| SBY-99-1296 | |
| SBY-99-1179 | |
| SBY-29-469 | |
| SBY-148-5201 | |
| SBR-27-146 | TAAGGTAGGACCTCCAACAATCACCAATACCTAAATTGCAAAAGTTCCGATTCTTTTTT 3240 |
| Jimmy Nardello | TAAGGTAGGACCTCCAACAATCACCAATACCTAAATTGCAAAAGTTCCGATTCTTTTTT 3240 |
| 10CA 3745-M | TAAGGTAGGACCTCCAACAATCACCAATACCTAAATTGCAAAAGTTCCGATTCTTTTTT 3240 |
| SBR-99-1193 | TAAGGTAGGACCTCCAACAATCACCAATACCTAAATTGCAAAAGTTCCGATTCTTTTTT 3240 |
| SBR-99-1299 | TAAGGTAGGACCTCCAACAATCACCAATACCTAAATTGCAAAAGTTCCGATTCTTTTTT 3240 |
| SBR-99-1300 | TAAGGTAGGACCTCCAACAATCACCAATACCTAAATTGCAAAAGTTCCGATTCTTTTTT 3240 |
| HAS-30-1017 | TAAGGTAGGACCTCCAACAATCACCAATACCTAAATTGCAAAAGTTCCGATTCTTTTTT 3240 |
| | ****************************************** |

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | GTAACAATCACCAATACCTAAATTAAATTTCAGTTAGTTTTTAGTTTTCTGTTTTTGGGA | 3420 |
| Jimmy Nardello | GTAACAATCACCAATACCTAAATTAAATTTCAGTTAGTTTTTAGTTTTCTGTTTTTGGGA | 3420 |
| 10CA 3745-M | GTAACAATCACCAATACCTAAATTAAATTTCAGTTAGTTTTTAGTTTTCTGTTTTTGGGA | 3420 |
| SBR-99-1193 | GTAACAATCACCAATACCTAAATTAAATTTCAGTTAGTTTTTAGTTTTCTGTTTTTGGGA | 3420 |
| SBR-99-1299 | GTAACAATCACCAATACCTAAATTAAATTTCAGTTAGTTTTTAGTTTTCTGTTTTTGGGA | 3420 |
| SBR-99-1300 | GTAACAATCACCAATACCTAAATTAAATTTCAGTTAGTTTTTAGTTTTCTGTTTTTGGGA | 3420 |
| HAS-30-1017 | GTAACAATCACCAATACCTAAATTAAATTTCAGTTAGTTTTTAGTTTTCTGTTTTTGGGA | 3420 |
| | ************************************************************ | |
| | | |
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | AGAGGAATACTTTCTTTTGCTATATAAGTAGGTACCTATAAGCATCAATATTT | 3480 |
| Jimmy Nardello | AGAGGAATACTTTCTTTTGCTATATAAGTAGGTACCTATAAGCATCAATATTT | 3480 |
| 10CA 3745-M | AGAGGAATACTTTCTTTTGCTATATAAGTAGGTACCTATAAGCATCAATATTT | 3480 |
| SBR-99-1193 | AGAGGAATACTTTCTTTTGCTATATAAGTAGGTACCTATAAGCATCAATATTT | 3480 |
| SBR-99-1299 | AGAGGAATACTTTCTTTTGCTATATAAGTAGGTACCTATAAGCATCAATATTT | 3480 |
| SBR-99-1300 | AGAGGAATACTTTCTTTTGCTATATAAGTAGGTACCTATAAGCATCAATATTT | 3480 |
| HAS-30-1017 | AGAGGAATACTTTCTTTTGCTATATAAGTAGGTACCTATAAGCATCAATATTT | 3480 |
| | ************************************************************ | |

| | | |
|---|---|---|
| SBY-99-1273 | --------- | |
| SMC-28-1234 | --------- | |
| SBY-99-1339 | --------- | |
| SBY-99-1296 | --------- | |
| SBY-99-1179 | --------- | |
| SBY-29-469 | --------- | |
| SBY-148-5201 | --------- | |
| SBR-27-146 | TCCACTTTTCCAAATCCAACCAAACAAACAAAAAGATTCAAGAAAGTTCCATTATAGAAACAAA | 3720 |
| Jimmy Nardello | TCCACTTTTCCAAATCCAACCAAACAAACAAAAAGATTCAAGAAAGTTCCATTATAGAAACAAA | 3720 |
| 10CA 3745-M | TCCACTTTTCCAAATCCAACCAAACAAACAAAAAGATTCAAGAAAGTTCCATTATAGAAACAAA | 3720 |
| SBR-99-1193 | TCCACTTTTCCAAATCCAACCAAACAAACAAAAAGATTCAAGAAAGTTCCATTATAGAAACAAA | 3720 |
| SBY-99-1299 | TCCACTTTTCCAAATCCAACCAAACAAACAAAAAGATTCAAGAAAGTTCCATTATAGAAACAAA | 3720 |
| SBR-99-1300 | TCCACTTTTCCAAATCCAACCAAACAAACAAAAAGATTCAAGAAAGTTCCATTATAGAAACAAA | 3720 |
| HAS-30-1017 | TCCACTTTTCCAAATCCAACCAAACAAACAAAAAGATTCAAGAAAGTTCCATTATAGAAACAAA | 3720 |
| CCS ORF | TCCACTTTTCCAAATCCAACCAAACAAACAAAAAGATTCAAGAAAGTTCCATTATAGAAACAAA | 138 |
| | ************************************************************ | |
| CCS | S T F P N P T K Q K D S R E F H Y R N K | |

FIG. 8 (continued)

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | AGCAGTACACATTTTTGTAGCTTTCTTGATTTAGCACCCACATCAAAGCCAGAGTCTTTA | 3780 |
| SBR-27-146 | AGCAGTACACATTTTTGTAGCTTTCTTGATTTAGCACCCACATCAAAGCCAGAGTCTTTA | 3780 |
| Jimmy Nardello | AGCAGTACACATTTTTGTAGCTTTCTTGATTTAGCACCCACATCAAAGCCAGAGTCTTTA | 3780 |
| 10CA 3745-M | AGCAGTACACATTTTTGTAGCTTTCTTGATTTAGCACCCACATCAAAGCCAGAGTCTTTA | 3780 |
| SBR-99-1193 | AGCAGTACACATTTTTGTAGCTTTCTTGATTTAGCACCCACATCAAAGCCAGAGTCTTTA | 3780 |
| SBR-99-1299 | AGCAGTACACATTTTTGTAGCTTTCTTGATTTAGCACCCACATCAAAGCCAGAGTCTTTA | 3780 |
| SBR-99-1300 | AGCAGTACACATTTTTGTAGCTTTCTTGATTTAGCACCCACATCAAAGCCAGAGTCTTTA | 3780 |
| HAS-30-1017 | AGCAGTACACATTTTTGTAGCTTTCTTGATTTAGCACCCACATCAAAGCCAGAGTCTTTA | 3780 |
| CCS ORF | ************************************************************ | 198 |
| CCS | S S T H F C S F L D L A P T S K P E S L | |

FIG. 8 (continued)

```
SBY-99-1273        ------------------------------------------------------------
SMO-28-1234        ------------------------------------------------------------
SBY-99-1339        ------------------------------------------------------------
SBY-99-1296        ------------------------------------------------------------
SBY-99-1179        ------------------------------------------------------------
SBY-29-469         ------------------------------------------------------------
SBY-148-5201       ------------------------------------------------------------
SBR-27-146         GATGTTAACATCTCATGGGTTGATACTGATCTGGACGGGGCTGAATTCGACGTGATCATC 3840
Jimmy Nardello     GATGTTAACATCTCATGGGTTGATACTGATCTGGACGGGGCTGAATTCGACGTGATCATC 3840
10CA_3745-M        GATGTTAACATCTCATGGGTTGATACTGATCTGGACGGGGCTGAATTCGACGTGATCATC 3840
SBR-99-1193        GATGTTAACATCTCATGGGTTGATACTGATCTGGACGGGGCTGAATTCGACGTGATCATC 3840
SBR-99-1299        GATGTTAACATCTCATGGGTTGATACTGATCTGGACGGGGCTGAATTCGACGTGATCATC 3840
SBR-99-1300        GATGTTAACATCTCATGGGTTGATACTGATCTGGACGGGGCTGAATTCGACGTGATCATC 3840
HAS-30-1017        GATGTTAACATCTCATGGGTTGATACTGATCTGGACGGGGCTGAATTCGACGTGATCATC 3840
CCS ORF            GATGTTAACATCTCATGGGTTGATACTGATCTGGACCGGGCTGAATTCGACGTGATCATC 258
                   ************************************ ***********************

CCS                D  V  N  I  S  W  V  D  T  D  L  D  G  A  E  F  D  V  I  I
```

FIG. 8 (continued)

| | |
|---|---|
| SBY-99-1273 | ------------------------------------------------------------ |
| SMO-28-1234 | ------------------------------------------------------------ |
| SBY-99-1339 | ------------------------------------------------------------ |
| SBY-99-1296 | ------------------------------------------------------------ |
| SBY-99-1179 | ------------------------------------------------------------ |
| SBY-29-469 | ------------------------------------------------------------ |
| SBY-148-5201 | ------------------------------------------------------------ |
| SBR-27-146 | ATTGGAACTGGCCCTGCCCGGGCTTCGGCTAGCTGAACAAGTTTCTAAATATGGTATTAAG 3900 |
| Jimmy Nardello | ATTGGAACTGGCCCTGCCCGGGCTTCGGCTAGCTGAACAAGTTTCTAAATATGGTATTAAG 3900 |
| 10CA_3745-M | ATTGGAACTGGCCCTGCCCGGGCTTCGGCTAGCTGAACAAGTTTCTAAATATGGTATTAAG 3900 |
| SBR-99-1193 | ATTGGAACTGGCCCTGCCCGGGCTTCGGCTAGCTGAACAAGTTTCTAAATATGGTATTAAG 3900 |
| SBR-99-1299 | ATTGGAACTGGCCCTGCCCGGGCTTCGGCTAGCTGAACAAGTTTCTAAATATGGTATTAAG 3900 |
| SBR-99-1300 | ATTGGAACTGGCCCTGCCCGGGCTTCGGCTAGCTGAACAAGTTTCTAAATATGGTATTAAG 3900 |
| HAS-30-1017 | ATTGGAACTGGCCCTGCCCGGGCTTCGGCTAGCTGAACAAGTTTCTAAATATGGTATTAAG 3900 |
| CCS ORF | ATTGGAACTGGCCCTGCCCGGGCTTCGGCTAGCTGAACAAGTTTCTAAATATGGTATTAAG 318 |
| | ************************************************************ |
| CCS | I G T G P A G L R L A E Q V S K Y G I K |

FIG. 8 (continued)

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | GTATGTTGCGTTGACCCTTCACCACTTTCCATGTGGCCAAATAATTATGGTGTTTGGGTT | 3960 |
| SBR-27-146 | GTATGTTGCGTTGACCCTTCACCACTTTCCATGTGGCCAAATAATTATGGTGTTTGGGTT | 3960 |
| Jimmy Nardello | GTATGTTGCGTTGACCCTTCACCACTTTCCATGTGGCCAAATAATTATGGTGTTTGGGTT | 3960 |
| 10CA 3745-M | GTATGTTGCGTTGACCCTTCACCACTTTCCATGTGGCCAAATAATTATGGTGTTTGGGTT | 3960 |
| SBR-99-1193 | GTATGTTGCGTTGACCCTTCACCACTTTCCATGTGGCCAAATAATTATGGTGTTTGGGTT | 3960 |
| SBR-99-1299 | GTATGTTGCGTTGACCCTTCACCACTTTCCATGTGGCCAAATAATTATGGTGTTTGGGTT | 3960 |
| SBR-99-1300 | GTATGTTGCGTTGACCCTTCACCACTTTCCATGTGGCCAAATAATTATGGTGTTTGGGTT | 3960 |
| HAS-30-1017 | GTATGTTGCGTTGACCCTTCACCACTTTCCATGTGGCCAAATAATTATGGTGTTTGGGTT | 3960 |
| CCS ORF | GTATGTTGCGTTGACCCTTCACCACTTTCCATGTGGCCAAATAATTATGGTGTTTGGGTT | 378 |
| | ************************************************************ | |
| CCS | V C C V D P S P L S M N P N N Y G V W V | |

| | |
|---|---|
| SBY-99-1273 | ---------------------------------------------------------------- |
| SMO-28-1234 | ---------------------------------------------------------------- |
| SBY-99-1339 | ---------------------------------------------------------------- |
| SBY-99-1296 | ---------------------------------------------------------------- |
| SBY-99-1179 | ---------------------------------------------------------------- |
| SBY-29-469 | ---------------------------------------------------------------- |
| SBY-148-5201 | ---------------------------------------------------------------- |
| SBR-27-146 | GTTCATATATAAGTGATCACAAGACTAAGTATTTGGACAGAGACCATATGTGTAGAGTAAGTAGA 4080 |
| Jimmy Nardello | GTTCATATATAAGTGATCACAAGACTAAGTATTTGGACAGAGACCATATGTGTAGAGTAAGTAGA 4080 |
| 10CA_3745-M | GTTCATATATAAGTGATCACAAGACTAAGTATTTGGACAGAGACCATATGTGTAGAGTAAGTAGA 4080 |
| SBR-99-1193 | GTTCATATATAAGTGATCACAAGACTAAGTATTTGGACAGAGACCATATGTGTAGAGTAAGTAGA 4080 |
| SBR-99-1299 | GTTCATATATAAGTGATCACAAGACTAAGTATTTGGACAGAGACCATATGTGTAGAGTAAGTAGA 4080 |
| SBR-99-1300 | GTTCATATATAAGTGATCACAAGACTAAGTATTTGGACAGAGACCATATGTGTAGAGTAAGTAGA 4080 |
| HAS-30-1017 | GTTCATATATAAGTGATCACAAGACTAAGTATTTGGACAGAGACCATATGTGTAGAGTAAGTAGA 4080 |
| CCS ORF | GTTCATATATAAGTGATCACAAGACTAAGTATTTGGACAGAGACCATATGTGTAGAGTAAGTAGA 498 |
| CCS | V H I S D H K T K Y L D R P Y G R V S R |

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | GCCAAGGTTTTGAAAGTGAAGCATGAAGAATTTGAGTCTTCGATTGTTTGTGATGATGGT | 4200 |
| Jimmy Nardello | GCCAAGGTTTTGAAAGTGAAGCATGAAGAATTTGAGTCTTCGATTGTTTGTGATGATGGT | 4200 |
| 10CA_3745-M | GCCAAGGTTTTGAAAGTGAAGCATGAAGAATTTGAGTCTTCGATTGTTGTGATGATGGT | 4200 |
| SBR-99-1193 | GCCAAGGTTTTGAAAGTGAAGCATGAAGAATTTGAGTCTTCGATTGTTTGTGATGATGGT | 4200 |
| SBR-99-1299 | GCCAAGGTTTTGAAAGTGAAGCATGAAGAATTTGAGTCTTCGATTGTTTCTGATGATGGT | 4200 |
| SBR-99-1300 | GCCAAGGTTTTGAAAGTGAAGCATGAAGAATTTGAGTCTTCGATTGTTTGTGATGATGGT | 4200 |
| HAS-30-1017 | GCCAAGGTTTTGAAAGTGAAGCATGAAGAATTTGAGTCTTCCATTGTTTCTCATGATGGT | 4200 |
| CCS ORF | GCCAAGGTTTTGAAAGTGAAGCATGAAGAATTTGAGTCTTCGATTGTTTGTGATGATGGT | 4200 |
| | ************************************************************ | |
| CCS | A K V L K V K H E E F E S S I V C D D G | 518 |

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | TATGACAAGCCAAGAAACCATGGTTATCAAGTTGCTCATGGGATTTTAGCAGAAGTTGAT | 4320 |
| Jimmy Nardello | TATGACAAGCCAAGAAACCATGGTTATCAAGTTGCTCATGGGATTTTAGCAGAAGTTGAT | 4320 |
| 10CA 3745-M | TATGACAAGCCAAGAAACCATGGTTATCAAGTTGCTCATGGGATTTTAGCAGAAGTTGAT | 4320 |
| SBR-99-1193 | TATGACAAGCCAAGAAACCATGGTTATCAAGTTGCTCATGGGATTTTAGCAGAAGTTGAT | 4320 |
| SBR-99-1299 | TATGACAAGCCAAGAAACCATGGTTATCAAGTTGCTCATGGGATTTTAGCAGAAGTTGAT | 4320 |
| SBR-99-1300 | TATGACAAGCCAAGAAACCATGGTTATCAAGTTGCTCATGGGATTTTAGCAGAAGTTGAT | 4320 |
| HAS-30-1017 | TATGACAAGCCAAGAAACCATGGTTATCAAGTTGCTCATGGGATTTTAGCAGAAGTTGAT | 4320 |
| CCS ORF | TATGACAAGCCAAGAAACCATGGTTATCAAGTTGCTCATGGGATTTTAGCAGAAGTTGAT | 738 |
| | ************************************************************ | |
| CCS | Y  D  K  P  R  N  H  G  Y  Q  V  A  H  G  I  L  A  E  V  D | |

FIG. 8 (continued)

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469  | ------------------------------------------------------------ | |
| SBY-148-5201 | ------------------------------------------------------------ | |
| SBR-27-146  | AATCATCCATTTGATTTGATTGGATAAAAATGATGCTTATGCTTATGGATTGGAGGGATTCTCATTTAGGT | 4380 |
| Jimmy Nardello | AATCATCCATTTGATTTGATTGGATAAAAATGATGCTTATGCTTATGGATTGGAGGGATTCTCATTTAGGT | 4380 |
| 10CA 3745-M | AATCATCCATTTGATTTGATTGGATAAAAATGATGCTTATGCTTATGGATTGGAGGGATTCTCATTTAGGT | 4380 |
| SBR-99-1193 | AATCATCCATTTGATTTGATTGGATAAAAATGATGCTTATGCTTATGGATTGGAGGGATTCTCATTTAGGT | 4380 |
| SBR-99-1299 | AATCATCCATTTGATTTCATTTGGATAAAAATGATGCTTATGCTTATGGATTGGAGGGATTCTCATTTAGGT | 4380 |
| SBR-99-1300 | AATCATCCATTTGATTTCATTTGGATAAAAATGATGCTTATGCTTATGCACGGATTGGAGGGATTCTCATTTAGGT | 4380 |
| HAS-30-1017 | AATCATCCATTTGATTTGATTGGATAAAAATGATGCTTATGCTTATGGATTGGAGGGATTCTCATTTAGGT | 4380 |
| CCS ORF | AATCATCCATTTGATTTGATTGGATAAAAATGATGCTTATGCTTATGGATTGGAGGGATTCTCATTTAGGT | 798 |
| | ************************************************************ | |
| CCS | N H P F D L D K M M L M D W R D S H L G | |

```
SBY-99-1273    ---------------------------------------------------------
SMO-28-1234    ---------------------------------------------------------
SBY-99-1339    ---------------------------------------------------------
SBY-99-1296    ---------------------------------------------------------
SBY-99-1179    ---------------------------------------------------------
SBY-29-469     ---------------------------------------------------------
SBY-148-5201   ---------------------------------------------------------
SBR-27-146     TTTGATAGGAATTTGGTATTCTTGGAAGAGACTTCTTTAGTGAGTCGGCCTATGTTATCG  4500
Jimmy Nardello TTTGATAGGAATTTGGTATTCTTGGAAGAGACTTCTTTAGTGAGTCGGCCTATGTTATCG  4500
10CA 3745-M    TTTGATAGGAATTTGGTATTCTTGGAAGAGACTTCTTTAGTGAGTCGGCCTATGTTATCG  4500
SBR-99-1193    TTTGATAGGAATTTGGTATTCTTGGAAGAGACTTCTTTAGTGAGTCGGCCTATGTTATCG  4500
SBR-99-1299    TTTGATAGGAATTTGGTATTCTTGGAAGAGACTTCTTTAGTGAGTCGGCCTATGTTATCG  4500
SBR-99-1300    TTTGATAGGAATTTGGTATTCTTGGAAGAGACTTCTTTAGTGAGTCGGCCTATGTTATCG  4500
HAS-30-1017    TTTGATAGGAATTTGGTATTCTTGGAAGAGACTTCTTTAGTGAGTCGGCCTATGTTATCG  4500
CCS ORF        TTTGATAGGAATTTGGTATTCTTGGAAGAGACTTCTTTAGTGAGTCGGCCTATGTTATCG   918
               ************************************************************

CCS            F  D  R  N  L  V  F  L  E  E  T  S  L  V  S  R  P  M  L  S
```

FIG. 8 (continued)

| | | |
|---|---|---|
| SBY-99-1273 | ---------------------------------------------------------- | |
| SMO-28-1234 | ---------------------------------------------------------- | |
| SBY-99-1339 | ---------------------------------------------------------- | |
| SBY-99-1296 | ---------------------------------------------------------- | |
| SBY-99-1179 | ---------------------------------------------------------- | |
| SBY-29-469 | ---------------------------------------------------------- | |
| SBY-148-5201 | ---------------------------------------------------------- | |
| SBR-27-146 | TATATGGAAGTGAAAAGAAGAAGGATGGTAGCAAGATTAAGACATTTGGGGATCAAAGTGAGA | 4560 |
| Jimmy Nardello | TATATGGAAGTGAAAAGAAGAAGGATGGTAGCAAGATTAAGACATTTGGGGATCAAAGTGAGA | 4560 |
| 10CA 3745-M | TATATGGAAGTGAAAAGAAGAAGGATGGTAGCAAGATTAAGACATTTGGGGATCAAAGTGAGA | 4560 |
| SBR-99-1193 | TATATGGAAGTGAAAAGAAGAAGGATGGTAGCAAGATTAAGACATTTGGGGATCAAAGTGAGA | 4560 |
| SBR-99-1299 | TATATGGAAGTGAAAAGAAGAAGGATGGTAGCAAGATTAAGACATTTGGGGATCAAAGTGAGA | 4560 |
| SBR-99-1300 | TATATGGAAGTGAAAAGAAGAAGGATGGTAGCAAGATTAAGACATTTGGGGATCAAAGTGAGA | 4560 |
| HAS-30-1017 | TATATGGAAGTGAAAAGAAGAAGGATGGTAGCAAGATTAAGACATTTGGGGATCAAAGTGAGA | 4560 |
| CCS ORF | TATATGGAAGTGAAAAGAAGAAGGATGGTAGCAAGATTAAGACATTTGGGGATCAAAGTGAGA | 978 |
| | ************************************************************ | |
| CCS | Y M E V K R R M V A R L R H H L G I K V R | |

FIG. 8 (continued)

```
SBY-99-1273    ------------------------------------------------------------
SMO-28-1234    ------------------------------------------------------------
SBY-99-1339    ------------------------------------------------------------
SBY-99-1296    ------------------------------------------------------------
SBY-99-1179    ------------------------------------------------------------
SBY-29-469     ------------------------------------------------------------
SBY-148-5201   ------------------------------------------------------------
SBR-27-146     AGTGTCCTTGAGGAAGAGAAGTGTGTGATCACTATGGGAGGACCACTTCCGCGGATTCCT 4620
Jimmy Nardello AGTGTCCTTGAGGAAGAGAAGTGTGTGATCACTATGGGAGGACCACTTCCGCGGATTCCT 4620
10CA 3745-M    AGTGTCCTTGAGGAAGAGAAGTGTGTGATCACTATGGGAGGACCACTTCCGCGGATTCCT 4620
SBR-99-1193    AGTGTCCTTGAGGAAGAGAAGTGTGTGATCACTATGGGAGGACCACTTCCGCGGATTCCT 4620
SBR-99-1299    AGTGTCCTTGAGGAAGAGAAGTGTGTGATCACTATGGGAGGACCACTTCCGCGGATTCCT 4620
SBR-99-1300    AGTGTCCTTGAGGAAGAGAAGTGTGTGATCACTATGGGAGGACCACTTCCGCGGATTCCT 4620
HAS-30-1017    AGTGTCCTTGAGGAAGAGAAGTGTGTGATCACTATGGGAGGACCACTTCCGCGGATTCCT 4620
CCS ORF        AGTGTCCTTGAGGAAGAGAAGTGTGTGATCACTATGGGAGGACCACTTCCGCGGATTCCT 1038
               ************************************************************

CCS            S  V  L  E  E  E  K  C  V  I  T  M  G  G  P  L  P  R  I  P
```

FIG. 8 (continued)

| | | |
|---|---|---|
| SBY-99-1273 | ------- | |
| SMO-28-1234 | ------- | |
| SBY-99-1339 | ------- | |
| SBY-99-1296 | ------- | |
| SBY-99-1179 | ------- | |
| SBY-29-469 | ------- | |
| SBY-148-5201 | ------- | |
| SBR-27-146 | CAAAATGTTATGGCTATTGGTGGTGGGACTTCAGGGATAGTTCATCCATCCATCCGTCTGGGTACACATG | 4680 |
| Jimmy Nardello | CAAAATGTTATGGCTATTGGTGGTGGGACTTCAGGGATAGTTCATCCATCCATCCGTCTGGGTACATG | 4680 |
| 10CA 3745-M | CAAAATGTTATGGCTATTGGTGGTGGGACTTCAGGGATAGTTCATCCATCCATCCGTCTGGGTACATG | 4680 |
| SBR-99-1193 | CAAAATGTTATGGCTATTGGTGGTGGGACTTCAGGGATAGTTCATCCATCCATCCGTCTGGGTACATG | 4680 |
| SBR-99-1299 | CAAAATGTTATGGCTATTGGTGGTGGGACTTCAGGGATAGTTCATCCATCCATCCGTCTGGGTACATG | 4680 |
| SBR-99-1300 | CAAAATGTTATGGCTATTGGTGGTGGGACTTCAGGGATAGTTCATCCATCCATCCGTCTGGGTACATG | 4680 |
| HAS-30-1017 | CAAAATGTTATGGCTATTGGTGGTGGGACTTCAGGGATAGTTCATCCATCCATCCGTCTGGGTACATG | 4680 |
| CCS ORF | CAAAATGTTATGGCTATTGGTGGTGGGACTTCAGGGATAGTTCATCCATCCTCTGGTCTGGGTACATG | 1098 |
| | ****************************************************************** | |
| CCS | Q N V M A I G G T S G I V H P S S G Y M | |

FIG. 8 (continued)

| | | |
|---|---|---|
| SBY-99-1273 | ------------------------------------------------------------ | |
| SMO-28-1234 | ------------------------------------------------------------ | |
| SBY-99-1339 | ------------------------------------------------------------ | |
| SBY-99-1296 | ------------------------------------------------------------ | |
| SBY-99-1179 | ------------------------------------------------------------ | |
| SBY-29-469 | ------------------------------------------------------------ | |
| SBY-148-5201 | ------------------------------------------------------------ | |
| SBR-27-146 | GTGGCTCGTAGCATGGCATTGGCACCAGTACTGGCTGAGGCCTGAGGCCTGAAAGCCTTGGC | 4740 |
| Jimmy Nardello | GTGGCTCGTAGCATGGCATTGGCACCAGTACTGGCTGAGGCCTGAGGCCTGAAAGCCTTGGC | 4740 |
| 10CA 3745-M | GTGGCTCGTAGCATGGCATTGGCACCAGTACTGGCTGAGGCCTGAGGCCTGAAAGCCTTGGC | 4740 |
| SBR-99-1193 | GTGGCTCGTAGCATGGCATTGGCACCAGTACTGGCTGAGGCCTGAGGCCTGAAAGCCTTGGC | 4740 |
| SBR-99-1299 | GTGGCTCGTAGCATGGCATTGGCACCAGTACTGGCTGAGGCCTGAGGCCTGAAAGCCTTGGC | 4740 |
| SBR-99-1300 | GTGGCTCGTAGCATGGCATTGGCACCAGTACTGGCTGAGGCCTGAGGCCTGAAAGCCTTGGC | 4740 |
| HAS-30-1017 | GTGGCTCGTAGCATGGCATTGGCACCAGTACTGGCTGAGGCCTGAGGCCTGAAAGCCTTGGC | 4740 |
| CCS ORF | GTGGCTCGTAGCATGGCATTGGCACCAGTACTGGCTGAGGCCTGAGGCCTGAAAGCCTTGGC | 1158 |
| | ************************************************************ | |
| CCS | V A R S M A L A P V L A E A I V E S L G | |

FIG. 8 (continued)

```
SBY-99-1273    ------------------------------------------------AGTTTGGAATGGTTTGTGGCCT 373
SMO-28-1234    ------------------------------------------------AGTTTGGAATGGTTTGTGGCCT 373
SBY-99-1339    ------------------------------------------------AGTTTGGAATGGTTTGTGGCCT 373
SBY-99-1296    ------------------------------------------------AGTTTGGAATGGTTTGTGGCCT 373
SBY-99-1179    ------------------------------------------------AGTTTGGAATGGTTTGTGGCCT 373
SBY-29-469     ------------------------------------------------AGTTTGGAATGGTTTGTGGCCT 373
SBY-148-5201   ------------------------------------------------AGTTTGGAATGGTTTGTGGCCT 373
SBR-27-146     TCAACAAGAATGATAAGAGAGGGTCTCAACTTTACCATAGAGTTTGGAATGGTTTGTGGCCT 4800
Jimmy Nardello TCAACAAGAATGATAAGAGAGGGTCTCAACTTTACCATAGAGTTTGGAATGGTTTGTGGCCT 4800
10CA_3745-M    TCAACAAGAATGATAAGAGAGGGTCTCAACTTTACCATAGAGTTTGGAATGGTTTGTGGCCT 4800
SBR-99-1193    TCAACAAGAATGATAAGAGAGGGTCTCAACTTTACCATAGAGTTTGGAATGGTTTGTGGCCT 4800
SBR-99-1299    TCAACAAGAATGATAAGAGAGGGTCTCAACTTTACCATAGAGTTTGGAATGGTTTGTGGCCT 4800
SBR-99-1300    TCAACAAGAATGATAAGAGAGGGTCTCAACTTTACCATAGAGTTTGGAATGGTTTGTGGCCT 4800
HAS-30-1017    TCAACAAGAATGATAAGAGAGGGTCTCAACTTTACCATAGAGTTTGGAATGGTTTGTGGCCT 4800
CCS ORF        TCAACAAGAATGATAAGAGACCGTCTCAACTTTACCATAGAGTTTGGAATGGTTTGTGGCCT 1218
               ********************  ***************************************

CCS            S  T  R  M  I  R  G  S  Q  L  Y  H  R  V  W  N  G  L  W  P
```

| | | |
|---|---|---|
| SBY-99-1273 | GATTTGGAAGGTACTAGGAGAGATTGTTTGATGCTTTCTTTGATGTTGATCCCAAGTACTGG | 493 |
| SMO-28-1234 | GATTTGGAAGGTACTAGGAGAGATTGTTTGATGCTTTCTTTGATGTTGATCCCAAGTACTGG | 493 |
| SBY-99-1339 | GATTTGGAAGGTACTAGGAGAGATTGTTTGATGCTTTCTTTGATGTTGATCCCAAGTACTGG | 493 |
| SBY-99-1296 | GATTTGGAAGGTACTAGGAGAGATTGTTTGATGCTTTCTTTGATGTTGATCCCAAGTACTGG | 493 |
| SBY-99-1179 | GATTTGGAAGGTACTAGGAGAGATTGTTTGATGCTTTCTTTGATGTTGATCCCAAGTACTGG | 493 |
| SBY-29-469 | GATTTGGAAGGTACTAGGAGAGATTGTTTGATGCTTTCTTTGATGTTGATCCCAAGTACTGG | 493 |
| SBY-148-5201 | GATTTGGAAGGTACTAGGAGAGATTGTTTGATGCTTTCTTTGATGTTGATCCCAAGTACTGG | 493 |
| SBR-27-146 | GATTTGGAAGGTACTAGGAGAGATTGTTTGATGCTTTCTTTGATGTTGATCCCAAGTACTGG | 4920 |
| Jimmy Nardello | GATTTGGAAGGTACTAGGAGAGATTGTTTGATGCTTTCTTTGATGTTGATCCCAAGTACTGG | 4920 |
| 10CA 3745-M | GATTTGGAAGGTACTAGGAGAGATTGTTTGATGCTTTCTTTGATGTTGATCCCAAGTACTGG | 4920 |
| SBR-99-1193 | GATTTGGAAGGTACTAGGAGAGATTGTTTGATGCTTTCTTTGATGTTGATCCCAAGTACTGG | 4920 |
| SBR-99-1299 | GATTTGGAAGGTACTAGGAGAGATTGTTTGATGCTTTCTTTGATGTTGATCCCAAGTACTGG | 4920 |
| SBR-99-1300 | GATTTGGAAGGTACTAGGAGAGATTGTTTGATGCTTTCTTTGATGTTGATCCCAAGTACTGG | 4920 |
| HAS-30-1017 | GATTTGGAAGGTACTAGGAGAGATTGTTTGATGCTTTCTTTGATGTTGATCCCAAGTACTGG | 4920 |
| CCS ORF | GATTTGGAAGGTACTAGGAGAGATTGTTTGATGCTTTCTTTGATGTTGATCCCAAGTACTGG | 1338 |
| CCS | D L E G T R R L F D A F F D V D P K Y W | |

FIG. 8 (continued)

| | | |
|---|---|---|
| SBY-99-1273 | CACGGGTTCCTTTCTTCAAGATTGTCTGTGTCAAAGAACTTGCTGTACTCAGTTTGTACCTT | 553 |
| SMO-28-1234 | CACGGGTTCCTTTCTTCAAGATTGTCTGTGTCAAAGAACTTGCTGTACTCAGTTTGTACCTT | 553 |
| SBY-99-1339 | CACGGGTTCCTTTCTTCAAGATTGTCTGTGTCAAAGAACTTGCTGTACTCAGTTTGTACCTT | 553 |
| SBY-99-1296 | CACGGGTTCCTTTCTTCAAGATTGTCTGTGTCAAAGAACTTGCTGTACTCAGTTTGTACCTT | 553 |
| SBY-99-1179 | CACGGGTTCCTTTCTTCAAGATTGTCTGTGTCAAAGAACTTGCTGTACTCAGTTTGTACCTT | 553 |
| SBY-29-469 | CACGGGTTCCTTTCTTCAAGATTGTCTGTGTCAAAGAACTTGCTGTACTCAGTTTGTACCTT | 553 |
| SBY-148-5201 | CACGGGTTCCTTTCTTCAAGATTGTCTGTGTCAAAGAACTTGCTGTACTCAGTTTGTACCTT | 553 |
| SBR-27-146 | CACGGGTTCCTTTCTTCAAGATTGTCTGTGTCAAAGAACTTGCTGTACTCAGTTTGTACCTT | 4980 |
| Jimmy Nardello | CACGGGTTCCTTTCTTCAAGATTGTCTGTGTCAAAGAACTTGCTGTACTCAGTTTGTACCTT | 4980 |
| 10CA 3745-M | CACGGGTTCCTTTCTTCAAGATTGTCTGTGTCAAAGAACTTGCTGTACTCAGTTTGTACCTT | 4980 |
| SBR-99-1193 | CACGGGTTCCTTTCTTCAAGATTGTCTGTGTCAAAGAACTTGCTGTACTCAGTTTGTACCTT | 4980 |
| SBR-99-1299 | CACGGGTTCCTTTCTTCAAGATTGTCTGTGTCAAAGAACTTGCTGTACTCAGTTTGTACCTT | 4980 |
| SBR-99-1300 | CACGGGTTCCTTTCTTCAAGATTGTCTGTGTCAAAGAACTTGCTGTACTCAGTTTGTACCTT | 4980 |
| HAS-30-1017 | CACGGGTTCCTTTCTTCAAGATTGTCTGTGTCAAAGAACTTGCTGTACTCAGTTTGTACCTT | 4980 |
| CCS ORF | CACGGGTTCCTTTCTTCAAGATTGTCTGTGTCAAAGAACTTGCTGTACTCAGTTTGTACCTT | 1398 |
| CCS | H G F L S R L S V K E L A V L S L Y L | |

| | | |
|---|---|---|
| SBY-99-1273 | GTTAAACTGCTGGGCAATCTAGCAATAGAGAGCCTTTGAATTAATATGATAGTTTTGAAG | 673 |
| SMO-28-1234 | GTTAAACTGCTGGGCAATCTAGCAATAGAGAGCCTTTGAATTAATATGATAGTTTTGAAG | 673 |
| SBY-99-1339 | GTTAAACTGCTGGGCAATCTAGCAATAGAGAGCCTTTGAATTAATATGATAGTTTTGAAG | 673 |
| SBY-99-1296 | GTTAAACTGCTGGGCAATCTAGCAATAGAGAGCCTTTGAATTAATATGATAGTTTTGAAG | 673 |
| SBY-99-1179 | GTTAAACTGCTGGGCAATCTAGCAATAGAGAGCCTTTGAATTAATATGATAGTTTTGAAG | 673 |
| SBY-29-469 | GTTAAACTGCTGGGCAATCTAGCAATAGAGAGCCTTTGAATTAATATGATAGTTTTGAAG | 673 |
| SBY-148-5201 | GTTAAACTGCTGGGCAATCTAGCAATAGAGAGCCTTTGAATTAATATGATAGTTTTGAAG | 673 |
| SBR-27-146 | GTTAAACTGCTGGGCAATCTAGCAATAGAGAGCCTTTGAATTAATATGATAGTTTTGAAG | 5100 |
| Jimmy Nardello | GTTAAACTGCTGGGCAATCTAGCAATAGAGAGCCTTTGAATTAATATGATAGTTTTGAAG | 5100 |
| 10CA 3745-M | GTTAAACTGCTGGGCAATCTAGCAATAGAGAGCCTTTGAATTAATATGATAGTTTTGAAG | 5100 |
| SBR-99-1193 | GTTAAACTGCTGGGCAATCTAGCAATAGAGAGCCTTTGAATTAATATGATAGTTTTGAAG | 5100 |
| SBR-99-1299 | GTTAAACTGCTGGGCAATCTAGCAATAGAGAGCCTTTGAATTAATATGATAGTTTTGAAG | 5100 |
| SBR-99-1300 | GTTAAACTGCTGGGCAATCTAGCAATAGAGAGCCTTTGAATTAATATGATAGTTTTGAAG | 5100 |
| HAS-30-1017 | GTTAAACTGCTGGGCAATCTAGCAATAGAGAGCCTTTGAATTAATATGATAGTTTTGAAG | 5100 |
| CCS ORF | GTTAAACTGCTGGGCAATCTAGCAATAGAGAGCCTTTGA | 1497 |
| CCS | V K L L G N L A I E S L * | |

FIG. 8 (continued)

| | | |
|---|---|---|
| SBY-99-1273 | CACTGCTTTCATTTTAATTTTAATTCTTAGGTTATTTTCATTTTAATTTCATCTTTTATCAATGCAAAAGTGAAAC | 733 |
| SMO-28-1234 | CACTGCTTTCATTTTAATTTTAATTCTTAGGTTATTTTCATTTTAATTTCATCTTTTATCAATGCAAAAGTGAAAC | 733 |
| SBY-99-1339 | CACTGCTTTCATTTTAATTTTAATTCTTAGGTTATTTTCATTTTAATTTCATCTTTTATCAATGCAAAAGTGAAAC | 733 |
| SBY-99-1296 | CACTGCTTTCATTTTAATTTTAATTCTTAGGTTATTTTCATTTTAATTTCATCTTTTATCAATGCAAAAGTGAAAC | 733 |
| SBY-99-1179 | CACTGCTTTCATTTTAATTTTAATTCTTAGGTTATTTTCATTTTAATTTCATCTTTTATCAATGCAAAAGTGAAAC | 733 |
| SBY-29-469 | CACTGCTTTCATTTTAATTTTAATTCTTAGGTTATTTTCATTTTAATTTCATCTTTTATCAATGCAAAAGTGAAAC | 733 |
| SBY-148-5201 | CACTGCTTTCATTTTAATTTTAATTCTTAGGTTATTTTCATTTTAATTTCATCTTTTATCAATGCAAAAGTGAAAC | 733 |
| SBR-27-146 | CACTGCTTTCATTTTAATTTTAATTCTTAGGTTATTTTCATTTTAATTTCATCTTTTATCAATGCAAAAGTGAAAC | 5160 |
| Jimmy Nardello | CACTGCTTTCATTTTAATTTTAATTCTTAGGTTATTTTCATTTTAATTTCATCTTTTATCAATGCAAAAGTGAAAC | 5160 |
| 10CA 3745-M | CACTGCTTTCATTTTAATTTTAATTCTTAGGTTATTTTCATTTTAATTTCATCTTTTATCAATGCAAAAGTGAAAC | 5160 |
| SBR-99-1193 | CACTGCTTTCATTTTAATTTTAATTCTTAGGTTATTTTCATTTTCATTTCATCTTTTCTCAATGCAAAAGTGAAAC | 5160 |
| SBR-99-1299 | CACTGCTTTCATTTTAATTTTAATTCTTAGGTTATTTTCATTTTCATTTCATCTTTTCTCAATGCAAAAGTGAAAC | 5160 |
| SBR-99-1300 | CACTGTTTTCATTTTAATTTTAATTCTTAGGTTATTTTCATTTTAATTTCATCTTTTCTCAATGCAAAAGTGAAAC | 5160 |
| HAS-30-1017 | CACTGTTTTCATTTTAATTTTAATTCTTAGGTTATTTTCATTTTAATTTCATCTTTTCTCAATGCAAAAGTGAAAC | 5160 |

NCANN0091135T0    NCANN00911317T0

| | | |
|---|---|---|
| SBY-99-1273 | TTGGACAAAAGTATAGAGCCCACAATCTGATACCAAGTCTGTATTTGGAAGCACTGGCTAA | 913 |
| SMO-28-1234 | TTGGACAAAAGTATAGAGCCACCAATCTGATACCAAGTCTGTATTTGGAAGCCACTGGCTAA | 913 |
| SBY-99-1339 | TTGGACAAAAGTATAGAGCCACCAATCTGATACCAAGTCTGTATTTGGAAGCACTGGCTAA | 913 |
| SBY-99-1296 | TTGGACAAAAGTATAGAGCCACCAATCTGATACCAAGTCTGTATTTGGAAGCACTGGCTAA | 913 |
| SBY-99-1179 | TTGGACAAAAGTATAGAGCCACCAATCTGATACCAAGTCTGTATTTGGAAGCACTGGCTAA | 913 |
| SBY-29-469 | TTGGACAAAAGTATAGAGCCACCAATCTGATACCAAGTCTGTATTTGGAAGCACTGGCTAA | 913 |
| SBY-148-5201 | TTGGACAAAAGTATAGAGCCACCAATCTGATACCAAGTCTGTATTTGGAAGCACTGGCTAA | 913 |
| SBR-27-146 | TTGGACAAAAGTATAGAGCCACCAATCTGATACCAAGTCTGTATTTGGAAGCACTGGCTAA | 5340 |
| Jimmy Nardello | TTGGACAAAAGTATAGAGCCACCAATCTGATACCAAGTCTGTATTTGGAAGCACTGGCTAA | 5340 |
| 10CA 3745-M | TTGGACAAAAGTATAGAGCCACCAATCTGATACCAAGTCTGTATTTGGAAGCACTGGCTAA | 5340 |
| SBR-99-1193 | TTGGACAAAAGTATAGAGCCACCAATCCGATACCAAGTCTGTATTTGGAAGCACTGTCTAA | 5326 |
| SBR-99-1299 | TTGGACAAAAGTATAGAGCCACCAATCCGATACCAAGTCTGTATTTGGAAGCACTGTCTAA | 5326 |
| SBR-99-1300 | TTGGACAAAAGTATAGAGCCACCAATCCGATACCAAGTCTGTATTTGGAAGCACTGTCTAA | 5326 |
| HAS-30-1017 | TTGGACAAAAGTATAGAGCCACCAATCTGATACCAAGTCTGTATTTGGAAGCACAGGCTAA | 5326 |
| | * * * | |
| | NCANN009113370 NCANN009113971 | |
| | NCANN009113371 | |

FIG. 8 (continued)

| | | |
|---|---|---|
| SBY-99-1273 | TTGTTATGGTTACCAAACACTTTGAATTGGCTGGATAAT----AACAGGAACTTTATGTT | 969 |
| SMO-28-1234 | TTGTTATGGTTACCAAACACTTTGAATTGGCTGGATAAT----AACAGGAAATTTATGTT | 969 |
| SBY-99-1339 | TTGTTATGGTTACCAAACACTTTGAATTGGCTGGATAAT----AACAGGAAATTTATGTT | 969 |
| SBY-99-1296 | TTGTTATGGTTACCAAACACTTTGAATTGGCTGGATAAT----AACAGGAAATTTATGTT | 969 |
| SBY-99-1179 | TTGTTATGGTTACCAAACACTTTGAATTGGCTGGATAAT----AACAGGAAATTTATGTT | 969 |
| SBY-29-469 | TTGTTATGGTTACCAAACACTTTGAATTGGCTGGATAAT----AACAGGAAATTTATGTT | 969 |
| SBY-148-5201 | TTGTTATGGTTACCAAACACTTTGAATTGGCTGGATAAT----AACAGGAAATTTATGTT | 5396 |
| SBR-27-146 | TTGTTATGGTTACCAAACACTTTGAATTGGCTGGATAAT----AACAGGAAATTTATGTT | 5396 |
| Jimmy Nardello | TTGTTATGGTTACCAAACACTTTGAATTGGCTGGATAAT----AACAGGAAATTTATGTT | 5396 |
| 10CA 3745-M | TTCTTATGGTTACCAAACACTTTGAATTGGCTGGATAAT----AACAGGAAATTTATGTT | 5386 |
| SBR-99-1193 | TTGTTATGGTTACCAAACACTTTGAATTGGCTGGATAATAACAAACAGGAAATTTATGTT | 5386 |
| SBR-99-1299 | TTGTTATGGTTACCAAACACTTTGAATTGGCTGGATAATAACAAACAGGAAATTTATGTT | 5386 |
| SBR-99-1300 | TTGTTATGGTTACCAAACACTTTGAATTGGCTGGATAATAACAAACAGGAAATTTATGTT | 5386 |
| HAS-30-1017 | TTGTTATGGTTACCAAACACTTTGAATTGGCTGGATAATAACAAACAGGAAATTTATGTT | 5386 |

NCANN009114170  NCANN009114370

FIG. 8 (continued)

```
SBY-99-1273       ATTAATCATTAACACAGCAAATTGGGAAAAGCAAGAATTATTAGGAAAGTTAATATATAGTGTCT 1029
SMO-28-1234       ATTAATCATTAACACAGCAAATTGGGAAAAGCAAGAATTATTAGGAAAGTTAATATATAGTGTCT 1029
SBY-99-1339       ATTAATCATTAACACAGCAAATTGGGAAAAGCAAGAATTATTAGGAAAGTTAATATATAGTGTCT 1029
SBY-99-1296       ATTAATCATTAACACAGCAAATTGGGAAAAGCAAGAATTATTAGGAAAGTTAATATATAGTGTCT 1029
SBY-99-1179       ATTAATCATTAACACAGCAAATTGGGAAAAGCAAGAATTATTAGGAAAGTTAATATATAGTGTCT 1029
SBY-29-469        ATTAATCATTAACACAGCAAATTGGGAAAAGCAAGAATTATTAGGAAAGTTAATATATAGTGTCT 1029
SBY-148-5201      ATTAATCATTAACACAGCAAATTGGGAAAAGCAAGAATTATTAGGAAAGTTAATATATAGTGTCT 5456
SBR-27-146        ATTAATCATTAACACAGCAAATTGGGAAAAGCAAGAATTATTAGGAAAGTTAATATATAGTGTCT 5456
Jimmy Nardello    ATTAATCATTAACACAGCAAATTGGGAAAAGCAAGAATTATTAGGAAAGTTAATATATAGTGTCT 5456
10CA_3745-M       ATTAATCATTAACACAGCAAATTGGGAAAAGCAAGAATTATTAGGAAAGTTAATATATAGTGTCT 5446
SBR-99-1193       TTTAATCATTAACACAGCAAATTGGGAAAAGCAAGAATTATTAGGAAAGTTAATATATAGTGTCT 5446
SBR-99-1299       TTTAATCATTAACACAGCAAATTGGGAAAAGCAAGAATTATTAGGAAAGTTAATATATAGTGTCT 5446
SBR-99-1300       TTTAATCATTAACACAGCAAATTGGGAAAAGCAAGAATTATTAGGAAAGTTAATATATAGTGTCT 5446
HAS-30-1017       TTTAATCATTAACACAGCAAATTGGGAAAAGCAAGAATTATTAGGAAAGTTAATATATAGTGTCT 5446
NCANN005134316
                  *
```

FIG. 8 (continued)

| | |
|---|---|
| SBY-99-1273 | TGGTTATTCTAATGGAGTGGGTTATGCAAATTAAGTTCCCTTATCAAAGTTTGGTTTATG 1089 |
| SMO-28-1234 | TGGTTATTCTAATGGAGTGGGTTATGCAAATTAAGTTCCCTTATCAAAGTTTGGTTTATG 1089 |
| SBY-99-1339 | TGGTTATTCTAATGGAGTGGGTTATGCAAATTAAGTTCCCTTATCAAAGTTTGGTTTATG 1089 |
| SBY-99-1296 | TGGTTATTCTAATGGAGTGGGTTATGCAAATTAAGTTCCCTTATCAAAGTTTGGTTTATG 1089 |
| SBY-99-1179 | TGGTTATTCTAATGGAGTGGGTTATGCAAATTAAGTTCCCTTATCAAAGTTTGGTTTATG 1089 |
| SBY-29-469 | TGGTTATTCTAATGGAGTGGGTTATGCAAATTAAGTTCCCTTATCAAAGTTTGGTTTATG 1089 |
| SBY-148-5201 | TGGTTATTCTAATGGAGTGGGTTATGCAAATTAAGTTCCCTTATCAAAGTTTGGTTTATG 1089 |
| SBR-27-146 | TGGTTATTCTAATGGAGTGGGTTATGCAAATTAAGTTCCCTTATCAAAGTTTGGTTTATG 5516 |
| Jimmy Nardello | TGGTTATTCTAATGGAGTGGGTTATGCAAATTAAGTTCCCTTATCAAAGTTTGGTTTATG 5516 |
| 10CA 3745-M | TGGTTATTCTAATGGAGTGGGTTATGCAAATTAAGTTCCCTTATCAAAGTTTGGTTTATG 5516 |
| SBR-99-1193 | TGGTTATTCTAATGGAGTGGGTTATGCAAATTAAGTTCCCTTATCAAAGTTTGGTTTATG 5506 |
| SBR-99-1299 | TGGTTATTCTAATGGAGTGGGTTATGCAAATTAAGTTCCCTTATCAAAGTTTGGTTTATG 5506 |
| SBR-99-1300 | TGGTTATTCTAATGGAGTGGGTTATGCAAATTAAGTTCCCTTATCAAAGTTTGGTTTATG 5506 |
| HAS-30-1017 | TGGTTATTCTAATGGAGTGGGTTATGCAAATTAAGTTCCCTGTCAAAGTTTGGTTTATG 5506 |
| | * |
| NCANN009113571 | |

```
SBY-99-1273       ATTATGAGGATGCAATGCAATAGGTTTAATTAATTACCAGTTATCTGTAAATTGTCTTCGTTGCC 1269
SMO-28-1234       ATTATGAGGATGCAATGCAATAGGTTTAATTAATTACCAGTTATCTGTAAATTGTCTTCGTTGCC 1269
SBY-99-1339       ATTATGAGGATGCAATGCAATAGGTTTAATTAATTACCAGTTATCTGTAAATTGTCTTCGTTGCC 1269
SBY-99-1296       ATTATGAGGATGCAATGCAATAGGTTTAATTAATTACCAGTTATCTGTAAATTGTCTTCGTTGCC 1269
SBY-99-1179       ATTATGAGGATGCAATGCAATAGGTTTAATTAATTACCAGTTATCTGTAAATTGTCTTCGTTGCC 1269
SBY-29-469        ATTATGAGGATGCAATGCAATAGGTTTAATTAATTACCAGTTATCTGTAAATTGTCTTCGTTGCC 1269
SBY-148-5201      ATTATGAGGATGCAATGCAATAGGTTTAATTAATTACCAGTTATCTGTAAATTGTCTTCGTTGCC 1269
SBR-27-146        ATTATGAGGATGCAATGCAATAGGTTTAATTAATTACCAGTTATCTGTAAATTGTCTTCGTTGCC 1269
Jimmy Nardello    ATTATGAGGATGCAATGCAATAGGTTTAATTAATTACCAGTTATCTGTAAATTGTCTTCGTTGCC 5696
10CA 3745-M       ATTATGAGGATGCAATGCAATAGGTTTAATTAATTACCAGTTATCTGTAAATTGTCTTCGTTGCC 5696
SBR-99-1193       ATTATGAGGATGCAATGCAATAGGTTTAATTAATTACCAGTTATCTGTAAATTGTCTTCGTTGCC 5686
SBR-99-1299       ATTATGAGGATGCAATGCAATAGGTTTAATTAATTACCAGTTATCTGTAAATTGTCTCTTTGCC 5686
SBR-99-1300       ATTATGAGGATGCAATGCAATAGGTTTAATTAATTACCAGTTATCTGTAAATTGTCTTCTTGCC 5686
HAS-30-1017       ATTATGAGGATGCAATGCAATAGGTTTAATTAATTACCAGTTATCTGTAAATTGTCTTCTTGCC 5686
                                                                 *                          NCANN009113771

SBY-99-1273       ATTATTTTAAAAGTTTAAT----AAGTGTAACATCTACAAAGAGTTGATAA 1316
SMO-28-1234       ATTATTTTAAAAGTTTAAT----AAGTGTAACATCTACAAAGAGTTGATAA 1316
SBY-99-1339       ATTATTTTAAAAGTTTAAT----AAGTGTAACATCTACAAAGAGTTGATAA 1316
SBY-99-1296       ATTATTTTAAAAGTTTAAT----AAGTGTAACATCTACAAAGAGTTGATAA 1316
SBY-99-1179       ATTATTTTAAAAGTTTAAT----AAGTGTAACATCTACAAAGAGTTGATAA 1316
SBY-29-469        ATTATTTTAAAAGTTTAAT----AAGTGTAACATCTACAAAGAGTTGATAA 1316
SBY-148-5201      ATTATTTTAAAAGTTTAAT----AAGTGTAACATCTACAAAGAGTTGATAA 1316
SBR-27-146        ATTATTTTAAAAGTTTAAT----AAGTGTAACATCTACAAAGAGTTGATAA 1316
Jimmy Nardello    ATTATTTTAAAAGTTTAAT----AAGTGTAACATCTACAAAGAGTTGATAA 5743
10CA 3745-M       ATTATTTTAAAAGTTTAAT----AAGTGTAACATCTACAAAGAGTTGATAA 5743
SBR-99-1193       ATTATTTTAAAAGTTTAATAACAAGTGTAACAAGTGTAACATCTACAAAGAGTTGATAA 5736
SBR-99-1299       ATTATTTTAAAAGTTTAATAACAAGTGTAACAAGTGTAACATCTACAAAGAGTTGATAA 5736
SBR-99-1300       ATTATTTTAAAAGTTTAATAACAAGTGTAACAAGTGTAACATCTACAAAGAGTTGATAA 5736
HAS-30-1017       ATTATTTTAAAAGTTTAATAACAAGTGTAACAAGTGTAACATCTACAAAGAGTTGATAA 5736
                                      ***                                NCANN009114171
```

FIG. 8 (continued)

SEQUENCE LISTING

```
<160> NUMBER OF SEQ ID NOS: 99

<210> SEQ ID NO 1
<211> LENGTH: 1497
<212> TYPE: DNA
<213> ORGANISM: Capsicum annuum

<400> SEQUENCE: 1
atggaaaccc ttctaaagcc ttttccatct cctttacttt ccattcctac tcctaacatg      60
tatagtttca aacacaactc cacttttcca aatccaacca aacaaaaaga ttcaagaaag     120
ttccattata gaaacaaaag cagtacacat ttttgtagct ttcttgattt agcacccaca     180
tcaaagccag agtctttaga tgttaacatc tcatgggttg atactgatct ggacggggct     240
gaattcgacg tgatcatcat tggaactggc cctgccgggc ttcggctagc tgaacaagtt     300
tctaaatatg gtattaaggt atgttgcgtt gacccttcac cactttccat gtggccaaat     360
aattatggtg tttgggttga tgagtttgaa aagttgggat tagaagattg tctagatcat     420
aagtggcctg tgagttgtgt tcatataagt gatcacaaga ctaagtattt ggacagacca     480
```

```
tatggtagag taagtagaaa gaagttgaag ttgaaattgt tgaatagttg tgttgaaaat      540
agagtgaagt tttataaagc caaggttttg aaagtgaagc atgaagaatt tgagtcttcg      600
attgtttgtg atgatggtag gaagataagc ggtagcttga ttgttgatgc aagtggctat      660
gctagtgatt ttatagagta tgacaagcca agaaaccatg gttatcaagt tgctcatggg      720
attttagcag aagttgataa tcatccattt gatttggata aaatgatgct tatggattgg      780
agggattctc atttaggtaa tgagccatat ctgagggtga agaatactaa agaaccaaca      840
ttcttgtatg caatgccatt tgataggaat ttggtattct tggaagagac ttctttagtg      900
agtcggccta tgttatcgta tatggaagtg aaaagaagga tggtagcaag attaagacat      960
ttggggatca aagtgagaag tgtccttgag gaagagaagt gtgtgatcac tatgggagga     1020
ccacttccgc ggattcctca aaatgttatg gctattggtg ggacttcagg gatagttcat     1080
ccatcgtctg ggtacatggt ggctcgtagc atggcattgg caccagtact ggctgaggcc     1140
atcgtcgaaa gccttggctc aacaagaatg ataagagggg ctcaacttta ccatagagtt     1200
tggaatggtt tgtggccttc ggatagaaga cgtgttagaa atgttattg tttcggaatg       1260 gagactttgt tgaagcttga tttggaaggt actaggagat tgtttgatgc tttctttgat     1320
gttgatccca agtactggca cgggttcctt tcttcaagat tgtctgtcaa agaacttgct     1380
gtactcagtt tgtaccttt tggacatgcc tctaatttgg ctaggttgga tattgttaca      1440
aagtgcactg tccccttggt taaactgctg ggcaatctag caatagagag cctttga       1497
```

<210> SEQ ID NO 2
<211> LENGTH: 20
<212> TYPE: DNA
<213> ORGANISM: Artificial sequence
<220> FEATURE:
<223> OTHER INFORMATION: Primer

<400> SEQUENCE: 2

```
caactccact tttccaaatc                                                    20
```

<210> SEQ ID NO 3
<211> LENGTH: 20
<212> TYPE: DNA
<213> ORGANISM: Artificial sequence
<220> FEATURE:
<223> OTHER INFORMATION: Primer

<400> SEQUENCE: 3

```
ggttgatact gatctggacg                                                    20
```

<210> SEQ ID NO 4
<211> LENGTH: 21
<212> TYPE: DNA
<213> ORGANISM: Artificial sequence
<220> FEATURE:
<223> OTHER INFORMATION: Primer

<400> SEQUENCE: 4

```
gtgagtcggc ctatgttatc g                                                  21
```

<210> SEQ ID NO 5
<211> LENGTH: 21
<212> TYPE: DNA
<213> ORGANISM: Artificial sequence
<220> FEATURE:
<223> OTHER INFORMATION: Primer

<400> SEQUENCE: 5
gtgagtcggc ctatgttatc g                                              21

<210> SEQ ID NO 6
<211> LENGTH: 20
<212> TYPE: DNA
<213> ORGANISM: Artificial sequence
<220> FEATURE:
<223> OTHER INFORMATION: Primer

<400> SEQUENCE: 6
tgttgatccc aagtactggc                                                20

<210> SEQ ID NO 7
<211> LENGTH: 22
<212> TYPE: DNA
<213> ORGANISM: Artificial sequence
<220> FEATURE:
<223> OTHER INFORMATION: Primer

<400> SEQUENCE: 7
agacttggta tcagattgtg gc                                             22

<210> SEQ ID NO 8
<211> LENGTH: 20
<212> TYPE: DNA
<213> ORGANISM: Artificial sequence
<220> FEATURE:
<223> OTHER INFORMATION: Primer

<400> SEQUENCE: 8
agccacaatc cgataccaag                                                20

<210> SEQ ID NO 9
<211> LENGTH: 20
<212> TYPE: DNA
<213> ORGANISM: Artificial sequence
<220> FEATURE:
<223> OTHER INFORMATION: Primer

<400> SEQUENCE: 9
gagggacaag agtggagcag                                                20

<210> SEQ ID NO 10
<211> LENGTH: 20
<212> TYPE: DNA
<213> ORGANISM: Artificial sequence
<220> FEATURE:
<223> OTHER INFORMATION: Primer

<400> SEQUENCE: 10
tcgaaagcct tggctcaaca                                                20

<210> SEQ ID NO 11
<211> LENGTH: 23
<212> TYPE: DNA
<213> ORGANISM: Artificial sequence
<220> FEATURE:
<223> OTHER INFORMATION: Primer

<400> SEQUENCE: 11
ttttgtatct ccctttccca gaa                                            23

<210> SEQ ID NO 12
<211> LENGTH: 26

```
<212> TYPE: DNA
<213> ORGANISM: Artificial sequence
<220> FEATURE:
<223> OTHER INFORMATION: Primer

<400> SEQUENCE: 12
tctctaacac gtcttctatc cgaagg                                          26

<210> SEQ ID NO 13
<211> LENGTH: 18
<212> TYPE: DNA
<213> ORGANISM: Artificial sequence
<220> FEATURE:
<223> OTHER INFORMATION: Primer

<400> SEQUENCE: 13
agaatgataa gagggtct                                                   18

<210> SEQ ID NO 14
<211> LENGTH: 18
<212> TYPE: DNA
<213> ORGANISM: Artificial sequence
<220> FEATURE:
<223> OTHER INFORMATION: Probe

<400> SEQUENCE: 14
cttttagagt ttggaatg                                                   18

<210> SEQ ID NO 15
<211> LENGTH: 25
<212> TYPE: DNA
<213> ORGANISM: Artificial sequence
<220> FEATURE:
<223> OTHER INFORMATION: Primer

<400> SEQUENCE: 15
ccaaacactt tgaattggct ggata                                           25

<210> SEQ ID NO 16
<211> LENGTH: 36
<212> TYPE: DNA
<213> ORGANISM: Artificial sequence
<220> FEATURE:
<223> OTHER INFORMATION: Primer

<400> SEQUENCE: 16
actatattaa ctttcctaat aattcttgct ttccca                               36

<210> SEQ ID NO 17
<211> LENGTH: 22
<212> TYPE: DNA
<213> ORGANISM: Artificial sequence
<220> FEATURE:
<223> OTHER INFORMATION: Probe

<400> SEQUENCE: 17
tgctgttaat gattaataac at                                              22

<210> SEQ ID NO 18
<211> LENGTH: 20
<212> TYPE: DNA
<213> ORGANISM: Artificial sequence
<220> FEATURE:
<223> OTHER INFORMATION: Probe

<400> SEQUENCE: 18
```

```
ctgttaatga ttaaaaacat                                                    20
```

<210> SEQ ID NO 19
<211> LENGTH: 206
<212> TYPE: DNA
<213> ORGANISM: Capsicum annuum
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (88)..(91)
<223> OTHER INFORMATION: n is a, c, g, or t

<400> SEQUENCE: 19

```
agccacaatc cgataccaag tctgtatttg gaagcacngn ctaattgtta tggttaccaa        60
acactttgaa ttggctggat aataacannn nggaaattta tgttwttaat cattaacagc       120
aaattgggaa agcaagaatt attaggaaag ttaatatagt gtcttggtta ttctaatgga       180
gtgggttatg caaattaagt tccctt                                            206
```

<210> SEQ ID NO 20
<211> LENGTH: 206
<212> TYPE: DNA
<213> ORGANISM: Capsicum annuum
<220> FEATURE:
<221> NAME/KEY: misc_feature
<222> LOCATION: (38)..(38)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (88)..(91)
<223> OTHER INFORMATION: n is a, c, g, or t

<400> SEQUENCE: 20

```
agccacaatc cgataccaag tctgtatttg gaagcacngn ctaattgtta tggttaccaa        60
acactttgaa ttggctggat aataacannn nggaaattta tgttwttaat cattaacagc       120
aaattgggaa agcaagaatt attaggaaag ttaatatagt gtcttggtta ttctaatgga       180
gtgggttatg caaattaagt tccctt                                            206
```

<210> SEQ ID NO 21
<211> LENGTH: 5105
<212> TYPE: DNA
<213> ORGANISM: Capsicum annuum
<220> FEATURE:
<221> NAME/KEY: misc_feature
<222> LOCATION: (4775)..(4775)
<223> OTHER INFORMATION: A may be either A or a deletion

<400> SEQUENCE: 21

```
tgttgaatgg aaaatattgg aagaatttca tttcatttta caaaaataaa gagtgtagag        60
ggtattttg taaatcaata ttttttctat aaaaaatata taagaaatat tattttaata       120
catcaaatca aatactgtat aagaaataat gttaacataa ttaatgcaag tatagctaat       180
accaacatta ctaatgcaag tattactaat acaccatatt ctatattaat cttatatact       240
ctaccaaacg accctaagtg tgtatctata tcctccgaga atttggaatt tgcaaattcc       300
```

```
aagttttgta tctcccttc ccagaaatta agataattct ggtgctttta gcattagaaa       360
agtatttatt gggtagggaa atgtcatgac ttcacagcat taagcatcaa gggtataact       420
taatgaaata gtggtcaatg aattatattg agaatgacga ggtctctgtt ccaactttgg       480
tagactttgg aaatgctcgt ctggacgccg cccattcttt ctagtcttgg tgccattcta       540
tttggtctga gactggcatg atgccaaatt ctaacctttt cacaatgagc attcgaccta       600
ctcttctttt ttacgactct atttgaccta ctaggcattg gccaacttgg ctaaccactt       660
gaggaactag agttcggatt caatagaatc taataatttt aatcaaaaga cttcatgtat       720
attgaaaaat ctatttataa ctaactttaa atcggccttt acgtatcgac gtaatcaaaa       780
ttgtgtcagc ttgccacgtg gggtctagta tgagtttgaa attggtcata ggggccccaa       840
ttccactaat acagctgccg tccatgcact acaagacaaa tacaccacta tgtttgttag       900
tgcttggtaa atgtaaaaca aactttgat gagaatctat tcgtggcatc gaagtgctgc        960
aaattggctt ttacctctgc tacttcaagc ctcactgatt ttcaccccaa ctttctcatt      1020 tcccttcaa ggatttgatt ttccagttgg gcatgttaaa acaacaatt ttcctcaaaa        1080 ctgtagaaat gatttytcat attttaatca gtcaaattat ttaaacaaga agttgatttt      1140
tttttaattt ttttttttac aaaaaaattt caaatgtcaa gtaagatttt tcaaattgaa      1200
actgaataag ctgcgacttt agaaacaaaa aactaagata agtaaaaata ccaaaaagag      1260
tgaatcacat caattgaatt cttccaacag ttcgtttttt agtttctgtt ttgggaagag      1320
gagtactaca aggtaggacc tccaacaatc aacaatatct aagttgcaaa agttttgtg      1380 cgttttttag tttctgtttc gagaagagga atactacaag ttcgtttttt agtttctgtt      1440
ttgggaagag gagtactgca aggtaggacc tccaacaatt atcaatatct aaattgcaaa      1500
aatttcagtt cgttttttagt ttctgtttcg ggaagaggaa tactacaagt tcgttttta       1560 gtttctatt tgggaagagg agtactacaa ggtaggacct ccaataccta aattgcaaaa       1620
atttcagttc gttttttagt ttcagtttag ggaagaggaa tactacaagg taggacctcc      1680
aacaatcatc agtacctaaa ttgcaaaaat ttcagttcgt ttttagttt atgtttggga       1740 agaagaatac tacaaggcag tggcggagct accttatgat taggggttc atccgaacct      1800 ccttcgacgg aaattatac tatttttata agtgaaatt attttttatg tatatataat       1860
tgatgttgaa ccccttcgg ttagttcatg tatctatatt tttttatttt gaaccccgat       1920
gaaaattttg gctccgccac tgctacaagg taggacctcc aacaatcacc aatacctaaa      1980 ttgcaaaat tcagtttgt tttttagttt ctgtttggg aagaggaata ctacaaggta        2040
ggacctccaa caatcaccaa tacctaaatt gcaacgtttt tttagtttct gttttgggaa      2100
gaggaatact acatggtagg gcctccaaca atcaccaata cctaaattgc aaaaatttca      2160
gttcgtattt tcgtttctat tttgggaagt ggaatagtat aaggtaggac ctccaacaat      2220
caccaatacc taaattaaag ttccgattca tttttagtt tctgttttgg aaagagaaat      2280
actacaaggt agggcctaca acaatcacca gtacctaaat tgtaaaaatt tcagttcgtt      2340
ttttagtttc tattttgaga agaggaatgc tacaaggtag ggcctacaac aatcaccagt      2400
acctaaattg taaaaatttc agttcgtttt ttagttctg ttttgggaag aggaatacta      2460
caaggtaggg ccttcaacaa tcagcaatac ctaaattaca aaaatttcaa ttcgtttttt      2520
agtttctgtt ttgggaagag gaatactaca aggcagtggc ggagctacct tatgattagg      2580
ggttcatccg aacctccttc gacggaaaat tatactattt ttatatagta aaaattattt      2640
```

```
tttatgtata tataattgat gttgaacccc cttcggttag tttgtgtatc tatatttttt    2700
tattttgaac ctccttgata aaaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctatttttgg gaagtggaat    3000 agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttcttttttt    3240
agtttctgtt ttggaaagag aaatactaca agataggacc ttcaacaatc accaatacct    3300
aaattgcaaa aacttcagtt cattttttag tttctgtttt gggaagaaga atacttcaag    3360
gtaacaatca ccaatacctaa aawwaaattt cagttagttt tttagtttct gttttggga    3420 agaggaatac tttcttttgc tatataaagc caaagtaggt acctataagc atcaatattt    3480
tgtattgctt agtgattccc ctagttcggt atttcatttt ttttcactat actatatcac    3540
ctcctctcat aaatagccat tataaatctt gcattttctc taatggaaac ccttctaaag    3600
ccttttccat ctcctttact ttccattcct actcctaaca tgtatagttt caaacacaac    3660
tccacttttc caaatccaac caaacaaaaa gattcaagaa agttccatta tagaaacaaa    3720
agcagtacac atttttgtag ctttcttgat ttagcaccca catcaaagcc agagtcttta    3780
gatgttaaca tctcatgggt tgatactgat ctggacgggg ctgaattcga cgtgatcatc    3840 attgaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
tatgacaagc caagaaacca tggttatcaa gttgctcatg ggattttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtacctt    4980
tttggacatg cctctaattt ggctaggttg gatattgtta caaagtgcac tgtccccttg    5040
```

```
gttaaactgc tgggcaatct agcaatagag agcctttgaa ttaatatgat agttttgaag    5100
cactg                                                                5105
```

<210> SEQ ID NO 22
<211> LENGTH: 678
<212> TYPE: DNA
<213> ORGANISM: Capsicum annuum

<400> SEQUENCE: 22

```
tgttgaatgg aaaatattgg aagaatttca tttcatttta caaaaataaa gagtgtagag      60 ggtattttg taaatcaata ttttttctat aaaaaatata taagaaatat tattttaata     120
catcaaatca aatactgtat aagaaataat gttaacataa ttaatgcaag tatagctaat     180
accaacatta ctaatgcaag tattactaat acaccatatt ctatattaat cttatatact     240
ctaccaaacg accctaagtg tgtatctata tcctccgaga atttggaatt tgcaaattcc     300 aagtttgta tctcccttc ccagaaatta agataattct ggtgctttta gagtttggaa     360
tggtttgtgg ccttcggata aagacgtgt tagagaatgt tattgtttcg aatggagac     420 tttgttgaag cttgatttgg aaggtactag gagattgttt gatgctttct ttgatgttga     480
tcccaagtac tggcacgggt tcctttcttc aagattgtct gtcaaagaac ttgctgtact     540
cagtttgtac cttttggac atgcctctaa tttggctagg ttggatattg ttacaaagtg     600
cactgtcccc ttggttaaac tgctgggcaa tctagcaata gagagccttt gaattaatat     660
gatagttttg aagcactg                                                  678
```

<210> SEQ ID NO 23
<211> LENGTH: 1000
<212> TYPE: DNA
<213> ORGANISM: Capsicum annuum
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:

<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 23

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga    180
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ytttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnn nnncattgga caaaagtata gagccacaat cngataccaa     540
gtctgtattt ggaagcacng nctaattgtt atggttacca acactttga attggctgga    600
taataacann nnggaatttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata   840
tgttatttaa atgaaggact gaatgattat gaggatgcaa tgcataggtt taattaccag   900
ttatctgtaa attgtcttcn ttgccattat tttaaaagtt taatnnnaag tgtaacatct   960
acaaagagtt gataattaca aagcagctac tagttttttag                         1000
```

<210> SEQ ID NO 24
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 24

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga    180
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcatttt aatttcttag gttattttca    360
tcttttmtca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacng nctaattgtt atggttacca aacactttga attggctgga    600
taataacann nnggaantttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                        1000
```

<210> SEQ ID NO 25
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (503)..(503)
<223> OTHER INFORMATION: G is either G or a deletion
<220> FEATURE:
<221> NAME/KEY: misc_feature
<222> LOCATION: (532)..(532)

```
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 25
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt acctttttgg acatgcctct aatttggcta ggttggatat     240
tgttacaaag tgcactgtcc ccttggttaa actgctgggc aatctagcaa tagagagcct     300
ttgaattaat atgatagttt tgaagcactg nttttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgt atggttgtcg atgcattgga caaaagtata gagccacaat cngataccaa     540
gtctgtattt ggaagcacng nctaattgtt atggttacca aacactttga attggctgga     600
taataacann nnggaanttt atgttattaa tcattaacag caaattggga aagcaagaat     660
tattaggaaa gttaatatag tgtcttggtt attctaatgg agtgggttat gcaaattaag     720
ttcccttntc aaagtttggt ttatgaactg ctccactcnt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
ttatctgtaa attgtcttcn ttgccattat tttaaaagtt taatnnnaag tgtaacatct     960
acaaagagtt gataattaca aagcagctac tagtttttag                          1000

<210> SEQ ID NO 26
<211> LENGTH: 986
<212> TYPE: DNA
<213> ORGANISM: Capsicum annuum
```

```
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (518)..(518)
<223> OTHER INFORMATION: n is a, c, g, or t
<220> FEATURE:
<221> NAME/KEY: misc_feature
<222> LOCATION: (545)..(545)
<223> OTHER INFORMATION: n is a, c, g, or t
<220> FEATURE:
<221> NAME/KEY: misc_feature
<222> LOCATION: (547)..(547)
<223> OTHER INFORMATION: n is a, c, g, or t
<220> FEATURE:
<221> NAME/KEY: misc_feature
<222> LOCATION: (595)..(598)
<223> OTHER INFORMATION: n is a, c, g, or t
<220> FEATURE:
<221> NAME/KEY: misc_feature
<222> LOCATION: (603)..(603)
<223> OTHER INFORMATION: n is a, c, g, or t
<220> FEATURE:
<221> NAME/KEY: misc_feature
<222> LOCATION: (714)..(714)
<223> OTHER INFORMATION: n is a, c, g, or t
<220> FEATURE:
<221> NAME/KEY: misc_feature
<222> LOCATION: (745)..(745)
<223> OTHER INFORMATION: n is a, c, g, or t
<220> FEATURE:
<221> NAME/KEY: misc_feature
<222> LOCATION: (790)..(790)
<223> OTHER INFORMATION: n is a, c, g, or t
<220> FEATURE:
<221> NAME/KEY: misc_feature
<222> LOCATION: (906)..(906)
<223> OTHER INFORMATION: n is a, c, g, or t
<220> FEATURE:
<221> NAME/KEY: misc_feature
<222> LOCATION: (931)..(933)
<223> OTHER INFORMATION: n is a, c, g, or t

<400> SEQUENCE: 26
tagagtttgg aatggtttgt ggccttcgga tagaagacgt gttagagaat gttattgttt    60
cggaatggag actttgttga agcttgattt ggaaggtact aggagattgt ttgatgcttt   120
ctttgatgtt gatcccaagt actggcacgg gttcctttct tcaagattgt ctgtcaaaga   180
acttgctgta ctcagtttgt accttttlgg acatgcctct aatttggcta ggttggatat   240
tgttacaaag tgcactgtcc ccttggttaa actgctgggc aatctagcaa tagagagcct   300
ttgaattaat atgatagttt tgaagcactg ntttcatttt aatttcttag gttattttca   360
tcttttntca atgcaaaagt gaaacaaaag ctatacacat tgtcatcgtt gttcaaactc   420
agacaagttt gcctagctct atgtatttat ccttaacata tgtattcatc aaattcgaaa   480
tatacaatgc attggacaaa agtatagagc cacaatcnga taccaagtct gtatttggaa   540
gcacngncta attgttatgg ttaccaaaca ctttgaattg gctggataat aacannnngg   600
aantttatgt tattaatcat taacagcaaa ttgggaaagc aagaattatt aggaaagtta   660
atatagtgtc ttggttattc taatggagtg ggttatgcaa attaagttcc cttntcaaag   720
tttggtttat gaactgctcc actcntgtcc ctcttaaaag ccttaatccc aacatgtacc   780
accaaagaan tgagctgctc catcagatcc tttgagaatg ttaatatgtt atttaaatga   840
```

```
aggactgaat gattatgagg atgcaatgca taggtttaat taccagttat ctgtaaattg    900
tcttcnttgc cattatttta aaagtttaat nnnaagtgta acatctacaa agagttgata    960
attacaaagc agctactagt ttttag                                         986
```

```
<210> SEQ ID NO 27
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 27
```

```
tagagtttgg aatggtttgt ggccttcgga tagaagacgt gttagagaat gttattgttt     60
cggaatggag actttgttga agcttgattt ggaaggtact aggagattgt ttgatgcttt    120
ctttgatgtt gatcccaagt actggcacgg gttccttcct tcaagattgt ctgtcaaaga   180
acttgctgta ctcagtttgt accttttggg acatgcctct aatttggcta ggttggatat    240
tgttacaaag tgcactgtcc ccttggttaa actgctgggc aatctagcaa tagagagcct   300
ttgaattaat atgatagttt tgaagcactg ntttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa   480
tatacaatgn nnnnnnnnnn nncattggaa caaaagtata gagccacaat cygataccaa    540
```

-continued

```
gtctgtattt ggaagcacng nctaattgtt atggttacca aacactttga attggctgga      600
taataacann nnggaantt atgttattaa tcattaacag caaattggga aagcaagaat      660
tattaggaaa gttaatatag tgtcttggtt attctaatgg agtgggttat gcaaattaag     720
ttcccttntc aaagtttggt ttatgaactg ctccactcnt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
ttatctgtaa attgtcttcn ttgccattat tttaaaagtt taatnnnaag tgtaacatct     960
acaaagagtt gataattaca aagcagctac tagtttttag                          1000
```

<210> SEQ ID NO 28
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 28

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga    180
```

```
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacwg nctaattgtt atggttacca aacactttga attggctgga    600
taataacann nnggaanttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                         1000

<210> SEQ ID NO 29
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
```

```
<222> LOCATION: (945)..(947)
<223> OTHER INFORMATION: n is a, c, g, or t

<400> SEQUENCE: 29
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt acctttttgg acatgcctct aatttggcta ggttggatat     240
tgttacaaag tgcactgtcc ccttggttaa actgctgggc aatctagcaa tagagagcct     300
ttgaattaat atgatagttt tgaagcactg ntttcatttt aatttcttag gttattttca     360
tctttntca atgcaaaagt gaaacaaaag ctatacacat tgtcatcgtt gttcaaactc       420
agacaagttt gcctagctct atgtatttat ccttaacata tgtattcatc aaattcgaaa     480
tatacaatgn nnnnnnnnn nnncattgga caaaagtata gagccacaat cngataccaa      540
gtctgtattt ggaagcacng kctaattgtt atggttacca aacactttga attggctgga    600
taataacann nnggaantt atgttattaa tcattaacag caaattggga aagcaagaat      660
tattaggaaa gttaatatag tgtcttggtt attctaatgg agtgggttat gcaaattaag     720
ttcccttntc aaagtttggt ttatgaactg ctccactcnt gtccctctta aaagccttaa     780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagttttag                            1000

<210> SEQ ID NO 30
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (612)..(612)
<223> OTHER INFORMATION: A may be either A or a deletion
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
```

```
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 30
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt accttttggg acatgcctct aatttggcta ggttggatat     240
tgttacaaag tgcactgtcc ccttggtaa actgctgggc aatctagcaa tagagagcct     300
ttgaattaat atgatagttt tgaagcactg nttttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnn nnncattgga caaaagtata gagccacaat cngataccaa     540
gtctgtattt ggaagcacng nctaattgtt atggttacca aacactttga attggctgga     600
taataacaaa caggaantt tatgttattaa tcattaacag caaattggga aagcaagaat     660
tattaggaaa gttaatatag tgtcttggtt attctaatgg agtgggttat gcaaattaag     720 ttccctntc aaagttggt ttatgaactg ctccactcnt gtccctctta aaagccttaa     780
tcccaacatg taccaccaaa gaantgagct gctccatcag atcctttgag aatgttaata     840 tgttattaa atgaaggact gaatgattat gaggatgcaa tgcataggtt taattaccag     900
ttatctgtaa attgtcttcn ttgccattat tttaaaagtt taatnnnaag tgtaacatct     960
acaaagagtt gataattaca aagcagctac tagtttttag                            1000

<210> SEQ ID NO 31
<211> LENGTH: 996
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
```

<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (613)..(613)
<223> OTHER INFORMATION: n is a, c, g, or t
<220> FEATURE:
<221> NAME/KEY: misc_feature
<222> LOCATION: (724)..(724)
<223> OTHER INFORMATION: n is a, c, g, or t
<220> FEATURE:
<221> NAME/KEY: misc_feature
<222> LOCATION: (755)..(755)
<223> OTHER INFORMATION: n is a, c, g, or t
<220> FEATURE:
<221> NAME/KEY: misc_feature
<222> LOCATION: (800)..(800)
<223> OTHER INFORMATION: n is a, c, g, or t
<220> FEATURE:
<221> NAME/KEY: misc_feature
<222> LOCATION: (916)..(916)
<223> OTHER INFORMATION: n is a, c, g, or t
<220> FEATURE:
<221> NAME/KEY: misc_feature
<222> LOCATION: (941)..(943)
<223> OTHER INFORMATION: n is a, c, g, or t

<400> SEQUENCE: 31

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt accttttttgg acatgcctct aatttggcta ggttggatat    240
tgttacaaag tgcactgtcc ccttggttaa actgctgggc aatctagcaa tagagagcct     300
ttgaattaat atgatagttt tgaagcactg ntttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnnn nnncattgga caaaagtata gagccacaat cngataccaa     540
gtctgtattt ggaagcacng nctaattgtt atggttacca aacactttga attggctgga    600
taataacagg aantttatgt tattaatcat taacagcaaa ttgggaaagc aagaattatt    660
aggaaagtta atatagtgtc ttggttattc taatggagtg ggttatgcaa attaagttcc    720
cttntcaaag tttggtttat gaactgctcc actcntgtcc ctcttaaaag ccttaatccc    780
aacatgtacc accaaagaan tgagctgctc catcagatcc tttgagaatg ttaatatgtt    840
atttaaatga aggactgaat gattatgagg atgcaatgca taggtttaat taccagttat    900
ctgtaaattg tcttcnttgc cattattta aaagtttaat nnnaagtgta acatctacaa      960
agagttgata attacaaagc agctactagt ttttag                              996
```

<210> SEQ ID NO 32
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:

<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 32

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga    180
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg nttttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacng nctaattgtt atggttacca aacactttga attggctgga    600
taataacann nnggaamttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagttttttag                         1000
```

<210> SEQ ID NO 33
<211> LENGTH: 1000

```
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 33
tagagtttgg aatggtttgt ggccttcgga tagaagacgt gttagagaat gttattgttt     60
cggaatggag actttgttga agcttgattt ggaaggtact aggagattgt ttgatgcttt    120 cttttgatgtt gatcccaagt actggcacgg gttcctttct tcaagattgt ctgtcaaaga   180
acttgctgta ctcagtttgt accttttggg acatgcctct aatttggcta ggttggatat    240
tgttacaaag tgcactgtcc ccttggttaa actgctgggc aatctagcaa tagagagcct    300
ttgaattaat atgatagttt tgaagcactg nttcattttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacng nctaattgtt atggttacca acactttga attggctgga    600 taataacann nnggaatttt atgttattaa tcattaacag caaattggga aagcaagaat    660
tattaggaaa gttaatatag tgtcttggtt attctaatgg agtgggttat gcaaattaag    720
ttcccttrtc aaagtttggt ttatgaactg ctccactcnt gtccctctta aaagccttaa    780
```

```
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagttttag                         1000
```

<210> SEQ ID NO 34
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 34

```
tagagtttgg aatggtttgt ggccttcgga tagaagacgt gttagagaat gttattgttt     60
cggaatggag actttgttga agcttgattt ggaaggtact aggagattgt ttgatgcttt    120
ctttgatgtt gatcccaagt actggcacgg gttcctttct tcaagattgt ctgtcaaaga    180
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg ntttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
```

```
tatacaatgn nnnnnnnnnn nnncattgga caaaagtata gagccacaat cngataccaa    540
gtctgtattt ggaagcacng nctaattgtt atggttacca aacactttga attggctgga    600
taataacann nnggaanttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactckt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttcn ttgccattat tttaaaagtt taatnnnaag tgtaacatct    960
acaaagagtt gataattaca aagcagctac tagtttttag                          1000

<210> SEQ ID NO 35
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (945)..(947)
<223> OTHER INFORMATION: n is a, c, g, or t

<400> SEQUENCE: 35
tagagtttgg aatggtttgt ggccttcgga tagaagacgt gttagagaat gttattgttt     60
cggaatggag actttgttga agcttgattt ggaaggtact aggagattgt ttgatgcttt    120
```

```
ctttgatgtt gatcccaagt actggcacgg gttcctttct tcaagattgt ctgtcaaaga       180
acttgctgta ctcagtttgt accttttggg acatgcctct aatttggcta ggttggatat       240
tgttacaaag tgcactgtcc ccttggttaa actgctgggc aatctagcaa tagagagcct       300
ttgaattaat atgatagttt tgaagcactg ntttcatttt aatttcttag gttattttca       360
tcttttntca atgcaaaagt gaaacaaaag ctatacacat tgtcatcgtt gttcaaactc       420
agacaagttt gcctagctct atgtatttat ccttaacata tgtattcatc aaattcgaaa       480
tatacaatgn nnnnnnnnnn nnncattgga caaaagtata gagccacaat cngataccaa       540
gtctgtattt ggaagcacng nctaattgtt atggttacca acactttga attggctgga       600 taataacann nnggaanttt atgttattaa tcattaacag caaattggga aagcaagaat       660
tattaggaaa gttaatatag tgtcttggtt attctaatgg agtgggttat gcaaattaag       720
ttcccttntc aaagtttggt ttatgaactg ctccactcnt gtccctctta aaagccttaa       780
tcccaacatg taccaccaaa gaaytgagct gctccatcag atcctttgag aatgttaata       840
tgttatttaa atgaaggact gaatgattat gaggatgcaa tgcataggtt taattaccag       900
ttatctgtaa attgtcttcn ttgccattat tttaaaagtt taatnnnaag tgtaacatct       960
acaaagagtt gataattaca aagcagctac tagttttag                             1000

<210> SEQ ID NO 36
<211> LENGTH: 1000
<212> TYPE: DNA
<213> ORGANISM: Capsicum annum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
```

<220> FEATURE:
<221> NAME/KEY: misc_feature
<222> LOCATION: (945)..(947)
<223> OTHER INFORMATION: n is a, c, g, or t

<400> SEQUENCE: 36

```
tagagtttgg aatggtttgt ggccttcgga tagaagacgt gttagagaat gttattgttt     60
cggaatggag actttgttga agcttgattt ggaaggtact aggagattgt ttgatgcttt    120
ctttgatgtt gatcccaagt actggcacgg gttcctttct tcaagattgt ctgtcaaaga    180
acttgctgta ctcagtttgt acctttttgg acatgcctct aatttggcta ggttggatat    240
tgttacaaag tgcactgtcc ccttggttaa actgctgggc aatctagcaa tagagagcct    300
ttgaattaat atgatagttt tgaagcactg nttttcatttt aatttcttag gttattttca    360
tcttttntca atgcaaaagt gaaacaaaag ctatacacat tgtcatcgtt gttcaaactc    420
agacaagttt gcctagctct atgtatttat ccttaacata tgtattcatc aaattcgaaa    480
tatacaatgn nnnnnnnnnn nnncattgga caaaagtata gagccacaat cngataccaa    540
gtctgtattt ggaagcacng nctaattgtt atggttacca aacactttga attggctgga    600
taataacann nnggaanttt atgttattaa tcattaacag caaattggga aagcaagaat    660
tattaggaaa gttaatatag tgtcttggtt attctaatgg agtgggttat gcaaattaag    720
ttcccttntc aaagtttggt ttatgaactg ctccactcnt gtccctctta aaagccttaa    780
tcccaacatg taccaccaaa gaantgagct gctccatcag atcctttgag aatgttaata    840
tgttatttaa atgaaggact gaatgattat gaggatgcaa tgcataggtt taattaccag    900
ttatctgtaa attgtcttck ttgccattat tttaaaagtt taatnnnaag tgtaacatct    960
acaaagagtt gataattaca aagcagctac tagtttttag                         1000
```

<210> SEQ ID NO 37
<211> LENGTH: 1000
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:

```
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t
<220> FEATURE:
<221> NAME/KEY: misc_feature
<222> LOCATION: (947)..(947)
<223> OTHER INFORMATION: C may be either C or a deletion

<400> SEQUENCE: 37
tagagtttgg aatggtttgt ggccttcgga tagaagacgt gttagagaat gttattgttt    60
cggaatggag actttgttga agcttgattt ggaaggtact aggagattgt ttgatgcttt   120
ctttgatgtt gatcccaagt actggcacgg gttcctttct tcaagattgt ctgtcaaaga   180
acttgctgta ctcagtttgt accttttggg acatgcctct aatttggcta ggttggatat   240
tgttacaaag tgcactgtcc ccttggttaa actgctgggc aatctagcaa tagagagcct   300
ttgaattaat atgatagttt tgaagcactg nttttcatttt aatttcttag gttattttca   360
tcttttntca atgcaaaagt gaaacaaaag ctatacacat tgtcatcgtt gttcaaactc   420
agacaagttt gcctagctct atgtatttat ccttaacata tgtattcatc aaattcgaaa   480
tatacaatgn nnnnnnnnnn nnncattgga caaaagtata gagccacaat cngataccaa   540
gtctgtattt ggaagcacng nctaattgtt atggttacca aacactttga attggctgga   600
taataacann nnggaanttt atgttattaa tcattaacag caaattggga aagcaagaat   660
tattaggaaa gttaatatag tgtcttggtt attctaatgg agtgggttat gcaaattaag   720
ttcccttntc aaagtttggt ttatgaactg ctccactcnt gtccctctta aaagccttaa   780
tcccaacatg taccaccaaa gaantgagct gctccatcag atcctttgag aatgttaata   840
tgttatttaa atgaaggact gaatgattat gaggatgcaa tgcataggtt taattaccag   900
ttatctgtaa attgtcttcn ttgccattat tttaaaagtt taataacaag tgtaacatct   960
acaaagagtt gataattaca aagcagctac tagttttag                          1000

<210> SEQ ID NO 38
<211> LENGTH: 997
<212> TYPE: DNA
<213> ORGANISM: Capsicum annuum
<220> FEATURE:
<221> NAME/KEY: misc_feature
<222> LOCATION: (331)..(331)
<223> OTHER INFORMATION: n is a, c, g, or t
<220> FEATURE:
<221> NAME/KEY: misc_feature
<222> LOCATION: (367)..(367)
<223> OTHER INFORMATION: n is a, c, g, or t
<220> FEATURE:
<221> NAME/KEY: misc_feature
<222> LOCATION: (490)..(503)
<223> OTHER INFORMATION: n is a, c, g, or t
<220> FEATURE:
<221> NAME/KEY: misc_feature
<222> LOCATION: (532)..(532)
<223> OTHER INFORMATION: n is a, c, g, or t
<220> FEATURE:
<221> NAME/KEY: misc_feature
```

<222> LOCATION: (559)..(559)
<223> OTHER INFORMATION: n is a, c, g, or t
<220> FEATURE:
<221> NAME/KEY: misc_feature
<222> LOCATION: (561)..(561)
<223> OTHER INFORMATION: n is a, c, g, or t
<220> FEATURE:
<221> NAME/KEY: misc_feature
<222> LOCATION: (609)..(612)
<223> OTHER INFORMATION: n is a, c, g, or t
<220> FEATURE:
<221> NAME/KEY: misc_feature
<222> LOCATION: (617)..(617)
<223> OTHER INFORMATION: n is a, c, g, or t
<220> FEATURE:
<221> NAME/KEY: misc_feature
<222> LOCATION: (728)..(728)
<223> OTHER INFORMATION: n is a, c, g, or t
<220> FEATURE:
<221> NAME/KEY: misc_feature
<222> LOCATION: (759)..(759)
<223> OTHER INFORMATION: n is a, c, g, or t
<220> FEATURE:
<221> NAME/KEY: misc_feature
<222> LOCATION: (804)..(804)
<223> OTHER INFORMATION: n is a, c, g, or t
<220> FEATURE:
<221> NAME/KEY: misc_feature
<222> LOCATION: (920)..(920)
<223> OTHER INFORMATION: n is a, c, g, or t

<400> SEQUENCE: 38

```
tagagtttgg aatggtttgt ggccttcgga tagaagacgt gttagagaat gttattgttt      60
cggaatggag actttgttga agcttgattt ggaaggtact aggagattgt ttgatgcttt     120
ctttgatgtt gatcccaagt actggcacgg gttcctttct tcaagattgt ctgtcaaaga     180
acttgctgta ctcagtttgt acctttttgg acatgcctct aatttggcta ggttggatat     240
tgttacaaag tgcactgtcc ccttggttaa actgctgggc aatctagcaa tagagagcct     300
ttgaattaat atgatagttt tgaagcactg ntttcatttt aatttcttag gttattttca     360
tcttttntca atgcaaaagt gaaacaaaag ctatacacat tgtcatcgtt gttcaaactc     420
agacaagttt gcctagctct atgtatttat ccttaacata tgtattcatc aaattcgaaa     480
tatacaatgn nnnnnnnnn nnncattgga caaaagtata gagccacaat cngataccaa     540
gtctgtattt ggaagcacng nctaattgtt atggttacca aacactttga attggctgga     600
taataacann nnggaanttt atgttattaa tcattaacag caaattggga aagcaagaat     660
tattaggaaa gttaatatag tgtcttggtt attctaatgg agtgggttat gcaaattaag     720
ttcccttntc aaagtttggt ttatgaactg ctccactcnt gtccctctta aaagccttaa     780
tcccaacatg taccaccaaa gaantgagct gctccatcag atcctttgag aatgttaata     840
tgttatttaa atgaaggact gaatgattat gaggatgcaa tgcataggtt taattaccag     900
ttatctgtaa attgtcttcn ttgccattat tttaaaagtt taataagtgt aacatctaca     960
aagagttgat aattacaaag cagctactag tttttag                             997
```

<210> SEQ ID NO 39
<211> LENGTH: 14
<212> TYPE: DNA
<213> ORGANISM: Capsicum annuum

<400> SEQUENCE: 39

```
tatggttgtc gatg                                                        14
```

<210> SEQ ID NO 40

```
<211> LENGTH: 5736
<212> TYPE: DNA
<213> ORGANISM: Capsicum annuum

<400> SEQUENCE: 40
tgttgaatgg aaaatattgg aagaatttca tttcatttta caaaaataaa gagtgtagag      60 ggtattttg taaatcaata ttttttctat aaaaaatata taagaaatat tattttaata     120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctccctttc ccagaaatta agataattct ggtgctttta gcattagaaa    360
agtatttatt gggtagggaa atgtcatgac ttcacagcat taagcatcaa gggtataact    420
taatgaaata gtggtcaatg aattatattg agaatgacga ggtctctgtt ccaactttgg    480
tagactttgg aaatgctcgt ctggacgccg cccattcttt ctagtcttgg tgccattcta    540
tttggtctga gactggcatg atgccaaatt ctaacctttt cacaatgagc attcgaccta    600
ctcttctttt ttacgactct atttgaccta ctaggcattg ccaacttggg ctaaccactt    660
gaggaactag agttcggatt caatagaatc taataatttt aatcaaaaga cttcatgtat    720
attgaaaaat ctatttataa ctaactttaa atcggccttt acgtatcgac gtaatcaaaa    780
ttgtgtcagc ttgccacgtg gggtctagta tgagtttgaa attggtcata ggggccccaa    840
ttccactaat acagctgccg tccatgcact acaagacaaa tacaccacta tgtttgttag    900
tgcttggtaa atgtaaaaca aacttttgat gagaatctat tcgtggcatc gaagtgctgc    960
aaattggctt ttacctctgc tacttcaagc ctcactgatt tcaccccaa ctttctcatt    1020 tccctttcaa ggatttgatt ttccagttgg gcatgttaaa acaacaatt ttcctcaaaa    1080 ctgtagaaat gatttctcat attttaatca gtcaaattat ttaaacaaga agttgatttt    1140
tttttaattt ttttttttac aaaaaaattt caaatgtcaa gtaagatttt tcaaattgaa    1200
actgaataag ctgcgacttt agaaacaaaa aactaagata agtaaaaata ccaaaaagag    1260
tgaatcacat caattgaatt cttccaacag ttcgtttttt agtttctgtt ttgggaagag    1320
gagtactaca aggtaggacc tccaacaatc aacaatatct aagttgcaaa agttttgtg    1380 cgttttttag tttctgtttc gagaagagga atactacaag ttcgtttttt agtttctgtt    1440
ttgggaagag gagtactgca aggtaggacc tccaacaatt atcaatatct aaattgcaaa    1500
aatttcagtt cgttttttagt ttctgtttcg ggaagaggaa tactacaagt tcgttttta    1560 gtttctattt tgggaagagg agtactacaa ggtaggacct ccaataccta aattgcaaaa    1620
atttcagttc gttttttagt ttcagtttag ggaagaggaa tactacaagg taggacctcc    1680
aacaatcatc agtacctaaa ttgcaaaaat ttcagttcgt tttttagttt atgtttggga    1740
agaagaatac tacaaggcag tggcggagct accttatgat tagggggttc atccgaacct    1800
ccttcgacgg aaaattatac tatttttata agtgaaaatt atttttatg tatatataat    1860 tgatgttgaa cccccttcgg ttagttcatg tatctatatt tttttatttt gaaccccgat    1920
gaaaattttg gctccgccac tgctacaagg taggacctcc aacaatcacc aatacctaaa    1980
ttgcaaaaat ttcagtttgt tttttagttt ctgttttggg aagaggaata ctacaaggta    2040
ggacctccaa caatcaccaa tacctaaatt gcaacgtttt tttagtttct gttttgggaa    2100
gaggaatact acatgtgtagg gcctccaaca atcaccaata cctaaattgc aaaaatttca    2160 gttcgtatttt tcgtttctat tttgggaagt ggaatagtat aaggtaggac ctccaacaat    2220
```

```
caccaatacc taaattaaag ttccgattca ttttttagtt tctgttttgg aaagagaaat    2280
actacaaggt agggcctaca acaatcacca gtacctaaat tgtaaaaatt tcagttcgtt    2340
ttttagtttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacggaaaat tatactatttt ttatatagta aaaattattt    2640
tttatgtata tataattgat gttgaaccccc cttcggttag tttgtgtatc tatattttttt    2700 tattttgaac ctccttgata aaaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctattttgg gaagtggaat    3000
agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttcttttttt    3240
agtttctgtt ttgggaagag aaatactaca agataggacc ttcaacaatc accaatacct    3300
aaattgcaaa aacttcagtt catttttttag tttctgtttt gggaagaaga atacttcaag    3360
gtaacaatca ccaatacctaa attaaatttt cagttagttt tttagtttct gttttttggga    3420 agaggaatac tttcttttgc tatataaagc caaagtaggt acctataagc atcaatattt    3480
tgtattgctt agtgattccc ctagttcggt atttcatttt ttttcactat actatatcac    3540
ctcctctcat aaatagccat tataaatctt gcattttctc taatgaaaac ccttctaaag    3600 cctttttccat ctcctttact ttccattcct actcctaaca tgtatagttt caaacacaac    3660 tccactttttc caaatccaac caaacaaaaa gattcaagaa agttccatta tagaaacaaa    3720
agcagtacac attttttgtag ctttcttgat ttagcaccca catcaaagcc agagtcttta    3780
gatgttaaca tctcatgggt tgatactgat ctggacgggg ctgaattcga cgtgatcatc    3840
attggaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
tatgacaagc caagaaacca tggttatcaa gttgctcatg ggattttagc agaagttgat    4320
aatcatccat ttgatttgga taaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttggggat caaagtgaga    4560
```

-continued

```
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtacctt    4980
tttggacatg cctctaattt ggctaggttg gatattgtta caagtgcac tgtccccttg    5040
gttaaactgc tgggcaatct agcaatagag agcctttgaa ttaatatgat agttttgaag    5100
cactgttttc atttaatttt cttaggttat tttcatcttt tctcaatgca aaagtgaaac    5160
aaaagctata cacattgtca tcgttgttca aactcagaca agtttgccta gctctatgta    5220
tttatcctta acatatgtat tcatcaaatt cgaaatatac aatgcattgg acaaaagtat    5280
agagccacaa tccgatacca agtctgtatt tggaagcact gtctaattgt tatgttacc    5340
aaacactttg aattggctgg ataataacaa acaggaaatt tatgttttta atcattaaca    5400
gcaaattggg aaagcaagaa ttattaggaa agttaatata gtgtcttggt tattctaatg    5460
gagtgggtta tgcaaattaa gttcccttat caaagtttgg tttatgaact gctccactct    5520
tgtccctctt aaaagcctta atcccaacat gtaccaccaa agaattgagc tgctccatca    5580
gatcctttga gaatgttaat atgttattta aatgaaggac tgaatgatta tgaggatgca    5640
atgcataggt ttaattacca gttatctgta aattgtcttc tttgccatta tttttaaagt    5700
ttaataacaa gtgtaacatc tacaaagagt tgataa                              5736
```

```
<210> SEQ ID NO 41
<211> LENGTH: 5736
<212> TYPE: DNA
<213> ORGANISM: Capsicum annuum
<400> SEQUENCE: 41
tgttgaatgg aaatattggg aagaatttca tttcatttta caaaaataaa gagtgtagag      60
ggtattttg taaatcaata ttttttctat aaaaaatata taagaaatat tattttaata     120
catcaaatca aatactgtat aagaaataat gttaacataa ttaatgcaag tatagctaat     180
accaacatta ctaatgcaag tattactaat acaccatatt ctatattaat cttatatact     240
ctaccaaacg accctaagtg tgtatctata tcctccgaga atttggaatt tgcaaattcc     300
aagttttgta tctccctttc ccagaaatta agataattct ggtgctttta gcattagaaa     360
agtatttatt gggtagggaa atgtcatgac ttcacagcat taagcatcaa gggtataact     420
taatgaaata gtggtcaatg aattatattg agaatgacga ggtctctgtt ccaactttgg     480
tagactttgg aaatgctcgt ctggacgccg cccattcttt ctagtcttgg tgccattcta     540
tttggtctga gactggcatg atgccaaatt ctaaccttt cacaatgagc attcgaccta     600
ctcttctttt ttacgactct atttgaccta ctaggcattg gccaacttgg ctaaccactt     660
gaggaactag agttcggatt caatagaatc taataatttt aatcaaaaga cttcatgtat     720
attgaaaaat ctatttataa ctaactttaa atcggccttt acgtatcgac gtaatcaaaa     780
ttgtgtcagc ttgccacgtg gggtctagta tgagtttgaa attggtcata ggggccccaa     840
ttccactaat acagctgccg tccatgcact acaagacaaa tacaccacta tgttgttag      900
tgcttggtaa atgtaaaaca aacttttgat gagaatctat tcgtggcatc gaagtgctgc    960
```

```
aaattggctt ttacctctgc tacttcaagc ctcactgatt ttcaccccaa ctttctcatt     1020
tccctttcaa ggatttgatt ttccagttgg gcatgttaaa aacaacaatt ttcctcaaaa     1080
ctgtagaaat gatttctcat atttaatca gtcaaattat ttaaacaaga agttgatttt      1140 ttttaattt tttttttac aaaaaaattt caaatgtcaa gtaagatttt tcaaattgaa       1200
actgaataag ctgcgacttt agaaacaaaa aactaagata agtaaaaata ccaaaaagag     1260
tgaatcacat caattgaatt cttccaacag ttcgttttt agtttctgtt ttgggaagag      1320
gagtactaca aggtaggacc tccaacaatc aacaatatct aagttgcaaa agttttgtg     1380 cgttttttag tttctgtttc gagaagagga atactacaag ttcgtttttt agtttctgtt    1440
ttgggaagag gagtactgca aggtaggacc tccaacaatt atcaatatct aaattgcaaa    1500
aatttcagtt cgttttagt ttctgtttcg ggaagaggaa tactacaagt tcgtttttta    1560 gtttctatttt tgggaagagg agtactacaa ggtaggacct ccaataccta aattgcaaaa   1620
atttcagttc gttttagt ttcagtttag ggaagaggaa tactacaagg taggacctcc     1680
aacaatcatc agtacctaaa ttgcaaaaat ttcagttcgt tttagtttt atgtttggga    1740 agaagaatac tacaaggcag tggcggagct accttatgat taggggttc atccgaacct    1800 ccttcgacgg aaaattatac tatttttata agtgaaaatt attttttatg tatatataat    1860
tgatgttgaa ccccttcgg ttagttcatg tatctatatt tttttatttt gaaccccgat     1920
gaaaattttg gctccgccac tgctacaagg taggacctcc aacaatcacc aatacctaaa   1980
ttgcaaaaat ttcagtttgt tttagttt ctgttttggg aagaggaata ctacaaggta    2040
ggacctccaa caatcaccaa tacctaaatt gcaacgtttt tttagtttct gttttgggaa   2100
gaggaatact acatggtagg gcctccaaca atcaccaata cctaaattgc aaaaatttca   2160 gttcgtatt tcgtttctat tttgggaagt ggaatagtat aaggtaggac ctccaacaat    2220
caccaatacc taaattaaag ttccgattca tttttagtt tctgtttttgg aaagagaaat   2280 actacaaggt agggcctaca acaatcacca gtacctaaat tgtaaaaatt tcagttcgtt   2340
ttttagtttc tattttgaga agaggaatgc tacaaggtag gcctacaac aatcaccagt    2400 acctaaattg taaaaatttc agttcgtttt tagtttctg ttttgggaag aggaatacta   2460
caaggtaggg ccttcaacaa tcagcaatac ctaaattaca aaaatttcaa ttcgtttttt   2520
agtttctgtt ttgggaagag gaatactaca aggcagtggc ggagctacct tatgattagg   2580
ggttcatccg aacctccttc gacggaaaat tatactattt ttatatagta aaaattattt   2640
tttatgtata taattgat gttgaaccc cttcggttag tttgtgtatc tatattttt    2700 tattttgaac ctccttgata aaaattttg actccgccat tgctacaagg tagaacctcc    2760
aacaatcacc aatacctaaa ttgcaaaaat ttcagttcgt tttttaattt ctgttttggg   2820
aagaggaata ctacaaggcc tccaacaatc accaatacct aaattgcaaa aatttcagtt   2880 tgtttttag tttctgtttt gggaagagga atactacaag gtaaggcctc caacaatcac   2940
caatacctaa attgcaaaaa tttcagttcg tattttcgtt tctattttgg gaagtggaat   3000
agtataaggt aggacctcca acaatcacca atacctaaat tgcaaaagtt ccgattcatt   3060
ttttagtttc tgttttggaa agagaaatac tacaaggtag ggtctccaac aatcaccagt   3120
acctaaattg taaaaatttc agttcgtttt ttagtttcta ttttgggaag tggaatagta   3180
taaggtagga cctccaacaa tcaccaatac ctaaattgca aaagttccga ttcttttttt   3240
agtttctgtt ttggaaagag aaatactaca agataggacc ttcaacaatc accaatacct   3300
```

```
aaattgcaaa aacttcagtt cattttttag tttctgtttt gggaagaaga atacttcaag    3360
gtaacaatca ccaataccta aattaaattt cagttagttt tttagtttct gttttggga    3420 agaggaatac tttcttttgc tatataaagc caaagtaggt acctataagc atcaatattt    3480
tgtattgctt agtgattccc ctagttcggt atttcatttt ttttcactat actatatcac    3540
ctcctctcat aaatagccat tataaatctt gcattttctc taatgaaaac ccttctaaag    3600 cctttccat ctcctttact ttccattcct actcctaaca tgtatagttt caaacacaac    3660 tccactttc caaatccaac caaacaaaaa gattcaagaa agttccatta tagaaacaaa    3720
agcagtacac attttgtag ctttcttgat ttagcaccca catcaaagcc agagtcttta    3780
gatgttaaca tctcatgggt tgatactgat ctggacgggg ctgaattcga cgtgatcatc    3840
attggaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
tatgacaagc caagaaacca tggttatcaa gttgctcatg ggattttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag atttgttgat gctttctttg atgttgatcc caagtactgg    4920
cacgggttcc tttcttcaag attgtctgtc aaagaacttg ctgtactcag tttgtacctt    4980
tttggacatg cctctaattt ggctaggttg gatattgtta caagtgcac tgtccccttg    5040 gttaaactgc tgggcaatct agcaatagag agcctttgaa ttaatatgat agttttgaag    5100
cactgttttc attttaattt cttaggttat tttcatcttt tctcaatgca aaagtgaaac    5160
aaaagctata cacattgtca tcgttgttca aactcagaca agtttgccta gctctatgta    5220
tttatcctta acatatgtat tcatcaaatt cgaaatatac aatgcattgg acaaaagtat    5280
agagccacaa tccgatacca agtctgtatt tggaagcact gtctaattgt tatggttacc    5340
aaacactttg aattggctgg ataataacaa acaggaaatt tatgttttta atcattaaca    5400
gcaaattggg aaagcaagaa ttattaggaa agttaatata gtgtcttggt tattctaatg    5460
gagtgggtta tgcaaattaa gttcccttat caaagtttgg tttatgaact gctccactct    5520
tgtccctctt aaaagcctta atcccaacat gtaccaccaa agaattgagc tgctccatca    5580
gatcctttga gaatgttaat atgttatta aatgaaggac tgaatgatta tgaggatgca    5640
atgcataggt ttaattacca gttatctgta aattgtcttc tttgccatta ttttaaaagt    5700
```

```
ttaataacaa gtgtaacatc tacaaagagt tgataa                                 5736
```

<210> SEQ ID NO 42
<211> LENGTH: 5736
<212> TYPE: DNA
<213> ORGANISM: Capsicum annuum

<400> SEQUENCE: 42

```
tgttgaatgg aaaatattgg aagaatttca tttcatttta caaaaataaa gagtgtagag     60
ggtattttg taaatcaata ttttttctat aaaaaatata taagaaatat tattttaata    120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctcccttc ccagaaatta agataattct ggtgcttta gcattagaaa     360
agtatttatt gggtagggaa atgtcatgac ttcacagcat taagcatcaa gggtataact    420
taatgaaata gtggtcaatg aattatattg agaatgacga ggtctctgtt ccaactttgg    480
tagactttgg aaatgctcgt ctggacgccg cccattcttt ctagtcttgg tgccattcta    540
tttggtctga actggcatg atgccaaatt ctaacctttt cacaatgagc attcgaccta    600
ctcttctttt ttacgactct atttgaccta ctaggcattg gccaacttgg ctaaccactt    660
gaggaactag agttcggatt caatagaatc taataatttt aatcaaaaga cttcatgtat    720
attgaaaaat ctatttataa ctaactttaa atcggccttt acgtatcgac gtaatcaaaa    780
ttgtgtcagc ttgccacgtg gggtctagta tgagtttgaa attggtcata ggggccccaa    840
ttccactaat acagctgccg tccatgcact acaagacaaa tacaccacta tgtttgttag    900
tgcttggtaa atgtaaaaca aacttttgat gagaatctat tcgtggcatc gaagtgctgc    960
aaattggctt ttacctctgc tacttcaagc ctcactgatt tcaccccaa ctttctcatt    1020
tccctttcaa ggatttgatt ttccagttgg gcatgttaaa acaacaatt ttcctcaaaa    1080
ctgtagaaat gatttctcat attttaatca gtcaaattat ttaaacaaga agttgatttt    1140
ttttaatt ttttttttac aaaaaaattt caaatgtcaa gtaagatttt tcaaattgaa     1200
actgaataag ctgcgacttt agaaacaaaa aactaagata agtaaaaata ccaaaaagag    1260
tgaatcacat caattgaatt cttccaacag ttcgtttttt agtttctgtt ttgggaagag    1320
gagtactaca aggtaggacc tccaacaatc aacaatatct aagttgcaaa gttttttgtg    1380
cgttttttag tttctgtttc gagaagagga atactacaag ttcgtttttt agtttctgtt    1440
ttgggaagag gagtactgca aggtaggacc tccaacaatt atcaatatct aaattgcaaa    1500
aatttcagtt cgttttttagt ttctgtttcg gaagaggaa tactacaagt tcgttttta    1560
gtttctatt tgggaagagg agtactacaa ggtaggacct ccaataccta aattgcaaaa    1620
atttcagttc gttttttagt ttcagtttag ggaagaggaa tactacaagg taggacctcc    1680
aacaatcatc agtacctaaa ttgcaaaaat ttcagttcgt tttttagttt atgtttggga    1740
agaagaatac tacaaggcag tggcggagct acctatgat taggggttc atccgaacct     1800
ccttcgacgg aaaattatac tatttttata agtgaaaatt attttttatg tatatataat    1860
tgatgttgaa ccccctcgg ttagttcatg tatctatatt tttttatttt gaaccccgat     1920
gaaaattttg gctccgccac tgctacaagg taggacctcc aacaatcacc aatacctaaa    1980
ttgcaaaaat ttcagtttgt ttttagtttt ctgtttggg aagaggaata ctacaaggta    2040
```

```
ggacctccaa caatcaccaa tacctaaatt gcaacgtttt tttagtttct gttttgggaa    2100
gaggaatact acatggtagg gcctccaaca atcaccaata cctaaattgc aaaaatttca    2160
gttcgtattt tcgtttctat tttgggaagt ggaatagtat aaggtaggac ctccaacaat    2220
caccaatacc taaattaaag ttccgattca ttttttagtt tctgttttgg aaagagaaat    2280
actacaaggt agggcctaca acaatcacca gtacctaaat tgtaaaaatt tcagttcgtt    2340
ttttagtttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacggaaaat tatactattt ttatatagta aaaattattt    2640
tttatgtata tataattgat gttgaacccc cttcggttag tttgtgtatc tatattttt    2700 tattttgaac ctccttgata aaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctattttgg gaagtggaat    3000
agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttctttttt    3240 agtttctgtt ttggaaagag aaatactaca agataggacc ttcaacaatc accaatacct    3300
aaattgcaaa aacttcagtt cattttttag tttctgtttt gggaagaaga atacttcaag    3360
gtaacaatca ccaatacctA aattaaattt cagttagttt tttagtttct gttttggga    3420 agaggaatac tttcttttgc tatataaagc caaagtaggt acctataagc atcaatattt    3480
tgtattgctt agtgattccc ctagttcggt atttcatttt ttttcactat actatatcac    3540
ctcctctcat aaatagccat tataaatctt gcattttctc taatggaaac ccttctaaag    3600
ccttttccat ctcctttact ttccattcct actcctaaca tgtatagttt caaacacaac    3660 tccactttc caaatccaac caaacaaaaa gattcaagaa agttccatta tagaaacaaa    3720
agcagtacac atttttgtag ctttcttgat ttagcaccca catcaaagcc agagtcttta    3780
gatgttaaca tctcatgggt tgatactgat ctggacgggg ctgaattcga cgtgatcatc    3840
attggaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
tatgacaagc caagaaacca tggttatcaa gttgctcatg ggattttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
```

```
tttgatagga atttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtacctt    4980
tttggacatg cctctaattt ggctaggttg gatattgtta caagtgcac tgtccccttg     5040 gttaaactgc tgggcaatct agcaatagag agcctttgaa ttaatatgat agttttgaag    5100
cactgttttc atttaatttt cttaggttat tttcatcttt tctcaatgca aaagtgaaac    5160
aaaagctata cacattgtca tcgttgttca aactcagaca agtttgccta gctctatgta    5220
tttatcctta acatatgtat tcatcaaatt cgaaatatac aatgcattgg acaaaagtat    5280
agagccacaa tccgatacca agtctgtatt tggaagcact gtctaattgt tatggttacc    5340
aaacactttg aattggctgg ataataacaa acaggaaatt tatgttttta atcattaaca    5400
gcaaattggg aaagcaagaa ttattaggaa agttaatata gtgtcttggt tattctaatg    5460
gagtgggtta tgcaaattaa gttcccttat caaagtttgg tttatgaact gctccactct    5520
tgtccctctt aaaagcctta atcccaacat gtaccaccaa agaattgagc tgctccatca    5580
gatcctttga gaatgttaat atgttattta aatgaaggac tgaatgatta tgaggatgca    5640
atgcataggt ttaattacca gttatctgta aattgtcttc tttgccatta ttttaaaagt    5700
ttaataacaa gtgtaacatc tacaaagagt tgataa                              5736
```

<210> SEQ ID NO 43
<211> LENGTH: 5736
<212> TYPE: DNA
<213> ORGANISM: Capsicum annuum

<400> SEQUENCE: 43

```
tgttgaatgg aaatattgg aagaatttca tttcatttta caaaaataaa gagtgtagag      60 ggtattttg taaatcaata tttttctat aaaaaatata aagaaatat tattttaata       120 catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctccctttc ccagaaatta agataattct ggtgctttta gcattagaaa    360
agtatttatt gggtagggaa atgtcatgac ttcacagcat taagcatcaa gggtataact    420
taatgaaata gtggtcaatg aattatattg agaatgacga ggtctctgtt ccaactttgg    480
tagactttgg aaatgctcgt ctggacgccg cccattcttt ctagtcttgg tgccattcta    540
tttggtctga gactggcatg atgccaaatt ctaaccttttt cacaatgagc attcgaccta    600
ctcttctttt ttacgactct atttgaccta ctaggcattg gccaacttgg ctaaccactt    660
gaggaactag agttcggatt caatagaatc taataatttt aatcaaaaga cttcatgtat    720
attgaaaaat ctatttataa ctaactttaa atcggccttt acgtatcgac gtaatcaaaa    780
```

```
ttgtgtcagc ttgccacgtg gggtctagta tgagtttgaa attggtcata ggggcccaa      840 ttccactaat acagctgccg tccatgcact acaagacaaa tacaccacta tgtttgttag      900
tgcttggtaa atgtaaaaca aacttttgat gagaatctat tcgtggcatc gaagtgctgc      960
aaattggctt ttacctctgc tacttcaagc ctcactgatt ttcacccccaa ctttctcatt    1020 tccctttcaa ggatttgatt ttccagttgg gcatgttaaa aacaacaatt ttcctcaaaa    1080
ctgtagaaat gatttctcat attttaatca gtcaaattat ttaaacaaga agttgatttt    1140 ttttaattt tttttttttac aaaaaaattt caaatgtcaa gtaagatttt tcaaattgaa    1200
actgaataag ctgcgacttt agaaacaaaa aactaagata agtaaaaata ccaaaaagag    1260
tgaatcacat caattgaatt cttccaacag ttcgtttttt agtttctgtt ttgggaagag    1320
gagtactaca aggtaggacc tccaacaatc aacaatatct aagttgcaaa agttttttgtg   1380 cgttttttag tttctgtttc gagaagagga atactacaag ttcgtttttt agtttctgtt    1440
ttgggaagag gagtactgca aggtaggacc tccaacaatt atcaatatct aaattgcaaa    1500
aatttcagtt cgtttttagt ttctgtttcg ggaagaggaa tactacaagt tcgttttta    1560 gtttctattt tgggaagagg agtactacaa ggtaggacct ccaataccta aattgcaaaa    1620
atttcagttc gttttttagt ttcagtttag ggaagaggaa tactacaagg taggacctcc    1680
aacaatcatc agtacctaaa ttgcaaaaat ttcagttcgt ttttttagttt atgtttggga    1740 agaagaatac tacaaggcag tggcggagct accttatgat tagggggttc atccgaacct    1800
ccttcgacgg aaaattatac tattttttata agtgaaaatt attttttttatg tatatataat  1860 tgatgttgaa ccccccttcgg ttagttcatg tatctatatt tttttattttt gaaccccgat    1920 gaaaattttg gctccgccac tgctacaagg taggacctcc aacaatcacc aatacctaaa    1980
ttgcaaaaat ttcagtttgt ttttttagttttt ctgttttggg aagaggaata ctacaaggta  2040
ggacctccaa caatcaccaa tacctaaatt gcaacgtttt tttagtttct gttttgggaa    2100
gaggaatact acatggtagg gcctccaaca atcaccaata cctaaattgc aaaaatttca    2160 gttcgtatttt tcgtttctat tttgggaagt ggaatagtat aaggtaggac ctccaacaat   2220
caccaatacc taaattaaag ttccgattca tttttttagtt tctgttttgg aaagagaaat    2280
actacaaggt agggcctaca acaatcacca gtacctaaat tgtaaaaatt tcagttcgtt    2340
ttttagtttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgttttttt   2520 agtttctgtt ttgggaagag gaatactaca aggcagtggc ggagctacct tatgattagg    2580
ggttcatccg aacctccttc gacggaaaat tatactattt ttatatagta aaaattattt    2640
tttatgtata tataattgat gttgaacccc cttcggttag tttgtgtatc tatattttttt   2700 tattttgaac ctccttgata aaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880
tgttttttag tttctgtttt gggaagagga atactacaag gtaaggcctc caacaatcac    2940
caatacctaa attgcaaaaa tttcagttcg tattttcgtt tctatttttgg gaagtggaat    3000 agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgttttt ttagtttcta ttttgggaag tggaatagta   3180
```

```
taaggtagga cctccaacaa tcaccaatac ctaaattgca aaagttccga ttctttttt   3240
agtttctgtt ttggaaagag aaatactaca agataggacc ttcaacaatc accaatacct   3300
aaattgcaaa aacttcagtt cattttttag tttctgtttt gggaagaaga atacttcaag   3360
gtaacaatca ccaataccta aattaaattt cagttagttt tttagtttct gttttttggga   3420
agaggaatac tttcttttgc tatataaagc caaagtaggt acctataagc atcaatattt   3480
tgtattgctt agtgattccc ctagttcggt atttcatttt ttttcactat actatatcac   3540
ctcctctcat aaatagccat tataaatctt gcattttctc taatggaaac ccttctaaag   3600
cctttttccat ctcctttact ttccattcct actcctaaca tgtatagttt caaacacaac   3660
tccacttttc caaatccaac caaacaaaaa gattcaagaa agttccatta tagaaacaaa   3720
agcagtacac attttgtag ctttcttgat ttagcaccca catcaaagcc agagtcttta   3780
gatgttaaca tctcatgggt tgatactgat ctggaccggg ctgaattcga cgtgatcatc   3840
attggaactg gccctgccgg gcttcggcta gctgaacaag tttctaaata tggtattaag   3900
gtatgttgcg ttgaccccttc accactttcc atgtggccaa ataattatgg tgtttgggtt   3960
gatgagtttg aaaagttggg attagaagat tgtctagatc ataagtggcc tgtgagttgt   4020
gttcatataa gtgatcacaa gactaagtat ttggacagac catatggtag agtaagtaga   4080
aagaagttga agttgaaatt gttgaatagt tgtgttgaaa atagagtgaa gttttataaa   4140
gccaaggttt tgaaagtgaa gcatgaagaa tttgagtctt cgattgtttg tgatgatggt   4200
aggaagataa gtggtagctt gattgttgat gcaagtggct atgctagtga ttttatagag   4260
tatgacaagc caagaaacca tggttatcaa gttgctcatg ggattttagc agaagttgat   4320
aatcatccat ttgatttgga taaaatgatg cttatggatt ggagggattc tcatttaggt   4380
aatgagccat atctgagggt gaagaatact aaagaaccaa cattcttgta tgcaatgcca   4440
tttgatagga atttggtatt cttggaagag acttctttag tgagtcggcc tatgttatcg   4500
tatatggaag tgaaaagaag gatggtagca agattaagac atttggggat caaagtgaga   4560
agtgtccttg aggaagagaa gtgtgtgatc actatgggag gaccacttcc gcggattcct   4620
caaaatgtta tggctattgg tgggacttca gggatagttc atccatcgtc tgggtacatg   4680
gtggctcgta gcatggcatt ggcaccagta ctggctgagg ccatcgtcga aagccttggc   4740
tcaacaagaa tgataagagg gtctcaactt taccatagag tttggaatgg tttgtggcct   4800
tcggatagaa gacgtgttag agaatgttat tgtttcggaa tggagacttt gttgaagctt   4860
gatttggaag gtactaggag attgtttgat gctttctttg atgttgatcc caagtactgg   4920
cacgggttcc tttcttcaag attgtctgtc aaagaacttg ctgtactcag tttgtacctt   4980
tttggacatg cctctaattt ggctaggttg atattgtta caagtgcac tgtccccttg   5040
gttaaactgc tgggcaatct agcaatagag agcctttgaa ttaatatgat agtttgaag   5100
cactgttttc attttaattt cttaggttat tttcatcttt tctcaatgca aaagtgaaac   5160
aaaagctata cacattgtca tcgttgttca aactcagaca agtttgccta gctctatgta   5220
tttatcctta acatatgtat tcatcaaatt cgaaatatac aatgcattgg acaaaagtat   5280
agagccacaa tctgatacca agtctgtatt tggaagcaca ggctaattgt tatggttacc   5340
aaacactttg aattggctgg ataataacaa acaggaaatt tatgttttta atcattaaca   5400
gcaaattggg aaagcaagaa ttattaggaa agttaatata gtgtcttggt tattctaatg   5460
gagtgggtta tgcaaattaa gttcccttgt caaagtttgg tttatgaact gctccactct   5520
```

```
tgtccctctt aaaagcctta atcccaacat gtaccaccaa agaattgagc tgctccatca    5580
gatcctttga gaatgttaat atgttattta aatgaaggac tgaatgatta tgaggatgca    5640
atgcataggt ttaattacca gttatctgta aattgtcttc tttgccatta ttttaaaagt    5700
ttaataacaa gtgtaacatc tacaaagagt tgataa                              5736

<210> SEQ ID NO 44
<211> LENGTH: 5743
<212> TYPE: DNA
<213> ORGANISM: Capsicum annuum

<400> SEQUENCE: 44
tgttgaatgg aaatattgg aagaatttca tttcatttta caaaaataaa gagtgtagag      60
ggtatttttg taaatcaata ttttttctat aaaaaatata taagaaatat tattttaata    120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctcccttc ccagaaatta agataattct ggtgctttta gcattagaaa    360
agtatttatt gggtagggaa atgtcatgac ttcacagcat taagcatcaa gggtataact    420
taatgaaata gtggtcaatg aattatattg agaatgacga ggtctctgtt ccaactttgg    480
tagactttgg aaatgctcgt ctggacgccg cccattcttt ctagtcttgg tgccattcta    540
tttggtctga gactggcatg atgccaaatt ctaaccttt cacaatgagc attcgaccta     600
ctcttctttt ttacgactct atttgaccta ctaggcattg gccaacttgg ctaaccactt    660
gaggaactag agttcggatt caatagaatc taataatttt aatcaaaaga cttcatgtat    720
attgaaaaat ctatttataa ctaactttaa atcggccttt acgtatcgac gtaatcaaaa    780
ttgtgtcagc ttgccacgtg gggtctagta tgagtttgaa attggtcata ggggccccaa    840
ttccactaat acagctgccg tccatgcact acaagacaaa tacaccacta tgtttgttag    900
tgcttggtaa atgtaaaaca aacttttgat gagaatctat tcgtggcatc gaagtgctgc    960
aaattggctt ttacctctgc tacttcaagc ctcactgatt tcaccccaa ctttctcatt    1020 tcccttttcaa ggatttgatt ttccagttgg gcatgttaaa acaacaatt ttcctcaaaa    1080 ctgtagaaat gatttctcat attttaatca gtcaaattat ttaaacaaga agttgatttt    1140 ttttttaattt ttttttttac aaaaaaattt caaatgtcaa gtaagatttt tcaaattgaa    1200
actgaataag ctgcgacttt agaaacaaaa aactaagata agtaaaaata ccaaaaagag    1260
tgaatcacat caattgaatt cttccaacag ttcgtttttt agtttctgtt ttgggaagag    1320
gagtactaca aggtaggacc tccaacaatc aacaatatct aagttgcaaa agttttgtg     1380 cgtttttag tttctgtttc gagaagagga atactacaag ttcgtttttt agtttctgtt    1440
ttgggaagag gagtactgca aggtaggacc tccaacaatt atcaatatct aaattgcaaa    1500
aatttcagtt cgttttagt ttctgtttcg ggaagaggaa tactacaagt tcgttttta     1560 gtttctattt tgggaagagg agtactacaa ggtaggacct ccaataccta aattgcaaaa    1620
atttcagttc gttttagt ttcagtttag ggaagaggaa tactacaagg taggacctcc     1680
aacaatcatc agtacctaaa ttgcaaaaat ttcagttcgt ttttagtttt atgtttggga    1740
agaagaatac tacaaggcag tggcggagct accttatgat tagggggttc atccgaacct    1800
ccttcgacgg aaaattatac tatttttata agtgaaaatt attttttatg tatatataat    1860
tgatgttgaa ccccctcgg ttagttcatg tatctatatt tttttatttt gaaccccgat     1920
```

```
gaaaattttg gctccgccac tgctacaagg taggacctcc aacaatcacc aatacctaaa    1980
ttgcaaaaat ttcagtttgt tttttagttt ctgttttggg aagaggaata ctacaaggta    2040
ggacctccaa caatcaccaa tacctaaatt gcaacgtttt tttagtttct gttttgggaa    2100
gaggaatact acatggtagg gcctccaaca atcaccaata cctaaattgc aaaaatttca    2160
gttcgtattt tcgtttctat tttgggaagt ggaatagtat aaggtaggac ctccaacaat    2220
caccaatacc taaattaaag ttccgattca ttttttagtt tctgttttgg aaagagaaat    2280
actacaaggt agggcctaca acaatcacca gtacctaaat tgtaaaaatt tcagttcgtt    2340
ttttagtttc tattttgaga agaggaatgc tacaaggtag ggcctacaac aatcaccagt    2400
acctaaattg taaaaatttc agttcgtttt ttagtttctg ttttgggaag aggaatacta    2460
caaggtaggg ccttcaacaa tcagcaatac ctaaattaca aaaatttcaa ttcgtttttt    2520
agtttctgtt ttgggaagag gaatactaca aggcagtggc ggagctacct tatgattagg    2580
ggttcatccg aacctccttc gacggaaaat tatactattt ttatatagta aaaattattt    2640
tttatgtata tataattgat gttgaacccc cttcggttag tttgtgtatc tatattttt    2700 tattttgaac ctccttgata aaaattttg actccgccat tgctacaagg tagaacctcc    2760
aacaatcacc aatacctaaa ttgcaaaaat ttcagttcgt tttttaattt ctgttttggg    2820
aagaggaata ctacaaggcc tccaacaatc accaatacct aaattgcaaa aatttcagtt    2880 tgtttttag tttctgtttt gggaagagga atactacaag gtaaggcctc caacaatcac    2940
caatacctaa attgcaaaaa tttcagttcg tattttcgtt tctattttgg gaagtggaat    3000
agtataaggt aggacctcca acaatcacca atacctaaat tgcaaaagtt ccgattcatt    3060
ttttagtttc tgtttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttctttttt    3240 agtttctgtt ttgaaagag aaatactaca agataggacc ttcaacaatc accaatacct    3300
aaattgcaaa aacttcagtt catttttag tttctgtttt gggaagaaga atacttcaag    3360
gtaacaatca ccaatacta aattaaattt cagttagttt tttagtttct gttttggga    3420 agaggaatac tttcttttgc tatataaagc caaagtaggt acctataagc atcaatattt    3480
tgtattgctt agtgattccc ctagttcggt atttcatttt ttttcactat actatatcac    3540
ctcctctcat aaatagccat tataaatctt gcattttctc taatggaaac ccttctaaag    3600
ccttttccat ctcctttact ttccattcct actcctaaca tgtatagttt caaacacaac    3660 tccactttc caaatccaac caaacaaaaa gattcaagaa agttccatta tagaaacaaa    3720
agcagtacac attttgtag ctttcttgat ttagcaccca catcaaagcc agagtcttta    3780
gatgttaaca tctcatgggt tgatactgat ctggacgggg ctgaattcga cgtgatcatc    3840
attggaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtggct atgctagtga ttttatagag    4260
```

```
tatgacaagc caagaaacca tggttatcaa gttgctcatg ggattttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga agccttggc    4740 tcaacaagaa tgataagagg gtctcaactt taccatagag tttggaatgg tttgtggcct    4800
tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtacctt    4980 tttgacatg cctctaattt ggctaggttg atattgtta caaagtgcac tgtccccttg    5040
gttaaactgc tgggcaatct agcaatagag agcctttgaa ttaatatgat agttttgaag    5100
cactgctttc attttaattt cttaggttat tttcatcttt tatcaatgca aaagtgaaac    5160
aaaagctata cacattgtca tcgttgttca aactcagaca agtttgccta gctctatgta    5220
tttatcctta acatatgtat tcatcaaatt cgaaatatac aatgtatggt tgtcgatgca    5280
ttggacaaaa gtatagagcc acaatctgat accaagtctg tatttggaag cactggctaa    5340
ttgttatggt taccaaacac tttgaattgg ctggataata caggaaatt tatgttatta    5400 atcattaaca gcaaattggg aaagcaagaa ttattaggaa agttaatata gtgtcttggt    5460
tattctaatg gagtgggtta tgcaaattaa gttcccttat caaagtttgg tttatgaact    5520
gctccactcg tgtccctctt aaaagcctta atcccaacat gtaccaccaa agaactgagc    5580
tgctccatca gatcctttga gaatgttaat atgttattta aatgaaggac tgaatgatta    5640
tgaggatgca atgcataggt ttaattacca gttatctgta aattgtcttc gttgccatta    5700
ttttaaaagt ttaataagtg taacatctac aaagagttga taa    5743
```

<210> SEQ ID NO 45
<211> LENGTH: 5743
<212> TYPE: DNA
<213> ORGANISM: Capsicum annuum

<400> SEQUENCE: 45

```
tgttgaatgg aaaatattgg aagaatttca tttcatttta caaaaataaa gagtgtagag      60
ggtatttttg taaatcaata ttttttctat aaaaaatata taagaaatat tattttaata     120
catcaaatca aatactgtat aagaaataat gttaacataa ttaatgcaag tatagctaat     180
accaacatta ctaatgcaag tattactaat acaccatatt ctatattaat cttatatact     240
ctaccaaacg accctaagtg tgtatctata tcctccgaga atttggaatt tgcaaattcc     300
aagttttgta tctccctttc ccagaaatta agataattct ggtgctttta gcattagaaa     360
agtatttatt gggtagggaa atgtcatgac ttcacagcat taagcatcaa gggtataact     420
taatgaaata gtggtcaatg aattatattg agaatgacga ggtctctgtt ccaactttgg     480
tagactttgg aaatgctcgt ctggacgccg cccattcttt ctagtcttgg tgccattcta     540
tttggtctga gactggcatg atgccaaatt ctaacctttt cacaatgagc attcgaccta     600
ctcttctttt ttacgactct atttgaccta ctaggcattg gccaacttgg ctaaccactt     660
```

-continued

```
gaggaactag agttcggatt caatagaatc taataatttt aatcaaaaga cttcatgtat      720
attgaaaaat ctatttataa ctaactttaa atcggccttt acgtatcgac gtaatcaaaa      780
ttgtgtcagc ttgccacgtg gggtctagta tgagtttgaa attggtcata ggggccccaa      840
ttccactaat acagctgccg tccatgcact acaagacaaa taccactact tgtttgttag      900
tgcttggtaa atgtaaaaca aacttttgat gagaatctat tcgtggcatc gaagtgctgc      960
aaattggctt ttacctctgc tacttcaagc ctcactgatt tcaccccaa ctttctcatt      1020 tcccttcaa ggatttgatt ttccagttgg gcatgttaaa acaacaatt ttcctcaaaa       1080 ctgtagaaat gatttctcat attttaatca gtcaaattat ttaaacaaga agttgatttt      1140 ttttaattt tttttttac aaaaaattt caaatgtcaa gtaagatttt tcaaattgaa        1200
actgaataag ctgcgacttt agaaacaaaa aactaagata agtaaaaata ccaaaaagag     1260
tgaatcacat caattgaatt cttccaacag ttcgtttttt agtttctgtt ttgggaagag     1320
gagtactaca aggtaggacc tccaacaatc aacaatatct aagttgcaaa agtttttgtg     1380
cgttttttag tttctgtttc gagaagagga atactacaag ttcgtttttt agtttctgtt     1440
ttgggaagag gagtactgca aggtaggacc tccaacaatt atcaatatct aaattgcaaa     1500
aatttcagtt cgttttagt ttctgtttcg ggaagaggaa tactacaagt tcgttttta       1560 gtttctatttt tgggaagagg agtactacaa ggtaggacct ccaataccta aattgcaaaa     1620
atttcagttc gttttagt ttcagtttag ggaagaggaa tactacaagg taggacctcc        1680
aacaatcatc agtacctaaa ttgcaaaaat ttcagttcgt ttttagtttt atgtttggga     1740
agaagaatac tacaaggcag tggcggagct accttatgat taggggttc atccgaacct     1800 ccttcgacgg aaaattatac tattttata agtgaaaatt attttttatg tatatataat     1860
tgatgttgaa ccccctttcgg ttagttcatg tatctatatt ttttatttt gaaccccgat     1920 gaaaattttg gctccgccac tgctacaagg taggacctcc aacaatcacc aatacctaaa     1980
ttgcaaaaat ttcagtttgt tttttagttt ctgtttggg aagaggaata ctacaaggta      2040
ggacctccaa caatcaccaa tacctaaatt gcaacgtttt tttagtttct gttttgggaa     2100
gaggaatact acatggtagg gcctccaaca atcaccaata cctaaattgc aaaaatttca     2160 gttcgtatt tcgtttctat tttgggaagt ggaatagtat aaggtaggac ctccaacaat      2220
caccaatacc taaattaaag ttccgattca tttttagtt tctgttttgg aaagagaaat      2280
actacaaggt agggcctaca acaatcacca gtacctaaat tgtaaaaatt tcagttcgtt     2340
ttttagtttc tattttgaga agaggaatgc tacaaggtag ggcctacaac aatcaccagt     2400
acctaaattg taaaaatttc agttcgtttt ttagtttctg ttttgggaag aggaatacta     2460
caaggtaggc ccttcaacaa tcagcaatac ctaaattaca aaaatttcaa ttcgtttttt     2520
agtttctgtt ttgggaagag gaatactaca aggcagtggc ggagctacct tatgattagg     2580
ggttcatccg aacctccttc gacgaaaat tatactattt ttatatagta aaaattattt     2640
tttatgtata tataattgat gttgaacccc cttcggttag tttgtgtatc tatatttttt     2700
tattttgaac ctccttgata aaaattttg actccgccat tgctacaagg tagaacctcc     2760
aacaatcacc aatacctaaa ttgcaaaaat ttcagttcgt tttttaattt ctgttttggg     2820
aagaggaata ctacaaggcc tccaacaatc accaatacct aaattgcaaa aatttcagtt     2880
tgttttttag tttctgtttt gggaagagga atactacaag gtaaggcctc caacaatcac     2940
caatacctaa attgcaaaaa tttcagttcg tattttcgtt tctattttgg gaagtggaat     3000
```

```
agtataaggt aggacctcca acaatcacca atacctaaat tgcaaaagtt ccgattcatt    3060
ttttagtttc tgttttggaa agagaaatac tacaaggtag ggtctccaac aatcaccagt    3120
acctaaattg taaaaatttc agttcgtttt ttagtttcta ttttgggaag tggaatagta    3180
taaggtagga cctccaacaa tcaccaatac ctaaattgca aaagttccga ttcttttttt    3240
agtttctgtt ttggaaagag aaatactaca agataggacc ttcaacaatc accaataccT    3300
aaattgcaaa aacttcagtt catttttag tttctgtttt gggaagaaga atacttcaag    3360
gtaacaatca ccaataccta aattaaattt cagttagttt tttagtttct gttttgggA    3420 agaggaatac tttcttttgc tatataaagc caaagtaggt acctataagc atcaatattT    3480
tgtattgctt agtgattccc ctagttcggt atttcatttt ttttcactat actatatcac    3540
ctcctctcat aaatagccat tataaatctt gcattttctc taatgaaaac ccttctaaag    3600
ccttttccat ctcctttact ttccattcct actcctaaca tgtatagttt caaacacaac    3660
tccacttttc caaatccaac caaacaaaaa gattcaagaa agttccatta tagaaacaaa    3720
agcagtacac atttttgtag ctttcttgat ttagcaccca catcaaagcc agagtcttta    3780
gatgttaaca tctcatgggt tgatactgat ctggacgggg ctgaattcga cgtgatcatc    3840
attggaactg gccctgccgg gcttcggcta gctgaacaag tttctaaata tggtattaag    3900
gtatgttgcg ttgacccttc accactttcc atgtggccaa ataattatgg tgtttgggtt    3960
gatgagtttg aaaagttggg attagaagat tgtctagatc ataagtggcc tgtgagttgt    4020
gttcatataa gtgatcacaa gactaagtat ttggacagac catatggtag agtaagtaga    4080
aagaagttga agttgaaatt gttgaatagt tgtgttgaaa atagagtgaa gttttataaa    4140
gccaaggttt tgaaagtgaa gcatgaagaa tttgagtctt cgattgtttg tgatgatggt    4200
aggaagataa gcggtagctt gattgttgat gcaagtgggt atgctagtga ttttatagag    4260
tatgacaagc caagaaacca tggttatcaa gttgctcatg ggattttagc agaagttgat    4320
aatcatccat ttgatttgga taaaatgatg cttatggatt ggagggattc tcatttaggt    4380
aatgagccat atctgagggt gaagaatact aaagaaccaa cattcttgta tgcaatgcca    4440
tttgatagga atttggtatt cttggaagag acttctttag tgagtcggcc tatgttatcg    4500
tatatggaag tgaaaagaag gatggtagca agattaagac atttggggat caaagtgaga    4560
agtgtccttg aggaagagaa gtgtgtgatc actatgggag gaccacttcc gcggattcct    4620
caaaatgtta tggctattgg tgggacttca gggatagttc atccatcgtc tgggtacatg    4680
gtggctcgta gcatggcatt ggcaccagta ctggctgagg ccatcgtcga aagccttggc    4740
tcaacaagaa tgataagagg gtctcaactt taccatagag ttggaatgg tttgtggcct    4800 tcggatagaa gacgtgttag agaatgttat tgtttcggaa tggagacttt gttgaagctt    4860
gatttggaag gtactaggag attgtttgat gctttctttg atgttgatcc caagtactgg    4920
cacgggttcc tttcttcaag attgtctgtc aaagaacttg ctgtactcag tttgtacctt    4980
tttggacatg cctctaattt ggctaggttg atattgtta caaagtgcac tgtccccttg    5040
gttaaactgc tgggcaatct agcaatagag agcctttgaa ttaatatgat agttttgaag    5100
cactgctttc atttttaattt cttaggttat tttcatcttt tatcaatgca aaagtgaaac    5160
aaaagctata cacattgtca tcgttgttca aactcagaca agtttgccta gctctatgta    5220
tttatcctta acatatgtat tcatcaaatt cgaaatatac aatgtatggt tgtcgatgca    5280
ttggacaaaa gtatagagcc acaatctgat accaagtctg tatttggaag cactggctaa    5340
ttgttatggt taccaaacac tttgaattgg ctggataata acaggaaatt tatgttatta    5400
```

```
atcattaaca gcaaattggg aaagcaagaa ttattaggaa agttaatata gtgtcttggt    5460
tattctaatg gagtgggtta tgcaaattaa gttcccttat caaagtttgg tttatgaact    5520
gctccactcg tgtccctctt aaaagcctta atcccaacat gtaccaccaa agaactgagc    5580
tgctccatca gatcctttga gaatgttaat atgttattta aatgaaggac tgaatgatta    5640
tgaggatgca atgcataggt ttaattacca gttatctgta aattgtcttc gttgccatta    5700
ttttaaaagt ttaataagtg taacatctac aaagagttga taa                     5743

<210> SEQ ID NO 46
<211> LENGTH: 5743
<212> TYPE: DNA
<213> ORGANISM: Capsicum annuum

<400> SEQUENCE: 46
tgttgaatgg aaatattgg aagaatttca tttcatttta caaaaataaa gagtgtagag      60 ggtattttg taaatcaata tttttctat aaaaaatata taagaaatat tattttaata     120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctccctttc ccagaaatta agataattct ggtgctttta gcattagaaa    360
agtatttatt gggtagggaa atgtcatgac ttcacagcat taagcatcaa gggtataact    420
taatgaaata gtggtcaatg aattatattg agaatgacga ggtctctgtt ccaactttgg    480
tagactttgg aaatgctcgt ctggacgccg cccattcttt ctagtcttgg tgccattcta    540
tttggtctga gactggcatg atgccaaatt ctacctttt cacaatgagc attcgaccta    600
ctcttctttt ttacgactct atttgaccta ctaggcattg gccaacttgg ctaaccactt    660
gaggaactag agttcggatt caatagaatc taataatttt aatcaaaaga cttcatgtat    720
attgaaaaat ctatttataa ctaactttaa atcggccttt acgtatcgac gtaatcaaaa    780
ttgtgtcagc ttgccacgtg gggtctagta tgagtttgaa attggtcata ggggccccaa    840
ttccactaat acagctgccg tccatgcact acaagacaaa tacaccacta tgtttgttag    900
tgcttggtaa atgtaaaaca aacttttgat gagaatctat tcgtggcatc gaagtgctgc    960
aaattggctt ttacctctgc tacttcaagc ctcactgatt ttcaccccaa ctttctcatt   1020 tcccttcaa ggatttgatt ttccagttgg gcatgttaaa acaacaatt ttcctcaaaa    1080 ctgtagaaat gatttctcat attttaatca gtcaaattat ttaaacaaga agttgatttt   1140 ttttaattt tttttttac aaaaaaattt caaatgtcaa gtaagatttt tcaaattgaa    1200
actgaataag ctgcgacttt agaaacaaaa aactaagata agtaaaaata ccaaaaagag   1260
tgaatcacat caattgaatt cttccaacag ttcgtttttt agtttctgtt ttgggaagag   1320
gagtactaca aggtaggacc tccaacaatc aacaatatct aagttgcaaa gttttttgtg   1380
cgttttttag tttctgtttc gagaagagga atactacaag ttcgtttttt agtttctgtt   1440
ttgggaagag gagtactgca aggtaggacc tccaacaatt atcaatatct aaattgcaaa   1500
aatttcagtt cgttttagt ttctgtttcg ggaagaggaa tactacaagt tcgttttta    1560 gtttctattt tgggaagagg agtactacaa ggtaggacct ccaatacctaa aattgcaaaa   1620 atttcagttc gttttttagt ttcagtttag ggaagaggaa tactacaagg taggacctcc   1680
aacaatcatc agtacctaaa ttgcaaaaat ttcagttcgt ttttagtttt atgtttggga   1740
```

```
agaagaatac tacaaggcag tggcggagct accttatgat taggggttc atccgaacct   1800 ccttcgacgg aaaattatac tatttttata agtgaaaatt attttttatg tatatataat   1860
tgatgttgaa ccccttcgg ttagttcatg tatctatatt tttttatttt gaaccccgat   1920
gaaaattttg gctccgccac tgctacaagg taggacctcc aacaatcacc aatacctaaa   1980
ttgcaaaaat ttcagtttgt ttttagtttt ctgttttggg aagaggaata ctacaaggta   2040
ggacctccaa caatcaccaa tacctaaatt gcaacgtttt tttagtttct gttttgggaa   2100
gaggaatact acatggtagg gcctccaaca atcaccaata cctaaattgc aaaaatttca   2160
gttcgtattt tcgtttctat tttgggaagt ggaatagtat aaggtaggac ctccaacaat   2220
caccaatacc taaattaaag ttccgattca tttttttagtt tctgttttgg aaagagaaat   2280
actacaaggt agggcctaca caatcacca gtacctaaat tgtaaaaatt tcagttcgtt   2340
ttttagtttc tattttgaga agaggaatgc tacaaggtag ggcctacaac aatcaccagt   2400
acctaaattg taaaaatttc agttcgtttt ttagtttctg ttttgggaag aggaatacta   2460
caaggtaggg ccttcaacaa tcagcaatac ctaaattaca aaaatttcaa ttcgtttttt   2520
agtttctgtt ttgggaagag gaatactaca aggcagtggc ggagctacct tatgattagg   2580
ggttcatccg aacctccttc gacggaaaat tatactattt ttatatagta aaaattattt   2640
tttatgtata taattgat gttgaacccc cttcggttag tttgtgtatc tatatttttt   2700
tattttgaac ctccttgata aaaattttg actccgccat tgctacaagg tagaacctcc   2760
aacaatcacc aatacctaaa ttgcaaaaat ttcagttcgt tttttaattt ctgttttggg   2820
aagaggaata ctacaaggcc tccaacaatc accaatacct aaattgcaaa aatttcagtt   2880
tgttttttag tttctgtttt gggaagagga atactacaag gtaaggcctc caacaatcac   2940
caatacctaa attgcaaaaa tttcagttcg tattttcgtt tctatttggg aagtggaat   3000 agtataaggt aggacctcca acaatcacca atacctaaat tgcaaaagtt ccgattcatt   3060
ttttagtttc tgttttggaa agagaaatac tacaaggtag ggtctccaac aatcaccagt   3120
acctaaattg taaaaatttc agttcgtttt ttagtttcta ttttgggaag tggaatagta   3180
taaggtagga cctccaacaa tcaccaatac ctaaattgca aaagttccga ttcttttttt   3240
agtttctgtt ttggaaagag aaatactaca agataggacc ttcaacaatc accaatacct   3300
aaattgcaaa aacttcagtt cattttttag tttctgtttt gggaagaaga atacttcaag   3360
gtaacaatca ccaataccta aattaaattt cagttagttt tttagtttct gttttgggga   3420
agaggaatac tttctttgc tatataaagc caaagtaggt acctataagc atcaatattt   3480
tgtattgctt agtgattccc ctagttcggt atttcatttt ttttcactat actatatcac   3540
ctcctctcat aaatagccat tataaatctt gcattttctc taatgaaaac ccttctaaag   3600 cctttccat ctccttact ttccattcct actcctaaca tgtatagttt caaacacaac   3660
tccacttttc caaatccaac caaacaaaaa gattcaagaa agttccatta tagaaacaaa   3720
agcagtacac attttgtag ctttcttgat ttagcaccca catcaaagcc agagtcttta   3780
gatgttaaca tctcatgggt tgatactgat ctggacgggg ctgaattcga cgtgatcatc   3840
attggaactg gccctgccgg gcttcggcta gctgaacaag tttctaaata tggtattaag   3900
gtatgttgcg ttgacccttc accactttcc atgtggccaa ataattatgg tgtttgggtt   3960
gatgagtttg aaaagttggg attagaagat tgtctagatc ataagtggcc tgtgagttgt   4020
gttcatataa gtgatcacaa gactaagtat ttggacagac catatggtag agtaagtaga   4080
aagaagttga agttgaaatt gttgaatagt tgtgttgaaa atagagtgaa gttttataaa   4140
```

| | |
|---|---|
| gccaaggttt tgaaagtgaa gcatgaagaa tttgagtctt cgattgtttg tgatgatggt | 4200 |
| aggaagataa gcggtagctt gattgttgat gcaagtggct atgctagtga ttttatagag | 4260 |
| tatgacaagc caagaaacca tggttatcaa gttgctcatg ggattttagc agaagttgat | 4320 |
| aatcatccat ttgatttgga taaaatgatg cttatggatt ggagggattc tcatttaggt | 4380 |
| aatgagccat atctgagggt gaagaatact aaagaaccaa cattcttgta tgcaatgcca | 4440 |
| tttgatagga atttggtatt cttggaagag acttctttag tgagtcggcc tatgttatcg | 4500 |
| tatatggaag tgaaaagaag gatggtagca agattaagac atttggggat caaagtgaga | 4560 |
| agtgtccttg aggaagagaa gtgtgtgatc actatgggag gaccacttcc gcggattcct | 4620 |
| caaaatgtta tggctattgg tgggacttca gggatagttc atccatcgtc tgggtacatg | 4680 |
| gtggctcgta gcatggcatt ggcaccagta ctggctgagg ccatcgtcga agccttggc | 4740 |
| tcaacaagaa tgataagagg gtctcaactt taccatagag tttggaatgg tttgtggcct | 4800 |
| tcggatagaa gacgtgttag agaatgttat tgtttcggaa tggagacttt gttgaagctt | 4860 |
| gatttggaag gtactaggag attgtttgat gctttctttg atgttgatcc caagtactgg | 4920 |
| cacgggttcc tttcttcaag attgtctgtc aaagaacttg ctgtactcag tttgtacctt | 4980 |
| tttggacatg cctctaattt ggctaggttg gatattgtta caaagtgcac tgtccccttg | 5040 |
| gttaaactgc tgggcaatct agcaatagag agcctttgaa ttaatatgat agttttgaag | 5100 |
| cactgctttc attttaattt cttaggttat tttcatcttt tatcaatgca aaagtgaaac | 5160 |
| aaaagctata cacattgtca tcgttgttca aactcagaca agtttgccta gctctatgta | 5220 |
| tttatcctta acatatgtat tcatcaaatt cgaaatatac aatgtatggt tgtcgatgca | 5280 |
| ttggacaaaa gtatagagcc acaatctgat accaagtctg tatttggaag cactggctaa | 5340 |
| tgttatggt taccaaacac tttgaattgg ctggataata acaggaaatt tatgttatta | 5400 |
| atcattaaca gcaaattggg aaagcaagaa ttattaggaa agttaatata gtgtcttggt | 5460 |
| tattctaatg gagtgggtta tgcaaattaa gttcccttat caaagtttgg tttatgaact | 5520 |
| gctccactcg tgtccctctt aaaagcctta atcccaacat gtaccaccaa gaaactgagc | 5580 |
| tgctccatca gatcctttga gaatgttaat atgttattta aatgaaggac tgaatgatta | 5640 |
| tgaggatgca atgcataggt ttaattacca gttatctgta aattgtcttc gttgccatta | 5700 |
| ttttaaaagt ttaataagtg taacatctac aaagagttga taa | 5743 |

<210> SEQ ID NO 47
<211> LENGTH: 1316
<212> TYPE: DNA
<213> ORGANISM: Capsicum annuum

<400> SEQUENCE: 47

| | |
|---|---|
| tgttgaatgg aaaatattgg aagaatttca tttcatttta caaaaataaa gagtgtagag | 60 |
| ggtatttttg taaatcaata tttttttctat aaaaaatata taagaaatat tattttaata | 120 |
| catcaaatca aatactgtat aagaaataat gttaacataa ttaatgcaag tatagctaat | 180 |
| accaacatta ctaatgcaag tattactaat acaccatatt ctatattaat cttatatact | 240 |
| ctaccaaacg accctaagtg tgtatctata tcctccgaga atttggaatt tgcaaattcc | 300 |
| aagttttgta tctcccttc ccagaaatta agataattct ggtgctttta gagtttggaa | 360 |
| tggtttgtgg cttcggata gaagacgtgt tagagaatgt tattgtttcg gaatggagac | 420 |
| tttgttgaag cttgatttgg aaggtactag gagattgttt gatgctttct ttgatgttga | 480 |

| | |
|---|---|
| tcccaagtac tggcacgggt tcctttcttc aagattgtct gtcaaagaac ttgctgtact | 540 |
| cagtttgtac cttttggac atgcctctaa tttggctagg ttggatattg ttacaaagtg | 600 |
| cactgtcccc ttggttaaac tgctgggcaa tctagcaata gagagccttt gaattaatat | 660 |
| gatagttttg aagcactgct ttcattttaa tttcttaggt tattttcatc ttttatcaat | 720 |
| gcaaaagtga acaaaagct atacacattg tcatcgttgt tcaaactcag acaagtttgc | 780 |
| ctagctctat gtatttatcc ttaacatatg tattcatcaa attcgaaata tacaatgtat | 840 |
| ggttgtcgat gcattggaca aaagtataga gccacaatct gataccaagt ctgtatttgg | 900 |
| aagcactggc taattgttat ggttaccaaa cactttgaat tggctggata ataacaggaa | 960 |
| atttatgtta ttaatcatta acagcaaatt gggaaagcaa gaattattag gaaagttaat | 1020 |
| atagtgtctt ggttattcta atggagtggg ttatgcaaat taagttccct tatcaaagtt | 1080 |
| tggtttatga actgctccac tcgtgtccct cttaaaagcc ttaatcccaa catgtaccac | 1140 |
| caaagaactg agctgctcca tcagatcctt tgagaatgtt aatatgttat ttaaatgaag | 1200 |
| gactgaatga ttatgaggat gcaatgcata ggtttaatta ccagttatct gtaaattgtc | 1260 |
| ttcgttgcca ttattttaaa agtttaataa gtgtaacatc tacaaagagt tgataa | 1316 |

<210> SEQ ID NO 48
<211> LENGTH: 1316
<212> TYPE: DNA
<213> ORGANISM: Capsicum annuum

<400> SEQUENCE: 48

| | |
|---|---|
| tgttgaatgg aaatattgg aagaatttca tttcatttta caaaaataaa gagtgtagag | 60 |
| ggtattttg taaatcaata ttttttctat aaaaaatata taagaaatat tattttaata | 120 |
| catcaaatca aatactgtat aagaaataat gttaacataa ttaatgcaag tatagctaat | 180 |
| accaacatta ctaatgcaag tattactaat acaccatatt ctatattaat cttatatact | 240 |
| ctaccaaacg accctaagtg tgtatctata tcctccgaga atttggaatt tgcaaattcc | 300 |
| aagttttgta tctcccttcc cagaaattta agataattct ggtgctttta gagtttggaa | 360 |
| tggtttgtgg ccttcggata gaagacgtgt tagagaatgt tattgtttcg gaatggagac | 420 |
| tttgttgaag cttgatttgg aaggtactag gagattgttt gatgctttct ttgatgttga | 480 |
| tcccaagtac tggcacgggt tcctttcttc aagattgtct gtcaaagaac ttgctgtact | 540 |
| cagtttgtac cttttggac atgcctctaa tttggctagg ttggatattg ttacaaagtg | 600 |
| cactgtcccc ttggttaaac tgctgggcaa tctagcaata gagagccttt gaattaatat | 660 |
| gatagttttg aagcactgct ttcattttaa tttcttaggt tattttcatc ttttatcaat | 720 |
| gcaaaagtga acaaaagct atacacattg tcatcgttgt tcaaactcag acaagtttgc | 780 |
| ctagctctat gtatttatcc ttaacatatg tattcatcaa attcgaaata tacaatgtat | 840 |
| ggttgtcgat gcattggaca aaagtataga gccacaatct gataccaagt ctgtatttgg | 900 |
| aagcactggc taattgttat ggttaccaaa cactttgaat tggctggata ataacaggaa | 960 |
| atttatgtta ttaatcatta acagcaaatt gggaaagcaa gaattattag gaaagttaat | 1020 |
| atagtgtctt ggttattcta atggagtggg ttatgcaaat taagttccct tatcaaagtt | 1080 |
| tggtttatga actgctccac tcgtgtccct cttaaaagcc ttaatcccaa catgtaccac | 1140 |
| caaagaactg agctgctcca tcagatcctt tgagaatgtt aatatgttat ttaaatgaag | 1200 |
| gactgaatga ttatgaggat gcaatgcata ggtttaatta ccagttatct gtaaattgtc | 1260 |
| ttcgttgcca ttattttaaa agtttaataa gtgtaacatc tacaaagagt tgataa | 1316 |

<210> SEQ ID NO 49
<211> LENGTH: 1316
<212> TYPE: DNA
<213> ORGANISM: Capsicum annuum

<400> SEQUENCE: 49

```
tgttgaatgg aaaatattgg aagaatttca tttcatttta caaaaataaa gagtgtagag      60
ggtattttg taaatcaata ttttttctat aaaaaatata taagaaatat tattttaata     120
catcaaatca aatactgtat aagaaataat gttaacataa ttaatgcaag tatagctaat     180
accaacatta ctaatgcaag tattactaat acaccatatt ctatattaat cttatatact     240
ctaccaaacg accctaagtg tgtatctata tcctccgaga atttggaatt tgcaaattcc     300
aagttttgta tctcccttc ccagaaatta agataattct ggtgctttta gagtttggaa     360
tggtttgtgg ccttcggata aagacgtgt tagagaatgt tattgtttcg aatggagac     420
tttgttgaag cttgatttgg aaggtactag gagattgttt gatgctttct ttgatgttga     480
tcccaagtac tggcacgggt tcctttcttc aagattgtct gtcaaagaac ttgctgtact     540
cagtttgtac cttttggac atgcctctaa tttggctagg ttggatattg ttacaaagtg     600
cactgtcccc ttggttaaac tgctgggcaa tctagcaata gagagccttt gaattaatat     660
gatagttttg aagcactgct ttcattttaa tttcttaggt tattttcatc ttttatcaat     720
gcaaaagtga acaaaagct atacacattg tcatcgttgt tcaaactcag acaagtttgc     780
ctagctctat gtatttatcc ttaacatatg tattcatcaa attcgaaata tacaatgtat     840
ggttgtcgat gcattggaca aagtataga gccacaatct gataccaagt ctgtatttgg     900
aagcactggc taattgttat ggttaccaaa cactttgaat tggctggata ataacaggaa     960
atttatgtta ttaatcatta acagcaaatt gggaaagcaa gaattattag gaaagttaat    1020
atagtgtctt ggttattcta atggagtggg ttatgcaaat taagttccct tatcaaagtt    1080
tggtttatga actgctccac tcgtgtccct cttaaaagcc ttaatcccaa catgtaccac    1140
caaagaactg agctgctcca tcagatcctt tgagaatgtt aatatgttat ttaaatgaag    1200
gactgaatga ttatgaggat gcaatgcata ggtttaatta ccagttatct gtaaattgtc    1260
ttcgttgcca ttattttaaa agtttaataa gtgtaacatc tacaaagagt tgataa        1316
```

<210> SEQ ID NO 50
<211> LENGTH: 1316
<212> TYPE: DNA
<213> ORGANISM: Capsicum annuum

<400> SEQUENCE: 50

```
tgttgaatgg aaaatattgg aagaatttca tttcatttta caaaaataaa gagtgtagag      60
ggtattttg taaatcaata ttttttctat aaaaaatata taagaaatat tattttaata     120
catcaaatca aatactgtat aagaaataat gttaacataa ttaatgcaag tatagctaat     180
accaacatta ctaatgcaag tattactaat acaccatatt ctatattaat cttatatact     240
ctaccaaacg accctaagtg tgtatctata tcctccgaga atttggaatt tgcaaattcc     300
aagttttgta tctcccttc ccagaaatta agataattct ggtgctttta gagtttggaa     360
tggtttgtgg ccttcggata aagacgtgt tagagaatgt tattgtttcg aatggagac     420
tttgttgaag cttgatttgg aaggtactag gagattgttt gatgctttct ttgatgttga     480
tcccaagtac tggcacgggt tcctttcttc aagattgtct gtcaaagaac ttgctgtact     540
```

```
cagtttgtac cttttggac atgcctctaa tttggctagg ttggatattg ttacaaagtg    600
cactgtcccc ttggttaaac tgctgggcaa tctagcaata gagagccttt gaattaatat    660
gatagttttg aagcactgct ttcatttaa tttcttaggt tattttcatc ttttatcaat    720
gcaaaagtga acaaaagct atacacattg tcatcgttgt tcaaactcag acaagtttgc    780
ctagctctat gtatttatcc ttaacatatg tattcatcaa attcgaaata tacaatgtat    840
ggttgtcgat gcattggaca aaagtataga gccacaatct gataccaagt ctgtatttgg    900
aagcactggc taattgttat ggttaccaaa cactttgaat tggctggata ataacaggaa    960
ctttatgtta ttaatcatta acagcaaatt gggaaagcaa gaattattag gaaagttaat   1020
atagtgtctt ggttattcta atggagtggg ttatgcaaat taagttccct tatcaaagtt   1080
tggtttatga actgctccac tcgtgtccct cttaaaagcc ttaatcccaa catgtaccac   1140
caaagaactg agctgctcca tcagatcctt tgagaatgtt aatatgttat ttaaatgaag   1200
gactgaatga ttatgaggat gcaatgcata ggtttaatta ccagttatct gtaaattgtc   1260
ttcgttgcca ttattttaaa agtttaataa gtgtaacatc tacaaagagt tgataa       1316

<210> SEQ ID NO 51
<211> LENGTH: 1316
<212> TYPE: DNA
<213> ORGANISM: Capsicum annuum

<400> SEQUENCE: 51
tgttgaatgg aaaatattgg aagaatttca tttcatttta caaaaataaa gagtgtagag     60
ggtattttg taaatcaata tttttctat aaaaaatata taagaaatat tattttaata    120
catcaaatca aatactgtat aagaaataat gttaacataa ttaatgcaag tatagctaat    180
accaacatta ctaatgcaag tattactaat acaccatatt ctatattaat cttatatact    240
ctaccaaacg accctaagtg tgtatctata tcctccgaga atttggaatt tgcaaattcc    300
aagttttgta tctccctttc ccagaaatta agataattct ggtgctttta gagtttggaa    360
tggtttgtgg ccttcggata aagacgtgt tagagaatgt tattgtttcg gaatggagac    420
tttgttgaag cttgatttgg aaggtactag gagattgttt gatgcttttct ttgatgttga    480
tcccaagtac tggcacgggt tccttttcttc aagattgtct gtcaaagaac ttgctgtact    540
cagtttgtac cttttggac atgcctctaa tttggctagg ttggatattg ttacaaagtg    600
cactgtcccc ttggttaaac tgctgggcaa tctagcaata gagagccttt gaattaatat    660
gatagttttg aagcactgct ttcatttaa tttcttaggt tattttcatc ttttatcaat    720
gcaaaagtga acaaaagct atacacattg tcatcgttgt tcaaactcag acaagtttgc    780
ctagctctat gtatttatcc ttaacatatg tattcatcaa attcgaaata tacaatgtat    840
ggttgtcgat gcattggaca aaagtataga gccacaatct gataccaagt ctgtatttgg    900
aagcactggc taattgttat ggttaccaaa cactttgaat tggctggata ataacaggaa    960
atttatgtta ttaatcatta acagcaaatt gggaaagcaa gaattattag gaaagttaat   1020
atagtgtctt ggttattcta atggagtggg ttatgcaaat taagttccct tatcaaagtt   1080
tggtttatga actgctccac tcgtgtccct cttaaaagcc ttaatcccaa catgtaccac   1140
caaagaactg agctgctcca tcagatcctt tgagaatgtt aatatgttat ttaaatgaag   1200
gactgaatga ttatgaggat gcaatgcata ggtttaatta ccagttatct gtaaattgtc   1260
ttcgttgcca ttattttaaa agtttaataa gtgtaacatc tacaaagagt tgataa       1316
```

<210> SEQ ID NO 52
<211> LENGTH: 1316
<212> TYPE: DNA
<213> ORGANISM: Capsicum annuum

<400> SEQUENCE: 52

```
tgttgaatgg aaatatattgg aagaatttca tttcatttta caaaaataaa gagtgtagag      60
ggtattttg taaatcaata tttttctat aaaaaatata taagaaatat tattttaata       120
catcaaatca aatactgtat aagaaataat gttaacataa ttaatgcaag tatagctaat      180
accaacatta ctaatgcaag tattactaat acaccatatt ctatattaat cttatatact      240
ctaccaaacg accctaagtg tgtatctata tcctccgaga atttggaatt tgcaaattcc      300
aagttttgta tctcccttc ccagaaatta agataattct ggtgctttta gagtttggaa       360
tggtttgtgg ccttcggata gaagacgtgt tagagaatgt tattgtttcg gaatggagac      420
tttgttgaag cttgatttgg aaggtactag gagattgttt gatgctttct ttgatgttga      480
tcccaagtac tggcacgggt tcctttcttc aagattgtct gtcaaagaac ttgctgtact      540
cagtttgtac cttttggac atgcctctaa tttggctagg ttggatattg ttacaaagtg       600
cactgtcccc ttggttaaac tgctgggcaa tctagcaata gagagccttt gaattaatat      660
gatagttttg aagcactgct ttcattttaa tttcttaggt tattttcatc ttttatcaat      720
gcaaagtga acaaaagct atacacattg tcatcgttgt tcaaactcag acaagtttgc        780
ctagctctat gtatttatcc ttaacatatg tattcatcaa attcgaaata tacaatgtat      840
ggttgtcgat gcattggaca aaagtataga gccacaatct gataccaagt ctgtatttgg      900
aagcactggc taattgttat ggttaccaaa cactttgaat tggctggata taacaggaa       960
atttatgtta ttaatcatta acagcaaatt gggaaagcaa gaattattag gaaagttaat     1020
atagtgtctt ggttattcta atggagtggg ttatgcaaat taagttccct tatcaaagtt     1080
tggtttatga actgctccac tcgtgtccct cttaaaagcc ttaatcccaa catgtaccac     1140
caaagaactg agctgctcca tcagatcctt tgagaatgtt aatatgttat ttaaatgaag     1200
gactgaatga ttatgaggat gcaatgcata ggtttaatta ccagttatct gtaaattgtc     1260
ttcgttgcca ttatttaaa agtttaataa gtgtaacatc tacaaagagt tgataa         1316
```

<210> SEQ ID NO 53
<211> LENGTH: 1316
<212> TYPE: DNA
<213> ORGANISM: Capsicum annuum

<400> SEQUENCE: 53

```
tgttgaatgg aaatatattgg aagaatttca tttcatttta caaaaataaa gagtgtagag      60
ggtattttg taaatcaata tttttctat aaaaaatata taagaaatat tattttaata       120
catcaaatca aatactgtat aagaaataat gttaacataa ttaatgcaag tatagctaat      180
accaacatta ctaatgcaag tattactaat acaccatatt ctatattaat cttatatact      240
ctaccaaacg accctaagtg tgtatctata tcctccgaga atttggaatt tgcaaattcc      300
aagttttgta tctcccttc ccagaaatta agataattct ggtgctttta gagtttggaa       360
tggtttgtgg ccttcggata gaagacgtgt tagagaatgt tattgtttcg gaatggagac      420
tttgttgaag cttgatttgg aaggtactag gagattgttt gatgctttct ttgatgttga      480
tcccaagtac tggcacgggt tcctttcttc aagattgtct gtcaaagaac ttgctgtact      540
cagtttgtac cttttggac atgcctctaa tttggctagg ttggatattg ttacaaagtg       600
```

-continued

| | |
|---|---|
| cactgtcccc ttggttaaac tgctgggcaa tctagcaata gagagccttt gaattaatat | 660 |
| gatagttttg aagcactgct ttcattttaa tttcttaggt tatttcatc ttttatcaat | 720 |
| gcaaaagtga acaaaagct atacacattg tcatcgttgt tcaaactcag acaagtttgc | 780 |
| ctagctctat gtatttatcc ttaacatatg tattcatcaa attcgaaata tacaatgtat | 840 |
| ggttgtcgat gcattggaca aaagtataga gccacaatct gataccaagt ctgtatttgg | 900 |
| aagcactggc taattgttat ggttaccaaa cactttgaat tggctggata ataacaggaa | 960 |
| atttatgtta ttaatcatta acagcaaatt gggaaagcaa gaattattag gaaagttaat | 1020 |
| atagtgtctt ggttattcta atggagtggg ttatgcaaat taagttccct tatcaaagtt | 1080 |
| tggtttatga actgctccac tcgtgtccct cttaaaagcc ttaatcccaa catgtaccac | 1140 |
| caaagaactg agctgctcca tcagatcctt tgagaatgtt aatatgttat ttaaatgaag | 1200 |
| gactgaatga ttatgaggat gcaatgcata ggtttaatta ccagttatct gtaaattgtc | 1260 |
| ttcgttgcca ttattttaaa agtttaataa gtgtaacatc tacaaagagt tgataa | 1316 |

<210> SEQ ID NO 54
<211> LENGTH: 5760
<212> TYPE: DNA
<213> ORGANISM: Capsicum annuum

<400> SEQUENCE: 54

| | |
|---|---|
| tgttgaatgg aaatatattgg aagaatttca tttcattttta caaaaataaa gagtgtagag | 60 |
| ggtattttg taaatcaata ttttttctat aaaaaatata taagaaatat tattttaata | 120 |
| catcaaatca aatactgtat aagaaataat gttaacataa ttaatgcaag tatagctaat | 180 |
| accaacatta ctaatgcaag tattactaat acaccatatt ctatattaat cttatatact | 240 |
| ctaccaaacg accctaagtg tgtatctata tcctccgaga atttggaatt tgcaaattcc | 300 |
| aagttttgta tctccctttc ccagaaatta agataattct ggtgcttta gcattagaaa | 360 |
| agtatttatt gggtagggaa atgtcatgac ttcacagcat taagcatcaa gggtataact | 420 |
| taatgaaata gtggtcaatg aattatattg agaatgacga ggtctctgtt ccaactttgg | 480 |
| tagactttgg aaatgctcgt ctggacgccg cccattcttt ctagtcttgg tgccattcta | 540 |
| tttggtctga aatggcatg atgccaaatt ctaccttttc acaatgagca ttcgacctac | 600 |
| tcttcttttt tcgactcatt tgacctacta ggcattggcc aacttggcta accacttgag | 660 |
| gaactagagt tcggattcaa tagaatctaa taattttaat caaaagactt catgtatatt | 720 |
| gaaaaatcta tttataacta actttaaatc ggcctttacg tatcgacgta atcaaaattg | 780 |
| tgtcagcttg ccacgtgggg tctagtatga gtttgaaatt ggtcataggg gccccaattc | 840 |
| cactaataca gctgccgtcc atgcactaca agacaaatac accactatgt tgttagtgc | 900 |
| ttggtaaatg taaaacaaac ttttgatgag aatctattcg tggcatcgaa gtgctgcaaa | 960 |
| ttggctttta cctctgctac ttcaagcctc actgattttc accccaactt tctcatttcc | 1020 |
| ctttcaagga tttgattttc cagttgggca tgttaaaaac aacaatttc ctcaaaactg | 1080 |
| tagaaatgat ttctcatatt ttaatcagtc aaattattta acaagaagt tgattttttt | 1140 |
| ttaattttt ttttttacaaa aaatttcaa atgtcaagta agattttca aattgaaact | 1200 |
| gaataagctg cgactttaga aacaaaaaac taagataagt aaaatacca aaagagtga | 1260 |
| atcacatcaa ttgaattctt ccaacagttc gttttttagt ttctgttttg ggaagaggag | 1320 |
| tactacaagg taggacctcc aacaatcaac aatatctaag ttgcaaaagt ttttgtgcgt | 1380 |
| ttttagttt ctgtttcgag aagaggaata ctacaagttc gttttttagt ttctgttttg | 1440 |

```
ggaagaggag tactgcaagg taggacctcc aacaattatc aatatctaaa ttgcaaaaat   1500
ttcagttcgt ttttagtttc tgtttcggga agaggaatac tacaagttcg ttttttagtt   1560
tctattttgg gaagaggagt actacaaggt aggacctcca atacctaaat tgcaaaatt    1620 tcagttcgtt ttttagtttc agtttaggga agaggaatac tacaaggtag gacctccaac   1680
aatcatcagt acctaaattg caaaaatttc agttcgtttt ttagtttatg ttttgggaag   1740
aagaatacta caaggcagtg gcggagctac cttatgatta gggggttcat ccgaacctcc   1800
ttcgacggaa aattatacta ttttttataag tgaaaattat ttttttatgta tatataattg  1860 atgttgaacc cccttcggtt agttcatgta tctatatttt tttattttga accccgatga   1920
aaattttggc tccgccactg ctacaaggta ggacctccaa caatcaccaa tacctaaatt   1980
gcaaaaattt cagtttgttt tttagttcct gttttgggaa gaggaatact acaaggtagg   2040
acctccaaca atcaccaata cctaaattgc aacgttttt agtttctgtt ttgggaagag    2100
gaatactaca tggtagggcc tccaacaatc accaatacct aaattgcaaa aatttcagtt   2160
cgtattttcg tttctattttt gggaagtgga atagtataag gtaggacctc caacaatcac   2220
caatacctaa attaaagttc cgattcatttt tttagtttct gttttggaaa gagaaatact   2280
acaaggtagg gcctacaaca atcaccagta cctaaattgt aaaaatttca gttcgttttt   2340
tagtttctat tttgagaaga ggaatgctac aaggtagggc ctacaacaat caccagtacc   2400
taaattgtaa aaatttcagt tcgttttttta gtttctgttt tgggaagagg aatactacaa   2460
ggtagggcct tcaacaatca gcaatacctaa aattacaaaa atttcaattc gttttttagt   2520
ttctgttttg ggaagaggaa tactacaagg cagtggcgga gctacctat gattaggggt    2580 tcatccgaac ctccttcgac ggaaaattat actatttttat atagtaaaaa attattttt    2640 atgtatatat aattgatgtt gaaccccctt cggttagttt gtgtatctat atttttttat   2700
tttgaacctc cttgataaaa aattttgact ccgccattgc tacaaggtag aacctccaac   2760
aatcaccaat acctaaattg caaaaattc agttcgtttt ttaatttctg ttttgggaag    2820
aggaatacta caaggcctcc aacaatcacc aatacctaaa ttgcaaaaat ttcagtttgt   2880
ttttagtttt ctgttttggg aagaggaata ctacaaggta aggcctccaa caatcaccaa   2940
tacctaaatt gcaaaaattt cagttcgtat ttttcgtttct atttttgggaa gtggaatagt  3000 ataaggtagg acctccaaca atcaccaata cctaaattgc aaaagttccg attcattttt   3060
tagtttctgt tttggaaaga gaaatactac aaggtagggt ctccaacaat caccagtacc   3120
taaattgtaa aaatttcagt tcgttttttta gtttctatt tgggaagtgg aatagtataa    3180
ggtaggacct ccaacaatca ccaatacta aattgcaaaa gttccgattc ttttttagt     3240 ttctgttttg gaaagagaaa tactacaagg taggaccttc aacaatcacc aatacctaaa   3300
ttgcaaaaac ttcagttcat ttttagttt ctgttttggg aagaagaata cttcaaggta    3360
acaatcacca atacctaaat taaaaatttc agttagtttt ttagtttctg ttttgggaa    3420 gaggaatact ttcttttgct atataaagcc aaagtaggta cctataagca tcaatatttt   3480
gtattgctta gtgattcccc tagttcggta tttcattttt tttcactata ctatatcacc   3540
tcctctcata aatagccatt ataaatcttg cattttctct aatggaaacc cttctaaagc   3600
cttttccatc tcctttactt tccattccta ctcctaacat gtatagtttc aaacacaact   3660
ccacttttcc aaatccaacc aaacaaaaag attcaagaaa gttccattat agaaacaaaa   3720
gcagtacaca ttttttgtagc tttcttgatt tagcaccac atcaaagcca gagtctttag   3780
```

| | |
|---|---|
| atgttaacat ctcatgggtt gatactgatc tggaccgggc tgaattcgac gtgatcatca | 3840 |
| ttggaactgg ccctgccggg cttcggctag ctgaacaagt ttctaaatat ggtattaagg | 3900 |
| tatgttgcgt tgacccttca ccactttcca tgtggccaaa taattatggt gtttgggttg | 3960 |
| atgagtttga aaagttggga ttagaagatt gtctagatca taagtggcct gtgagttgtg | 4020 |
| ttcatataag tgatcacaag actaagtatt tggacagacc atatggtaga gtaagtagaa | 4080 |
| agaagttgaa gttgaaattg ttgaatagtt gtgttgaaaa tagagtgaag ttttataaag | 4140 |
| ccaaggtttt gaaagtgaag catgaagaat tgagtcttc gattgtttgt gatgatggta | 4200 |
| ggaagataag tggtagcttg attgttgatg caagtggcta tgctagtgat tttatagagt | 4260 |
| atgacaagcc aagaaaccat ggttatcaag ttgctcatgg gatttagca gaagttgata | 4320 |
| atcatccatt tgatttggat aaaatgatgc ttatggattg gagggattct catttaggta | 4380 |
| atgagccata tctgagggtg aagaatacta agaaccaac attcttgtat gcaatgccat | 4440 |
| ttgataggaa tttggtattc ttggaagaga cttctttagt gagtcggcct atgttatcgt | 4500 |
| atatggaagt gaaaagaagg atggtagcaa gattaagaca tttggggatc aaagtgagaa | 4560 |
| gtgtccttga ggaagagaag tgtgtgatca ctatgggagg accacttccg cggattcctc | 4620 |
| aaaatgttat ggctattggt gggacttcag ggatagttca tccatcgtct gggtacatgg | 4680 |
| tggctcgtag catggcattg gcaccagtac tggctgaggc catcgtcgaa agccttggct | 4740 |
| caacaagaat gataagaggg tctcaacttt accatagagt ttggaatggt ttgtggcctt | 4800 |
| cggatagaag acgtgttaga gaatgttatt gtttcggaat ggagactttg ttgaagcttg | 4860 |
| atttggaagg tactaggaga ttgtttgatg ctttctttga tgttgatccc aagtactggc | 4920 |
| acgggttcct ttcttcaaga ttgtctgtca agaacttgc tgtactcagt ttgtacctt | 4980 |
| ttggacatgc ctctaatttg gctaggttgg atattgttac aaagtgcact gtccccttgg | 5040 |
| ttaaactgct gggcaatcta gcaatagaga gcctttgaat taatatgata gttttgaagc | 5100 |
| actgttttca ttttaattc ttaggttatt ttcatctttt ctcaatgcaa aagtgaaaca | 5160 |
| aaagctatac acattgtcat cgttgttcaa actcagacaa gtttgcctag ctctatgtat | 5220 |
| ttatccttaa catatgtatt catcaaattc gaaatataca atgcattgga caaaagtata | 5280 |
| gagccacaat ctgataccaa gtctgtattt ggaagcacag gctaattgtt atggttacca | 5340 |
| aacactttga attggctgga taataacaaa caggaaattt atgttattaa tcattaacag | 5400 |
| caaattggga agcaagaat tattaggaaa gttaatatag tgtcttggtt attctaatgg | 5460 |
| agtgggttat gcaaattaag ttcccttgtc aaagtttggt ttatgaactg ctccactctt | 5520 |
| gtccctctta aaagccttaa tcccaacatg taccaccaaa gaattgagct gctccatcag | 5580 |
| atcctttgag aatgttaata tgttatttaa atgaaggact gaatgattat gaggatgcaa | 5640 |
| tgcataggtt taattaccag ttatctgtaa attgtcttct ttgccattat tttaaaagtt | 5700 |
| taataacaag tgtaacatct acaaagagtt gataattaca aagcagctac tagttttagg | 5760 |

<210> SEQ ID NO 55
<211> LENGTH: 498
<212> TYPE: PRT
<213> ORGANISM: Capsicum annuum

<400> SEQUENCE: 55

Met Glu Thr Leu Leu Lys Pro Phe Pro Ser Pro Leu Leu Ser Ile Pro
1               5                   10                  15

Thr Pro Asn Met Tyr Ser Phe Lys His Asn Ser Thr Phe Pro Asn Pro
                20                  25                  30

```
Thr Lys Gln Lys Asp Ser Arg Lys Phe His Tyr Arg Asn Lys Ser Ser
         35                  40                  45

Thr His Phe Cys Ser Phe Leu Asp Leu Ala Pro Thr Ser Lys Pro Glu
     50                  55                  60

Ser Leu Asp Val Asn Ile Ser Trp Val Asp Thr Asp Leu Asp Gly Ala
 65                  70                  75                  80

Glu Phe Asp Val Ile Ile Ile Gly Thr Gly Pro Ala Gly Leu Arg Leu
                     85                  90                  95

Ala Glu Gln Val Ser Lys Tyr Gly Ile Lys Val Cys Val Asp Pro
                100                 105                 110

Ser Pro Leu Ser Met Trp Pro Asn Asn Tyr Gly Val Trp Val Asp Glu
                115                 120                 125

Phe Glu Lys Leu Gly Leu Glu Asp Cys Leu Asp His Lys Trp Pro Val
                130                 135                 140

Ser Cys Val His Ile Ser Asp His Lys Thr Lys Tyr Leu Asp Arg Pro
145                 150                 155                 160

Tyr Gly Arg Val Ser Arg Lys Lys Leu Lys Leu Lys Leu Leu Asn Ser
                165                 170                 175

Cys Val Glu Asn Arg Val Lys Phe Tyr Lys Ala Lys Val Leu Lys Val
                180                 185                 190

Lys His Glu Glu Phe Glu Ser Ser Ile Val Cys Asp Asp Gly Arg Lys
                195                 200                 205

Ile Ser Gly Ser Leu Ile Val Asp Ala Ser Gly Tyr Ala Ser Asp Phe
                210                 215                 220

Ile Glu Tyr Asp Lys Pro Arg Asn His Gly Tyr Gln Val Ala His Gly
225                 230                 235                 240

Ile Leu Ala Glu Val Asp Asn His Pro Phe Asp Leu Asp Lys Met Met
                245                 250                 255

Leu Met Asp Trp Arg Asp Ser His Leu Gly Asn Glu Pro Tyr Leu Arg
                260                 265                 270

Val Lys Asn Thr Lys Glu Pro Thr Phe Leu Tyr Ala Met Pro Phe Asp
                275                 280                 285

Arg Asn Leu Val Phe Leu Glu Glu Thr Ser Leu Val Ser Arg Pro Met
                290                 295                 300

Leu Ser Tyr Met Glu Val Lys Arg Arg Met Val Ala Arg Leu Arg His
305                 310                 315                 320

Leu Gly Ile Lys Val Arg Ser Val Leu Glu Glu Lys Cys Val Ile
                325                 330                 335

Thr Met Gly Gly Pro Leu Pro Arg Ile Pro Gln Asn Val Met Ala Ile
                340                 345                 350

Gly Gly Thr Ser Gly Ile Val His Pro Ser Ser Gly Tyr Met Val Ala
                355                 360                 365

Arg Ser Met Ala Leu Ala Pro Val Leu Ala Glu Ala Ile Val Glu Ser
370                 375                 380

Leu Gly Ser Thr Arg Met Ile Arg Gly Ser Gln Leu Tyr His Arg Val
385                 390                 395                 400

Trp Asn Gly Leu Trp Pro Ser Asp Arg Arg Val Arg Glu Cys Tyr
                405                 410                 415

Cys Phe Gly Met Glu Thr Leu Leu Lys Leu Asp Leu Glu Gly Thr Arg
                420                 425                 430

Arg Leu Phe Asp Ala Phe Phe Asp Val Asp Pro Lys Tyr Trp His Gly
                435                 440                 445
```

```
Phe Leu Ser Ser Arg Leu Ser Val Lys Glu Leu Ala Val Leu Ser Leu
            450                 455                 460
Tyr Leu Phe Gly His Ala Ser Asn Leu Ala Arg Leu Asp Ile Val Thr
465                 470                 475                 480
Lys Cys Thr Val Pro Leu Val Lys Leu Leu Gly Asn Leu Ala Ile Glu
                485                 490                 495
Ser Leu

<210> SEQ ID NO 56
<211> LENGTH: 1983
<212> TYPE: DNA
<213> ORGANISM: Capsicum annuum

<400> SEQUENCE: 56
```

| | | | | | |
|---|---|---|---|---|---|
| atgtatgcat | cgtctgccag | ggacggtatc | ccggggaaat | ggtgtaacgc | tcgccgtaag | 60 |
| cagctacctt | tattgatatc | caaggacttt | cctgcagagt | tgtatcattc | tttaccttgt | 120 |
| aagagtttgg | aaaatgggca | tcaagaag | gttaaaggag | taaaagccac | actagctgaa | 180 |
| gctccagcta | ctcctacaga | aagagtaac | tctgaggttc | cacagaagaa | gttgaaagta | 240 |
| cttgtggcag | tggtgggat | tggaggatta | gttttttgctt | tggcaggaaa | gaagaggggg | 300 |
| tttgatgtgt | tagtgtttga | gagagatata | agtgctataa | gaggtgaggg | gcaatataga | 360 |
| ggtccaattc | agatacagag | caatgcattg | gctgctttgg | aagcaattga | tatggatgtt | 420 |
| gctgaagaga | tcatgaatgc | tggctgtatc | actggtcaaa | ggattaatgg | cttggtcgat | 480 |
| ggtatttctg | gcaactggta | ttgcaagttt | gatacgttca | ctccagctgt | ggaacgtgga | 540 |
| cttcctgtga | caagagtcat | cagccgcatg | actttgcaac | agattcttgc | acgtctgcag | 600 |
| ggggaggatg | taattatgaa | tgaaagccat | gtagtaaatt | ttgcggatga | tggggagacg | 660 |
| gttactgtga | atcctgagtt | atgccaacaa | tacacaggtg | atcttctggt | tggtgctgat | 720 |
| ggcataaggt | ctaaggtacg | gactaatttg | ttcggaccga | gtgaactaac | ttactctggt | 780 |
| tacacttgtt | atactggaat | tgcagatttc | gtccctgctg | atattgacac | agctggctac | 840 |
| cgagtcttt | tgggccacaa | acagtacttt | gtttcttcag | atgtgggtgg | aggcaagatg | 900 |
| cagtggtatg | catttcacaa | tgaaccagct | ggtggtgtgg | atgctccaaa | cggtaaaaag | 960 |
| gaaagattgc | ttaaaatatt | tgggggatgg | tgtgacaacg | ttatagacct | ttcagtcgcc | 1020 |
| acagatgaag | atgcaattct | tcgtcgtgac | atctatgata | gaccccccaac | atttagttgg | 1080 |
| ggaaaaggtc | gtgttacatt | gcttgggac | tctgtccatg | ctatgcagcc | taatttgggt | 1140 |
| caaggaggat | gcatggccat | agaggatagc | tatcaactag | cactggaact | tgagaaagca | 1200 |
| tggagccgaa | gtgctgagtc | cggaagccct | atggatgtca | tctcatcttt | acggagctat | 1260 |
| gaaagtgcta | gaaaactccg | agttggagtt | atccatggac | tggctagaat | ggctgcaatc | 1320 |
| atggcatcag | cttacaaggc | ctatcttggt | gtcggactgg | gtccattatc | attcattacc | 1380 |
| aagtttagga | taccacatcc | tggaagagtt | ggtgaagat | tttttattga | cttgggaatg | 1440 |
| ccgcttatgt | taagctgggt | tctaggaggc | aacggggaaa | agcttgaagg | cagaatacaa | 1500 |
| cattgcagac | tatctgagaa | agcaaatgac | caattgagaa | attggttga | agatgatgat | 1560 |
| gctttagagc | gtgctactga | tgcagagtgg | ctattgcttc | ctgccgggaa | tagcaatgct | 1620 |
| gctttagaaa | ctctcgtttt | aagcagagat | gagaacatgc | cttgcactat | cgggtctgtc | 1680 |
| tcacatgcaa | acattcctgg | aaaatcagtt | gttattcctt | tgtctcaggt | gtccgatatg | 1740 |
| cacgcccgga | tatcctacaa | tggtggcgca | tttctcggca | ctgctttccg | aagtgaccat | 1800 |

| | |
|---|---:|
| ggcacttggt ttatagataa cgaaggcaga agatatcggg tgtctccaaa cttcccaatg | 1860 |
| cggtttcatt catcagatgt aatcgtattt ggttctgata aggcagcatt tcgtataaag | 1920 |
| gctatgaaat ttgccccaaa aactgctgca aaagaagatc gtcaagcagt gggggcagct | 1980 |
| tag | 1983 |

<210> SEQ ID NO 57
<211> LENGTH: 613
<212> TYPE: DNA
<213> ORGANISM: Capsicum annuum
<220> FEATURE:
<221> NAME/KEY: misc_feature
<222> LOCATION: (59)..(59)
<223> OTHER INFORMATION: n is a, c, g, or t
<220> FEATURE:
<221> NAME/KEY: misc_feature
<222> LOCATION: (475)..(475)
<223> OTHER INFORMATION: n is a, c, g, or t

<400> SEQUENCE: 57

| | |
|---|---:|
| ctgtagctcc acattgcttc ctacatagga cttgctcaga atagaactcg aaaaagagna | 60 |
| ccaattgaat gtaaatactt caacaactta ggtagggaca tcttatattg ctaaatacag | 120 |
| tgcccactct gcacagacta ggcatacaaa gcattccggc ccatcttagt gaagaaacat | 180 |
| gatatttgtt cacgtccatt agtttgtttg tacccgtctt tagttgttat ctattcgtga | 240 |
| tatcaagaat ataagactg gtggcttat tcacgtaaat tgtagtcctt gcctcagtag | 300 |
| taaaattttg tttcytgtca atagaggtac agtctttaga ttcaacttcc tcccttgtcc | 360 |
| atgcagtttg tgcttcttct gatgttgcgt acaatgctgc caataatcgt cggtgttgct | 420 |
| ggagataact cggtaatatt ggtcatggtt agtgtcacag ttatatttcc tttgnaaatg | 480 |
| aaaattctgc ttttcctcg gttcatttat atgttcatct ttatagttat tagtgttgaa | 540 |
| agctattgga atcctactgg cagtctatgt tgtggtgaaa acttttattg ctgtacgaca | 600 |
| tcggaggcat cag | 613 |

<210> SEQ ID NO 58
<211> LENGTH: 2007
<212> TYPE: DNA
<213> ORGANISM: Capsicum annuum

<400> SEQUENCE: 58

| | |
|---|---:|
| ggggatcgac attgatccaa ctgccaaaat tgtccttagg acagtaagga gtatgagaca | 60 |
| atccattaga tctagctcct ccttcccta c atgcagatga ccctaaccag tggatcgata | 120 |
| aatttccttt aaccattggc taaaagtgag ttgagaaaaa ataaagaga aacctaatt t | 180 |
| acttccctca gtgacccctt tgtcttccat gcttcaagta tgtgtacctt tgacatgttt | 240 |
| ctgctgctat ggttatcaga caatgcgacg atgcatttct gcatccgtgg tgtgttttct | 300 |
| tctgtgcctt ttgacatcgt gtttcatttt cctctttatg tttgctaaca gtttgatttt | 360 |
| aagaggcctt gctaaagaga tggatgtctt ctgtttctta cgagctatct ctgcttcttt | 420 |
| agcccttcaa gataccttaa cagtgcattt gttaatactc tcttgtagca ctagcagata | 480 |
| actactgcat ataccatttc tatttctctt cttcttgtta aagtaattgc cgtagttgta | 540 |
| ctactgatcg ttctagtctc ttgaaaatac tgctatcctg ccttttcttg aatcattacc | 600 |
| ttttgaagaa ctcagcacat tttttcagtt tggtgtctct gaggcatgat taaccacttt | 660 |
| caataaaaat ttcatgcat atgacagaat gtgtatgcac tgactttgtt ggaacctaag | 720 |
| taaacagcaa ccatcttcat gcctttcttg accaaagaag ttgctgacac ggctttgaca | 780 |

| | |
|---|---|
| tctgcatgtt tgttatccac agttcagaag ttacagccta catcctctag acctcactca | 840 |
| ataatttagc aacttttcct tgcattatgt gtttacttcc atttgtttga tcatttactt | 900 |
| ggttaacatg tagaattgga gttgtatctg ggaaagctat atttgcacaa ccacttgatg | 960 |
| aatattggaa gaagaaactt caggagaaac cagccgcaaa agaaaatgat gtaagcacct | 1020 |
| catagcgttt ggtgatctga gcttaatatc gtagtatttt tctgttggcc gttactctat | 1080 |
| aaaaatgcct tgtgtatcca caacctcatc caaataacta attacatgat gctctagaaa | 1140 |
| tttcatcctt cagttgtttg tatgagactg cccatcaaaa ctatccacgt ttttaatctt | 1200 |
| gtcgcgaaat attacatatc aattgggata aaattgtgcc catgttactt tacgtttctt | 1260 |
| tgaagtattt ggatgaagta ttcatgtggt cagaaccaaa attgatcatt tagaaaggat | 1320 |
| gctgattact gaatgtaatg tcatcaagca taatttgttc ctttaatttg gaattatctg | 1380 |
| tactcggcac tagtgtgtgt ccctttcctt ggttctgttg tgcactggct tggcgctaat | 1440 |
| ttagaacatc tgcattaaac gcctggacta aatgctgata tttaatgctg aaatgtgtgt | 1500 |
| aataatcaca attgacgctg gtaatatag atttctcatca gattataatc ttacagatga | 1560 |
| tctccatgag gtagggtcag tgggttaagg gttctctttt atagtgtaaa agttaattta | 1620 |
| ttcgtttagt tggttgcaga gcattacata gcttttaata ttctctttac ttaacagaac | 1680 |
| tatgatcact tcaactgagt gaagaaaagg aaaagaacca ctgacaggag acagagaaat | 1740 |
| tacgggcata attacattca ctcgacaaac atgaattgaa atacaatcaa tcaacaagga | 1800 |
| caaaccaatg atatacagyt gtactatcca agattccctt ggcaaaagaa tgtaatactc | 1860 |
| taggaagttt aacaaataaa agttgtcttc cccaagattc taatcgaaac ttctaatttg | 1920 |
| gaaccaagat ccaaggacca ttaagtatgt gtaaacatag agagaggcat atactaacag | 1980 |
| tagtagaaga tttcccaccc acatacc | 2007 |

<210> SEQ ID NO 59
<211> LENGTH: 336
<212> TYPE: DNA
<213> ORGANISM: Capsicum annuum

<400> SEQUENCE: 59

| | |
|---|---|
| gtcaattctt tgtttcttgc agagctagta cttttttgtct tgttggacca atccctttac | 60 |
| aytggagggg gtccttgttt gctttctcct ctgaaaaatg tacgtattga ctgcaacatg | 120 |
| gtctacaagg aagaactttc ttttgcatat acaacaatag agacgttaat aaattctctt | 180 |
| tggaaaacta ctttattact gttctgatta ttcaatagct acttggatca ataatgatgt | 240 |
| aagagacaca atagcaatac taggtttagg gacttgtgtt atcttctctt tgttgcattc | 300 |
| agaatgaagg gacgattcta taactgctgt ctgtca | 336 |

<210> SEQ ID NO 60
<211> LENGTH: 963
<212> TYPE: DNA
<213> ORGANISM: Capsicum annuum

<400> SEQUENCE: 60

| | |
|---|---|
| ggttttcttg tttgcatgcg ccattgctct tctagcttct tcatcaatgg tttctgctga | 60 |
| agttatcgag cattcttttc aagtatataa ctctcctctt tttatttcct atttatgcaa | 120 |
| attaggttct ccttttttgc acccatctc gagaaaataa atgaaatt tacatatata | 180 |
| tatatataga ggtgtcaaaa aaaagtttg tgttaataaa tgagtatgct attgactcac | 240 |

| | |
|---|---:|
| ccaattgtta tttgagttga aatggattaa acgatgggtc ataacctaac tcttctttt | 300 |
| ttgcaatttg tctaagtata gccctaagta attttttttt ctttgtcctg gttatacata | 360 |
| acatatcaaa tagaagttta tttctggaaa aaaagacatt ttaacaaggt aaatgttttg | 420 |
| tgaagacttt cctttgatc caagggtcta gcggaagcaa cctttcaacc tcacaagagt | 480 |
| cggggtgaag tttgtataca tcccactccg tcagacctca ttgtggtatt acaatggata | 540 |
| agctattgtt gttgttgtaa atgttttgtg agtgataaga ttatgtattt ggttggtgta | 600 |
| ggtgcaaaac cttactataa acaggttatg ccgtagacaa gtaataaatg cagtaaatgg | 660 |
| aagtcttcct ggtccaactc tacatgtacg tgagggcgac accmttgttg ttcatgtctt | 720 |
| caataaatta ccatacgatc tcactatcca ttggtatgtc attcacgtta atttaattaa | 780 |
| aggatttaac ttatatacat tgctagcgca tagaaatttt atactatcaa tgttaatta | 840 |
| atcacaagag gttgttattt cattttaat atcaaaatta ataccatact aaagcgtaac | 900 |
| gtgtggttac cataagatct ccaatcaaat cttctttct ttttcctatc aaatttcact | 960 |
| ttc | 963 |

<210> SEQ ID NO 61
<211> LENGTH: 2014
<212> TYPE: DNA
<213> ORGANISM: Capsicum annuum

<400> SEQUENCE: 61

| | |
|---|---:|
| ggatgtaata aatcattttg ttttatctga ggaagtatga agaagagtaa tacttcaccc | 60 |
| aaaagcttca ttaataaaat tcagaaaggt aaacagtaac ttacagtatc aactggaatt | 120 |
| gaaaagccaa cacccgatga tgcaccggaa ggagaatata tagcagtatt tattccaata | 180 |
| aggtttccag aactatctag aagtggtcct ccactgttac cgggattgat tgctgcgtct | 240 |
| gtctgaataa catcttggat tggacggcca gtagctgcag aattgatttc tcttctaagg | 300 |
| ccactagaaa catataaatt aatcagttat attaaagaaa atgtatgata aatagcatat | 360 |
| actttataca wcaccaacac atcttgcttt tgcgtataat atatccatt actgcgagat | 420 |
| atggttattg catatgtaat acgtttgctt cttggatttt atggatgcaa ggctctagac | 480 |
| agtgacaacc aaccaatcta tcctataaca atctgctttc tgccatattt cagaaatgaa | 540 |
| aacaaaaggt ggaccttacg gaaagatgag gagtattgga cacacttgaa agatataatc | 600 |
| tccctttgtc gttcaaaaag caaagaaaag atagagatca agaaagccac caacattgaa | 660 |
| aaactcgtat ttcagttgaa atggatgaag aagattaatc aaaactctct acttcatctc | 720 |
| aattctaaac aaaggaaaga aggttacttc atttttattt atttaattc ctctcattta | 780 |
| cttccttcac tttgttagtc attaattcca caagccttct accaagattt tgagtgtccc | 840 |
| atattcattt tattttatct cctatcttca cacaacactg ttagcaccat ttcactggaa | 900 |
| tatctgaaca ttaggaactt gtgcacaata atatgaaata gtaaatacc tgataacacc | 960 |
| agtggtgagt gtatgatcaa gtccaaactg caacatattt acataaaaga ccagtcatca | 1020 |
| ggtgttttcca gatgaaaatt aaaagagaag taaatatta atgtttcata gtaaattata | 1080 |
| cgaatacaga ggaaaagag gcgtgaaggg ggaaggcta cccaaatata agaaacatgc | 1140 |
| acccatttca acaagagatc tagttccaat gtgtaagtca agtacgttga ttttaatgta | 1200 |
| agtcagtgcg aaattttggc agaagttgga gcactagatt aaaggaggga attgttatgc | 1260 |
| tctaaacttg ggggaaaaca agcagttaaa aatattagca ggctggtaaa ggttcagaag | 1320 |
| tagcagctaa cttcagatg ggctaatggg caaagatttg aaacagaaga cagaaataag | 1380 |

```
ttgtactctc tatcagttgt ttttttttct tgcacaaatt ttcgtaataa gaaaaatgca    1440
ctagaaatct gtatgcaaag ttatactttc taactgttgt aatgctcatg aacgcctgca    1500
agccaaattg catagactct gcatttcgat gccgcacgcg tgtcggatgc tccaaaaata    1560
cacttctttt tatatttgga gaatccggca cgcaccccact gacattttg aagagtccaa    1620 gcaacatagc ctgcaagaca attgttttct cgaaagcaag gactgaatat gaaatggacc    1680
aaactagttt agagaaggga caatagacca gactaaaagc gctatcatta aaagggtag    1740 ctcggtgcac taaagctatt gctatgcgcg gtgtccggag aagggcccca ccacaagggt    1800
gtatcgtacg cagccttacc ttgcatttct gccagaggct gtttccaaga ctttaacccg    1860
tgacctcctg ataacatgac aacaacttta ccagttactc caaggctccc cttcaaaagt    1920
gctatcatta catgaataga attctctatc aggtttgtat ttcatcacat acaggatttc    1980
caatagcaaa tacttttga ccaacgagca agtc                                 2014

<210> SEQ ID NO 62
<211> LENGTH: 1216
<212> TYPE: DNA
<213> ORGANISM: Capsicum annuum

<400> SEQUENCE: 62
ccttagcttg cgtctctctt gatctcgatt cctctggtgc ttcttttgaa ttacattcca      60
attctttctc gttttgtaa ttttcttgac ttttggcctc tgcacccagt tgcacatatg     120
gggtaatgct gtctttgggc gtaccattga cgccagtgct gcttgttgga acagtttcct    180
ccctctctaa tgtaagtaga ggatatgctg cttgatcttg tagctgctta gttgcattgc    240
tttcactgct caccatgtta tccattgcta tctccttttc cggaacctta acagatgtca    300
atgatgtcaa atgttctgtt atttcttctt gctcattcct tgttttttcc tcttgttcac    360
ctcctacttg ggtaattgga gcattttcag tctttaattc ttctttctgt gtttcttttg    420
tttcatcgca tgttatcatc tctccgaaac ctgctgctgt ttttctttct gatccaaaag    480
gttccaaact tcctctttca ggttcacttg ttgttgttcc ctgctcttgc tgtacctgtg    540
ttgtgytgtt gtttgaggaa tcttggccgg tgctctctct taagtcttct tcttgttcct    600
cctatgagtt catatcttac cgtcagaaat cttgattgaa ttgttgcgcg agtaaatagg    660
ggagacagag gggtgtatga aaagattgga ataatgtatt ttgcttctat ttttttagct    720 ttttttcctca ctgtttatag tctagatcca gttttataat tcagaattat gatttcttgt    780
agcagattgc aaatcggcat ttatgttata ctctgcctgt gtatatgaaa tgtttcatgc    840
agttgaccat gcataatgtt ttcacggcaa catctttca atcccctctt tgcacgagaa    900
tacaaaaact gaaaataata tatagtcatc tagagatttg tgaccttaac taacttggag    960
ttgtggctta gatgttgtca tcgttgttgt tctgaaatat tgtgcagcag gagaaccaaa   1020
tttctaggtt cataaacatg caataaactc atagattctc gtagatgct aatcagctaa    1080 cgttgtaagt tcttgttcat ttaccttgtt agtattgtcc tccaccctca tttcttctga   1140
agaaagttca attgcgttct ccactccacg cacgtcttta acctcttctg tggttaggtt   1200 ggcttttga aggttc                                                    1216

<210> SEQ ID NO 63
<211> LENGTH: 25
<212> TYPE: DNA
<213> ORGANISM: Artificial sequence
<220> FEATURE:
```

<223> OTHER INFORMATION: primer

<400> SEQUENCE: 63
cgtaaattgt agtccttgcc tcagt                                    25

<210> SEQ ID NO 64
<211> LENGTH: 25
<212> TYPE: DNA
<213> ORGANISM: Artificial sequence
<220> FEATURE:
<223> OTHER INFORMATION: primer

<400> SEQUENCE: 64
ggacaaggga ggaagttgaa tctaa                                    25

<210> SEQ ID NO 65
<211> LENGTH: 19
<212> TYPE: DNA
<213> ORGANISM: Artificial sequence
<220> FEATURE:
<223> OTHER INFORMATION: Primer

<400> SEQUENCE: 65
ctctattgac aagaaacaa                                           19

<210> SEQ ID NO 66
<211> LENGTH: 17
<212> TYPE: DNA
<213> ORGANISM: Artificial sequence
<220> FEATURE:
<223> OTHER INFORMATION: Primer

<400> SEQUENCE: 66
ctattgacag gaaacaa                                             17

<210> SEQ ID NO 67
<211> LENGTH: 23
<212> TYPE: DNA
<213> ORGANISM: Artificial sequence
<220> FEATURE:
<223> OTHER INFORMATION: Primer

<400> SEQUENCE: 67
ctggtccaac tctacatgta cgt                                      23

<210> SEQ ID NO 68
<211> LENGTH: 29
<212> TYPE: DNA
<213> ORGANISM: Artificial sequence
<220> FEATURE:
<223> OTHER INFORMATION: Primer

<400> SEQUENCE: 68
ccaatggata gtgagatcgt atggtaatt                                29

<210> SEQ ID NO 69
<211> LENGTH: 16
<212> TYPE: DNA
<213> ORGANISM: Artificial sequence
<220> FEATURE:
<223> OTHER INFORMATION: Primer

<400> SEQUENCE: 69
agggcgacac cattgt                                              16

```
<210> SEQ ID NO 70
<211> LENGTH: 16
<212> TYPE: DNA
<213> ORGANISM: Artificial sequence
<220> FEATURE:
<223> OTHER INFORMATION: Primer

<400> SEQUENCE: 70
agggcgacac ccttgt                                                    16

<210> SEQ ID NO 71
<211> LENGTH: 28
<212> TYPE: DNA
<213> ORGANISM: Artificial sequence
<220> FEATURE:
<223> OTHER INFORMATION: Primer

<400> SEQUENCE: 71
caatcaatca acaaggacaa accaatga                                       28

<210> SEQ ID NO 72
<211> LENGTH: 29
<212> TYPE: DNA
<213> ORGANISM: Artificial sequence
<220> FEATURE:
<223> OTHER INFORMATION: Primer

<400> SEQUENCE: 72
ctagagtatt acattctttt gccaaggga                                      29

<210> SEQ ID NO 73
<211> LENGTH: 22
<212> TYPE: DNA
<213> ORGANISM: Artificial sequence
<220> FEATURE:
<223> OTHER INFORMATION: Primer

<400> SEQUENCE: 73
atcttggata gtacagctgt at                                             22

<210> SEQ ID NO 74
<211> LENGTH: 22
<212> TYPE: DNA
<213> ORGANISM: Artificial sequence
<220> FEATURE:
<223> OTHER INFORMATION: Primer

<400> SEQUENCE: 74
atcttggata gtacaactgt at                                             22

<210> SEQ ID NO 75
<211> LENGTH: 27
<212> TYPE: DNA
<213> ORGANISM: Artificial sequence
<220> FEATURE:
<223> OTHER INFORMATION: Primer

<400> SEQUENCE: 75 gtacttttg tcttgttgga ccaatcc                                         27

<210> SEQ ID NO 76
<211> LENGTH: 24
<212> TYPE: DNA
<213> ORGANISM: Artificial sequence
<220> FEATURE:
<223> OTHER INFORMATION: Primer
```

<400> SEQUENCE: 76
accatgttgc agtcaatacg taca                                          24

<210> SEQ ID NO 77
<211> LENGTH: 16
<212> TYPE: DNA
<213> ORGANISM: Artificial sequence
<220> FEATURE:
<223> OTHER INFORMATION: Primer

<400> SEQUENCE: 77 cccctccaa tgtaaa                                                    16

<210> SEQ ID NO 78
<211> LENGTH: 16
<212> TYPE: DNA
<213> ORGANISM: Artificial sequence
<220> FEATURE:
<223> OTHER INFORMATION: Primer

<400> SEQUENCE: 78 cccctccag tgtaaa                                                    16

<210> SEQ ID NO 79
<211> LENGTH: 35
<212> TYPE: DNA
<213> ORGANISM: Artificial sequence
<220> FEATURE:
<223> OTHER INFORMATION: Primer

<400> SEQUENCE: 79
tcagttatat taaagaaaat gtatgataaa tagca                              35

<210> SEQ ID NO 80
<211> LENGTH: 31
<212> TYPE: DNA
<213> ORGANISM: Artificial sequence
<220> FEATURE:
<223> OTHER INFORMATION: Primer

<400> SEQUENCE: 80
gcagtaaatg gatatattat acgcaaaagc a                                  31

<210> SEQ ID NO 81
<211> LENGTH: 19
<212> TYPE: DNA
<213> ORGANISM: Artificial sequence
<220> FEATURE:
<223> OTHER INFORMATION: Primer

<400> SEQUENCE: 81
atgtgttggt gttgtataa                                                19

<210> SEQ ID NO 82
<211> LENGTH: 19
<212> TYPE: DNA
<213> ORGANISM: Artificial sequence
<220> FEATURE:
<223> OTHER INFORMATION: Primer

<400> SEQUENCE: 82
atgtgttggt gatgtataa                                                19

<210> SEQ ID NO 83
<211> LENGTH: 22

-continued

```
<212> TYPE: DNA
<213> ORGANISM: Artificial sequence
<220> FEATURE:
<223> OTHER INFORMATION: Primer

<400> SEQUENCE: 83
gttgttccct gctcttgctg ta                                              22

<210> SEQ ID NO 84
<211> LENGTH: 20
<212> TYPE: DNA
<213> ORGANISM: Artificial sequence
<220> FEATURE:
<223> OTHER INFORMATION: Primer

<400> SEQUENCE: 84
caccggccaa gattcctcaa                                                 20

<210> SEQ ID NO 85
<211> LENGTH: 18
<212> TYPE: DNA
<213> ORGANISM: Artificial sequence
<220> FEATURE:
<223> OTHER INFORMATION: Primer

<400> SEQUENCE: 85
cctgtgttgt gttgttgt                                                   18

<210> SEQ ID NO 86
<211> LENGTH: 17
<212> TYPE: DNA
<213> ORGANISM: Artificial sequence
<220> FEATURE:
<223> OTHER INFORMATION: Primer

<400> SEQUENCE: 86
ctgtgttgtg ctgttgt                                                    17

<210> SEQ ID NO 87
<211> LENGTH: 526
<212> TYPE: DNA
<213> ORGANISM: Capsicum annuum

<400> SEQUENCE: 87
cccaataayc caatactaat aacttaataa tatttttatc ggttcgattt atcgatcggc     60
tcaactacca aaaggaacaa aaaaataaat agagtactac aacaaccata gatgagtgaa    120
caagcgtcaa acatcagcct cagtttagta acccaaacaa gctacaatga caagccacct    180
ggccataaaa tcttcaccat tgctgcttca tggaccattg attggttctc aatcttcttt    240
gccccaccac caccaccacc ctcactatca cccacaattt ccacttcctt tttttccctcc   300 tcaaaagcct aactaacaca cattggccta actaaaattc tcataaatca ccttcacttc    360 ttttttttcat tagattatac attagttgtt tggtctcaat cttcctttca cttccttttgg  420 cctaattaac agtttatata aatcaacttc acttcttttt ttcactaaaa catacagtga    480
aagagaaaca caagagtctt ttcttgaact ggagttctag tgaaag                   526

<210> SEQ ID NO 88
<211> LENGTH: 638
<212> TYPE: DNA
<213> ORGANISM: Capsicum annuum

<400> SEQUENCE: 88
```

```
taaaaaatag tagttaattt tgaatgaaga cttacaaata cgaaaatcta taaaagaaat      60
tcatgaagga aactggccta taattgtata tacatagaga attagtatat atttaggaaa     120
tggtagaata agaaacaatg accatcactt tctctataca tttaggaaat ggtagaataa     180
gaaacaatga ccatcacttt ttccacgttc tttagaagaa agccaaataa tctctgtatt     240
tgttgaatct gttttgttta tcaatcttct acaatgtctg atgtttctat aaaatgctgt     300
acaaatttcc cgtttatgct gtccccacga ctttgcgctc ttccttcgct tcagcagttt     360
ttgaaggaaa tttcattgtc tttacacgaa atgctgccyg cataacataa acaaatggat     420
ttgaatgagt aataagctac tgccaatgcc aacgtatctt taaagcata tcaagcaaga     480 atttcacgaa tcacacctta tcagaaccaa atacgattac atctgatgaa tgaaaacgca     540
tagggaagtt tggagacacc cgatatcttc tgccttcatt actacataat gcagaacaat     600
gtaattcttt tgtcttcata gactaataaa tgtgatgc                            638
```

<210> SEQ ID NO 89
<211> LENGTH: 509
<212> TYPE: DNA
<213> ORGANISM: Capsicum annuum

<400> SEQUENCE: 89

```
ggcagcattt cgtgtaaaga caatgaaatt tccttcaaaa actgctgaag cgaaggaaga     60
gcgcaaagtc gtggggacag cataaacggg aaatttgtac agcatttat agaaacatca    120 gacattgtag aagattgata aacaaaacag attcaacaaa tacagagatt atttggcttt    180
cttctaaaga acgtggaaaa agtgatggtc attgtttctt attctaccat ttcctaaatg    240
tatagagaaa gtgatggtca ttgtttctta ttctaccatt tcctaaatat atactaattc    300
tctatgtata tacaattata ggccagtttc cttcatgaat ttcttttata gattttcgta    360
tttgtaagtc ttcattcaaa attaactact attttttact tttatttcta acktgcatta    420 tttttttactt ttatttctaa cttgcatttt atgttcattg ttgattttat acataataaa    480
atgaaacaaa tagaaaaaaa taataaatt                                       509
```

<210> SEQ ID NO 90
<211> LENGTH: 5
<212> TYPE: DNA
<213> ORGANISM: Capsicum annuum

<400> SEQUENCE: 90

```
caggc                                                                   5
```

<210> SEQ ID NO 91
<211> LENGTH: 5
<212> TYPE: DNA
<213> ORGANISM: Capsicum annuum

<400> SEQUENCE: 91

```
cgggc                                                                   5
```

<210> SEQ ID NO 92
<211> LENGTH: 29
<212> TYPE: DNA
<213> ORGANISM: Artificial sequence
<220> FEATURE:
<223> OTHER INFORMATION: Primer

<400> SEQUENCE: 92

```
cagcagtttt tgaaggaaat ttcattgtc                                        29
```

<210> SEQ ID NO 93
<211> LENGTH: 25
<212> TYPE: DNA
<213> ORGANISM: Artificial sequence
<220> FEATURE:
<223> OTHER INFORMATION: Primer

<400> SEQUENCE: 93
ggcattggca gtagcttatt actca                                          25

<210> SEQ ID NO 94
<211> LENGTH: 17
<212> TYPE: DNA
<213> ORGANISM: Artificial sequence
<220> FEATURE:
<223> OTHER INFORMATION: Probe

<400> SEQUENCE: 94
atgttatgcg ggcagca                                                   17

<210> SEQ ID NO 95
<211> LENGTH: 17
<212> TYPE: DNA
<213> ORGANISM: Artificial sequence
<220> FEATURE:
<223> OTHER INFORMATION: Probe

<400> SEQUENCE: 95
atgttatgca ggcagca                                                   17

<210> SEQ ID NO 96
<211> LENGTH: 5752
<212> TYPE: DNA
<213> ORGANISM: Capsicum annuum

<400> SEQUENCE: 96
cccaataatc caatactaat aacttaataa tattttatc ggttcgattt atcgatcggc      60
tcaactacca aaaggaacaa aaaaataaat agagtactac aacaaccata gatgagtgaa    120
caagcgtcaa acatcagcct cagtttagta acccaaacaa gctacaatga caagccacct    180
ggccataaaa tcttcaccat tgctgcttca tggaccattg attggttctc aatcttcttt    240
gccccaccac caccaccacc ctcactatca cccacaattt ccacttcctt ttttccctcc    300
tcaaaagcct aactaacaca cattggccta actaaaattc tcataaatca ccttcacttc    360 ttttttcat tagattatac attagttgtt tggtctcaat cttcctttca cttcctttgg      420
cctaattaac agtttatata aatcaacttc acttcttttt ttcactaaaa catacagtga    480
aagagaaaca caagagtctt tcttgaact ggagttctag tgaaagatgt attcaactgt      540
gttttacact tcagttcatc cctccacttc agttttttca agaaaacagc tacctttatt    600
gatatccaag gactttcctg cagagttgta tcattcttta ccttgtaaga gtttggaaaa    660
tgggcatatc aagaaggtta aaggagtaaa agccacacta gctgaagctc cagctactcc    720
tacagagaag agtaactctg aggttccaca gaagaagttg aaagtacttg tggcaggtgg    780
tgggattgga ggattagttt ttgctttggc agcaaagaaa aaggggtttg atgtattggt    840
gtttgagaga gatttaagtg ctataagagg tgagggcaa tatagaggtc caattcagat      900
acagagcaat gcattggctg ctttggaagc aattgatatg gatgttgctg aagagatcat    960
gaatgctggc tgtatcactg gtcaaaggat taatggcttg gtcgatggta tttctggcaa   1020

```
ctggtaaatt cacatcactc tgatttgatt gtgctgatta agagcttgtg tgcctttttt    1080
gctactgtat ttactttcca aacttgttcg gttatgcttt acttaagccg agggtcttca    1140
ggaatagtct ctctaccttc acgagatatg attaaggtct gcgcacgcaa tacccttctc    1200
agaagggtaa tcacactggc tatgttgttg ttgtaattaa atgcttgtct gtcttttttt    1260
agttgagctt taactgagga taccccagga aaataatgaa ttctttgaaa tatttagccc    1320
tttaaaaaag tatagggaaa ataattcatt tagtcacaag tttattgaat catggttgcc    1380
aagcttattc gggaaaagga tcctatcttt accttcaaat ggcttcaatc agattgataa    1440
gttagtctta ttgttgtatg agcagcttat tgtgagaaca gtcccttta ttcttgaact    1500 gcgaacagtg acaatagttg ggtatcaggt attgcaagtt tgatacgttc actccagctg    1560
tggaacgtgg acttcctgtg acaagagtca tcagccgcat gactttgcaa cagattcttg    1620
cacgtgctgt aggggaggat gtaattatga atgaaagtaa tgtagtaaat tttgaggatg    1680
atggggagaa ggtaatgcta ggtttgatct ctttgttttc tgctattctc aaaatatcaa    1740
gaaagattat aacttttctt aatttcattt gcatcattgt taattgttgt ttcttattca    1800
tcaattttcg ttaaagcttc tcatgtgctg tgtgaaatca ggttactgtg gttcttgaga    1860
atggacaacg gtttacaggt gatcttctgg ttggtgctga tggcataagg tctaaggtat    1920
tcaaaatcag tctcattata tttctttcta ttattactac ttcggttaac aaggatagag    1980
taacttgttt atattttact ttgagattgt ggttccacgt taaaaaattg tctgttgact    2040
gataggcctg agtccgtatt atgcagtgaa ccttttattg attattctag ttgattcaga    2100
agatcacaaa catttccgtt gtgttgtagg tacggactaa tttgttcgga cacagtgaag    2160
ctacttactc tggttacact tgttatactg gaattgcaga tttcgttcct gctgatattg    2220
acacagttgg gtatgatatt ctttcttacc ggattgtgtt tccactcatg cccttatccc    2280
tgctggtgcc gttacactca cacgaggttt tcatagtaga gattaaattg agatttcttt    2340
tctgaaggta ccgagtcttt tgggccacaa acagtactt tgtttcttca gatgtgggtg    2400
gaggcaagat gcagtggtat gcatttcaca atgaaccagc tggtggtgtg gatgctccaa    2460
acggtaaaat tttaggccg cttaaaacta tttactatag ttcaggatat agacatactt    2520
actagaagac gtttttgaat gcttaacttg taacgtttat ttaacccaag gggtttctta    2580 agaattttc ctcattgagg cctggttata gtgttgcaat aaggtaaaga acaactcaag    2640
attagaataa gatagactca aatgtattat gagtcggaaa gttttgaatt gaagttgctg    2700
actctatgaa ttaggagttg tttaatattt tgtctgttca tgctgcaggt aaaaaggaaa    2760
gattgcttaa aatatttggg ggatggtgtg acaacgttat agacctatta gttgccacag    2820
atgaagatgc aattcttcgt cgtgacatct atgatagacc gccaacattt aattggggaa    2880
gaggtcgtgt tacattgctt ggggactcag tccatgctat gcagcctaat ttgggtcaag    2940
gaggatgcat ggcctataga gtacaccact gtgtttatca tctttgtcaa atacacagta    3000
ttgtaaggtt gtgtatgaca ctgaactttt ccatgtacaa ctacaggata gctatcaact    3060
agcactggaa cttgagaaag catggagccg aagtgctgag tccggaagcc ctatggatgt    3120
catctcatct ttaaggaggt aatccattat ttattggctc aagtgctgta gtctggttgg    3180
ttgagtacag gctgccagtt catgataatt gaaaaaacat ttgcaattgg ttgaggtctt    3240
taacttcacc ccaccaccag cccagtagga ctgctttaaa tgcctcaact gaaaatggat    3300
tgatttgaac agctgccgtg tctgccagtt cgctgatcct ttaatgaatt tccttttct    3360 gcagctatga aagtgctaga aaacttcgag ttggagttat ccatggactg gctagaatgg    3420
```

```
ctgcaatcat ggcatcaact tacaaggcct atcttggtgt cggacttggt ccattatcag    3480
tatgaaaaac tatctatcac ttgaaattgg aatggcatag ccaatttgcg tgattgcgca    3540
gagctcttct tataatagat gttttttct attatttgtg cagttttga ccaagtatag     3600 gataccacat cctggaagag ttggtggaag agtatttgtg gacttgggaa tgcctctaat   3660
gttaagttgg gttctaggag gcaacgggta ggaatatgcg agctgtattc cagcattttc   3720
ttgcttcagt atttttgaaca tgattttggt ttctatgtga atccgtgatg agttgctgg   3780 agatcttgga agttgatatc ctgtggtttg actcgtcttt tttcttttct tgcagcgaca   3840
agcttgaggg tagaatacaa cattgcaggc tatctgagaa agtatgtagc gtaaggaact   3900
atgcactcaa cacacgaaca cagaaaagat ttctggcttc cattgctact taattaaggt   3960
ccaactatgg attttacggg tgtgttaata tactgtactg tggtgatgaa ggcaaatgat   4020
caattgagaa gatggtttga agatgatgat gctttagagc gtgctactga tgcagagtga   4080
gttaatggaa cgtaatattt aaaaatttca tttttacatg tctcattttc ctagtttgct   4140
ttctaatttg gtgcttacgt tttatctttc aggtggttac tgttacctgc agcgaatggc   4200
aattctgctt tagaaactat tgttttaagc agagatgagg atgtccttg cactatcggg   4260 tatgctttta ggttacggct tattggaaag attgttcata gctttgctgt tagatcctgg   4320
cagtttgcac aaagtaatct ttgttaacgt ttggttcata tgagtaagag gtacaacatt   4380
taaatgactt aattccccctt tgagaagatg gttgaagtca ttttattggc taaatgaaca   4440
tttaaagcaa gagtataaag gctacacagc atgacatctt tcttagatta tctgaattca   4500
tacttaaagc tcttaatgta tgcataacta tacaaaaaaa ttcatgcatc gtgatgcatc   4560
cattgcaaat atatccccat caatctccta gctctaatca acaaatccga tccatgcgca   4620
tcctatcaaa agtgcgtaga cattaatgga atgccacttt gcccaacttg gctgtaaggg   4680
aagaaacttg aatgaggtat tgtttcatta gaagagctac taacgtcttt aggtttcagg   4740
tctgtctcgc atacaaacat tcccggaaaa tcagtagttt tacctttgcc acaggtgatt   4800
gctatagctc agtatcctgg acattcttgt ggttaatgca tggcttagat tgtctatttt   4860 cttttgttaat cacaggtgtc tgaaatgcat gcccaaatat cctgcaaaaa caacgcattt   4920
tttgtaactg attttcagag tgaacatggt acttgggtta tagagtaagc tccatgagtt   4980
ctttatacaa ctgtactata agtgcatcac atttattagt ctatgaagac aaaagaatta   5040
cattgttctg cattatgtag taatgaaggc agaagatatc gggtgtctcc aaacttccct   5100
atgcgttttc attcatcaga tgtaatcgta tttggttctg ataaggtgtg attcgtgaaa   5160
ttcttgcttg atatgctta aaagatacgt tggcattggc agtagcttat tactcattca    5220
aatccatttg tttatgttat gcaggcagca tttcgtgtaa agacaatgaa atttccttca   5280
aaaactgctg aagcgaagga agagcgcaaa gtcgtgggga cagcataaac gggaaatttg   5340
tacagcattt tatagaaaca tcagacattg tagaagatta taaacaaaa cagattcaac    5400 aaatacagag attatttggc tttcttctaa agaacgtgga aaaagtgatg gtcattgttt   5460
cttattctac catttcctaa atgtatagag aaagtgatgg tcattgtttc ttattctacc   5520
atttcctaaa tatatactaa ttctctatgt atatacaatt ataggccagt ttccttcatg   5580
aatttctttt atagatttc gtatttgtaa gtcttcattc aaaattaact actatttttt   5640
acttttattt ctaacgtgca ttatttttta cttttatttc taacttgcat tttatgttca   5700
ttgttgattt tatacataat aaaatgaaac aaatagaaaa aaataataaa tt            5752
```

<210> SEQ ID NO 97
<211> LENGTH: 5752
<212> TYPE: DNA
<213> ORGANISM: Capsicum annuum

<400> SEQUENCE: 97

| | | | | | |
|---|---|---|---|---|---|
| cccaataacc | caatactaat | aacttaataa | tattttttatc | ggttcgattt | atcgatcggc | 60 |
| tcaactacca | aaaggaacaa | aaaaataaat | agagtactac | aacaaccata | gatgagtgaa | 120 |
| caagcgtcaa | acatcagcct | cagtttagta | acccaaacaa | gctacaatga | caagccacct | 180 |
| ggccataaaa | tcttcaccat | tgctgcttca | tggaccattg | attggttctc | aatcttcttt | 240 |
| gccccaccac | caccaccacc | ctcactatca | cccacaattt | ccacttcctt | tttcccctcc | 300 |
| tcaaaagcct | aactaacaca | cattggccta | actaaaattc | tcataaatca | ccttcacttc | 360 |
| ttttttttcat | tagattatac | attagttgtt | tggtctcaat | cttcctttca | cttcctttgg | 420 |
| cctaattaac | agtttatata | aatcaacttc | acttctttt | ttcactaaaa | catacagtga | 480 |
| aagagaaaca | caagagtctt | ttcttgaact | ggagttctag | tgaaagatgt | attcaactgt | 540 |
| gttttacact | tcagttcatc | cctccacttc | agttttttca | agaaaacagc | tacctttatt | 600 |
| gatatccaag | gactttcctg | cagagttgta | tcattcttta | ccttgtaaga | gtttggaaaa | 660 |
| tgggcatatc | aagaaggtta | aaggagtaaa | agccacacta | gctgaagctc | cagctactcc | 720 |
| tacagagaag | agtaactctg | aggttccaca | gaagaagttg | aaagtacttg | tggcaggtgg | 780 |
| tgggattgga | ggattagttt | ttgctttggc | agcaaagaaa | aaggggtttg | atgtattggt | 840 |
| gtttgagaga | gatttaagtg | ctataagagg | tgagggcaa | tatagaggtc | caattcagat | 900 |
| acagagcaat | gcattggctg | ctttggaagc | aattgatatg | gatgttgctg | aagagatcat | 960 |
| gaatgctggc | tgtatcactg | gtcaaaggat | taatggcttg | gtcgatggta | tttctggcaa | 1020 |
| ctggtaaatt | cacatcactc | tgatttgatt | gtgctgatta | agagcttgtg | tgcctttttt | 1080 |
| gctactgtat | ttactttcca | aacttgttcg | gttatgcttt | acttaagccg | agggtcttca | 1140 |
| ggaatagtct | ctctaccttc | acgagatatg | attaaggtct | gcgcacgcaa | tacccttctc | 1200 |
| agaagggtaa | tcacactggc | tatgttgttg | ttgtaattaa | atgcttgtct | gtcttttttt | 1260 |
| agttgagctt | taactgagga | taccccagga | aaataatgaa | ttctttgaaa | tatttagccc | 1320 |
| tttaaaaaag | tatagggaaa | ataattcatt | tagtcacaag | tttattgaat | catgggttgcc | 1380 |
| aagcttattc | gggaaaagga | tcctatcttt | accttcaaat | ggcttcaatc | agattgataa | 1440 |
| gttagtctta | ttgttgtatg | agcagcttat | tgtgagaaca | gtccctttat | ttcttgaact | 1500 |
| gcgaacagtg | acaatagttg | ggtatcaggt | attgcaagtt | tgatacgttc | actccagctg | 1560 |
| tggaacgtgg | acttcctgtg | acaagagtca | tcagccgcat | gactttgcaa | cagattcttg | 1620 |
| cacgtgctgt | aggggaggat | gtaattatga | atgaaagtaa | tgtagtaaat | tttgaggatg | 1680 |
| atggggagaa | ggtaatgcta | ggtttgatct | ctttgtttc | tgctattctc | aaaatatcaa | 1740 |
| gaaagattat | aacttttctt | aatttcattt | gcatcattgt | taattgttgt | ttcttattca | 1800 |
| tcaattttcg | ttaaagcttc | tcatgtgctg | tgtgaaatca | ggttactgtg | gttcttgaga | 1860 |
| atggacaacg | gtttacaggt | gatcttctgg | ttggtgctga | tggcataagg | tctaaggtat | 1920 |
| tcaaaatcag | tctcattata | tttctttcta | ttattactac | ttcggttaac | aaggatagag | 1980 |
| taacttgttt | atattttact | ttgagattgt | ggttccacgt | taaaaaattg | tctgttgact | 2040 |
| gataggcctg | agtccgtatt | atgcagtgaa | ccttttattg | attattctag | ttgattcaga | 2100 |
| agatcacaaa | catttccgtt | gtgttgtagg | tacggactaa | tttgttcgga | cacagtgaag | 2160 |

```
ctacttactc tggttacact tgttatactg gaattgcaga tttcgttcct gctgatattg    2220
acacagttgg gtatgatatt ctttcttacc ggattgtgtt tccactcatg cccttatccc    2280
tgctggtgcc gttacactca cacgaggttt tcatagtaga gattaaattg agatttcttt    2340
tctgaaggta ccgagtcttt tgggccaca aacagtactt tgtttcttca gatgtgggtg     2400
gaggcaagat gcagtggtat gcatttcaca atgaaccagc tggtggtgtg gatgctccaa    2460
acggtaaaat tttaggccg cttaaaacta tttactatag ttcaggatat agacatactt     2520
actagaagac gttttgaat gcttaacttg taacgttat ttaacccaag gggtttctta      2580 agaattttc ctcattgagg cctggttata gtgttgcaat aaggtaaaga acaactcaag     2640
attagaataa gatagactca aatgtattat gagtcggaaa gttttgaatt gaagttgctg    2700
actctatgaa ttaggagttg tttaatattt tgtctgttca tgctgcaggt aaaaaggaaa    2760
gattgcttaa aatatttggg ggatggtgtg acaacgttat agacctatta gttgccacag    2820
atgaagatgc aattcttcgt cgtgacatct atgatagacc gccaacattt aattggggaa    2880
gaggtcgtgt tacattgctt ggggactcag tccatgctat gcagcctaat ttgggtcaag    2940
gaggatgcat ggcccatagag gtacaccact gtgtttatca tctttgtcaa atacacagta   3000
ttgtaaggtt gtgtatgaca ctgaacttt ccatgtacaa ctacaggata gctatcaact     3060
agcactggaa cttgagaaag catggagccg aagtgctgag tccggaagcc ctatggatgt    3120
catctcatct ttaaggaggt aatccattat ttattggctc aagtgctgta gtctggttgg    3180
ttgagtacag gctgccagtt catgataatt gaaaaaacat ttgcaattgg ttgaggtctt    3240
taacttcacc ccaccaccag cccagtagga ctgctttaaa tgcctcaact gaaaatggat    3300
tgatttgaac agctgccgtg tctgccagtt cgctgatcct ttaatgaatt tccttttct    3360 gcagctatga aagtgctaga aaacttcgag ttggagttat ccatggactg gctagaatgg    3420
ctgcaatcat ggcatcaact tacaaggcct atcttggtgt cggacttggt ccattatcag    3480
tatggaaaac tatctatcac ttgaaattgg aatggcatag ccaatttgcg tgattgcgca   3540
gagctcttct tataatagat gtttttttct attatttgtg cagttttga ccaagtatag     3600 gataccacat cctggaagag ttggtggaag agtatttgtg gacttgggaa tgcctctaat    3660
gttaagttgg gttctaggag gcaacgggta ggaatatgcg agctgtattc cagcattttc    3720
ttgcttcagt attttgaaca tgattttggt ttctatgtga atccgtgatg agtttgctgg    3780
agatcttgga agttgatatc ctgtggtttg actcgtcttt tttcttttct tgcagcgaca    3840
agcttgaggg tagaatacaa cattgcaggc tatctgagaa agtatgtagc gtaaggaact    3900
atgcactcaa cacacgaaca cagaaaagat ttctggcttc cattgctact taattaaggt    3960
ccaactatga attttacggg tgtgttaata tactgtactg tggtgatgaa ggcaaatgat    4020
caattgagaa gatggttga agatgatgat gctttagagc gtgctactga tgcagagtga    4080
gttaatggaa cgtaatattt aaaaatttca ttttacatg tctcattttc ctagtttgct    4140
ttctaatttg gtgcttacgt tttatctttc aggtggttac tgttacctgc agcgaatggc    4200
aattctgctt tagaaactat tgttttaagc agagatgagg atgtcccttg cactatcggg    4260 tatgcttta ggttacggct tattggaaag attgttcata gctttgctgt tagatcctgg     4320
cagtttgcac aaagtaatct ttgttaacgt ttggttcata tgagtaagag gtacaacatt    4380
taaatgactt aattccccctt tgagaagatg gttgaagtca ttttattggc taaatgaaca   4440
tttaaagcaa gagtataaag gctacacagc atgacatctt tcttagatta tctgaattca    4500
```

| | |
|---|---|
| tacttaaagc tcttaatgta tgcataacta tacaaaaaaa ttcatgcatc gtgatgcatc | 4560 |
| cattgcaaat atatccccat caatctccta gctctaatca acaaatccga tccatgcgca | 4620 |
| tcctatcaaa agtgcgtaga cattaatgga atgccacttt gcccaacttg gctgtaaggg | 4680 |
| aagaaacttg aatgaggtat tgtttcatta aagagctac taacgtcttt aggtttcagg | 4740 |
| tctgtctcgc atacaaacat tcccggaaaa tcagtagttt tacctttgcc acaggtgatt | 4800 |
| gctatagctc agtatcctgg acattcttgt ggttaatgca tggcttagat tgtctatttt | 4860 |
| ctttgttaat cacaggtgtc tgaaatgcat gcccaaatat cctgcaaaaa caacgcattt | 4920 |
| tttgtaactg attttcagag tgaacatggt acttgggtta tagagtaagc tccatgagtt | 4980 |
| ctttatacaa ctgtactata agtgcatcac atttattagt ctatgaagac aaaagaatta | 5040 |
| cattgttctg cattatgtag taatgaaggc agaagatatc gggtgtctcc aaacttccct | 5100 |
| atgcgttttc attcatcaga tgtaatcgta tttggttctg ataaggtgtg attcgtgaaa | 5160 |
| ttcttgcttg atatgcttta aaagatacgt tggcattggc agtagcttat tactcattca | 5220 |
| aatccatttg tttatgttat gcgggcagca tttcgtgtaa agacaatgaa atttccttca | 5280 |
| aaaactgctg aagcgaagga agagcgcaaa gtcgtgggga cagcataaac gggaaatttg | 5340 |
| tacagcattt tatagaaaca tcagacattg tagaagatta ataacaaaa cagattcaac | 5400 |
| aaatacagag attatttggc tttcttctaa agaacgtgga aaaagtgatg gtcattgttt | 5460 |
| cttattctac catttcctaa atgtatagag aaagtgatgg tcattgtttc ttattctacc | 5520 |
| atttcctaaa tatatactaa ttctctatgt atatacaatt ataggccagt ttccttcatg | 5580 |
| aatttctttt atagattttc gtatttgtaa gtcttcattc aaaattaact actatttttt | 5640 |
| actttatttt ctaacttgca ttatttttta cttttatttc taacttgcat tttatgttca | 5700 |
| ttgttgattt tatacataat aaaatgaaac aaatagaaaa aataataaaa tt | 5752 |

<210> SEQ ID NO 98
<211> LENGTH: 1971
<212> TYPE: DNA
<213> ORGANISM: Capsicum annuum

<400> SEQUENCE: 98

| | |
|---|---|
| atgtattcaa ctgtgtttta cacttcagtt catccctcca cttcagtttt ttcaagaaaa | 60 |
| cagctacctt tattgatatc caaggacttt cctgcagagt tgtatcattc tttaccttgt | 120 |
| aagagtttgg aaaatgggca tatcaagaag gttaaaggag taaaagccac actagctgaa | 180 |
| gctccagcta ctcctacaga gaagagtaac tctgaggttc cacagaagaa gttgaaagta | 240 |
| cttgtggcag gtggtgggat tggaggatta gttttttgctt tggcagcaaa gaaaaagggg | 300 |
| tttgatgtat tggtgtttga gagagattta agtgctataa gaggtgaggg gcaatataga | 360 |
| ggtccaattc agatacagag caatgcattg gctgctttgg aagcaattga tatggatgtt | 420 |
| gctgaagaga tcatgaatgc tggctgtatc actggtcaaa ggattaatgg cttggtcgat | 480 |
| ggtatttctg gcaactggta ttgcaagttt gatacgttca ctccagctgt ggaacgtgga | 540 |
| cttcctgtga caagagtcat cagccgcatg actttgcaac agattcttgc acgtgctgta | 600 |
| ggggaggat taattatgaa tgaaagtaat gtagtaaatt ttgaggatga tggggagaag | 660 |
| gtaatgctag gtttgatctc tttgtttttct gctacaggtg atcttctggt tggtgctgat | 720 |
| ggcataaggt ctaaggtacg gactaatttg ttcggacaca gtgaagctac ttactctggt | 780 |
| tacacttgtt atactggaat tgcagattcc gttcctgctg atattgacac agttgggtac | 840 |
| cgagtctttt tgggccacaa acagtacttt gtttcttcag atgtgggtgg aggcaagatg | 900 |

```
cagtggtatg catttcacaa tgaaccagct ggtggtgtgg atgctccaaa cggtaaaaag      960
gaaagattgc ttaaaatatt tgggggatgg tgtgacaacg ttatagacct attagttgcc     1020
acagatgaag atgcaattct tcgtcgtgac atctatgata daccgccaac atttaattgg     1080
ggaagaggtc gtgttacatt gcttggggac tcagtccatg ctatgcagcc taatttgggt     1140
caaggaggat gcatggccat agaggatagc tatcaactag cactggaact tgagaaagca     1200
tggagccgaa gtgctgagtc cggaagccct atggatgtca tctcatcttt aaggagctat     1260
gaaagtgcta gaaaacttcg agttggagtt atccatggac tggctagaat ggctgcaatc     1320
atggcatcaa cttacaaggc ctatcttggt gtcggacttg gtccattatc agtatggacc     1380
aagtatagga taccacatcc tggaagagtt ggtggaagag tatttgtgga cttgggaatg     1440
cctctaatgt taagttgggt tctaggaggc aacgggagaa tacaacattg caggctatct     1500
gagaaagcaa atgatcaatt gagaagatgg tttgaagatg atgatgcttt agagcgtgct     1560
actgatgcag agtggttact gttacctgca gcgaatggca attctgcttt agaaactatt     1620
gttttaagca gagatgagga tgtcccttgc actatcgggt ctgtctcgca tacaaacatt     1680
cccggaaaat cagtagtttt accttttgcca caggtgtctg aaatgcatgc ccaaatatcc     1740
tgcaaaaaca acgcattttt tgtaactgat tttcagagtg aacatggtac ttgggttata     1800
gataatgaag gcagaagata tcgggtgtct ccaaacttcc ctatgcgttt tcattcatca     1860
gatgtaatcg tatttggttc tgataaggca gcatttcgtg taaagacaat gaaatttcct     1920
tcaaaaactg ctgaagcgaa ggaagagcgc aaagtcgtgg ggacagcata a              1971

<210> SEQ ID NO 99
<211> LENGTH: 5752
<212> TYPE: DNA
<213> ORGANISM: Capsicum annuum

<400> SEQUENCE: 99
cccaataacc caatactaat aacttaataa tatttttatc ggttcgattt atcgatcggc       60
tcaactacca aaggaacaa aaaaataaat agagtactac aacaaccata gatgagtgaa      120
caagcgtcaa acatcagcct cagtttagta acccaaacaa gctacaatga caagccacct      180
ggccataaaa tcttcaccat tgctgcttca tggaccattg attggttctc aatcttcttt      240
gccccaccac caccaccacc ctcactatca cccacaattt ccacttcctt ttttccctcc      300
tcaaagcct aactaacaca cattggccta actaaaattc tcataaatca ccttcacttc      360
ttttttcat tagattatac attagttgtt tggtctcaat cttcctttca cttcctttgg      420
cctaattaac agtttatata aatcaacttc acttcttttt ttcactaaaa catacagtga      480
aagagaaaca caagagtctt tcttgaact ggagttctag tgaaagatgt attcaactgt      540
gttttacact tcagttcatc cctccacttc agttttttca agaaaacagc tacctttatt      600
gatatccaag gactttcctg cagagttgta tcattcttta ccttgtaaga gtttggaaaa      660
tgggcatatc aagaaggtta aaggagtaaa agccacacta gctgaagctc cagctactcc      720
tacagagaag agtaactctg aggttccaca gaagaagttg aaagtacttg tggcaggtgg      780
tgggattgga ggattagttt ttgcttggc agcaaagaaa aaggggtttg atgtattggt      840
gtttgagaga gatttaagtg ctataagagg tgagggcaa tatagaggtc caattcagat      900
acagagcaat gcattggctg ctttggaagc aattgatatg gatgttgctg aagagatcat      960
gaatgctggc tgtatcactg gtcaaaggat taatggcttg gtcgatggta tttctggcaa     1020
```

-continued

```
ctggtaaatt cacatcactc tgatttgatt gtgctgatta agagcttgtg tgccttttt    1080 gctactgtat ttactttcca aacttgttcg gttatgcttt acttaagccg agggtcttca    1140
ggaatagtct ctctaccttc acgagatatg attaaggtct gcgcacgcaa taccettctc    1200 agaagggtaa tcacactggc tatgttgttg ttgtaattaa atgcttgtct gtcttttttt    1260
agttgagctt taactgagga tacccccagga aaataatgaa ttcttttgaaa tatttagccc    1320 tttaaaaaag tatagggaaa ataattcatt tagtcacaag tttattgaat catggttgcc    1380
aagcttattc gggaaaagga tcctatcttt accttcaaat ggcttcaatc agattgataa    1440
gttagtctta ttgttgtatg agcagcttat tgtgagaaca gtcccttat ttcttgaact    1500 gcgaacagtg acaatagttg ggtatcaggt attgcaagtt tgatacgttc actccagctg    1560
tggaacgtgg acttcctgtg acaagagtca tcagccgcat gactttgcaa cagattcttg    1620
cacgtgctgt agggggaggat gtaattatga atgaaagtaa tgtagtaaat tttgaggatg    1680
atggggagaa ggtaatgcta ggtttgatct ctttgttttc tgctattctc aaaatatcaa    1740
gaaagattat aacttttctt aatttcattt gcatcattgt taattgttgt ttcttattca    1800
tcaattttcg ttaaagcttc tcatgtgctg tgtgaaatca ggttactgtg gttcttgaga    1860
atggacaacg gttacaggt gatcttctgg ttggtgctga tggcataagg tctaaggtat    1920
tcaaaatcag tctcattata tttctttcta ttattactac ttcggttaac aaggatagag    1980
taacttgttt atatttact ttgagattgt ggttccacgt taaaaaattg tctgttgact    2040
gataggcctg agtccgtatt atgcagtgaa cctttattg attattctag ttgattcaga    2100
agatcacaaa catttccgtt gtgttgtagg tacggactaa tttgttcgga cacagtgaag    2160
ctacttactc tggttacact tgttatactg gaattgcaga tttcgttcct gctgatattg    2220
acacagttgg gtatgatatt ctttcttacc ggattgtgtt tccactcatg cccttatccc    2280
tgctggtgcc gttacactca cacgaggttt tcatagtaga gattaaattg agatttcttt    2340
tctgaaggta ccgagtcttt ttgggccaca acagtactt tgtttcttca gatgtgggtg    2400
gaggcaagat gcagtggtat gcatttcaca atgaaccagc tggtggtgtg gatgctccaa    2460
acggtaaaat ttttaggccg cttaaaacta tttactatag ttcaggatat agacatactt    2520
actagaagac gttttgaat gcttaacttg taacgtttat ttaacccaag gggtttctta    2580
agaatttttc ctcattgagg cctggttata gtgttgcaat aaggtaaaga acaactcaag    2640
attagaataa gatagactca aatgtattat gagtcggaaa gttttgaatt gaagttgctg    2700
actctatgaa ttaggagttg tttaatattt tgtctgttca tgctgcaggt aaaaaggaaa    2760
gattgcttaa aatatttggg ggatggtgtg acaacgttat agaccttatta gttgccacag    2820 atgaagatgc aattcttcgt cgtgacatct atgatagacc gccaacattt aattggggaa    2880
gaggtcgtgt tacattgctt ggggactcag tccatgctat gcagcctaat ttgggtcaag    2940
gaggatgcat ggccatagag gtacaccact gtgtttatca tctttgtcaa atacacagta    3000
ttgtaaggtt gtgtatgaca ctgaactttt ccatgtacaa ctacaggata gctatcaact    3060
agcactggaa cttgagaaag catggagccg aagtgctgag tccggaagcc ctatggatgt    3120
catctcatct ttaaggaggt aatccattat ttattggctc aagtgctgta gtctggttgg    3180
ttgagtacag gctgccagtt catgataatt gaaaaaacat ttgcaattgg ttgaggtctt    3240
taacttcacc ccaccaccag cccagtagga ctgctttaaa tgcctcaact gaaaatggat    3300
```

-continued

```
tgatttgaac agctgccgtg tctgccagtt cgctgatcct ttaatgaatt tcctttttct    3360
gcagctatga aagtgctaga aaacttcgag ttggagttat ccatggactg ctagaatgg     3420 ctgcaatcat ggcatcaact tacaaggcct atcttggtgt cggacttggt ccattatcag    3480
tatgaaaaac tatctatcac ttgaaattgg aatggcatag ccaatttgcg tgattgcgca    3540
gagctcttct tataatagat gttttttttct attatttgtg cagttttga ccaagtatag    3600 gataccacat cctggaagag ttggtggaag agtatttgtg gacttgggaa tgcctctaat    3660
gttaagttgg gttctaggag gcaacgggta ggaatatgcg agctgtattc cagcattttc    3720
ttgcttcagt attttgaaca tgattttggt ttctatgtga atccgtgatg agtttgctgg    3780
agatcttgga agttgatatc ctgtggtttg actcgtcttt tttcttttct tgcagcgaca    3840
agcttgaggg tagaatacaa cattgcaggc tatctgagaa agtatgtagc gtaaggaact    3900
atgcactcaa cacacgaaca cagaaaagat ttctggcttc cattgctact taattaaggt    3960
ccaactatgg attttacggg tgtgttaata tactgtactg tggtgatgaa ggcaaatgat    4020
caattgagaa gatggtttga agatgatgat gctttagagc gtgctactga tgcagagtga    4080
gttaatggaa cgtaatattt aaaaatttca tttttacatg tctcattttc ctagtttgct    4140
ttctaatttg gtgcttacgt tttatctttc aggtggttac tgttacctgc agcgaatggc    4200
aattctgctt tagaaactat tgttttaagc agagatgagg atgtcccttg cactatcggg    4260 tatgcttttta ggttacggct tattggaaag attgttcata gctttgctgt tagatcctgg    4320
cagtttgcac aaagtaatct tgttaacgt ttggttcata tgagtaagag gtacaacatt    4380
taaatgactt aattcccctt tgagaagatg gttgaagtca ttttattggc taaatgaaca    4440
tttaaagcaa gagtataaag gctacacagc atgacatctt tcttagatta ctgaattca    4500 tacttaaagc tcttaatgta tgcataacta tacaaaaaaa ttcatgcatc gtgatgcatc    4560
cattgcaaat atatccccat caatctccta gctctaatca acaaatccga tccatgcgca    4620
tcctatcaaa agtgcgtaga cattaatgga atgccacttt gcccaacttg gctgtaaggg    4680
aagaaacttg aatgaggtat tgtttcatta gaagagctac taacgtcttt aggtttcagg    4740
tctgtctcgc atacaaacat tcccggaaaa tcagtagttt tacctttgcc acaggtgatt    4800
gctatagctc agtatcctgg acattcttgt ggttaatgca tggcttagat tgtctatttt    4860
ctttgttaat cacaggtgtc tgaaatgcat gcccaaatat cctgcaaaaa caacgcattt    4920
tttgtaactg attttcagag tgaacatggt acttgggtta tagagtaagc tccatgagtt    4980
ctttatacaa ctgtactata agtgcatcac atttattagt ctatgaagac aaaagaatta    5040
cattgttctg cattatgtag taatgaaggc agaagatatc gggtgtctcc aaacttccct    5100
atgcgttttc attcatcaga tgtaatcgta tttggttctg ataaggtgtg attcgtgaaa    5160
ttcttgcttg atatgcttta aaagatacgt tggcattggc agtagcttat tactcattca    5220
aatccatttg tttatgttat gcaggcagca tttcgtgtaa agacaatgaa atttccttca    5280
aaaactgctg aagcgaagga agagcgcaaa gtcgtgggga cagcataaac gggaaatttg    5340
tacagcattt tatagaaaca tcagacattg tagaagattg ataaacaaaa cagattcaac    5400
aaatacagag attatttggc tttcttctaa agaacgtgga aaaagtgatg gtcattgttt    5460
cttattctac catttcctaa atgtatagag aaagtgatgg tcattgtttc ttattctacc    5520
atttcctaaa tatatactaa ttctctatgt atatacaatt ataggccagt ttccttcatg    5580 aatttcttt atagattttc gtatttgtaa gtcttcattc aaaattaact actatttttt     5640
```

```
acttttattt ctaacttgca ttatttttta cttttatttc taacttgcat tttatgttca    5700
ttgttgattt tatacataat aaaatgaaac aaatagaaaa aaataataaa tt            5752
```

SELECTION OF MATURE FRUIT COLOR IN PEPPER PLANTS

REFERENCE TO RELATED APPLICATIONS

This application is a divisional of U.S. application Ser. No. 14/304,722, filed Jun. 13, 2014, now U.S. Pat. No. 9,723,797, which claims the benefit of U.S. provisional application No. 61/863,765, filed Aug. 8, 2013, and U.S. provisional application No. 61/838,094, filed Jun. 21, 2013, each of which is herein incorporated by reference in its entirety.

BACKGROUND OF THE INVENTION

1. Incorporation of Sequence Listing

The sequence listing that is contained in the file named "SEMB011USD1-revised ST25.txt", which is 171 kilobytes as measured in the Microsoft Windows operating system and was created on Apr. 17, 2020, is filed electronically herewith and incorporated herein by reference.

2. Field of the Invention

The present invention relates to the field of plant breeding and, more specifically, to the development of pepper plants displaying a desired mature fruit color.

3. Description of Related Art

The goal of vegetable breeding is to produce varieties displaying one or more desirable traits, such as a desired mature fruit color. Pepper plants (*Capsicum* sp.) may display, for instance, a mature fruit color of red, red-orange, orange, or yellow as a result of the function of pigment biosynthetic pathway(s) which produce pigments such as carotenes and xanthophylls.

SUMMARY OF THE INVENTION

In one aspect, the invention provides a package of pepper fruits comprising at least two different colors of pepper fruits selected from the group consisting of: red, yellow, orange, and red-orange, wherein the peppers are grown from near isogenic pepper varieties. In one embodiment, the package comprises from about 1 to about 5 pepper fruits per color. In further embodiments, the pepper varieties are hybrid varieties. The package may contain, for example, at least three or at least four different colors of pepper fruits. The package may also comprise a green pepper fruit. In certain embodiments, the peppers are grown from at least two hybrid varieties that share a parent line. The hybrid varieties may also all share a parent line. In still further embodiments, the pepper varieties are *Capsicum annuum, C. baccatum, C. chinense, C. frutescens*, or *C. pubescens* varieties. In another embodiment, the pepper varieties are sweet peppers.

In another aspect, the invention provides a method of producing pepper fruits comprising: growing at least two near isogenic pepper lines that collectively comprise functional and non-functional Ccs and Ze alleles, and harvesting pepper fruit therefrom, wherein the pepper fruit are of at least two different colors selected from the group consisting of: red, yellow, orange, red-orange, and green. The method can further comprise, in one embodiment, packaging the pepper fruit in a single package, wherein the pepper fruit are of at least two different colors selected from the group consisting of: red, yellow, orange, red-orange, and green.

In still another aspect, the invention provides a container comprising seeds of at least two near isogenic pepper varieties, wherein the pepper varieties produce fruit of different fruit colors, and wherein the fruit colors are selected from the group consisting of: red, yellow, orange, and red-orange. In one embodiment, the container is defined as comprising seeds of at least three near isogenic pepper varieties that produce fruit of different fruit colors. In another embodiment, the container comprises seeds of at least four near isogenic pepper varieties that produce fruit of different fruit colors.

In still yet another aspect, the invention provides a method of producing pepper seed comprising: (a) producing a set of near isogenic inbred pepper lines that collectively comprise functional and non-functional Ccs and Ze alleles; (b) crossing said pepper lines to produce seed of near isogenic hybrid plants that comprise combinations of said alleles that result in red, yellow and orange fruit. In one embodiment of the method, producing a set of near isogenic lines comprises producing a plant that has been inbred but segregates for a Ccs or Ze allele. Producing a set of near isogenic lines may comprise, for example, producing a plant that has been inbred but segregates for Ccs and Ze alleles. In the method, the plant that has been inbred may be selfed for three or more generations. In certain embodiments of the method, producing a set of near isogenic inbred pepper lines comprises marker assisted selection for a Ccs or Ze allele. In other embodiments, producing a set of near isogenic inbred pepper lines comprises marker assisted selection for Ccs and Ze alleles. Marker assisted selection may comprise, in specific embodiments, detecting a deletion in a Ccs gene or the absence thereof. Marker assisted selection may also or alternatively comprise detecting a single nucleotide polymorphism in a Ze gene or the absence thereof. The near isogenic inbred pepper lines may, in one example, be homozygous for said Ccs and Ze alleles. In still further embodiments, the pepper lines are selected from the pepper species consisting of *Capsicum annuum, C. baccatum, C. chinense, C. frutescens*, and *C. pubescens*. In other embodiments, the pepper lines are sweet peppers.

In still yet another aspect, the invention provides a method of selecting a pepper plant for fruit color genotype comprising: (a) detecting the presence or absence of a polymorphism in the Zeaxanthin epoxidase (Ze) gene conferring said fruit color; and (b) selecting the plant based on the presence or absence of said polymorphism. In the method, detecting the presence or absence of a polymorphism in the Zeaxanthin epoxidase (Ze) gene may comprise detecting a genetic marker in linkage disequilibrium with said polymorphism. In another embodiment, detecting the presence or absence of a polymorphism in the Zeaxanthin epoxidase (Ze) gene comprises detecting the presence or absence of a single nucleotide polymorphism that is causative for said fruit color. In other embodiments, the method comprises detection of at least one genetic marker selected from the group consisting of: NE0235373, NE0240266, NE0239621, NE0240354, and NE0241248. In another embodiment, the method further comprises (c) crossing the selected plant from step (b) with a second pepper plant. In still other embodiments, the plant is a *Capsicum annuum* plant, and may be a sweet pepper plant.

BRIEF DESCRIPTION OF DRAWINGS

FIG. 2A) PCR amplicons obtained using different primer combinations in the Ccs gene. Primer combinations are listed on top of the panels. For each primer combination, four red and four yellow lines were used. FIG. 2B) Schematic representation of amplicons which were obtained; ATG and TGA respectively represent the start and stop codons of the Ccs gene. Next to each amplicon the expected amplicon size is indicated. Bars obtained with primers pd000285, pd000287, pd000279, and pd000187 represent amplicons obtained in red lines only; bars obtained with primers pd000277 and pd000190 represent amplicons obtained in all tested lines.

FIGS. 3A-3C: FIG. 3A) Schematic representation of the Ccs gene and flanking sequences in a red pepper background. FIG. 3B) Size and position of the deletion found in both yellow and orange lines. FIG. 3C) Observed color of 14 tested pepper lines and the genotypes obtained with TaqMan™ markers NCANN009113770 (based on the deletion) and NCANN005134316 (based on an A/T SNP in the 3'UTR).

FIG. 5: Alignment of the sequences of the Ze gene derived from pepper line CM334 (line labeled "contig36343", SEQ ID NO:99), representative yellow (SEQ ID NO:96) and orange (SEQ ID NO:97) pepper lines, and the predicted coding sequence (SEQ ID NO:98), with marker locations shown.

FIG. 8: Alignment of Ccs sequences from 14 pepper lines (SEQ ID NOs:40-53).

DETAILED DESCRIPTION OF THE INVENTION

The invention provides methods and compositions relating to pepper (*Capsicum* spp., such as *C. annuum*) plants, and pepper plant parts, including seeds and fruit, and derivatives of such pepper plants/lines to allow for identification of pepper plants and production of nearly isogenic varieties which produce mature fruit of a desired color or colors, such as red, red-orange, orange, and/or yellow fruit.

Thus, in one aspect, the novel identification of a genetic trait allowing for orange mature fruit color in peppers (*Capsicum* spp.) as residing at the "Ze" locus encoding Zeaxanthin Epoxidase ("ZE" or "ZEP") on pepper chromosome 2, is disclosed herein. In another aspect, a deletion in the Capsanthin-Capsorubin Synthase (CCS) gene (termed "Ccs") is identified as a causal mutation leading to non-red mature pepper fruit color, allowing for use of genetic markers linked to a known allele of the Ccs gene via marker assisted selection ("MAS") or marker assisted backcrossing ("MABC"), when breeding for diverse mature fruit color in pepper plants. Pepper plants comprising a genetic marker linked to a known allele of the CCS gene may thus be utilized to breed pepper plants which display a desired mature fruit color, including red, orange, red-orange, and yellow. Further, use of both Ze and Ccs-encoded traits, and associated genetic markers, allows for production of collections of pepper lines and plants which produce fruit displaying desired mature fruit color, including lines which produce mature fruit displaying one or more desired mature fruit colors such as red, red-orange, orange, and yellow, and any combination thereof.

Figure 1:
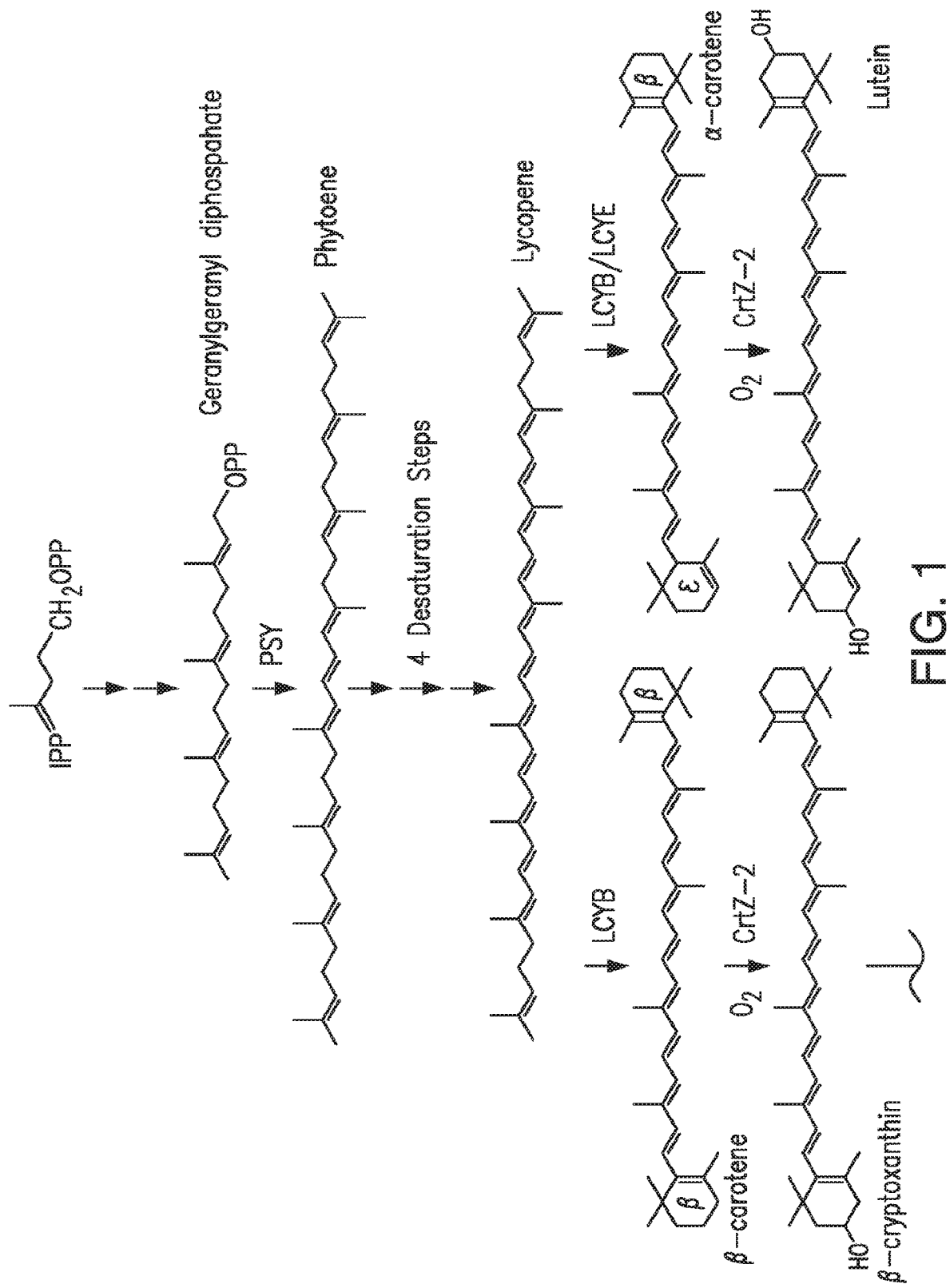
FIG. 1: Schematic presentation of the carotene and xanthophyll biosynthetic pathway in *Capsicum* sp. (from Guzman et al., *Plant Science* 179:49-59, 2010).
Figure 1:
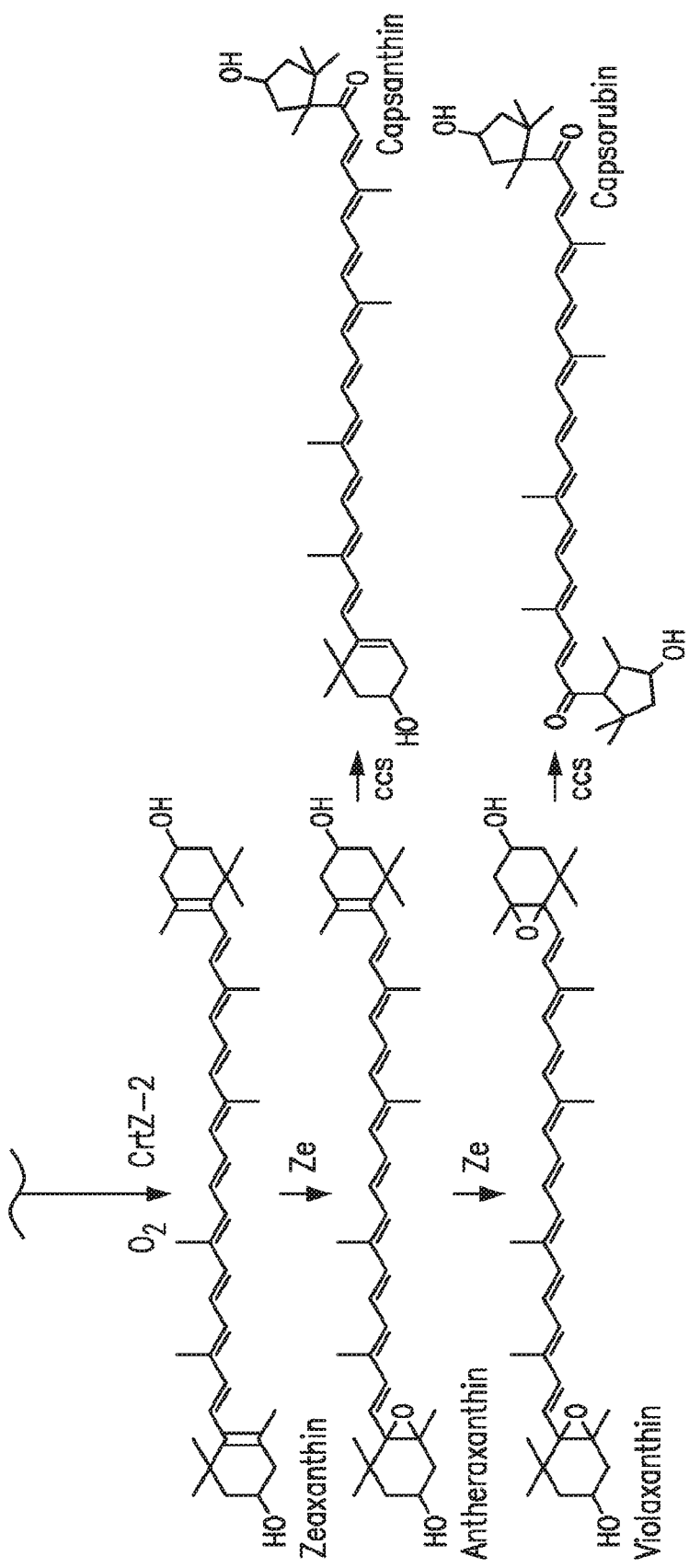

Plants with a functional carotenoid biosynthesis pathway upstream of compounds antheraxanthin and violaxanthin and a functional CCS protein are able to produce red pigments (carotenoids) in mature fruits, while plants that lack a functional CCS protein will not produce red fruits (Guzman et al. *Plant Sci.* 179:49-59, 2010; FIG. 1). Typically, these plants without a functional CCS protein have yellow or orange fruits. Carotenoids are largely responsible for the phenotypic colors of red, yellow, and orange pepper fruits. Due to the extensive conjugated double bond network and delocalized π-electrons, carotenoids absorb light in the visible range (400-500 nm) resulting in intense coloration of yellow, orange, and red (Britton, *FASEB J.* 9:1551-1558, 1995). The predominate carotenoids found in pepper fruits can be grouped according to their visual color class, which is based upon the number of conjugated double bonds. The major red carotenoids are capsanthin and capsorubin and absorb UV in the 470-475 nm range. The major orange carotenoids are zeaxanthin, β-carotene, and β-cryptoxanthin and absorb UV in the 450-455 nm range. The major yellow carotenoids are violaxanthin, antheraxanthin, and lutein and absorb UV in the 440-445 nm range. Thus, changes in the carotenoid profile have the potential to alter phenotypic fruit color.

Several enzymatic steps are required for the biosynthesis of carotenoids. Perturbations in the biosynthetic pathway can alter the carotenoid profile, ultimately resulting in phenotypic changes in fruit color. Capsanthin-Capsorubin Synthase and Zeaxanthin Epoxidase represent critical junctions in the pepper carotenoid biosynthetic pathway (FIG. 1). CCS is responsible for the formation of the red carotenoids capsanthin and capsorubin. ZEP catalyzes the epoxidation of the terminal 3-hydroxy-β-ionone ring structure of zeaxanthin, resulting in the formation of the di-epoxide violaxanthin via the mono-epoxide antheraxanthin. Both antheraxanthin and violaxanthin, in turn, serve as substrates for the CCS enzyme. Thus, the presence or absence of a fully functional CCS and/or ZEP enzyme impacts the biosynthesis of the red and yellow carotenoids, resulting in a change in carotenoid profile in mature fruit, and corresponding changes in fruit color.

Previously, the genetic basis of orange color in habanero peppers (*Capsicum chinense*) was reported to be due to a mutation in the gene encoding phytoene synthase ("Psy;" Thorup et al., *PNAS* 97:11192-11197, 2000). However, the orange line used in creating a polymorphic population for that mapping study was a habanero type pepper (*Capsicum chinense*), and the phytoene synthase gene was not known to contribute functional polymorphism affecting orange fruit color in elite *Capsicum annuum* peppers. Other research has implicated another carotenoid biosynthetic gene, encoding β-Carotene Hydroxylase, as involved in specifying fruit color (e.g. Borovsky et al. *TAG* 126:557-565, 2013). Thus, the identification of functional polymorphism (i.e. causal single nucleotide polymorphisms or "SNPs") in the gene encoding Zeaxanthin epoxidase correlating with a change in mature fruit color in *C. annuum* is surprising and unexpected. Pepper plants which produce, for instance, fruit with orange mature fruit color may thus be identified and bred using the presently disclosed genetic markers and trait source(s). Identification of causal polymorphisms in the Ccs gene provides further compositions and methods for pepper breeding, and may be used separately or in conjunction with disclosed Ze genetic markers and traits, to produce pepper plants displaying a mature fruit color of interest.

Commercial peppers are primarily of the species *Capsicum annuum* (e.g. bell peppers), *Capsicum frutescens* (Tabasco pepper), *Capsicum chinense* (Habanero pepper), and *Capsicum baccatum*. Pepper is an herbaceous species, generally grown as an annual crop, with fruits that vary in color, pungency, shape, and size. For instance, the fruit may be sweet or hot (pungent) and blocky or pointed, half-long, or of the Dulce Italiano or Corno di Toro types, among others. In view of the disclosed methods and compositions, pepper plants which produce fruit of different pungency levels and of various shapes, colors, and sizes are contemplated. Also contemplated are seeds, seed mixtures, cells, vegetative propagules, and fruit of the isogenic, nearly isogenic, or hybrid pepper lines which may thus be developed.

Utilizing genetic markers as disclosed herein, and/or markers genetically linked to these identified loci, and source lines, the methods described herein allow for production of nearly isogenic lines that differ in the mature fruit colors red, yellow, red-orange, and orange, and loci tightly linked to the color loci, but otherwise have essentially the same agronomic properties. These nearly isogenic lines can be used to produce nearly isogenic hybrids, which are of interest because each of the differently colored nearly isogenic hybrids have substantially the same horticultural properties, allowing growers to manage each variety in the same way. In contrast, current red, yellow and orange commercial varieties are typically distinct and may each have different pruning, nutritional, or pest control needs, adding complexity and expense to operations producing more than one color type. Additionally, the present invention allows for simplified breeding of pepper lines for producing multi-colored pepper packs, which have become increasingly popular. Additionally, breeding and hybrid lines may be produced and identified, for instance by transferring elite traits from typically more agronomically advanced red-fruited lines in order to improve orange and yellow-fruited germplasm. In addition the invention allows for the first time the production of substantially identical pepper fruits that differ in color. The invention thus also provides collections, including prepackaged collections, of near isogenic pepper fruit differing in color.

In one non-limiting example of a breeding method provided herein, the described color markers enable the consolidation of multiple breeding programs based on color into one multi-color breeding program. This can be achieved by crossing a red line that has both the intact Ccs and Ze alleles (CCSCCS ZEZE) with an orange line (ccsccs zeze) and maintaining both loci in a heterozygous state during breeding. In any given generation, a subset of plants heterozygous for both of these color loci can be subjected to MAS, and breeders may perform additional phenotypic selection on these plants as well. When the line is sufficiently genetically and phenotypically fixed after n generations, the line can be selfed and the progeny of the desired color genotype and phenotype can be selected using the markers for Ccs and Ze. This results in homozygous nearly isogenic lines that only differ in the mature fruit colors red, yellow, and orange, and loci tightly linked to the color loci. The invention thus provides, in one embodiment, a pepper plant comprising a desired mature fruit color trait, as well as a nearly isogenic pepper line comprising plants displaying a range of mature fruit colors. Diversity in the described color markers exists, for instance, in the commercial hybrids Orange Glory (ccsccs zeze), Derby (ccsccs ZEZE), Shanghai (ccsccs ZEZE), Aifos (CCSCCS ZEZE) and Darsena (CCSCCS ZEZE).

As used herein, "red," "red-orange," "orange," "yellow" and other contemplated fruit colors may be defined, for instance, by their visual color phenotype and absorption spectra of the underlying carotenoids. Yellow fruits appear yellow by visual assessment and the underlying carotenoids display a lambda max at approximately 442 nm; Orange fruits appear orange by visual assessment and the underlying carotenoids display a lambda max at approximately 454 nm; Red-Orange fruits appear red by visual assessment and the underlying carotenoids display a lambda max at approximately 454 nm; Red fruits appear red by visual assessment and the underlying carotenoids display a lambda max at approximately 474 nm. The visual contrast between Red-Orange and Red may usually be distinguishable upon side-by-side comparison but a grouping of only Red-Orange fruits would be visually assessed as being red in color.

As used herein, a "female parent" refers to a pepper plant that is the recipient of pollen from a male donor line, which pollen successfully pollinates an egg. A female parent can be any pepper plant that is the recipient of pollen.

As used herein, "male parent plant" refers to a parent plant that provides pollen to (i.e. is a pollinator for) a female line. They may be useful for breeding of progeny pepper plants, such as progeny plants which display a mature fruit color of interest.

As used herein, a "part of the pepper plant" is further defined as pollen, an ovule, a leaf, an embryo, a root, a root tip, an anther, a flower, a fruit, a stem, a cutting, a shoot, a seed, a protoplast, a cell, and a callus. A tissue culture of cells from a pepper plant may also be of use in propagating pepper plants of the present invention. As used herein, "tissue culture" refers to a composition comprising isolated cells of the same type(s) or of a different type, or of a collection of such cells, that may be organized into parts of a plant.

As used herein, a "hybrid pepper plant" includes a plant resulting directly or indirectly from crosses between populations, breeds or cultivars within the genus *Capsicum*. "Hybrid pepper plant" as used herein also refers to plants resulting directly or indirectly from crosses between different species, varieties or genotypes.

As used herein, a "marker" is a detectable polymorphism. Typically a marker is an indicator for the presence of at least one phenotype or genotype. Markers include, but are not limited to, single nucleotide polymorphisms (SNPs), small to large insertions and deletions, chromosomal rearrangements, cleavable amplified polymorphic sequences (CAPS), amplified fragment length polymorphisms (AFLPs), restriction fragment length polymorphisms (RFLPs), simple sequence repeats (SSRs), insertion(s)/deletion(s) ("INDEL"(s)), inter-simple sequence repeats (ISSR), and random amplified polymorphic DNA (RAPD) sequences. A marker may be inherited in codominant fashion (both alleles at a locus in a diploid heterozygote are readily detectable), with no environmental variance component, i.e., heritability of 1. A "nucleic acid marker" as used herein means a nucleic acid molecule that is capable of being a marker for detecting a polymorphism, phenotype, or both associated with a trait of interest. Stringent conditions for hybridization of a nucleic acid probe or primer to a marker sequence or a sequence flanking a marker sequence refers, for instance, to nucleic acid hybridization conditions of 1×SSC, and 65° C. As used herein, "marker assay" means a method for detecting a polymorphism at a particular locus using a particular method, e.g. measurement of at least one phenotype (such as a visually detectable trait, including disease resistance), restriction fragment length polymorphism (RFLP), single base extension, electrophoresis, sequence alignment, allelic specific oligonucleotide hybridization (ASO), random amplified polymorphic DNA (RAPD), microarray-based technologies, PCR-based technologies including TaqMan™, and nucleic acid sequencing technologies, etc.

As used herein, "near-isogenic" refers to a set of lines that are genetically highly similar (e.g. at least about 95% identical over the entire genome), but that differ with respect to chromosomal region(s) introduced from a "donor" parent line, such as a locus conferring fruit color as described herein. Near-isogenic varieties will generally share agronomic properties such that a farmer may apply substantially identical cultivation methods to grow a set of near isogenic varieties, and yield fruits that are essentially the same in appearance other than with respect to, for instance, fruit color.

Many useful traits that can be introduced by breeding strategies may also be introduced by genetic transformation techniques. Genetic transformation may therefore be used to insert a selected transgene, cisgene or intragene into a plant of the invention or may, alternatively, be used for the preparation of transgenes, cisgenes or intragenes which can be introduced by backcrossing. Methods for the transformation of plants that are well known to those of skill in the art and applicable to many crop species include, but are not limited to, electroporation, microprojectile bombardment, Agrobacterium-mediated transformation and direct DNA uptake by protoplasts. Exemplary nucleic acids which may be introduced to plants of this invention include, for example, DNA sequences or genes from another species, or even genes or sequences which originate with or are present in the same species, but are incorporated into recipient cells by genetic engineering methods rather than classical reproduction or breeding techniques.

One aspect of the current invention thus concerns methods for producing seed for pepper hybrids that grow to yield fruit displaying a desired mature fruit color, such as red, red-orange, orange, or yellow, and shades thereof. Plants of a female pepper parent displaying the desired color trait, may be used in certain embodiments for the development of new (e.g. hybrid) pepper varieties, for instance via marker assisted selection. Alternatively or in addition, a pepper line may be developed by introgressing one or more agronomic traits of interest into plant displaying a mature fruit color if interest.

The development of new varieties using one or more starting varieties is well known in the art. One or more presently disclosed genetic markers may be utilized in a marker assisted selection breeding method to create novel pepper lines or cultivars. Alternatively other mature fruit color-associated genetic markers may be identified by a skilled worker, and may be utilized in accordance with the invention. Thus novel varieties may be created by crossing lines displaying polymorphism at one or more fruit color-associated locus, followed by evaluation of fruit color characteristics of progeny plants, as well as genotyping, optionally evaluating other traits of agronomic interest. Thus, new varieties may be created by crossing with a second plant of a parental line chosen to exhibit one or more selected desirable characteristics or which exhibit the desired characteristic(s) when in hybrid combination. Once crosses have been made, selection may take place to identify new varieties.

The plants of the present invention are particularly well suited for the development of new lines based on the nature of the genetic background of the plants, particularly in view of available agronomically advanced traits of red-fruited parental lines, which allows for use in a method of producing seeds capable of growing into a pepper plant displaying a desired mature fruit color, as well as other agronomically useful traits such as, in specific embodiments, parthenocarpy, high seed yield, high seed germination, seedling vigor, high fruit yield, disease tolerance or resistance, and adaptability for soil and climate conditions. Consumer-driven traits, such as a fruit shape, color, texture, and taste are other examples of traits that may be incorporated into new lines of pepper plants developed in view of this invention.

Although the foregoing invention has been described in some detail by way of illustration and example for purposes of clarity and understanding, it will be obvious that certain changes and modifications may be practiced within the scope of the invention, as limited only by the scope of the appended claims.

All references cited herein are hereby expressly incorporated herein by reference.

EXAMPLES

Example 1

Capsanthin-Capsorubin Synthase (CCS) Marker Development

Pepper plants comprising a functional carotenoid biosynthesis pathway upstream of compounds antheraxanthin and violaxanthin and a functional CCS protein are able to produce red pigments (carotenoids) in mature fruits, while plants that lack a functional CCS protein will not produce red fruits (Guzman et al. *Plant Sci.* 179:49-59, 2010; FIG. 1). Typically, plants lacking a functional CCS have yellow or orange fruits. The CCS gene was mapped to the y locus on chromosome 6 of pepper and the trait of red vs. yellow fruit color was found to map to the bottom of chromosome 6 using an F2:F3 mapping population from a cross between a yellow blocky-shaped line (designated SBY-29-469) and a red Italian fryer line (designated SZZ-8T10901), as shown in Table 1.

TABLE 1

Map position of the y locus for red vs. yellow mature fruit color ("RY color").

| Marker | Chromosome | SBY-29-469/ SZZ-8T10901 F2:F3 | Map position (cM) |
| --- | --- | --- | --- |
| NE0239299 | 6 | 0 | 24.2 |
| NE0238978 | 6 | 8.5 | 30.2 |
| NE0238845 | 6 | 14.5 | 35.0 |
| NE0240908 | 6 | 33.7 | 62.6 |
| NE0235266 | 6 | 35.1 | 62.6 |
| NE0241110 | 6 | 44.5 | 70.6 |
| NE0237057 | 6 | 55.4 | 80.1 |
| NE0240567 | 6 | 64.4 | 89.3 |
| NE0238405 | 6 | 91.9 | 107.4 |
| RY_color* | 6 | 123.4 | 120.6 |
| NE0237488 | 6 | 126.4 | 121.8 |
| NE0237446 | 6 | 136.4 | 132.4 |

*Red (R) vs. yellow (Y) color scored as a binary trait in F3 families to permit inference of all three genotypic classes in the F2 generation.

Additionally, genome wide association mapping provided additional evidence that the position of a causal mutation for red vs. non-red mature fruit color on chromosome 6 is general across sweet pepper germplasm. Data obtained from 2,836 mapped SNPs from a total of 209 red, 122 yellow, and 17 orange lines of the sweet blocky, sweet mini, and sweet long fruit types was used in a case-control association mapping analysis implemented in a whole genome association analysis toolset (PLINK; Purcell et al., *Am. J. Hum. Genet.* 81:559-575, 2007). The SNP with the most significant association to the red- vs. non-red trait (NE0237110) occurred at position 120.7 cM on chromosome 6.

Figure 2A:
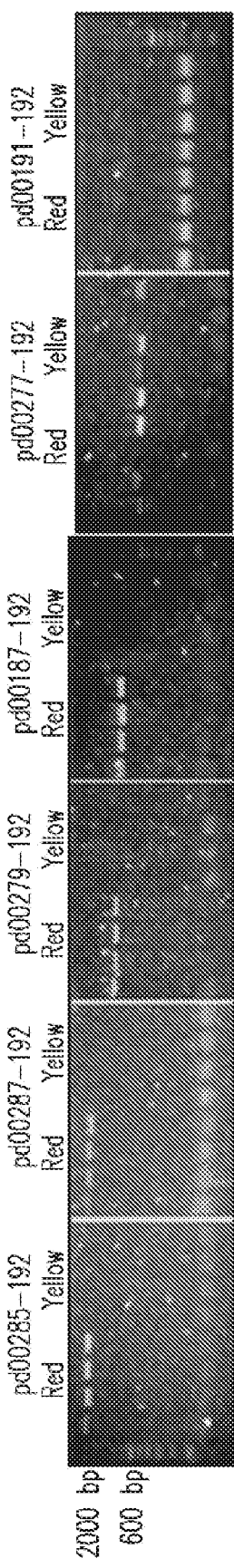
FIGS. 2A-2B: PCR analyses reveal a deletion in the Ccs gene of non-red lines, as only primer combinations pd00277-pd00192 and pd00190-pd00192 yielded amplification products in both red and non-red (yellow) assayed lines.
Figure 2B:
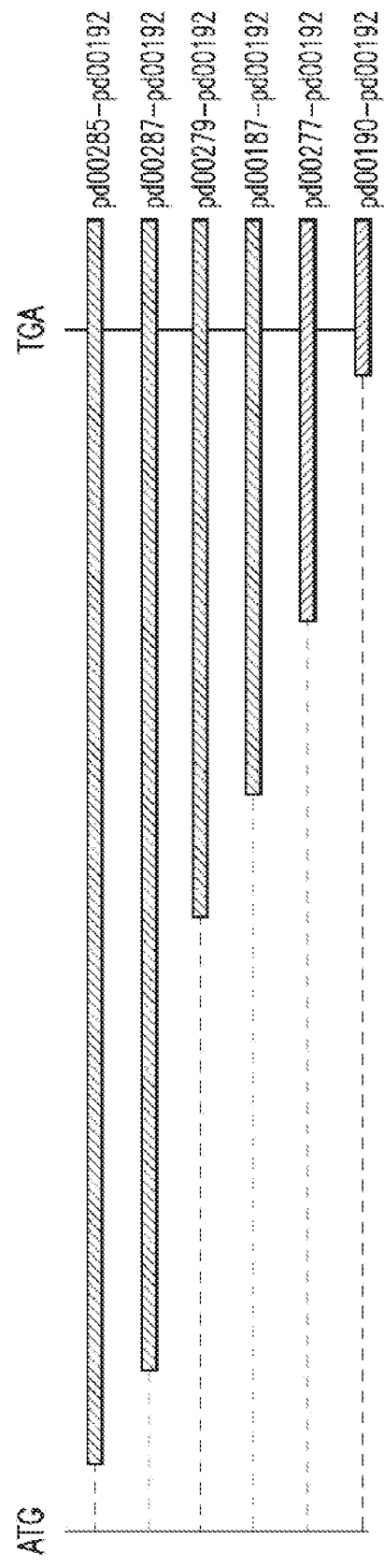

The Ccs gene sequence was previously deposited in Genbank (e.g. under accessions DQ907615.1 and X77289 (SEQ ID NO:1)). PCR analysis revealed that part of the CCS gene was deleted in certain studied pepper lines which produce non-red mature fruit. Primers were designed on parts of the CCS sequence and were used for PCR on red and non-red (yellow) lines (Table 2; SEQ ID NOs:2-9). Different forward primers were used, but in all PCR reactions primer pd00192 was used as reverse primer (Table 2; FIG. 2). Amplicons were always obtained from red lines, but in non-red lines amplicons were only obtained with primers that target the 3' region of the Ccs gene (FIG. 2). This inability to obtain amplicons is consistent with a deletion in the Ccs gene in non-red lines.

TABLE 2

Primers used to confirm deletion in Ccs gene of non-red lines (SEQ ID NOs: 2-9; see also FIG. 2).

| Primer | Sequence (5'-3') | Orientation | Expected fragment size (bp) | Amplicon obtained in Red | Amplicon obtained in Yellow |
|---|---|---|---|---|---|
| pd00285 | CAACTCCACTTTTCCAAATC | F | 1884 | Yes | No |
| pd00287 | GGTTGATACTGATCTGGACG | F | 1743 | Yes | No |
| pd00279 | GTGAGTCGGCCTATGTTATCG | F | 1066 | Yes | No |
| pd00187 | TGGTGGGACTTCAGGGATAG | F | 903 | Yes | No |
| pd00277 | TGTTGATCCCAAGTACTGGC | F | 639 | Yes | Yes |
| pd00190 | AGACTTGGTATCAGATTGTGGC | R | 418 | Yes | Yes |
| pd00191 | AGCCACAATCCGATACCAAG | F | 246 | Yes | Yes |
| pd00192 | GAGGGACAAGAGTGGAGCAG | R | N/A | N/A | N/A |

Genome walking experiments were performed to confirm the presence of a deletion in the Ccs gene of non-red lines. This analysis and additional sequencing showed that the Ccs gene contains an intact ORF in all red lines tested, while a 4472 bp deletion is present in all tested non-red lines (FIG. 3). The deletion covers most of the CCS ORF (1196 bp) and as a result only 351 bp of the sequence is conserved between red and non-red lines. Moreover, 3231 bp in the 5' UTR are absent in non-red lines compared to red lines. In the 3' UTR, a segment of 671 bp was conserved between red and non-red lines, albeit with several polymorphisms between these alleles. In total, 5750 bp of sequence was obtained from red pepper lines: 3582 bp of sequence was obtained from the 5' UTR, 671 bp from the 3' UTR, and the CCS ORF itself is 1497 bp in length. The observation that only red fruited lines have an intact Ccs gene leads to the conclusion that Capsanthin-Capsorubin Synthase is needed to convert the non-red carotenoids into the red carotenoids A TaqMan™ assay designated Q-NCANN009113770 was designed to assay the presence or absence of sequence at the 4472 bp deletion site in the Ccs gene. Primer and probe design for the NCANN009113770 assay are shown in Table 3 (SEQ ID NOs:10-14). Similarly performing assays can be designed by varying the position of the forward and reverse primers or by designing the primers against the complementary strand of DNA. The inferred fruit color phenotypes obtained with this marker on a line panel are shown in FIG. 3C. Another TaqMan™ assay designed for red vs. non-red marker assisted selection utilized marker NCANN005134316 (based on the A/T polymorphism in SEQ ID NO:19), and was designed to target an A/T SNP in the 3' UTR of Ccs. Primer and probe design for the NCANN009113770 assay are shown in Table 3 (SEQ ID NOs:15-18. This assay was predictive in approximately 95% of tested pepper germplasm. However, as shown in FIG. 3C, several lines with red fruits carry the A allele of NCANN005134316, associated with non-red fruits.

TABLE 3

Primers and probes used for TaqMan™ assays NCANN009113770 and NCANN005134316 (SEQ ID NOs: 10-18).

| Name | Description | Sequence | Allele |
|---|---|---|---|
| NCANN009113770_F1 | forward primer 1 | TCGAAAGCCTTGGCTCAACA | |
| NCANN009113770_F2 | forward primer 2 | TTTTGTATCTCCCTTTCCCAGAA | |
| NCANN009113770_R | reverse primer | TCTCTAACACGTCTTCTATCCGAAGG | |
| NCANN009113770_V | VIC probe | AGAATGATAAGAGGGTCT | INS |
| NCANN009113770_M | FAM probe | CTTTTAGAGTTTGGAATG | DEL |
| NCANN005134316_F | forward primer | CCAAACACTTTGAATTGGCTGGATA | |
| NCANN005134316_R | reverse primer | ACTATATTAACTTTCCTAATAATTCTTGCTTTCCCA | |
| NCANN005134316_V | VIC probe | TGCTGTTAATGATTAATAACAT | A* |
| NCANN005134316_M | FAM probe | CTGTTAATGATTAAAAACAT | T* |

*probes are designed on the reverse complement sequence

Table 4 shows an overview of the studied mutations found in the Ccs gene and flanking sequences (SEQ ID NOs:20-38). In total 13 additional SNPs and small indel mutations were identified in the 3' UTR of the Ccs gene (Table 4).

Three of these are indel mutations (of 3, 4 and 14 bp respectively). The other 10 mutations are SNPs. Two of these SNPs were only found in line HAS-30-1017, which is consistent with the fact that the Asian germplasm is genetically divergent from the sweet pepper germplasm. One line-specific SNP was found in line SBY-99-1273.

TABLE 4

Overview of mutations found in the CCS gene and flanking sequences.

| | Fruit color | NCANN005134316 [A/T] | NCANN009113770 [INS/DEL] | NCANN009113570 [T/c] | NCANN009114370 [A/c] | NCANN009113170 [C/a] | NCANN009113970 [TATGGTTGTCGATG/*] | NCANN009113370 [T/c] | NCANN009113971 [T/a] | NCANN009113371 [G/t] |
|---|---|---|---|---|---|---|---|---|---|---|
| SBR-99-1193 | Red | A | INS | T | A | c | * | c | t | t |
| SBR-99-1299 | Red | A | INS | T | A | c | * | c | t | t |
| SBR-99-1300 | Red | A | INS | T | A | c | * | c | t | t |
| HAS-30-1017 | Red | A | INS | T | A | c | TATGGTTGTCGATG | T | a | G |
| 10CA 3745-M | Red | T | INS | c | A | a | TATGGTTGTCGATG | T | T | G |
| SZZ-BT10901 | Red | T | INS | c | A | a | TATGGTTGTCGATG | T | T | G |
| SBR-27-146 | Red | T | INS | c | A | a | TATGGTTGTCGATG | T | T | G |
| SBY-148-5201 | Yellow | T | DEL | c | A | a | TATGGTTGTCGATG | T | T | G |
| SBY-29-469 | Yellow | T | DEL | c | A | a | TATGGTTGTCGATG | T | T | G |
| SBY-99-1179 | Yellow | T | DEL | c | A | a | TATGGTTGTCGATG | T | T | G |
| SBY-99-1273 | Yellow | T | DEL | c | C | A | TATGGTTGTCGATG | T | T | G |
| SBY-99-1296 | Yellow | T | DEL | c | A | a | TATGGTTGTCGATG | T | T | G |
| SBY-99-1339 | Yellow | T | DEL | c | A | a | TATGGTTGTCGATG | T | T | G |
| SMO-28-1234 | Change | T | DEL | c | A | a | TATGGTTGTCGATG | T | T | G |

| | Fruit color | NCANN009113970 [AACA/*] | NCANN009114370 [A/c] | NCANN009113571 [A/g] | NCANN009113171 [G/t] | NCANN009113371 [C/t] | NCANN009113771 [G/t] | NCANN009114171 [aac/*] |
|---|---|---|---|---|---|---|---|---|
| SBR-99-1193 | Red | AACA | A | A | t | t | t | aac |
| SBR-99-1299 | Red | AACA | A | A | t | t | t | aac |
| SBR-99-1300 | Red | AACA | A | A | t | t | t | aac |
| HAS-30-1017 | Red | AACA | A | A | t | t | t | aac |
| 10CA 3745-M | Red | * | A | A | G | C | G | * |
| SZZ-BT10901 | Red | * | A | A | G | C | G | * |
| SBR-27-146 | Red | * | A | A | G | C | G | * |
| SBY-148-5201 | Yellow | * | A | A | G | C | G | * |
| SBY-29-469 | Yellow | * | A | g | G | C | G | * |
| SBY-99-1179 | Yellow | * | A | A | G | C | G | * |
| SBY-99-1273 | Yellow | * | C | A | G | C | G | * |
| SBY-99-1296 | Yellow | * | A | A | G | C | G | * |
| SBY-99-1339 | Yellow | * | A | A | G | C | G | * |
| SMO-28-1234 | Change | * | A | A | G | C | G | * |

The INS/DEL identified by marker NCANN009113970 is given in SEQ ID NO: 39.

For accuracy tests, marker NCANN009113770 was validated on a panel of 615 leaf samples. The panel was derived from variety trials and predominantly contained lines that were developed for the Dutch greenhouse market. In all tested plants of visually-assessed fruit color, only two gave an unexpected genotype (Table 5), which are likely caused by a technical error, probably caused by a mistaken color description. Nonetheless, in this trial the marker is at least >99.6% accurate.

TABLE 5

Accuracy test results for marker NCANN009113770.

| Observed | Genotype | | | |
|---|---|---|---|---|
| | INSINS | INSDEL | DELDEL | — |
| | Inferred phenotype | | | |
| Phenotype | Red | Red | Not-red | — |
| Red | 294 | 22 | 1* | 12 |
| Yellow | 0 | 0 | 181 | 4 |
| Orange | 1* | 0 | 98 | 2 |

*conflict between inferred and observed phenotypes

In conclusion, marker NCANN009113770 is based on a large deletion mutation in the CCS gene; all available data suggests that this mutation prevents the formation of red pigment in non-red pepper fruits. The marker is thus highly predictive for mature fruit color.

Figure 8:
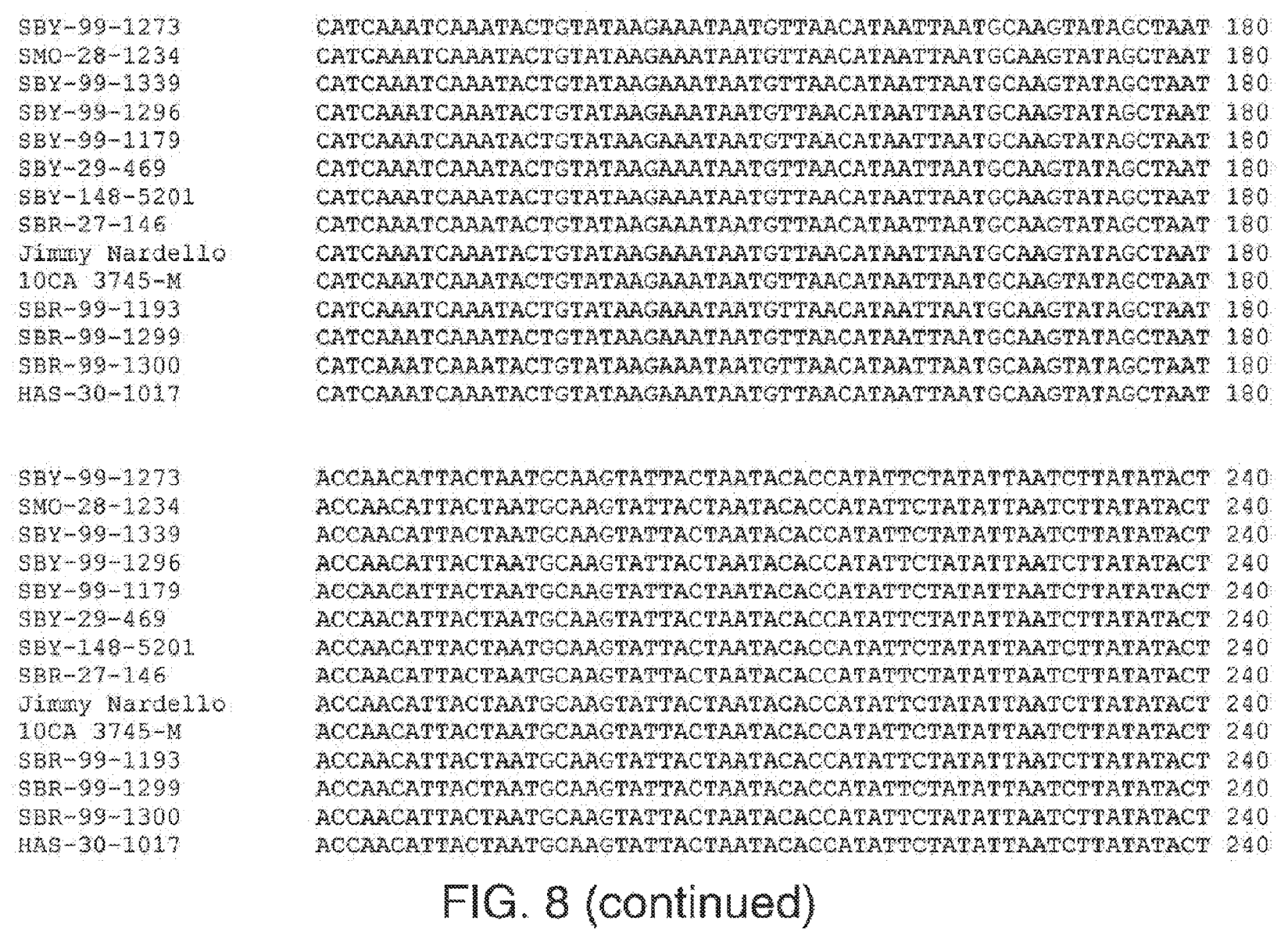
Figure 8:
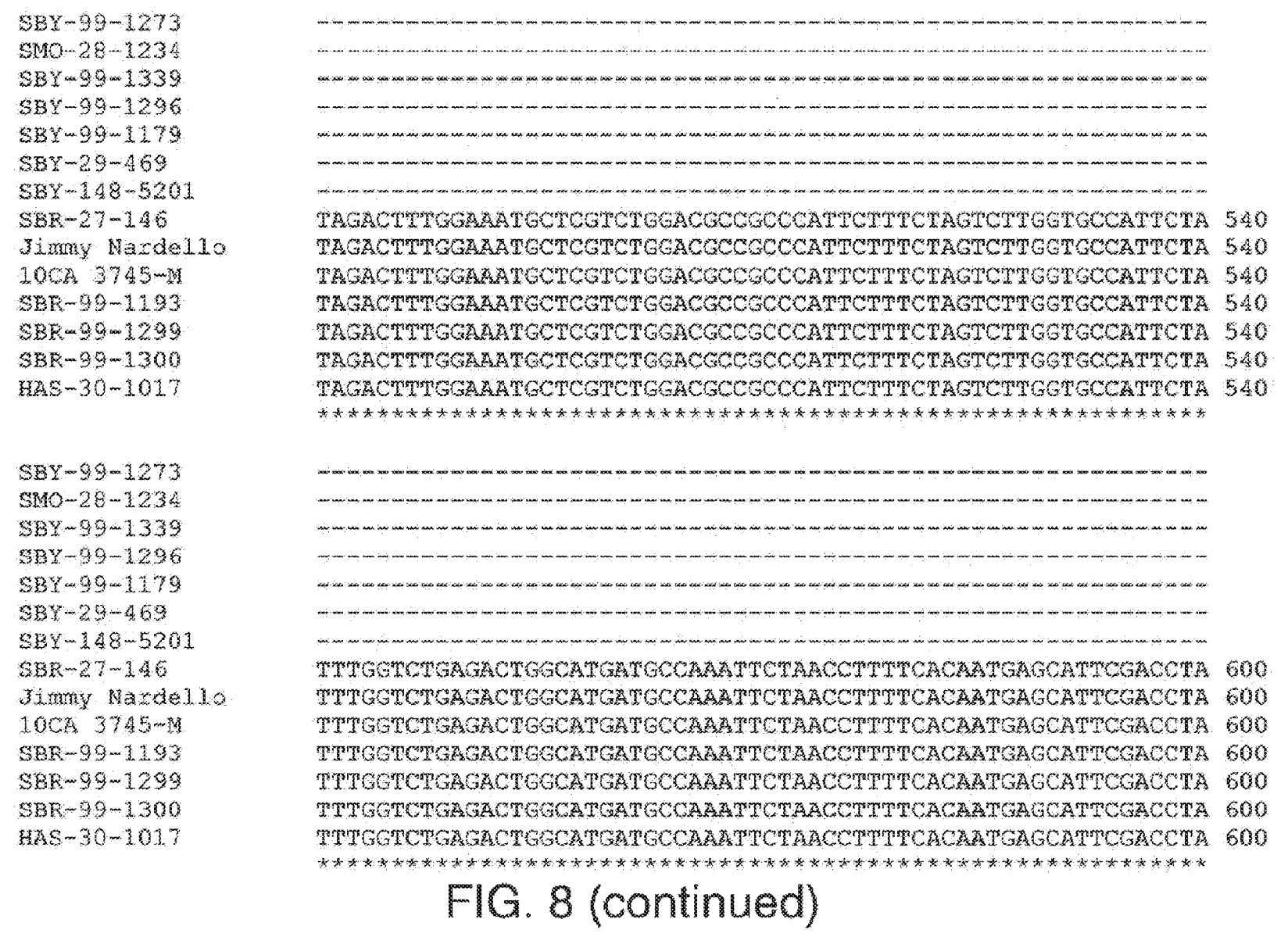
Figure 8:
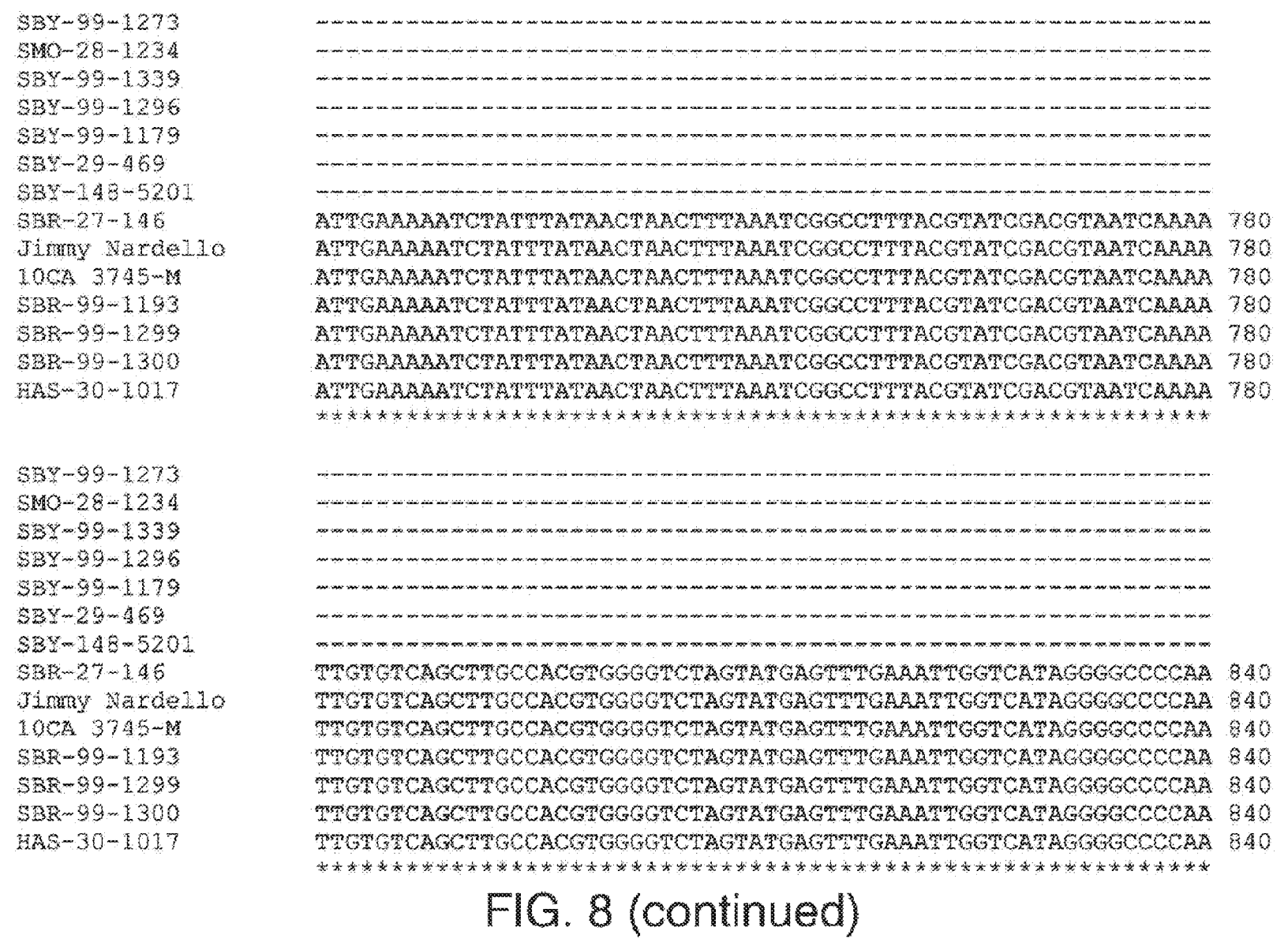
Figure 8:
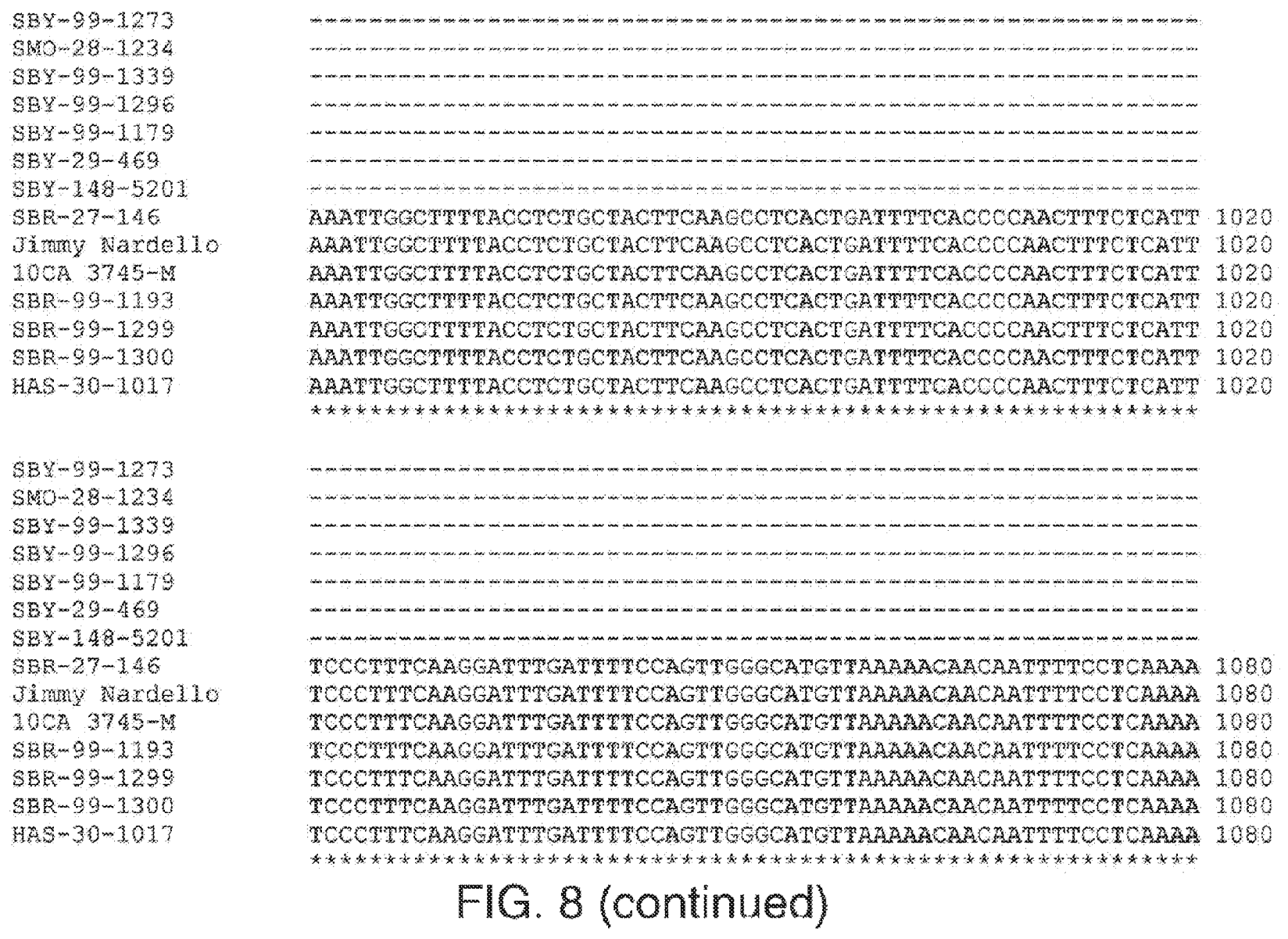
Figure 8:
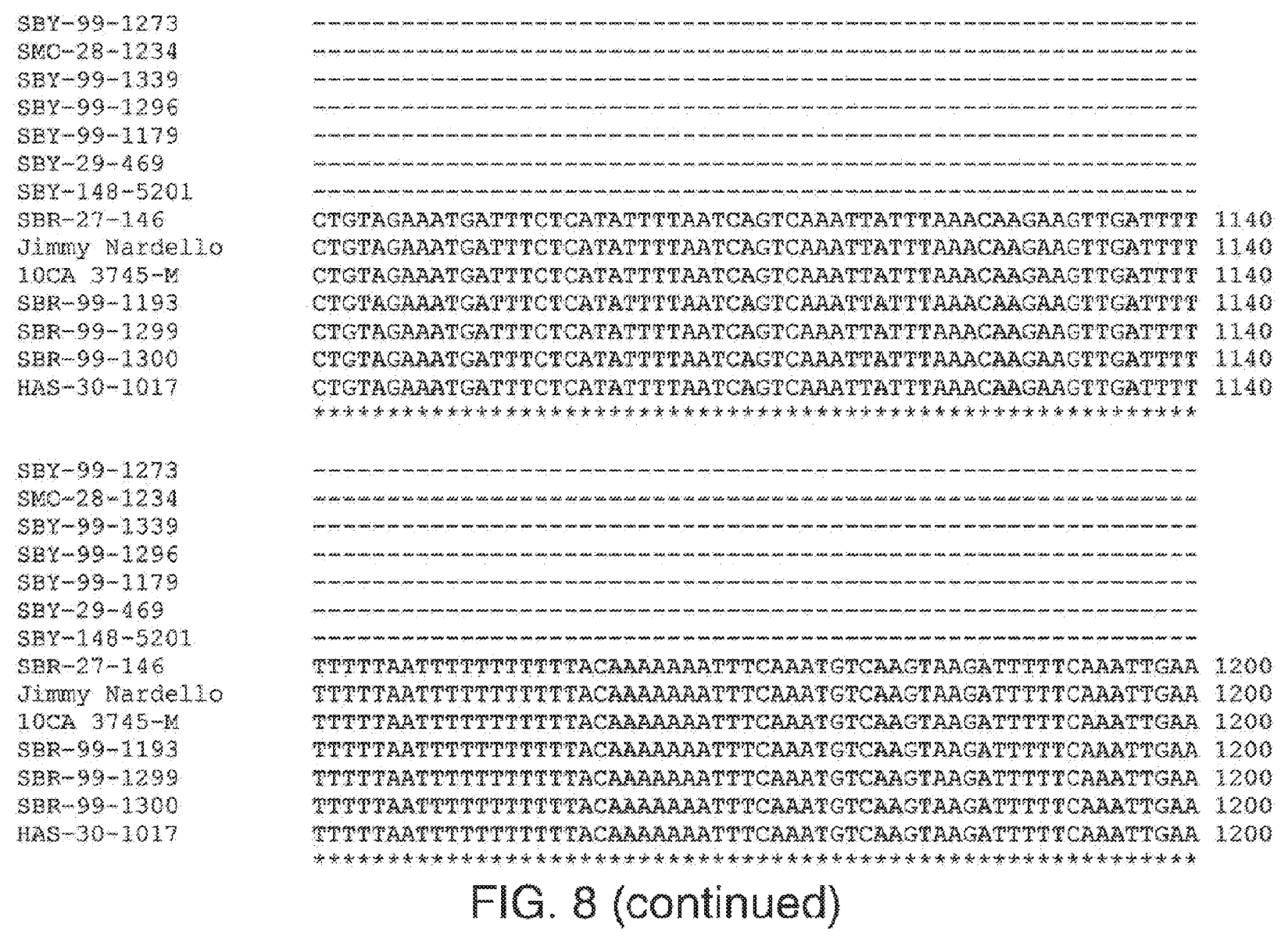
Figure 8:
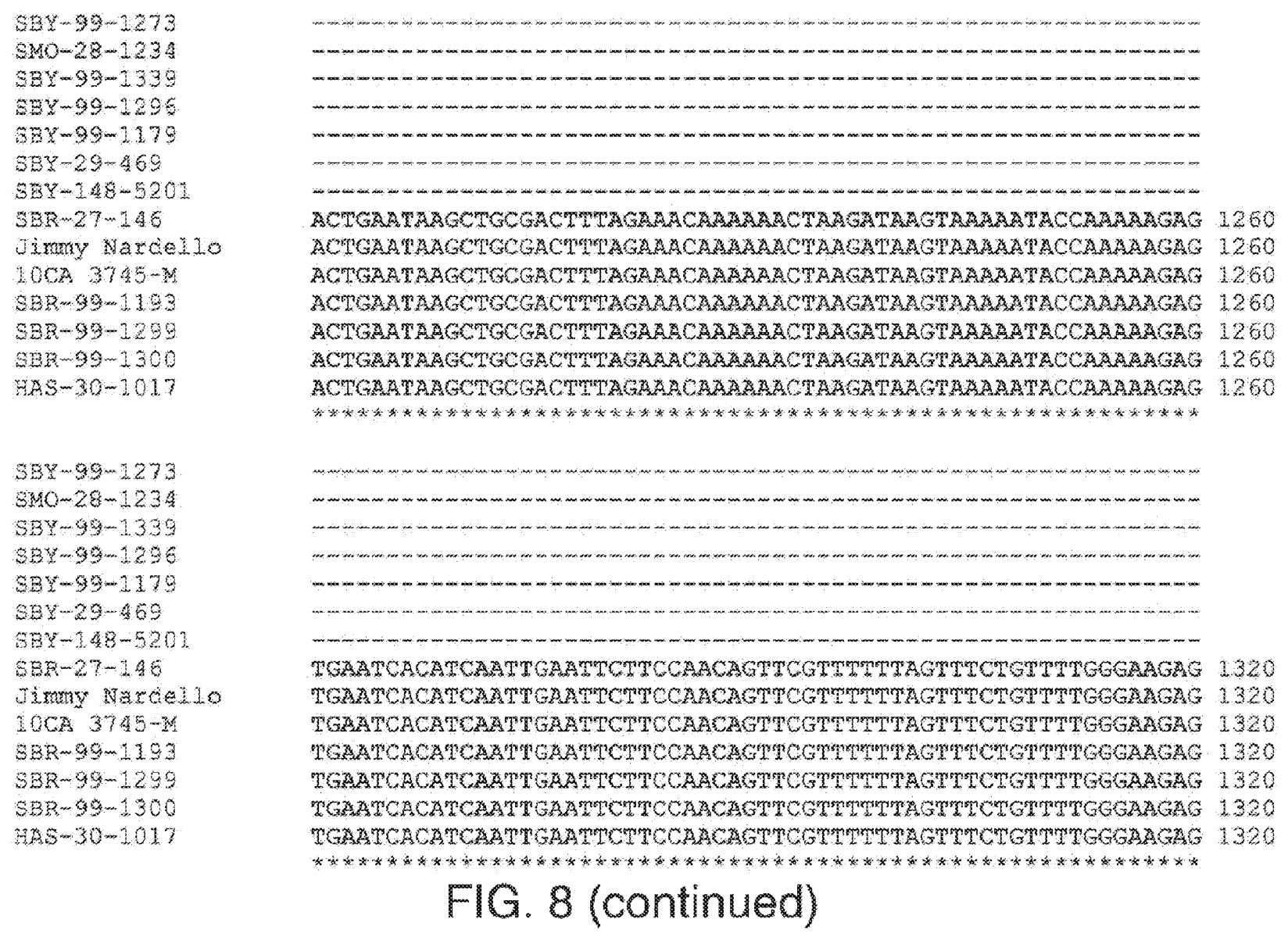
Figure 8:
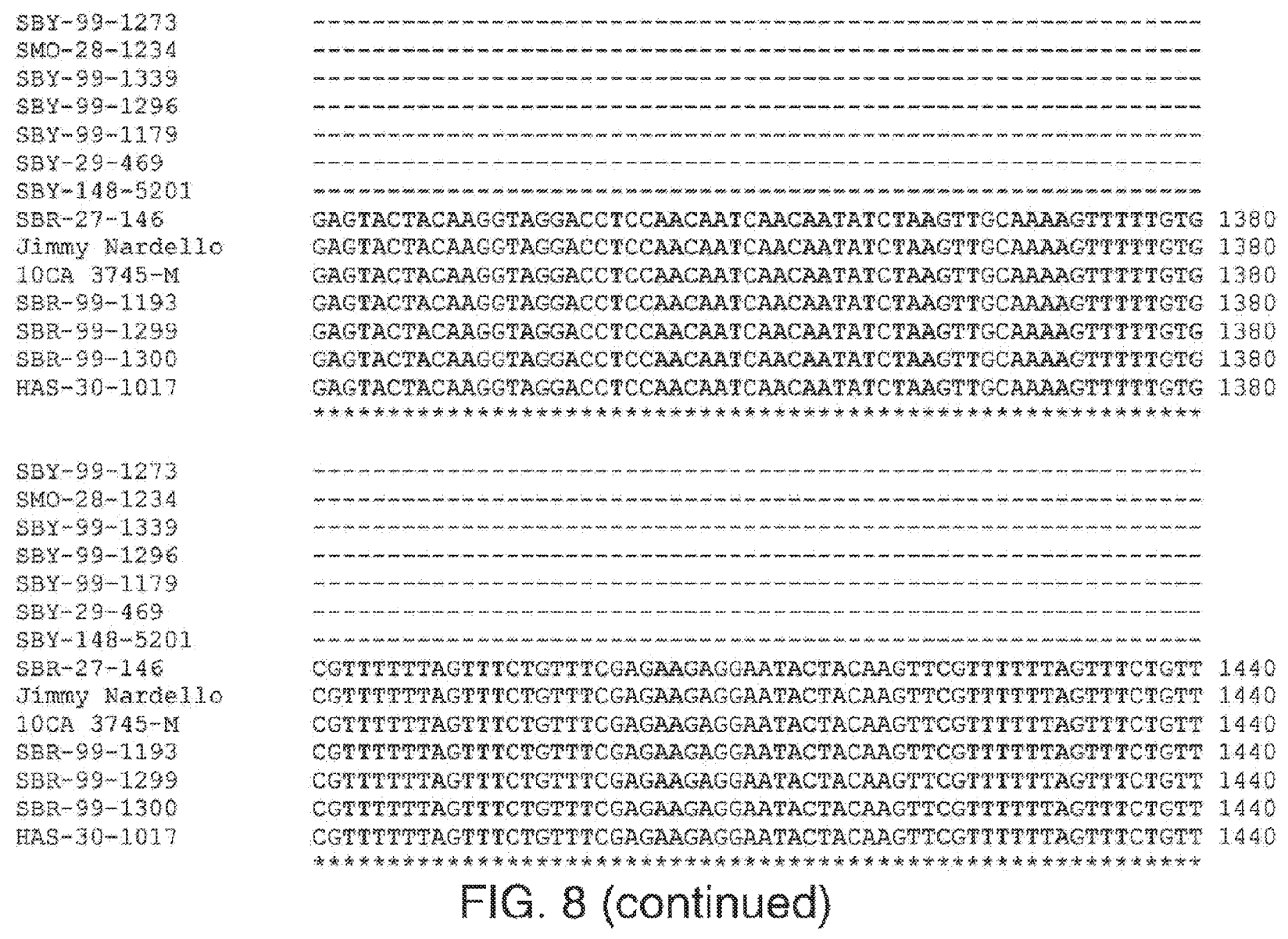
Figure 8:
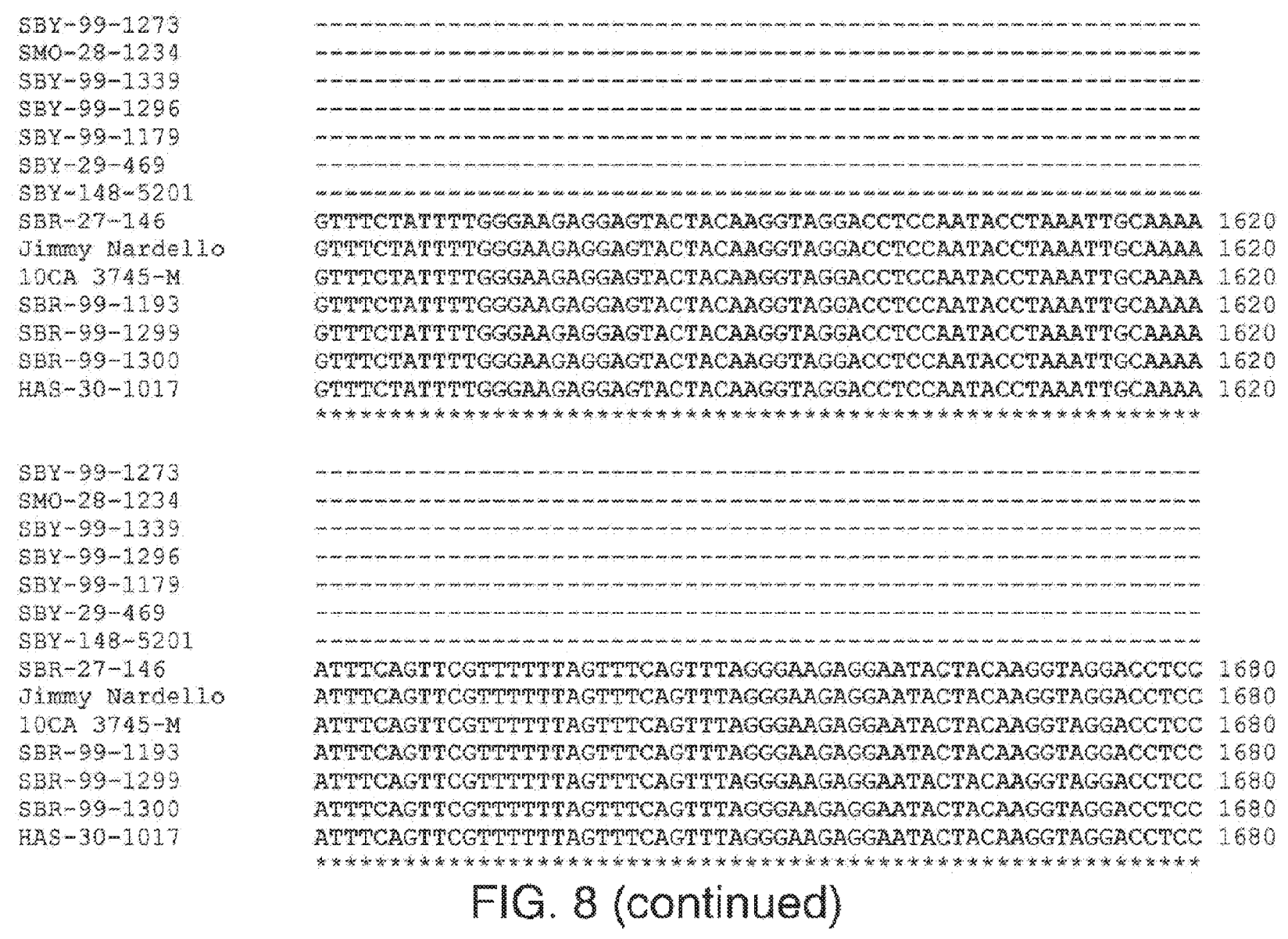
Figure 8:
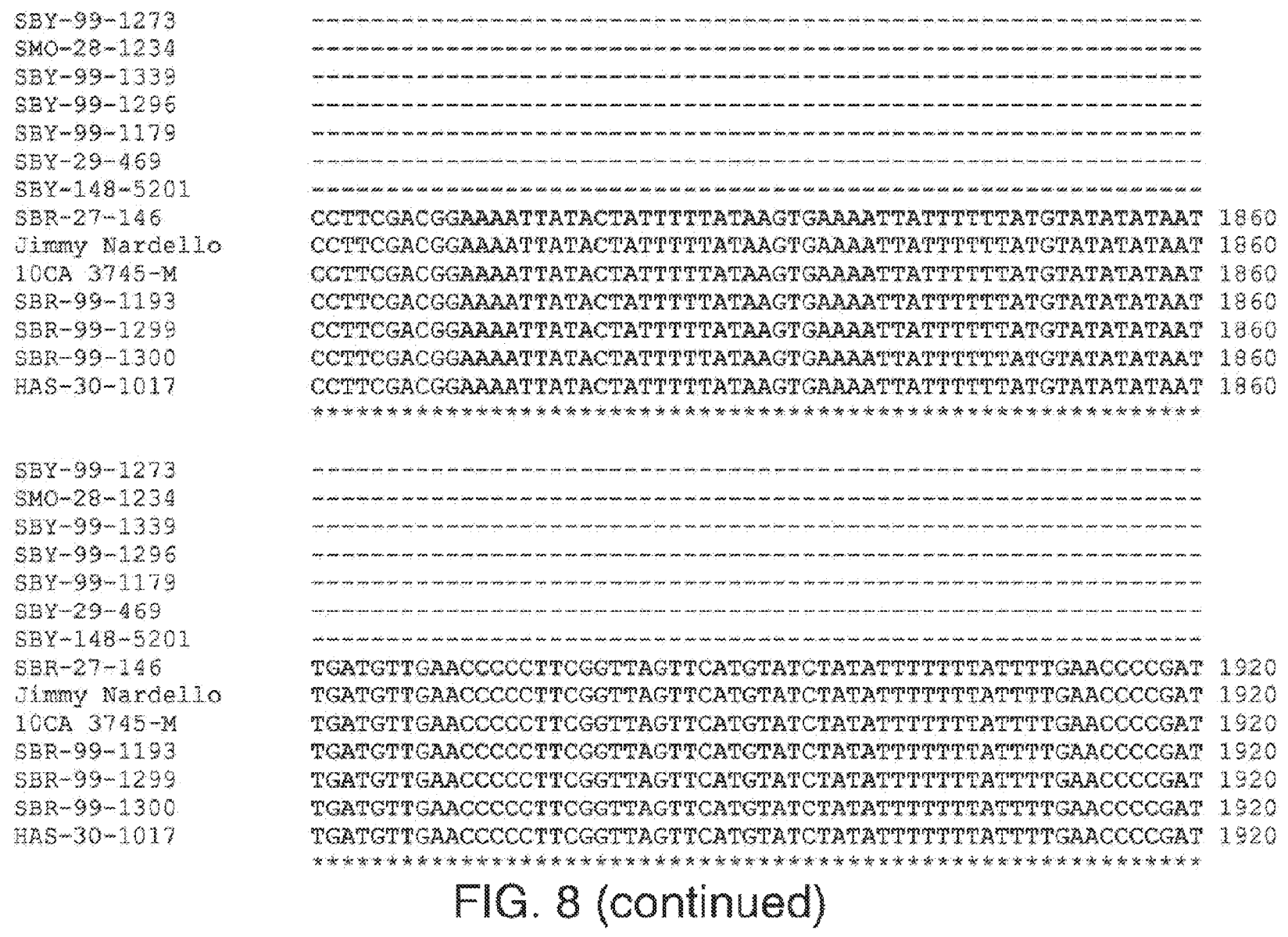
Figure 8:
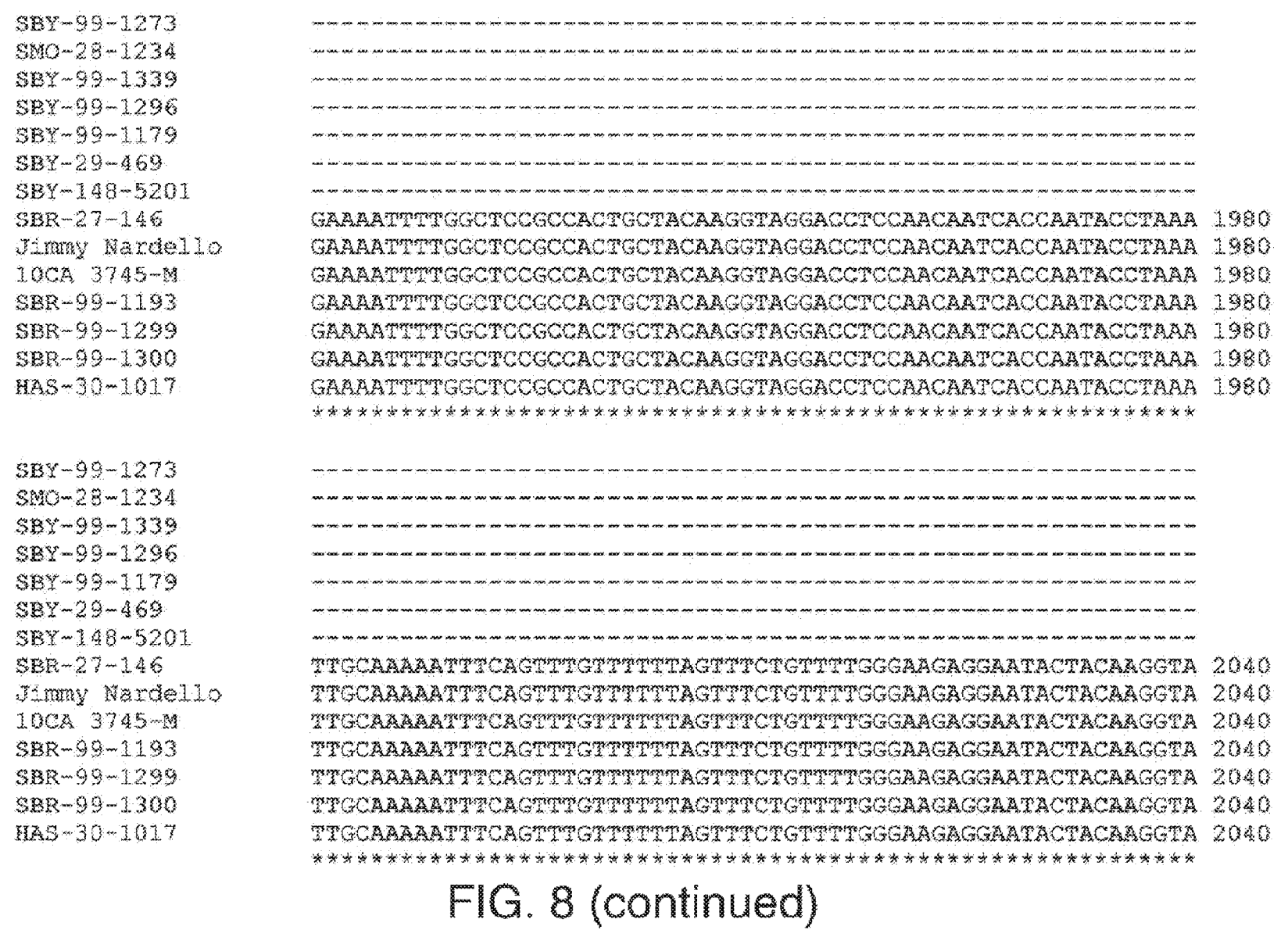
Figure 8:
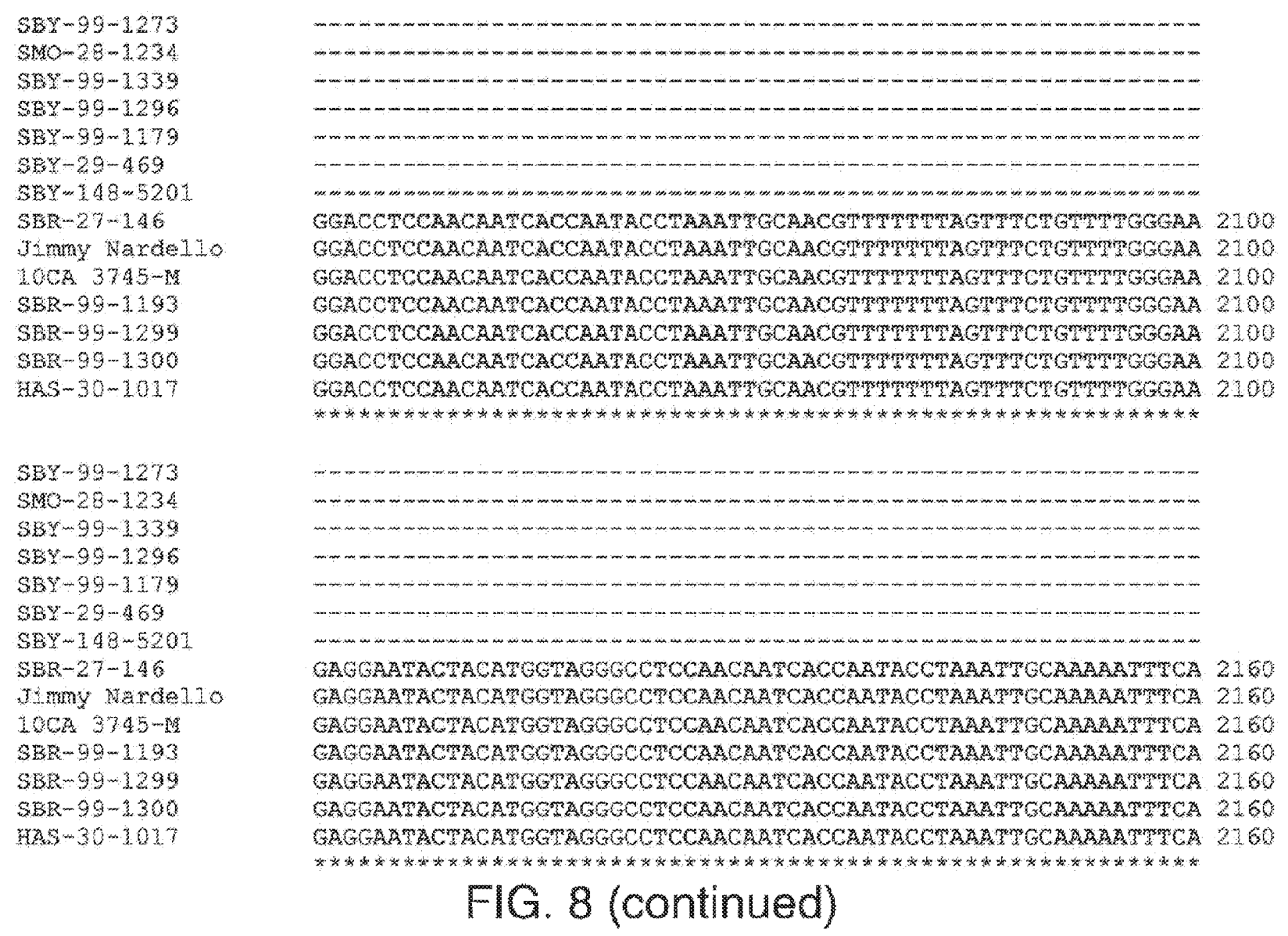
Figure 8:
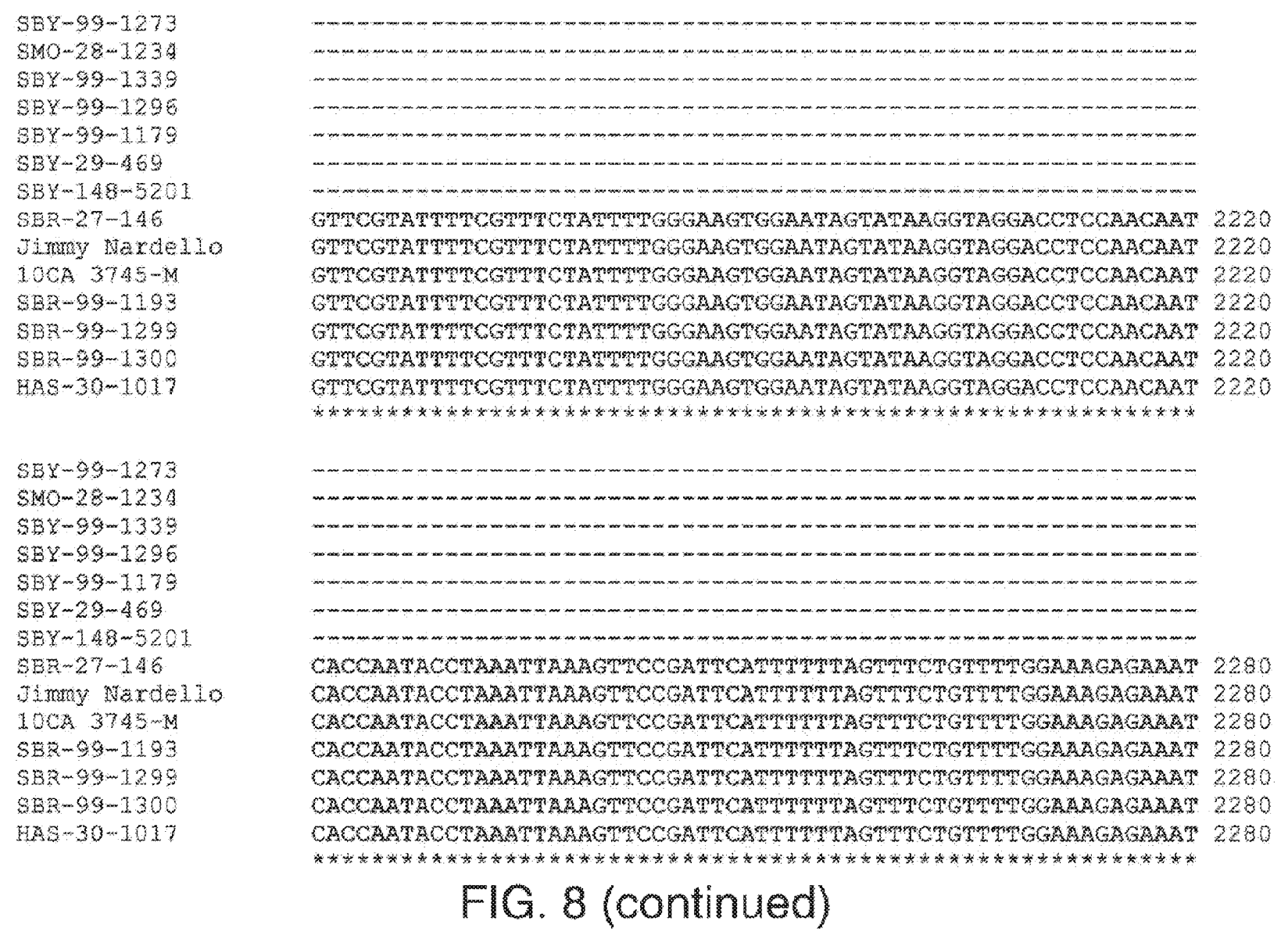
Figure 8:
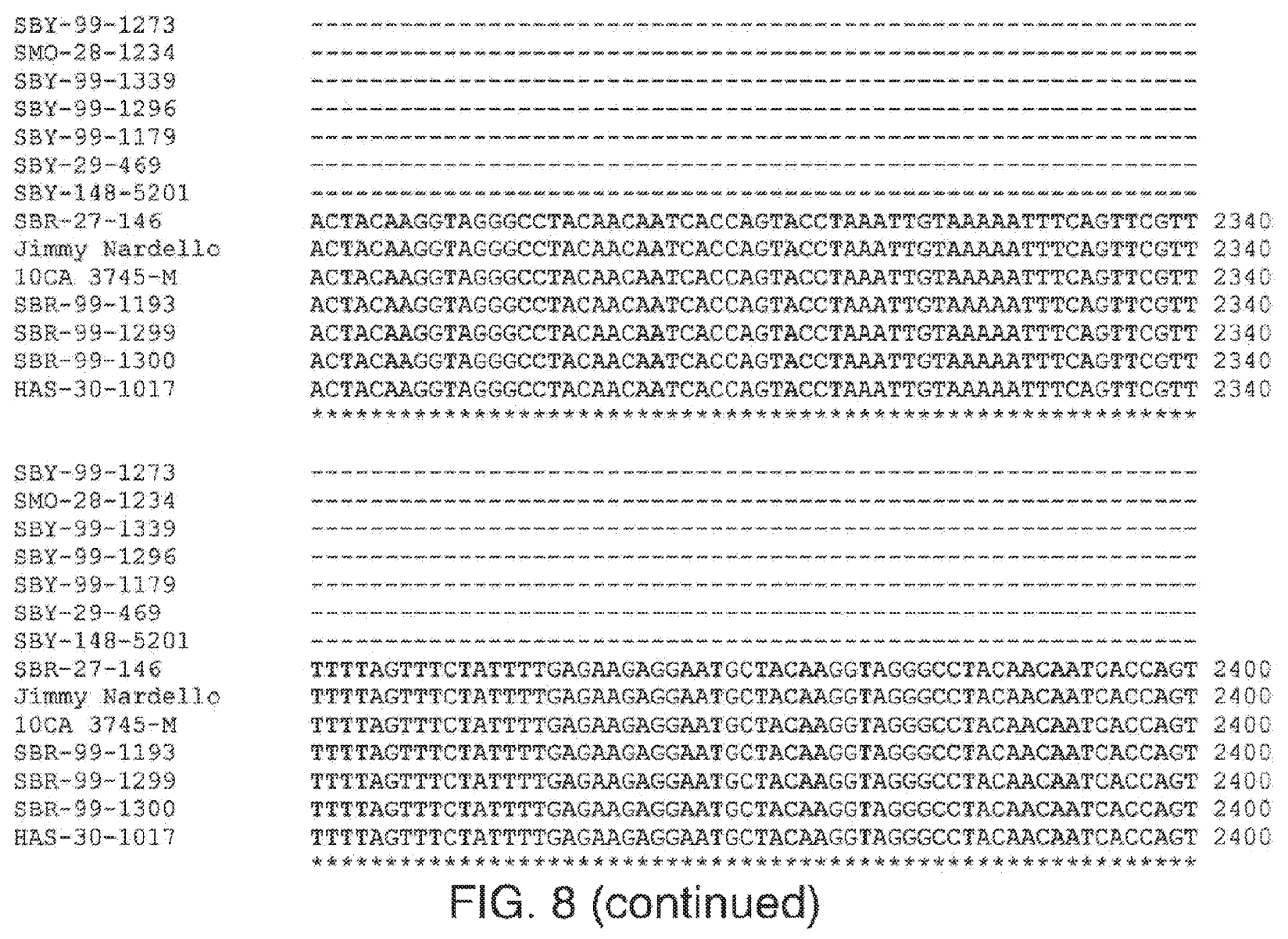
Figure 8:
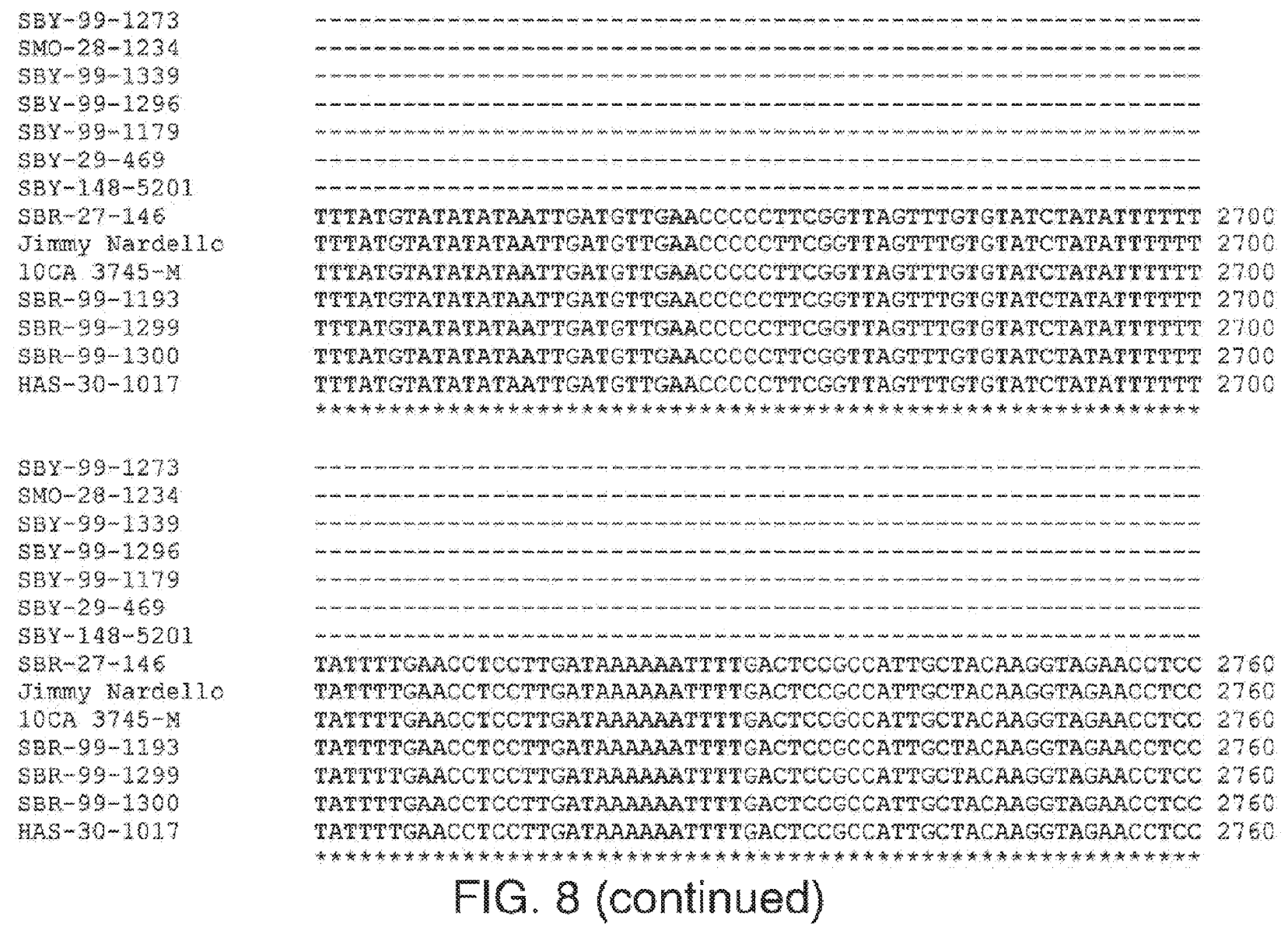
Figure 8:
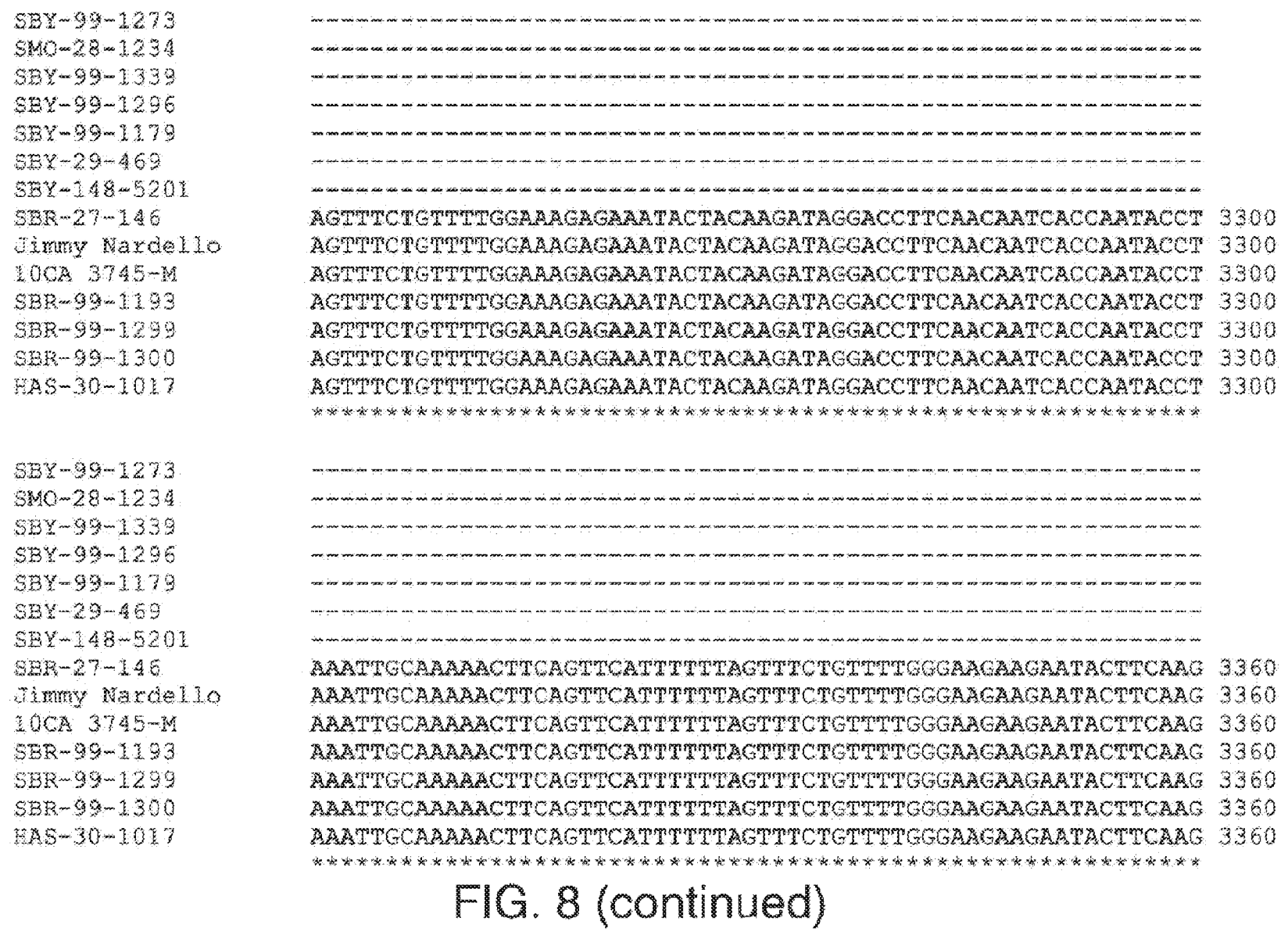
Figure 8:
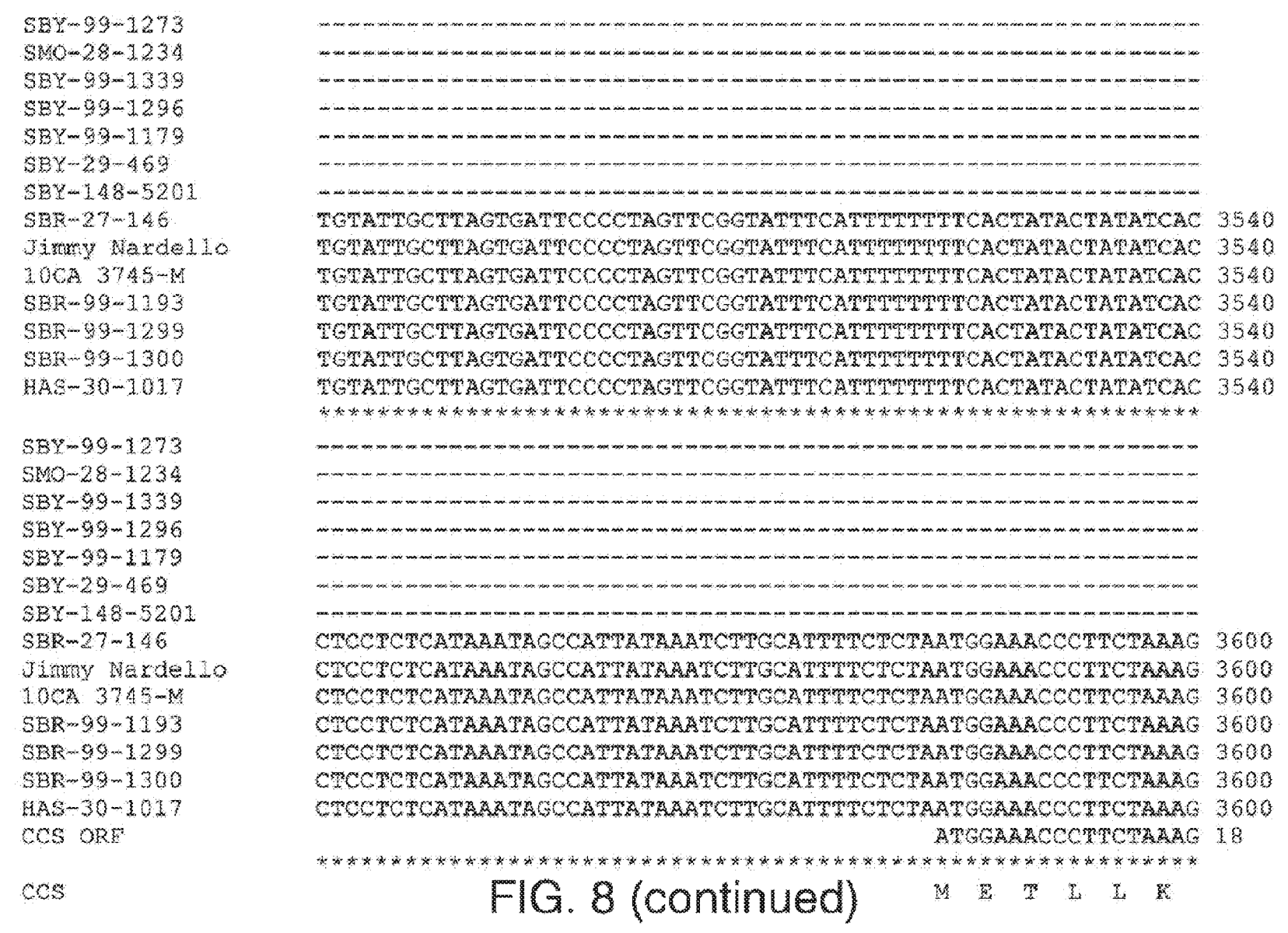
Figure 8:
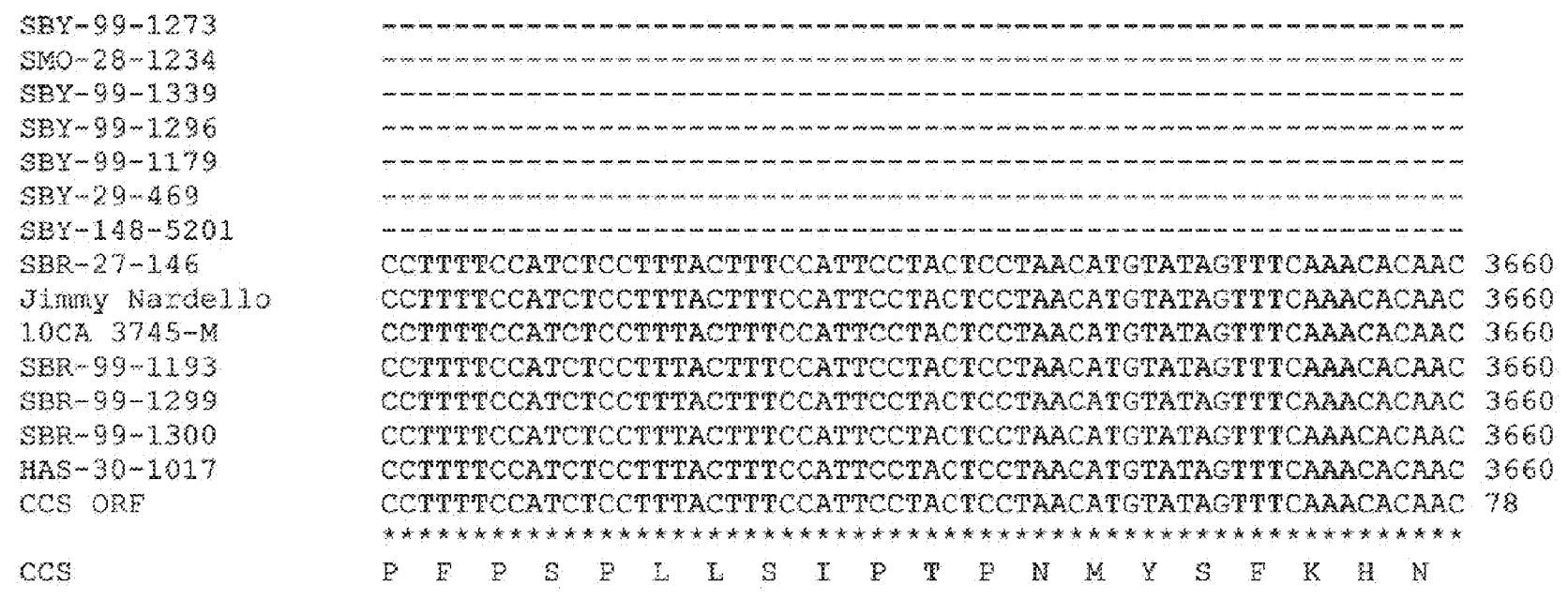
Figure 8:
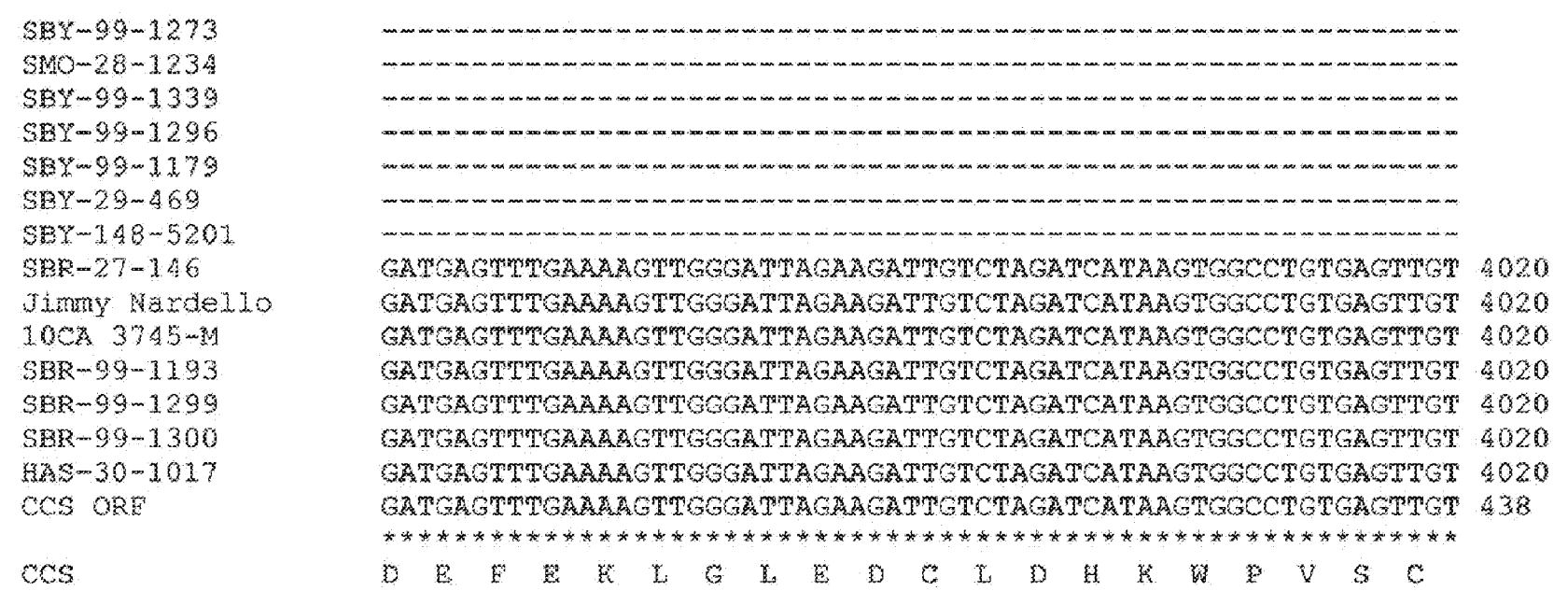
Figure 8:
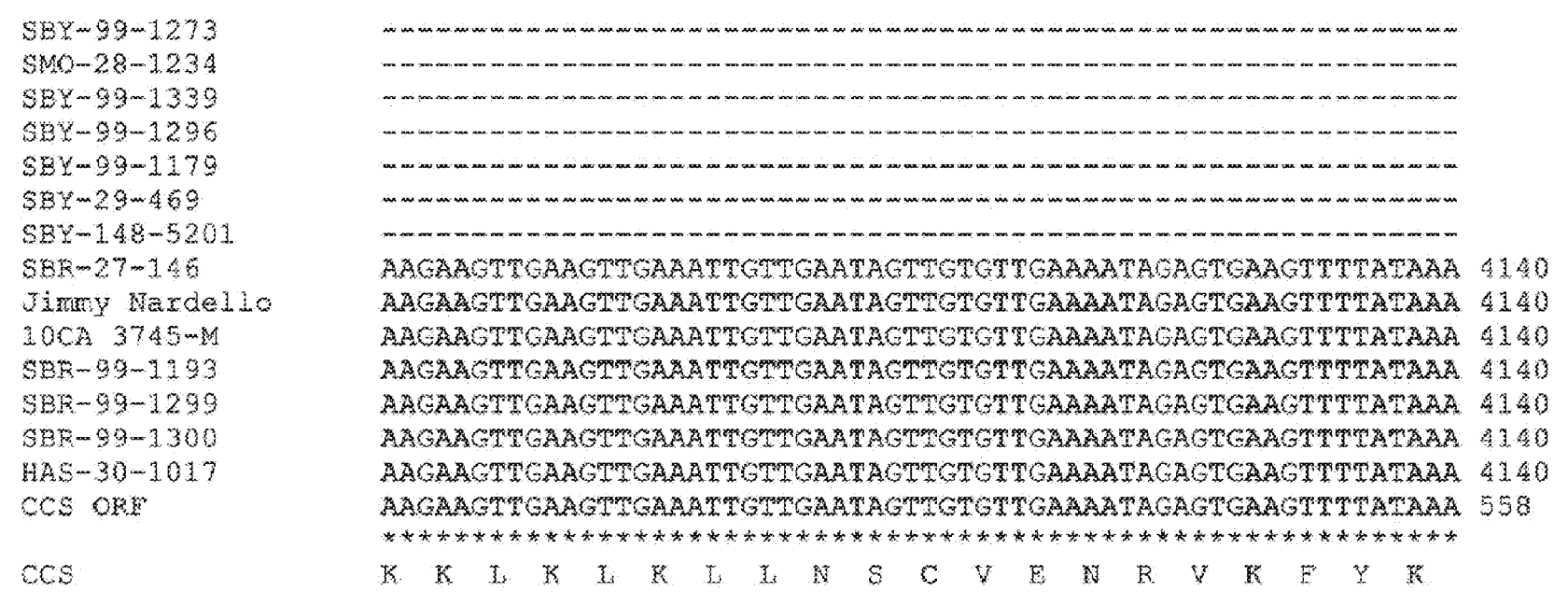
Figure 8:
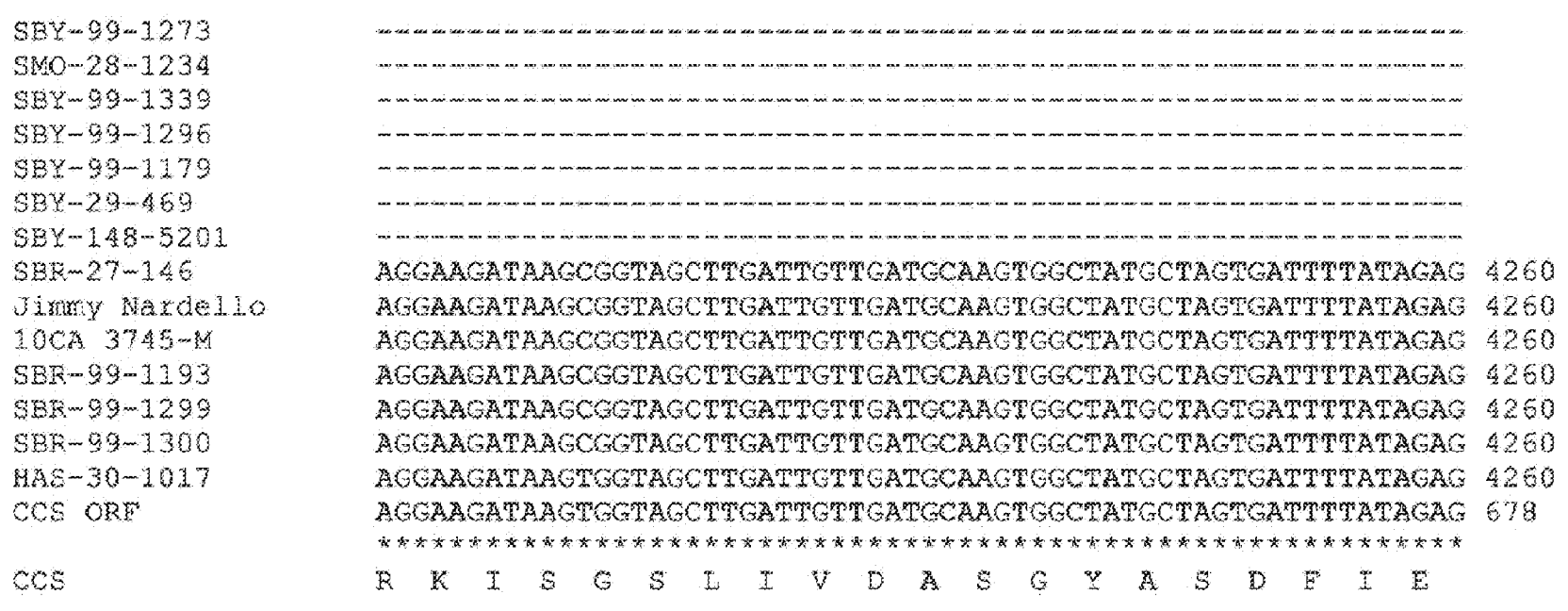
Figure 8:
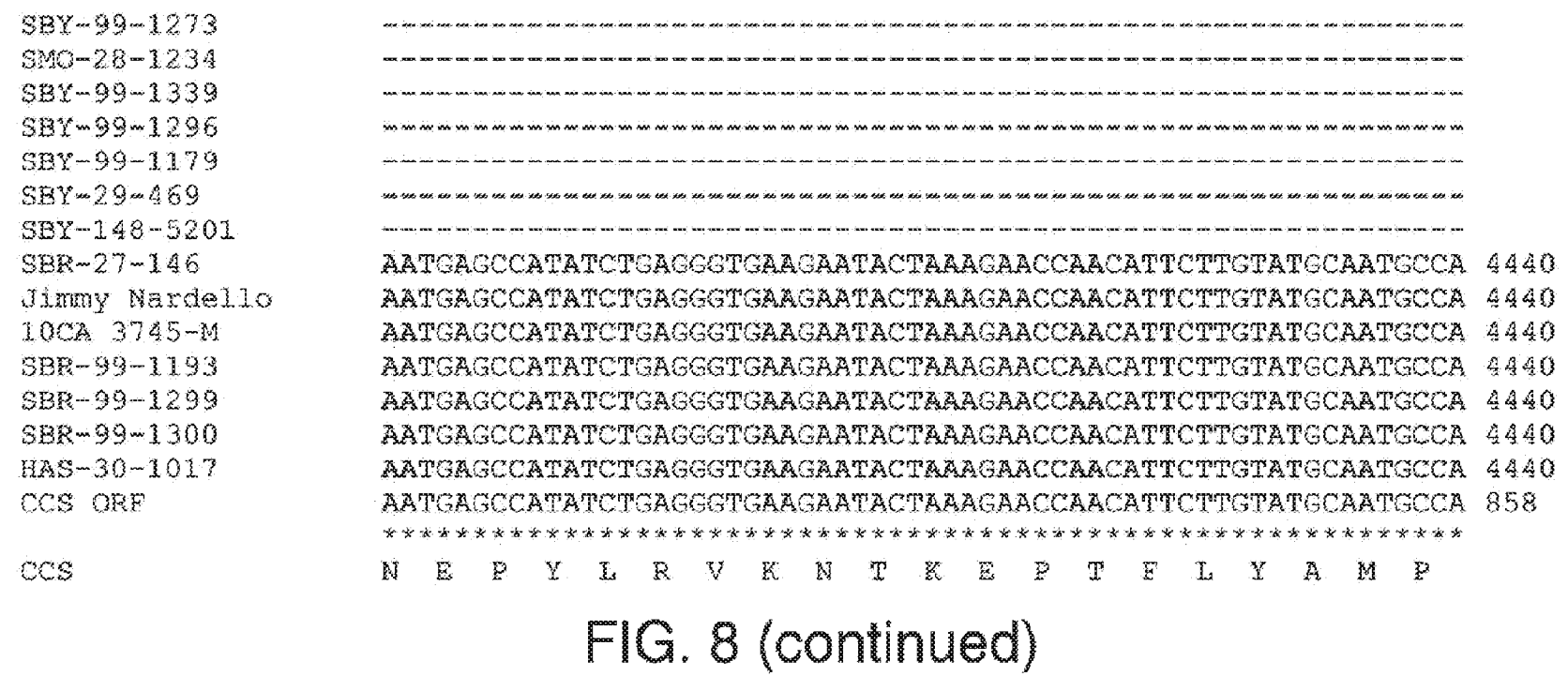
Figure 8:
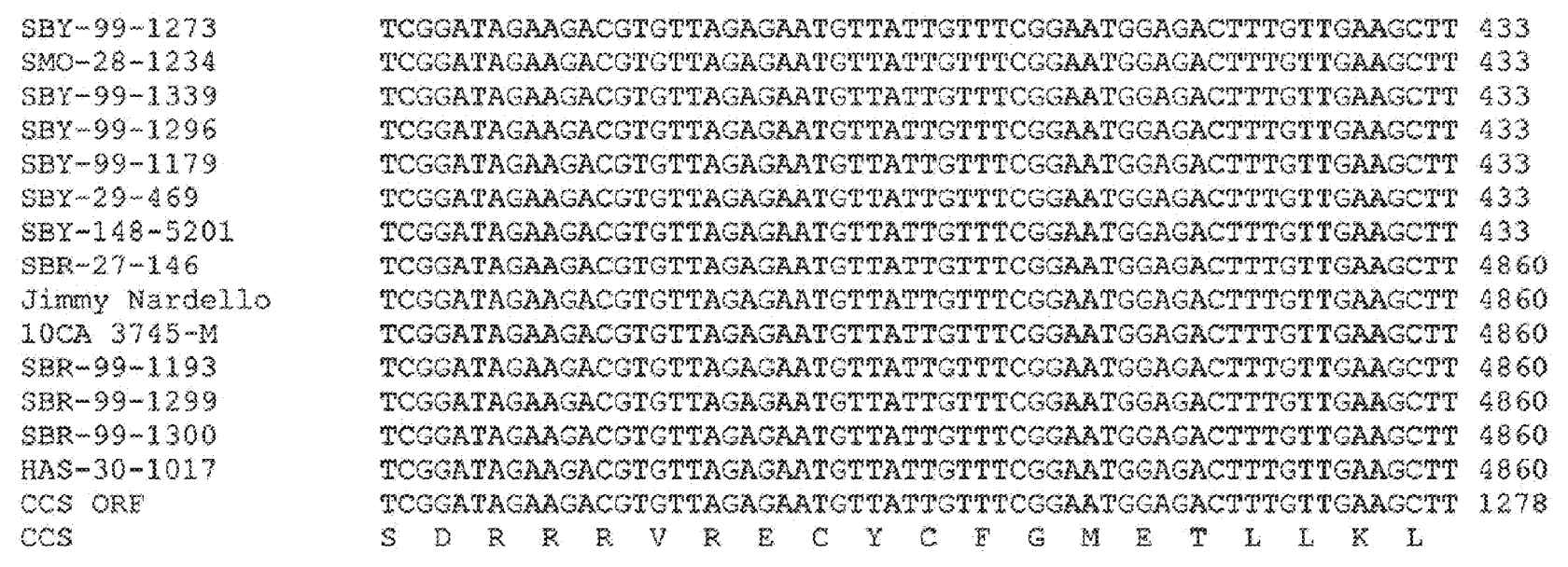
Figure 8:
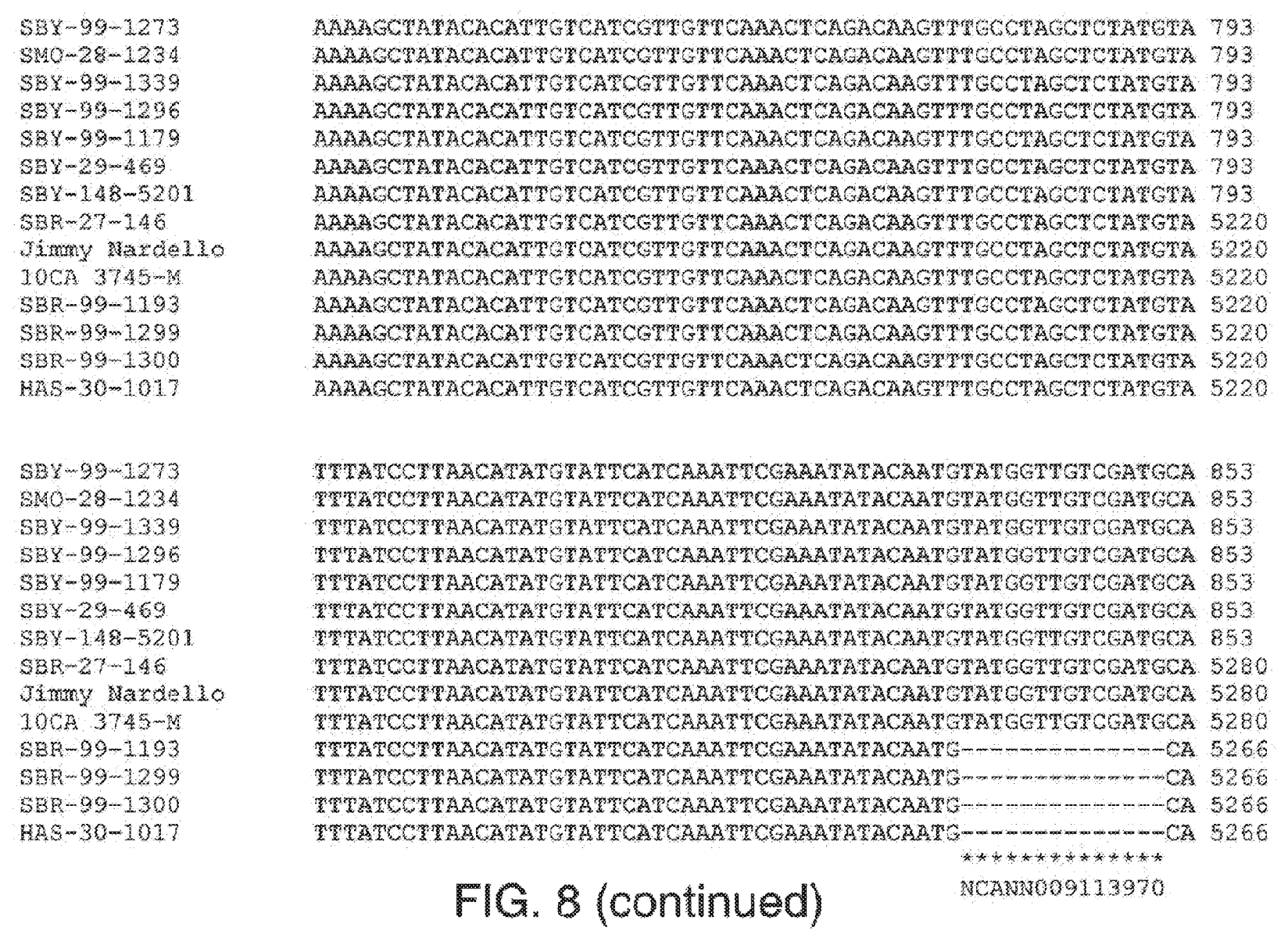
Figure 8:
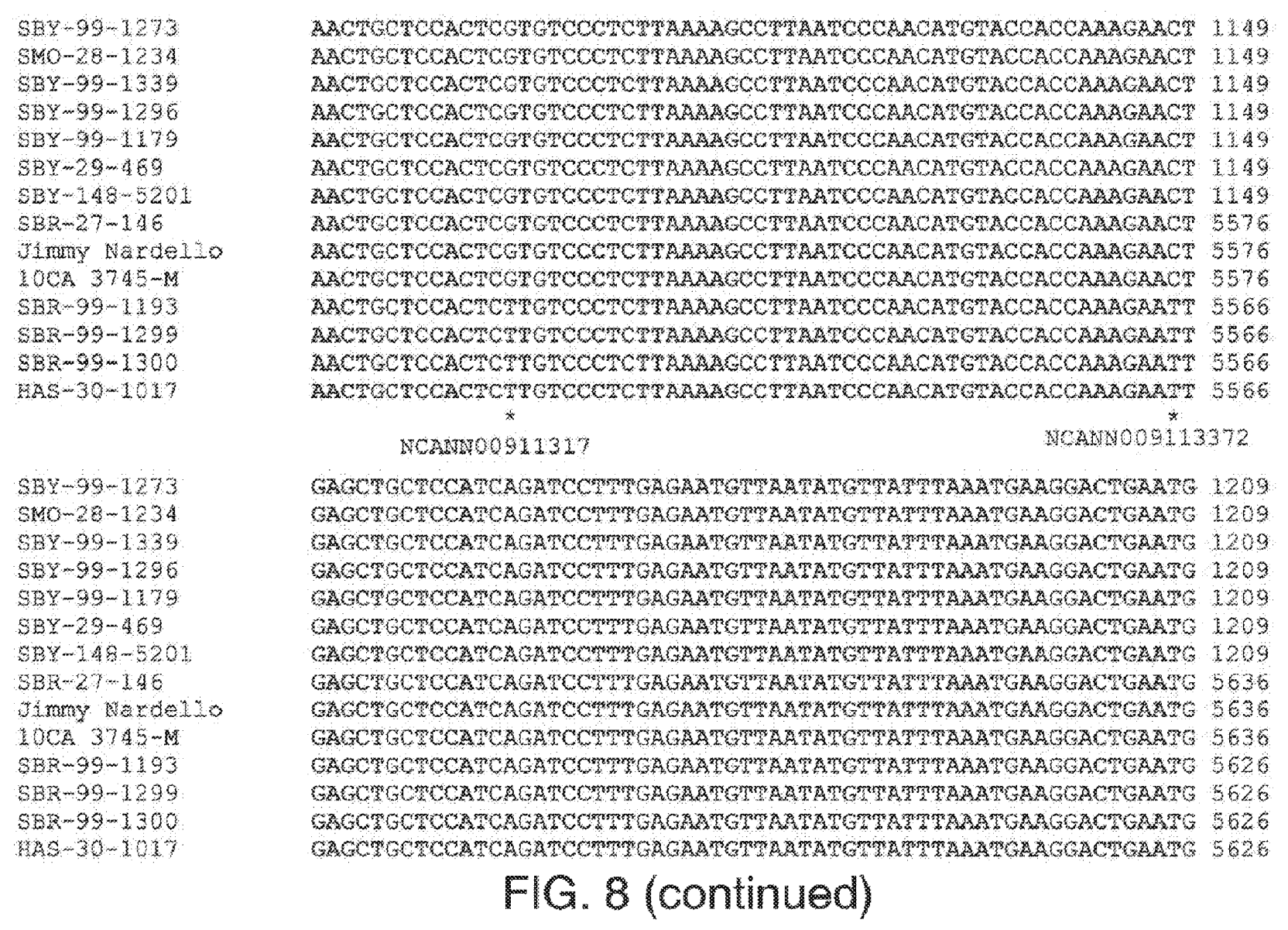

FIG. 8 gives an alignment of Ccs sequences from 14 pepper lines (SEQ ID NOs:40-53) showing the location of polymorphisms. A consensus CCS ORF sequence is given at SEQ ID NO:54. SNPs are indicated by asterisks. The predicted protein sequence of CCS is given at SEQ ID NO:55.

Of additional note is the discovery that plants can survive without a functional CCS gene. It follows that other mutations in the gene also may result in non-red fruit. An altered CCS genotype may therefore be provided by any suitable means; for example, EMS, MMS, other mutagen-derived, in situ-derived, or naturally-occurring mutations can provide an altered CCS genotype suitable for the development of the fruit color phenotypes described here. Color modulation of the fruit color phenotypes described here may also be achieved by transient disruption of CCS function at the time of fruit set and/or fruit color maturation.

Example 2

Zeaxanthin Epoxidase (Ze) Marker Development

The Zeaxanthin Epoxidase (Ze or ZEP hereafter) gene (Genbank X91491; SEQ ID NO:56) regulates the conversion of zeaxanthin to the yellow pigments antheraxanthin and violaxanthin. The gene is mapped to the lower part of chromosome 2 in pepper (Thorup et al. 2000) and the yellow-orange color polymorphism (YO_color) locus maps to the same region of chromosome 2. Map positions were derived from a linkage analysis study of an F2:F3 population (from a cross between a yellow line and an orange line) to arrive at a rough map position of 100.8 cM for the yellow-orange color locus (Tables 6-7).

TABLE 6

Map position of YO_color locus using an F2:F3 bi-parental mapping population. Nucleotide sequences around listed markers are given in SEQ ID NOs: 57-62.

| Marker | Chromosome | SBY-29-469/SMO-28-1234 F2:F3 | Map position (cM) |
|---|---|---|---|
| NE0235373 | 2 | 0 | 88.9 |
| NE0240266 | 2 | 2.9 | 94.2 |
| NE0237869 | 2 | n/a | 95.0 |
| YO_color* | 2 | 16.6 | 100.8 |
| NE0239621 | 2 | 22.4 | 103.6 |
| NE0240354 | 2 | 34.8 | 111.7 |
| NE0241248 | 2 | 37.1 | 113.6 |

*Yellow (Y) vs. orange (O) color scored as a binary trait in F3 families to permit inference of all three genotypic classes in the F2 generation.

TABLE 7

Primers and probes used for TaqMan ™ assay with markers of Table 6 (SEQ ID NOs: 63-86).

| Marker | Position | Primer or probe name | Sequence | Allele |
|---|---|---|---|---|
| NE0235373 | 88.9 | NE0235373_F | CGTAAATTGTAGTCCTTGCCTCAGT | |
| | | NE0235373_R | GGACAAGGGAGGAAGTTGAATCTAA | |
| | | NE0235373_V | CTCTATTGACAAGAAACAA | T |
| | | NE0235373_M | CTATTGACAGGAACAA | C |
| NE0240266 | 94.2 | NE0240266_F | CTGGTCCAACTCTACATGTACGT | |
| | | NE0240266_R | CCAATGGATAGTGAGATCGTATGGTAATT | |
| | | NE0240266_V | AGGGCGACACCATTGT | A |
| | | NE0240266_M | AGGGCGACACCCTTGT | C |
| NE0238769 | 95.0 | NE0238769_F | CAATCAATCAACAAGGACAAACCAATGA | |
| | | NE0238769_R | CTAGAGTATTACATTCTTTTGCCAAGGGA | |
| | | NE0238769_V | ATCTTGGATAGTACAGCTGTAT | C |
| | | NE0238769_M | ATCTTGGATAGTACAACTGTAT | T |
| NE0239621 | 103.6 | NE0239621_F | GTACTTTTTGTCTTGTTGGACCAATCC | |
| | | NE0239621_R | ACCATGTTGCAGTCAATACGTACA | |
| | | NE0239621_V | CCCCCTCCAATGTAAA | T |
| | | NE0239621_M | CCCCCTCCAGTGTAAA | C |
| NE0240354 | 111.7 | NE0240354_F | TCAGTTATATTAAAGAAAATGTATGATAAATAGCA | |
| | | NE0240354_R | GCAGTAAATGGATATATTATACGCAAAAGCA | |
| | | NE0240354_V | ATGTGTTGGTGTTGTATAA | A |
| | | NE0240354_M | ATGTGTTGGTGATGTATAA | T |

TABLE 7-continued

Primers and probes used for TaqMan ™ assay with markers of Table 6 (SEQ ID NOs: 63-86).

| Marker | Position | Primer or probe name | Sequence | Allele |
|---|---|---|---|---|
| NE0241248 | 113.6 | NE0241248_F | GTTGTTCCCTGCT CTTGCTGTA | |
| | | NE0241248_R | CACCGGCCAAGAT TCCTCAA | |
| | | NE0241248_V | CCTGTGTTGTGTT GTTGT | T |
| | | NE0241248_M | CTGTGTTGTGCTG TTGT | C |

Association mapping provided additional evidence that the position on chromosome 2 is common across the relevant pepper germplasm. Data obtained from assaying 2,836 mapped SNPs from a total of 122 yellow and 17 orange lines of the sweet blocky, sweet mini, and sweet long fruit types was used in a case-control association analysis implemented in PLINK. The strongest association between yellow- vs. orange color and a mapped SNP was detected for NE0238769 at position 95.04 cM on chromosome 2.

Figure 4:
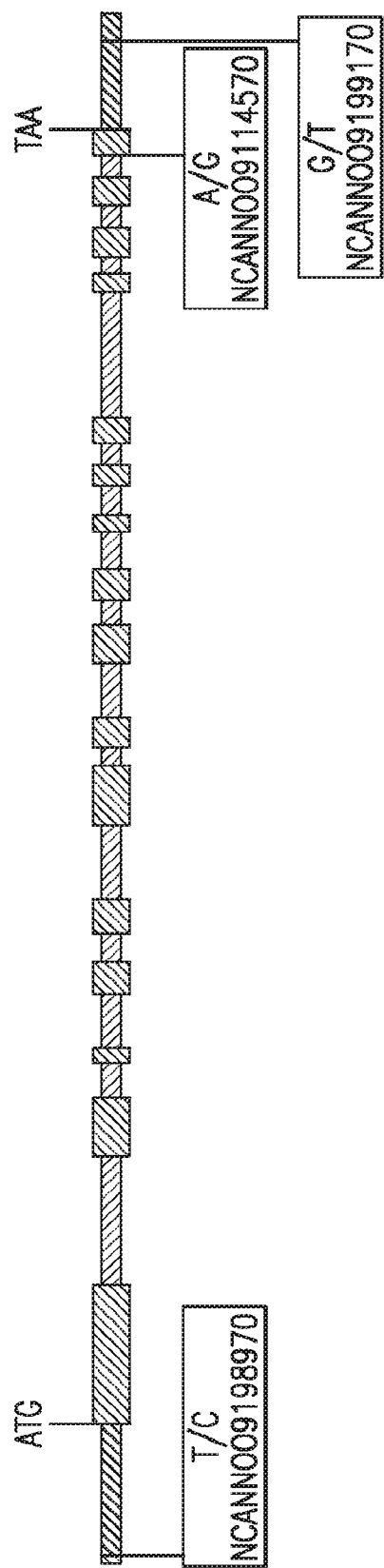
FIG. 4: The genomic structure of the Ze gene. Boxes set into top line represent coding regions (exons); other portions of the top line represent introns, and regions upstream of the ATG and downstream of the TAA represent the UTR. The start codon (ATG indicated on top line) and stop codon (TAA on top line) are also indicated, while the three identified SNPs are indicated on the bottom of the figure.

Only cDNA sequence was available for the *C. annuum* Ze gene in the public domain (Genbank X91491), and no SNPs were known to have been described in the coding sequence of the gene. Analysis of initial efforts to sequence the genomic gene sequence led to the conclusion that it was rich in introns (now known to be 15 introns in total) and extensive re-sequencing of genomic DNA was required to obtain the full sequence (introns and exons). In total 4803 bp were sequenced. The coding sequence (SEQ ID NO:56) comprises 1971 bp, corresponding to a 656 AA protein. This differs from Genbank X91491, which is 1983 bp in length, corresponding to a 660 AA protein. The coding sequence of SEQ ID NO:56 is divided over 16 exons. The 15 introns comprise 2831 bp while in total 950 bp are obtained from the UTR (Table 8). In total 3 SNPs were identified between yellow and orange lines (Table 8). The complete genomic organization of the Ze gene is represented in FIG. 4.

TABLE 8

Sizes in bp of coding and non-coding sequences in the pepper Ze gene.

| Coding sequence | | Non-Coding sequence | |
|---|---|---|---|
| | | 5' UTR | 526 |
| exon 1 | 497 | intron 1 | 505 |
| exon 2 | 196 | intron 2 | 150 |
| exon 3 | 42 | intron 3 | 213 |
| exon 4 | 101 | intron 4 | 117 |
| exon 5 | 116 | intron 5 | 285 |
| exon 6 | 212 | intron 6 | 86 |
| exon 7 | 90 | intron 7 | 226 |
| exon 8 | 123 | intron 8 | 104 |
| exon 9 | 99 | intron 9 | 163 |
| exon 10 | 31 | intron 10 | 130 |
| exon 11 | 65 | intron 11 | 96 |
| exon 12 | 86 | intron 12 | 480 |
| exon 13 | 55 | intron 13 | 81 |
| exon 14 | 89 | intron 14 | 96 |
| exon 15 | 85 | intron 15 | 99 |
| exon 16 | 84 | | |
| | | 3' UTR | 424 |
| Total | 1971 | | 3781 |

TABLE 9

SNPs identified in the Ze gene between orange and yellow lines (SEQ ID NOs: 87-89).

| Marker | Yellow allele | Orange allele | Location |
|---|---|---|---|
| NCANN009198970 | T | C | 5' UTR |
| NCANN009114570 | A | G | Intron 15 |
| NCANN009199170 | G | T | 3' UTR |

Figure 5:
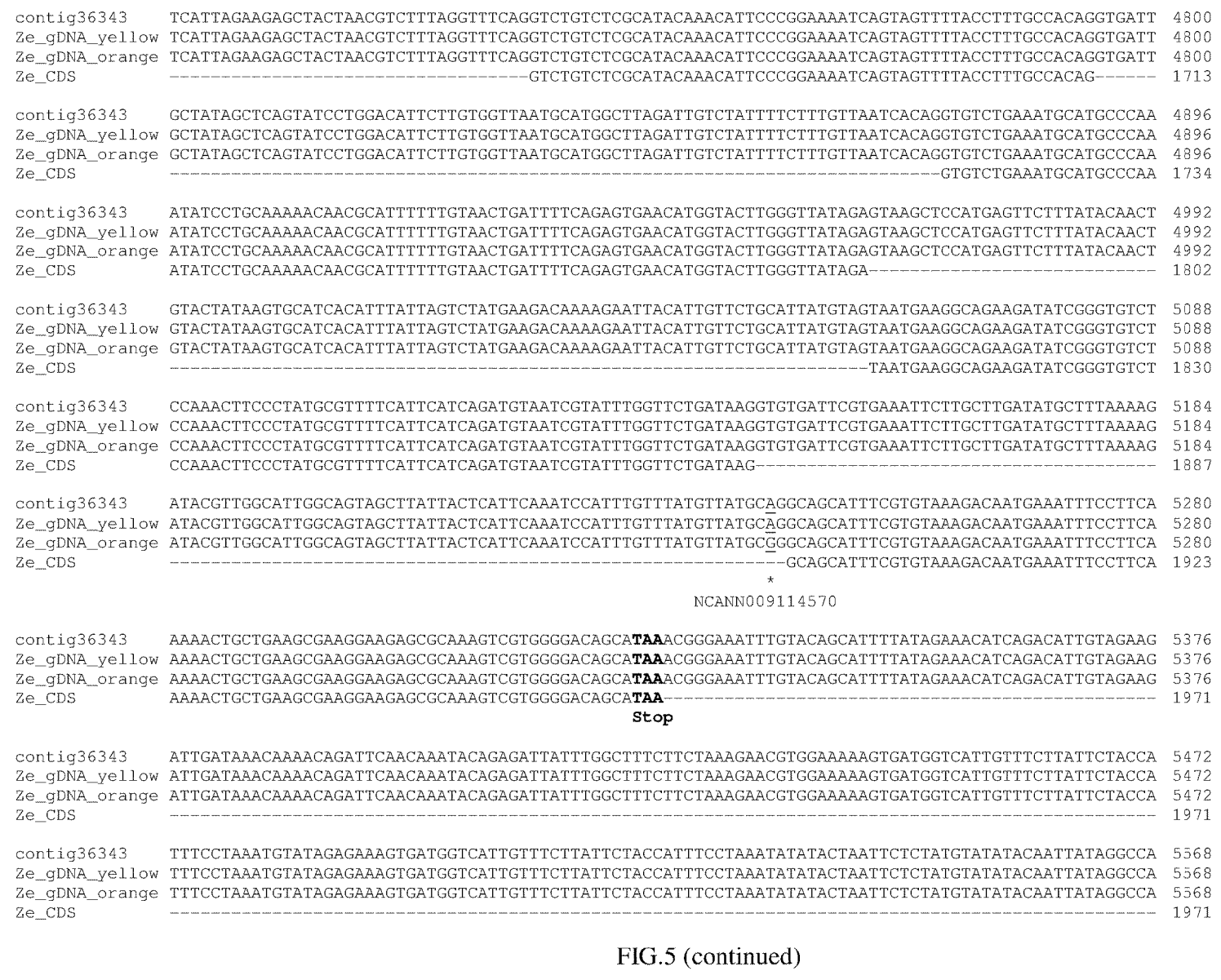

The [A/G] SNP in intron 15 (Table 9) is close to the intron-exon acceptor splice site and the allele found in orange lines (carrying the G allele) has a disrupted intron-exon acceptor site. In the Ze sequence of yellow fruited pepper lines, a typical acceptor splice site for an intron-exon barrier can be found on the borders of intron 15 and exon 16: CAGAGC (SEQ ID NO:90) (the ^ represents the actual splice site). The SNP in the allele found in orange lines has a sequence of CGGGC (SEQ ID NO:91), which is not a functional splice site. This SNP thus likely affects the plant's ability to produce a fully functional Zeaxanthin Epoxidase transcript and, as a result, significantly less yellow pigments are formed in plants carrying this allele in a homozygous state. As a result, these plants have orange fruits. The alignment in FIG. 5 shows the 3' region of the Ze gene and compares sequences of a yellow line to an orange line (SEQ ID NOs:96-97), the predicted coding sequence (SEQ ID NO:98), and a sequence from CM334 ("contig36343"; SEQ ID NO:99). All SNPs are indicated with an asterisk (*) and the marker names (MRNs) are indicated.

To carry out accuracy tests of marker NCANN009114570, a TaqMan™ assay was designed on the SNP NCANN009114570 (Table 10; SEQ ID NOs:92-95). For accuracy tests, marker NCANN009114570 was validated on a panel of 321 leaf samples. The panel was derived from variety trials and was dominated by lines bred for the Dutch greenhouse market. In all tested plants only one plant, out of 321 tested, gave an unexpected genotype, i.e. wherein the identified fruit color did not agree with the genotype at marker NCANN009114570 (yellow fruit expected for TT genotype; orange fruit expected for CC genotype), which was thought to be caused by an error in assignment of fruit color, as this is the same line used in CCS marker testing in which the phenotype and marker genotype did not agree. Thus, in this trial the marker was >99.6% accurate.

TABLE 10

Design details of TaqMan ™ assay NCANN009114570 (SEQ ID NOs: 92-95).

| Name | description | Sequence | Allele* |
|---|---|---|---|
| NCANN009114570_F | forward primer 1 | CAGCAGTTT TTGAAGGAA ATTTCATTG TC | |
| NCANN009114570_R | reverse primer | GGCATTGGC AGTAGCTTA TTACTCA | |
| NCANN009114570_V | VIC probe | ATGTTATGC GGGCAGCA | C |
| NCANN009114570_M | FAM probe | ATGTTATGC AGGCAGCA | T |

*probes are designed on the reverse complement sequence

Marker NCANN009114570 was designed on the reverse complement sequence of the Ze gene. The [A/G] SNP in the gene is therefore registered as a [C/T] SNP.

In conclusion, marker NCANN009114570 is based on a SNP that disrupts the production of a fully functional Zeaxanthin Epoxidase ("ZEP") transcript. The presence of this mutation appears almost perfectly correlated with the absence of yellow pigments in orange pepper fruits. The marker is highly predictive for mature fruit color in pepper and is a suitable marker for MAS and MABC applications.

This mutation yields a plant that can survive without a functional ZEP protein. It follows that other mutations in the gene also may result in the absence of yellow pigments in orange pepper fruits. An altered ZEP genotype may therefore be provided by any suitable means; for example, EMS, MMS, other mutagen-derived, in situ-derived, or naturally-occurring mutations can provide an altered ZEP genotype suitable for the development of the fruit color phenotypes described here. Color modulation of the fruit color phenotypes described here may also be achieved by transient disruption of ZEP function at the time of fruit set and/or fruit color maturation.

Example 3

Carotenoid Profiles of Red, Orange, and Yellow Pepper Fruits

The carotenoid profiles of various colored pepper fruits were measured, and those data used and to test the predictiveness of markers NCANN009113770 (CCS) and NCANN009114570 (ZEP) for determining the genotypes and phenotypes of the genes responsible for mature pepper fruit color. Carotenoid contents and profiles were analyzed in a panel of 133 pepper varieties representing red (n=55), orange (n=23), and yellow (n=55) mature fruit colors. The panel was selected from variety trials and contained lines predominantly for the Dutch greenhouse market. Carotenoid values were obtained using an Ultra high performance liquid chromatography (UHPLC) UV detection assay. Marker assay test results were obtained from DNA samples isolated from collected leaf samples.

Reversed Phase Ultra High Pressure Liquid Chromatography and UV DAD Detection of Carotenoid Pigments:

The pigment carotenoid content of the pepper samples was analyzed by reverse phase ultra high pressure liquid chromatography (UHPLC) UV DAD. All procedures were performed on ice, using amber glassware and/or reduced light where possible. Pepper samples were cut into pieces, removing and discarding the peduncle, seeds, and placental tissue, leaving only the pericarp. The pepper sample was weighed and an equal amount of nanopure water (1:1, weight/weight) was added. Samples were blended in a Vitamix blender (Vitamix Corporation, Cleveland, Ohio, USA) for approximately 30 seconds on high. The puree was transferred to a 50 mL centrifuge tube, and sample extraction and analysis was either performed immediately or stored at −80° C. Pureed pepper pericarp (0.5 g) was extracted with acetone:methanol:hexane (2:1:1, v/v/v, 0.5% BHT) containing 0.5 ppm β-apo-8'-carotenal (Sigma-Aldrich, St. Louis, USA). The extraction mixture was sonicated for 20 minutes on ice. After sonication, 1 M sodium chloride in water was added to the extraction mixture. Extraction vials were centrifuged and 1 ml aliquots of upper hexane phase were syringe filtered and placed in amber vials and either analyzed immediately or stored at −20° C. until analysis. Extracts were separated and analyzed using an Agilent 1260 UHPLC with quaternary pump and Waters BEH C18 column. The injection volume was 2 μl and the eluent flow was 0.375 μl/min. Detection and quantitation was by UV DAD by monitoring at 450±20 nm with no reference wavelength.

Data Processing:

Chromatograms were processed using Agilent Chemstation® software to integrate and identify peaks. Carotenoids were identified based upon relative retention time and UV absorption spectra in comparison to authentic standards. Carotenoids were quantified based upon generated relative response factors (RRF) using β-apo-8'-carotenal as an internal standard. Carotenoid esters were tentatively identified based upon absorption spectra, retention time and literature reference values. Retention characteristics of carotenoid esters were used to tentatively identify as either monoester or diester carotenoid pigments. Relative quantification was performed for monoester and diester carotenoid pigments using the calculated RRF values of the free carotenoid authentic standards.

Spectrophotometric Determination of Carotenoid Pigments.

UV absorption spectra (375-550 nm) were collected with a UV-Vis spectrophotometer. Briefly, 1.0 grams of pepper puree used was placed in a 50 ml conical tube. To the sample, 40 ml of 100% acetone was added. The tubes were shaken and placed in the dark at room temperature overnight. Prior to analysis, sample tubes were centrifuged for 15 minutes at 3000 rpm at room temperature (RT). A 1.0 ml aliquot was placed in a cuvette and spectra were recorded. Spectra were normalized to the spectra of pure acetone.

TABLE 11

Total carotenoid concentrations (μg/g FW) according to mature pepper fruit phenotype and genotype.

| Fruit Color | NCANN009113770 (INS/DEL) | NCANN009114570 (T/C) | Sample Number (n) | Capsanthin | Capsorubin | Zeaxanthin | β-carotene | β-cryptoxanthin |
|---|---|---|---|---|---|---|---|---|
| Red | INS | T | 36 | 60.80 ± 17.31 | 6.75 ± 2.05 | 1.57 ± 0.38 | 9.67 ± 3.46 | 0.94 ± 0.35 |
| Red | INS | H | 5 | 60.89 ± 21.54 | 5.67 ± 2.10 | 2.83 ± 1.15 | 9.48 ± 4.16 | 1.27 ± 0.56 |
| Red | INS | C | 2 | 25.38 ± 9.97 | 0.78 ± 0.14 | 23.92 ± 5.35 | 17.27 ± 7.11 | 1.91 ± 0.85 |
| Red | H | H | 6 | 64.28 ± 18.19 | 5.58 ± 2.05 | 3.21 ± 1.38 | 15.07 ± 6.16 | 1.79 ± 0.69 |
| Red | H | T | 6 | 49.85 ± 7.25 | 5.058 ± 0.92 | 2.08 ± 0.55 | 15.11 ± 5.15 | 1.23 ± 0.36 |
| Orange | DEL | C | 23 | ND | ND | 38.03 ± 9.98 | 14.07 ± 5.41 | 1.27 ± 0.44 |
| Yellow | DEL | T | 55 | ND | ND | 0.29 ± 0.12 | 0.94 ± 0.40 | 0.17 ± 0.13 |

| Fruit Color | NCANN009113770 (INS/DEL) | NCANN009114570 (T/C) | Sample Number (n) | Violaxanthin | Antheraxanthin | Lutein | α-Carotene |
|---|---|---|---|---|---|---|---|
| Red | INS | T | 36 | 2.58 ± 0.72 | 3.43 ± 0.99 | ND | ND |
| Red | INS | H | 5 | 2.53 ± 0.74 | 4.43 ± 1.65 | ND | ND |

TABLE 11-continued

Total carotenoid concentrations (μg/g FW) according to mature pepper fruit phenotype and genotype.

| | | | | | | | |
|---|---|---|---|---|---|---|---|
| Red | INS | C | 2 | 9.88 ± 3.95 | 0.14 ± 0.02 | ND | ND |
| Red | H | H | 6 | 3.47 ± 1.02 | 4.28 ± 1.42 | ND | ND |
| Red | H | T | 6 | 2.82 ± 0.41 | 3.32 ± 0.62 | ND | ND |
| Orange | DEL | C | 23 | 1.73 ± 0.50 | 6.66 ± 2.42 | 7.32 ± 1.21 | 0 ± 0 |
| Yellow | DEL | T | 55 | 10.32 ± 3.45 | 1.08 ± 0.41 | 3.47 ± 0.67 | 0.81 ± 0.38 |

*Mean ± SD;
ND—Not Detected;
H—Heterozygous

In red vs. non-red varieties, 55 phenotypic red varieties were analyzed for carotenoid content. As shown in Table 11, all lines phenotypically scored as red contained the red carotenoids capsanthin and capsorubin. Of the 78 non-red varieties (orange and yellow), no capsanthin or capsorubin pigments were detected in any samples tested. Marker NCANN009113770 was applied to the sample set to understand the predictability of red vs. non-red classification. As shown in Table 12, samples containing the CCS insertion (n=43) or heterozygotic (H) for the insertion (n=12), contained the red carotenoids capsanthin and capsorubin. Of the samples positive for the deletion (n=78), no capsanthin or capsorubin pigments were detected. These data indicate that the carotenoids capsanthin and capsorubin are indicative of red pepper fruits and that marker NCANN009113770 predicts the presence or absence of the red carotenoids capsanthin and capsorubin in this subset of red peppers.

Within the non-red varieties, varieties were scored as orange (n=23) or yellow (n=55) based upon visual appearance. As indicated in Table 11, all non-red varieties were positive for the CCS deletion according to the NCANN009113770 marker and were devoid of the red carotenoids capsanthin and capsorubin in their fruits. Among orange varieties, the highest concentration of carotenoids was evidenced from the orange carotenoid fraction, namely zeaxanthin and β-carotene. Zeaxanthin concentrations were highest in the orange varieties compared to both red and yellow varieties. Among yellow varieties, the highest concentration of carotenoids was evidenced in the yellow carotenoids, namely violaxanthin and lutein. The yellow carotenoid concentrations were significantly higher than orange carotenoids in the yellow pepper varieties.

The NCANN009114570 marker is predicted to specify the presence of a fully functional or impaired-function ZEP enzyme. Accordingly, perturbation in this enzyme (e.g. in translation or catalytic function) is expected to produce changes in the carotenoid profile namely through accumulation of zeaxanthin or production of the carotenoids antheraxanthin and violaxanthin. All yellow varieties (n=55) were positive for the T-allele, indicating presence of a fully functional ZEP enzyme. Yellow varieties accumulated the yellow carotenoid violaxanthin at the highest concentration. In comparison, all orange varieties were positive for the C-allele (Table 11), indicating the presence of a ZEP enzyme with reduced function. Accordingly, the orange varieties accumulated significant concentrations of zeaxanthin, implicating a non-functional ZEP protein. Further evidence of a impaired function ZEP is provided within the red varieties. Two red varieties that contained the CCS insertion also contained the C-allele of ZEP. These varieties, while still producing significantly lower concentrations of capsanthin and capsorubin, produced significantly higher concentration of zeaxanthin compared to other red varieties (Table 10). The zeaxanthin concentrations were similar to levels seen in orange varieties. These data indicate that the C-allele of the ZEP protein encodes a ZEP enzyme with significantly decreased function resulting in the accumulation of the orange carotenoid zeaxanthin.

To further understand the contribution of colored carotenoid fractions, color ratios were constructed based upon the total carotenoid concentration of the red, orange, or yellow carotenoid fractions. As shown in Table 12, for red varieties the red carotenoid fraction constitutes the largest pool of carotenoids when compared with the contribution of the orange or yellow carotenoids to the total carotenoid pool. In orange varieties, the orange carotenoid fraction constitutes the major carotenoid fraction compared to the yellow carotenoids. In yellow varieties, the yellow carotenoid fraction constitutes the largest carotenoid pool compared to the orange fraction. These data further indicate that mature pepper fruit color is driven by the underlying carotenoid profiles, which constitutes the red, orange, and yellow phenotypic appearance of pepper fruit colors.

Based upon the analytical data, red pepper fruits contain the red carotenoids capsanthin and capsorubin while they are not detected in non-red (orange or yellow) fruits. The presence of red carotenoids was associated with the presence of the CCS insertion (NCANN009113770) while the absence of red carotenoids is associated with the CCS

TABLE 12

Carotenoid color ratios according to mature pepper fruit phenotype and genotype.

| | | | | Carotenoid Color Ratio* | | |
|---|---|---|---|---|---|---|
| Fruit Color | NCANN009113770 (INS/DEL) | NCANN009114570 (T/C) | Sample Number (n) | Red Ratio $R_{Total}/(Y_{Total} + O_{Total})$ | Orange Ratio $O_{Total}/(R_{Total} + Y_{Total})$ | Yellow Ratio $Y_{Total}/(R_{Total} + O_{Total})$ |
| Red | INS | T | 36 | 3.76 ± 0.52 | 0.17 ± 0.03 | 0.08 ± 0.01 |
| Red | INS | H | 5 | 3.27 ± 0.54 | 0.19 ± 0.04 | 0.09 ± 0.01 |
| Red | INS | C | 2 | 0.49 ± 0.03 | 1.21 ± 0.10 | 0.14 ± 0.01 |
| Red | H | H | 6 | 2.60 ± 0.57 | 0.26 ± 0.06 | 0.09 ± 0.01 |
| Red | H | T | 6 | 2.33 ± 0.49 | 0.30 ± 0.06 | 0.08 ± 0.01 |
| Orange | DEL | C | 23 | NA | 3.37 ± 0.39 | 0.30 ± 0.03 |
| Yellow | DEL | T | 55 | NA | 0.09 ± 0.02 | 11.75 ± 2.92 |

*Mean ± SD deletion. In orange and yellow fruits, increased concentration of zeaxanthin is associated with orange mature pepper fruit color. Moreover, the increase in zeaxanthin is correlated with the C-allele of marker NCANN009114570. The presence of the ZEP T-allele results in shift in carotenoid fractions towards the yellow carotenoids, resulting in yellow fruit color. Further evidence of the ZEP function and prediction accuracy of marker NCANN009114570 is found in two varieties phenotypically described as red but predicted by this marker to be orange. The major carotenoid accumulated by these two varieties is the orange carotenoid zeaxanthin and the carotenoid distribution, as evidenced by the carotenoid ratios, is aligned with the observed orange carotenoid profiles. The analytical data combined with the marker information, indicate that the CCS and ZEP enzymes predict mature pepper fruit color.

Example 4

Linkage Disequilibrium Decay Surrounding Ccs and Ze

Markers based on causal genes are especially valuable for breeding and trait integration purposes when linkage disequilibrium (LD) around a trait locus is low. On the other hand, when LD around the causal mutation is relatively higher, then a linked marker in strong LD with the causal gene may suffice for most breeding applications. To better understand the value of the discovered mutations, for breeding, an LD analysis using marker data was performed for chromosomes 2 and 6 harboring the color loci Ze and Ccs, respectively. In total, 5191 SNP markers were used in this analysis. The analysis was performed on several pepper subpopulations (based on fruit type) and monomorphic markers within these populations were excluded in the analysis. In total, 882 pepper lines were used for the analysis.

LD was estimated using the $r^2$ metric (Hill and Robertson, TAG 38:226-231, 1968) and was calculated for all pairs of markers on LG6 and LG2 for each subpopulation. LD decay was examined using the equation: $LD_{ij}=1/(1+4b_j d_i)+e_{ij}$, where LD is the observed $r^2$ between the i-th marker pair in subpopulation j, $d_i$ is the genetic distance between the i-th marker pair in Morgans, $b_j$ is the coefficient of LD decay in subpopulation j, and $e_{ij}$ is the random residual. The extent of LD decay was taken to be the genetic distance required for LD to decay to $r^2=0.1$ or to 50% of the maximum estimated value, predicted using the aforementioned model.

LD appears to decay relatively rapidly in pepper: $r^2$ was estimated to reduce to 0.1 within 0.55 cM on LG6 and 1.65 cM on LG2 when elite hot and sweet pepper lines were considered together (e.g. see Table 13). Much of this diversity is attributable to hot pepper varieties: LD decays over 0.41 cM and 0.47 cM in LG6 and LG2, respectively. Conversely, for sweet pepper varieties, LD decays over 0.96 cM on LG6 and 2.47 cM on LG2. That is, for sweet peppers, LD appears to decay ~2.6 times slower on LH2 than LG6. Within sweet pepper varieties, the difference in LD decay is more substantial between bell (blocky; "SB") and mini ("SM") peppers, although LD and LD decay estimates are affected by sample size. For bell peppers, LD decays almost three times slower on LG2 than LG6, which is comparable to estimates of the total population studied.

Excluding all subpopulations with fewer than 20 lines, it takes up to 4.1 cM for LD to decay to $r^2=0.1$ on LG6 and up to 10 cM for LD to decay to $r^2=0.1$ on LG2. In consideration of immediate regions of the trait loci, LD decays to $r^2=0.1$ within 2 cM at the CCS locus and 4 cM at the Ze locus. Moreover, LD decay estimates surrounding the traits were very different to those observed for entire linkage groups. When only six relevant pepper types (where mature color varies and where color markers are thus most likely to be useful) were examined, LD decay surrounding Ccs was estimated as unchanged compared to the rest of the linkage group but was 1.5-times faster surrounding Ze than the rest of LG2. Thus, the presumptive causal mutation in Ze described here is of particular value when compared to a physically linked SNP since LD decays relatively rapidly around this locus.

TABLE 13

Summary of LD decay estimates on LG6 and LG2 for each subpopulation.

| Sub-population | N | LG6 | | LG2 | | LG2:LG6 | |
|---|---|---|---|---|---|---|---|
| | | cM to $\frac{1}{2}r^2_{max}$ | cM to $r^2 = 0.1$ | cM to $\frac{1}{2}r^2_{max}$ | cM to $r^2 = 0.1$ | cM to $\frac{1}{2}r^2_{max}$ | cM to $r^2 = 0.1$ |
| All | 882 | 0.06 | 0.55 | 0.18 | 1.65 | 2.99 | 2.99 |
| sweet | 537 | 0.11 | 0.96 | 0.27 | 2.47 | 2.57 | 2.57 |
| hot | 345 | 0.05 | 0.41 | 0.05 | 0.47 | 1.15 | 1.15 |
| bell | 319 | 0.21 | 1.87 | 0.60 | 5.43 | 2.90 | 2.90 |
| mini | 17 | 1.90 | 17.10 | 3.14 | 28.22 | 1.65 | 1.65 |
| red | 224 | 0.19 | 1.75 | 0.62 | 5.54 | 3.17 | 3.17 |
| yellow | 95 | 0.45 | 4.06 | 1.10 | 9.94 | 2.45 | 2.45 |
| orange | 17 | 1.07 | 9.67 | 5.78 | 52.06 | 5.39 | 5.39 |
| S[BM][RYO] | 339 | 0.40 | 1.78 | 0.62 | 5.56 | 1.55 | 3.12 |
| SBR | 221 | 0.40 | 1.80 | 0.71 | 6.36 | 1.77 | 3.53 |
| SBY | 89 | 0.66 | 4.11 | 0.68 | 6.09 | 1.03 | 1.48 |
| SBO | 12 | 1.64 | 12.99 | 4.99 | 44.87 | 3.03 | 3.45 |
| SMR | 5 | 13.05 | 115.66 | 12.06 | 108.54 | 0.92 | 0.94 |
| SMY | 6 | 52.51 | 470.75 | 9.60 | 86.39 | 0.18 | 0.18 |
| SMO | 6 | 14.26 | 126.53 | 47.19 | 424.75 | 3.31 | 3.36 |
| All (subregion) | 882 | 0.12 | 1.05 | 0.07 | 0.67 | 0.64 | 0.64 |
| S[BM][RYO] (subregion) | 339 | 0.61 | 1.93 | 0.42 | 3.82 | 0.69 | 1.97 |

S[BM]RYO indicates the combined population of six pepper types: SBR (i.e. sweet, bell, red subpopulation), SBY (i.e. sweet, bell, yellow subpopulation), SBO (i.e. sweet, bell, orange subpopulation), SMR (i.e. sweet, mini, red subpopulation), SMY (i.e. sweet, mini, yellow subpopulation), and SMO.
"cM to $\frac{1}{2}r^2_{max}$" is the genetic distance in cM for $r^2$ to decay to 50% of its predicted maximum;
"cM to $r^2 = 0.1$" is the genetic distance in cM for $r^2$ to decay to 0.1; L2:L6 is the ratio of LD decay estimates between LG2 and LG6.

Example 5

Breeding for Fruit Color Using Markers for Ccs and Ze

The identification of the presumptive causal SNPs in the two major color genes in pepper allows inference as to mature fruit color in pepper based on marker data. Table 14 shows the predicted fruit colors based on the markers NCANN009113770 (red vs. yellow; based on the Ccs gene) and NCANN009114570 (yellow vs. orange based on the Ze gene). The Ccs red allele is dominant to the yellow allele, and the yellow Ze allele is dominant to the orange allele. Therefore, a plant heterozygous for both genes has red fruits.

TABLE 14

Expected fruit colors based on Ccs and Ze genotypes.

|  |  |  | NCANN009113770 | | |
| --- | --- | --- | --- | --- | --- |
|  |  |  | INSINS CCSCCS | INSDEL CCSccs | DELDEL ccsccs |
| NCANN009114570 | AA | ZEZE | Red | Red | Yellow |
|  | AG | ZEze | Red | Red | Yellow |
|  | GG | zeze | Red* | Red* | Orange |

*Plants with a CCSCCSzeze genotype (red-orange fruits) are visually scored to have red fruits, however the carotenoid profile is more consistent with orange fruits. It is expected that the same is true of plants with the CCSccszeze genotype.

Figure 6:
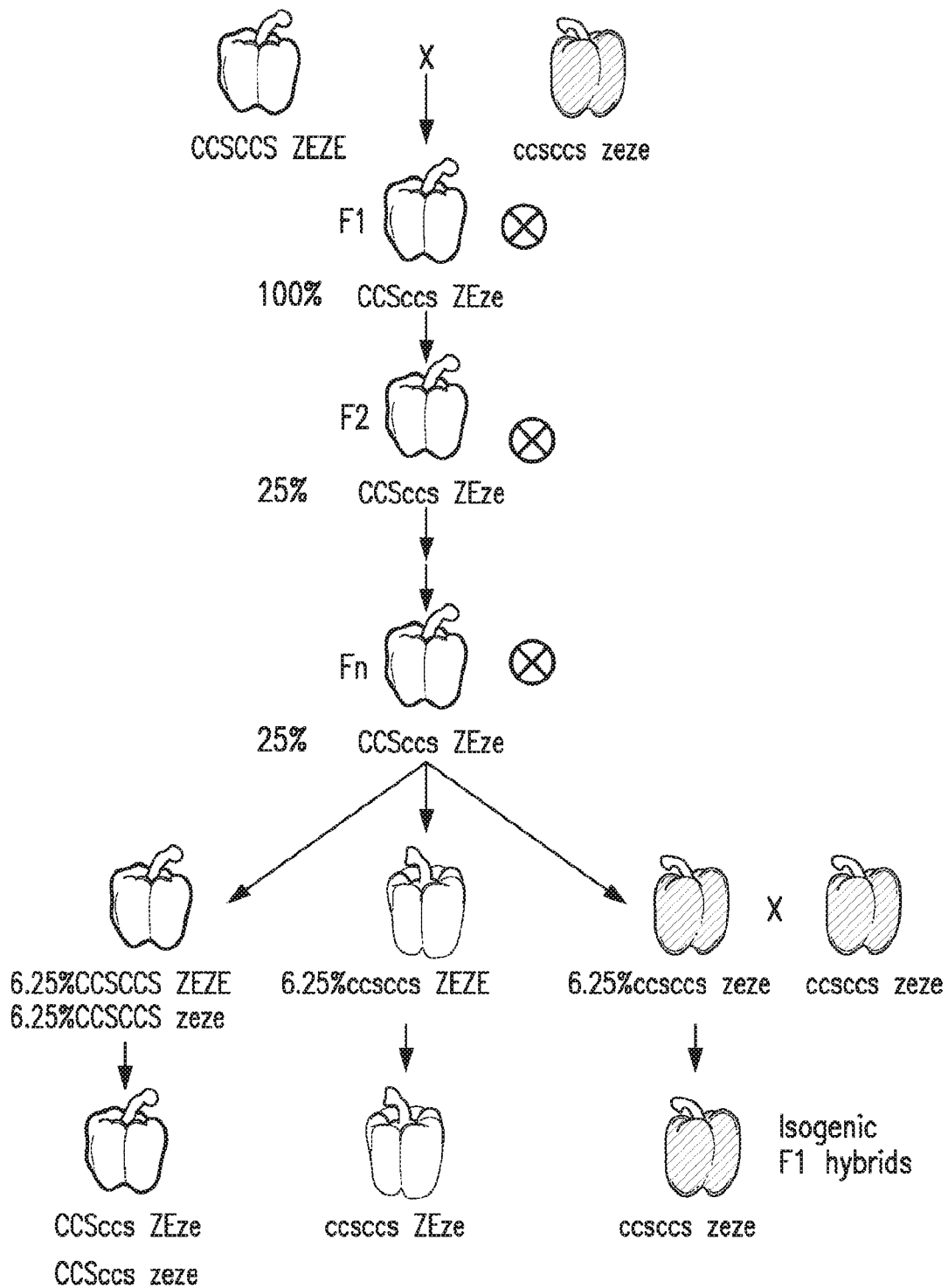
FIG. 6: An exemplary breeding scheme to create nearly isogenic orange, yellow, and red fruited pepper lines.

These two markers allow for marker assisted breeding in pepper for mature fruit color as described below. Sources of the genetic diversity described here exist in publically available germplasm. For example, diversity in the described color markers exists in the commercial hybrids Orange Glory (ccsccs zeze), Derby (ccsccs ZEZE), Shanghai (ccsccs ZEZE), Aifos (CCSCCS ZEZE) and Darsena (CCSCCS ZEZE). For instance, as discussed above, breeding for fruit color in peppers can be performed, wherein these color markers (or analogous linked markers) allow for simplification of multiple breeding programs based on color into one multi-color breeding program (FIG. 6). This can be achieved by crossing a red line that has both the intact Ccs and Ze alleles (CCSCCS ZEZE) with an orange line (ccsccs zeze) and maintaining both loci in a heterozygous state throughout the breeding process. In each generation, the subset of plants heterozygous for both color loci are selected with markers, and breeders may perform additional phenotypic selection on these plants. When the line is sufficiently genetically and phenotypically fixed after n generations the line can be selfed one final time and the progeny of the desired color genotype and phenotype can be selected using the markers for Ccs and Ze. This results in homozygous nearly isogenic lines that only differ in the mature fruit colors red, yellow and orange and loci tightly linked to the color loci. These nearly isogenic lines can be used to produce nearly isogenic hybrids, which are of interest because each of the differently colored nearly isogenic hybrids will have similar horticultural properties, allowing growers to manage each variety in the same way. Currently, red, yellow and orange commercial pepper varieties are each distinct and may each have different pruning, nutritional, or pest control needs, adding complexity and expense to operations producing more than one color type.

Figure 7:
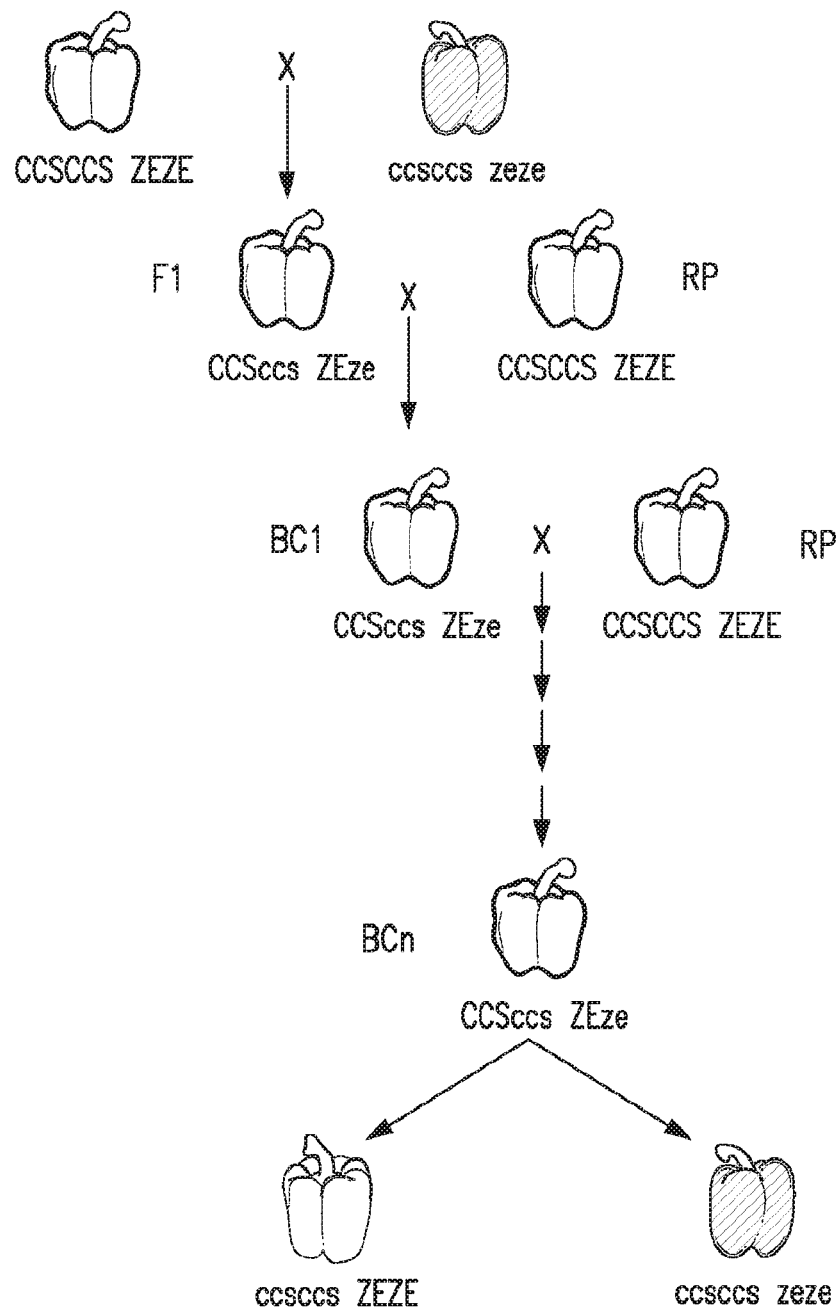
FIG. 7: Exemplary breeding scheme to create nearly isogenic orange, yellow, and red fruited pepper lines through marker assisted backcrossing ("MABC").

Isogenic inbred lines may also be created through marker assisted back crossing (MABC) using the new markers. Because red lines are typically the most advanced with respect to agronomic and disease traits, an improved orange or yellow line could be created by crossing an orange line with good color (color donor) to an elite red line with good agronomic and disease traits (recurrent parent). (FIG. 7).

Finally conventional marker-assisted breeding (MAS) can benefit greatly from the use of these color markers. Again, because red is the most economically important color and typically the most focused on for breeding efforts, MAS can be used to improve the orange and yellow germplasm. In a red by orange cross the red colored parent can be used to introduce more advanced agronomic traits while the orange parent is used to introduce the preferred color alleles. The color markers can be used to fix the color loci in the F2 generation and in subsequent generations, the lines with the best agronomic traits can be selected on a family basis. These methodologies may be used within and among any pepper species that are crossable in the genus *Capsicum*. For example these markers may be used to move these color mutations, and thus a desired fruit color phenotype, into any desired pepper genetic background.

What is claimed is:

1. A method of producing *Capsicum* pepper seed, said method comprising:
   (a) producing a set of near isogenic inbred *Capsicum* pepper lines that collectively comprise functional and non-functional Capsanthin-Capsorubin Synthase (Ccs) and Zeaxanthin epoxidase (ZE) alleles; and
   (b) crossing said pepper lines to produce seed of near isogenic hybrid plants that comprise combinations of said alleles that result in red, yellow and orange fruit; wherein said producing a set of near isogenic inbred pepper lines comprises marker assisted selection for a Ccs and/or a Ze allele, wherein marker assisted selection for said Ze allele comprises detecting the presence or absence of a Ze allele comprising a single nucleotide polymorphism in genetic marker NCANN009114570.

2. The method of claim 1, wherein producing a set of near isogenic lines comprises producing a plant that has been inbred but segregates for a Ccs or Ze allele.

3. The method of claim 1, wherein producing a set of near isogenic lines comprises producing a plant that has been inbred but segregates for Ccs and Ze alleles.

4. The method of claim 2, wherein the plant that has been inbred has been selfed for three or more generations.

5. The method of claim 1, wherein producing a set of near isogenic inbred pepper lines comprises marker assisted selection for a Ccs or Ze allele.

6. The method of claim 5, wherein producing a set of near isogenic inbred pepper lines comprises marker assisted selection for Ccs and Ze alleles.

7. The method of claim 5, wherein marker assisted selection comprises detecting a deletion in a Ccs allele or the absence thereof.

8. The method of claim 1, wherein the near isogenic inbred pepper lines are homozygous for said Ccs and Ze alleles.

9. The method of claim 1, wherein the pepper lines are selected from the pepper species consisting of *Capsicum annuum, C. baccatum, C. chinense, C. frutescens*, and *C. pubescens*.

10. The method of claim 1, wherein the pepper lines are sweet peppers.

11. A method of selecting a *Capsicum* pepper plant for fruit color genotype, said method comprising:
    (a) detecting in a *Capsicum* plant the presence or absence of a Zeaxanthin epoxidase (Ze) allele conferring said fruit color, wherein said Ze allele comprises a single nucleotide polymorphism in genetic marker NCANN009114570; and
    (b) selecting the plant based on the presence or absence of said allele.

12. The method of claim 11, wherein detecting the presence or absence of a Zeaxanthin epoxidase (Ze) allele comprises detecting a genetic marker in linkage disequilibrium with said polymorphism.

13. The method of claim 11, wherein detecting the presence or absence of a Zeaxanthin epoxidase (Ze) allele comprises detecting the presence or absence of a single nucleotide polymorphism that is causative for said fruit color.

14. The method of claim 11, further comprising:
    (c) crossing the selected plant from step (b) with a second *Capsicum* pepper plant.

15. The method of claim 11, wherein the plant is a *Capsicum annuum* plant.

16. The method of claim 15, wherein the plant is a sweet pepper plant.

* * * * *